US009045562B2

(12) United States Patent
Murphy et al.

(10) Patent No.: US 9,045,562 B2
(45) Date of Patent: Jun. 2, 2015

(54) COMPOSITIONS AND METHODS FOR MODULATING LYMPHOCYTE ACTIVITY

(75) Inventors: Kenneth M. Murphy, St. Louis, MO (US); Theresa L. Murphy, St. Louis, MO (US); John R. Sedy, St. Louis, MO (US); Michelle A. Hurchla Pyles, St. Louis, MO (US); Norihiko Watanabe, Chiba (JP); Jianfei Yang, Sandy Hook, CT (US)

(73) Assignee: Washington University, St. Louis, MO (US)

( * ) Notice: Subject to any disclaimer, the term of this patent is extended or adjusted under 35 U.S.C. 154(b) by 586 days.

(21) Appl. No.: 13/341,611

(22) Filed: Dec. 30, 2011

(65) Prior Publication Data

US 2012/0207759 A1 Aug. 16, 2012

Related U.S. Application Data

(60) Continuation of application No. 12/977,562, filed on Dec. 23, 2010, now Pat. No. 8,546,541, which is a continuation-in-part of application No. 11/875,537, filed on Oct. 19, 2007, now abandoned, which is a division of application No. 10/600,997, filed on Jun. 20, 2003, now Pat. No. 7,304,149, said application No. 12/977,562 is a continuation-in-part of application No. 11/719,356, filed as application No. PCT/US2005/041446 on Nov. 15, 2005, now Pat. No. 8,188,232.

(60) Provisional application No. 60/390,653, filed on Jun. 20, 2002, provisional application No. 60/438,593, filed on Jan. 6, 2003, provisional application No. 60/628,474, filed on Nov. 15, 2004.

(51) Int. Cl.
C07K 16/28 (2006.01)
C07K 14/705 (2006.01)
A61K 39/00 (2006.01)

(52) U.S. Cl.
CPC ..... *C07K 14/70521* (2013.01); *A61K 2039/505* (2013.01); *C07K 14/70532* (2013.01); *C07K 16/2818* (2013.01); *C07K 2317/76* (2013.01); *C07K 2319/00* (2013.01); *C07K 2319/30* (2013.01); *C07K 2317/34* (2013.01)

(58) Field of Classification Search
None
See application file for complete search history.

(56) References Cited

U.S. PATENT DOCUMENTS

| 7,153,950 | B2 * | 12/2006 | Clark et al. | 536/23.5 |
|---|---|---|---|---|
| 7,304,149 | B2 | 12/2007 | Murphy | |
| 7,479,544 | B2 | 1/2009 | Clark | |
| 7,605,229 | B2 * | 10/2009 | Clark et al. | 530/350 |
| 7,863,422 | B2 * | 1/2011 | Clark et al. | 530/387.1 |
| 8,188,232 | B1 | 5/2012 | Murphy | |
| 8,303,952 | B2 | 11/2012 | Murphy | |
| 2004/0091884 | A1 | 5/2004 | Clark | |
| 2004/0175380 | A1 | 9/2004 | Allison | |
| 2005/0272118 | A1 | 12/2005 | Clark | |
| 2007/0161061 | A1 | 7/2007 | Clark | |
| 2008/0269464 | A1 * | 10/2008 | Murphy et al. | 530/387.1 |
| 2009/0022713 | A1 | 1/2009 | Clark | |
| 2009/0081229 | A1 | 3/2009 | Clark | |
| 2009/0175855 | A1 | 7/2009 | Clark | |
| 2010/0310582 | A1 | 12/2010 | Murphy | |
| 2011/0230647 | A1 | 9/2011 | Murphy | |
| 2011/0236401 | A1 | 9/2011 | Murphy | |
| 2012/0214972 | A1 | 8/2012 | Murphy | |
| 2012/0232259 | A1 | 9/2012 | Murphy | |
| 2012/0322986 | A1 | 12/2012 | Murphy | |
| 2013/0034571 | A1 | 2/2013 | Murphy | |

FOREIGN PATENT DOCUMENTS

| AU | 2003215368 A1 | 5/2004 |
|---|---|---|
| AU | 2004325035 A1 | 5/2006 |
| BR | PI0419117 A | 12/2007 |
| CA | 2503125 A1 | 5/2004 |
| CA | 2586615 A1 | 5/2006 |
| CN | 101421298 A | 4/2009 |
| EP | 1560593 A1 | 8/2005 |
| EP | 1812465 A1 | 8/2007 |
| JP | 2006515167 T | 5/2006 |
| JP | 2008519599 T | 6/2008 |
| MX | 2007005612 A | 8/2007 |
| WO | 9940100 A1 | 8/1999 |
| WO | 0202624 A2 | 1/2002 |
| WO | 0206317 A2 | 1/2002 |
| WO | 0210187 A1 | 2/2002 |
| WO | 0216429 A2 | 2/2002 |
| WO | 0216581 A2 | 2/2002 |
| WO | 02072794 A2 | 9/2002 |
| WO | 2004000221 A3 | 12/2003 |
| WO | 2004039394 A1 | 5/2004 |

(Continued)

OTHER PUBLICATIONS

Sequence alignment, 2014, 2 pages.*
Notice of Allowance dated Jul. 19, 2010 from related U.S. Appl. No. 11/719,356, 4 pgs.
Notice of Allowance dated Sep. 23, 2010 from related U.S. Appl. No. 11/875,537, 4 pgs.
Notice of Allowance dated Mar. 16, 2012 from related U.S. Appl. No. 12/796,392, 5 pgs.
Non-final Office action dated Jun. 20, 2012 from related U.S. Appl. No. 12/977,562, 6 pgs.
Notice of Allowance dated Jun. 25, 2012 from related U.S. Appl. No. 12/796,392, 5 pgs.
Final Office action dated Oct. 18, 2012 from related U.S. Appl. No. 12/977,562, 6 pgs.

(Continued)

*Primary Examiner* — Ilia Ouspenski
(74) *Attorney, Agent, or Firm* — Polsinelli PC

(57) ABSTRACT

The present invention provides a novel lymphocyte inhibitory receptor termed BTLA which is expressed on both T and B cells, and identifies HVEM as interacting with BTLA. Methods and compositions for modulating BTLA-mediated signaling and interfering with the interaction of BTLA and HVEM for therapeutic, diagnostic and research purposes are also provided.

5 Claims, 99 Drawing Sheets

(56) References Cited

FOREIGN PATENT DOCUMENTS

| WO | 2004096976 A3 | 11/2004 |
|---|---|---|
| WO | 2006054961 A2 | 5/2006 |
| WO | 2007001459 A3 | 1/2007 |
| WO | 2008112840 A2 | 9/2008 |

OTHER PUBLICATIONS

Notice of Allowance dated Oct. 26, 2012 from related U.S. Appl. No. 11/875,537, 5 pgs.
Notice of Allowance dated Oct. 28, 2010 from related U.S. Appl. No. 11/719,356, 4 pgs.
Non-final Office action dated Jan. 09, 2013 from related U.S. Appl. No. 13/645,748, 5 pgs.
Non-final Office action dated Jan. 28, 2013 from related U.S. Appl. No. 13/474,101, 10 pgs.
Abbas, "T-cell stimulation: an abundance of B7s", Nature Medicine, 1999, pp. 1345-1346, vol. 5, No. 12.
Anderson, "Paradoxical inhibition of T-cell function in response to CTLA-4 blockade; heterogeneity within the human T-cell population", Nature Medicine, 2000, pp. 211-214, vol. 6, No. 2.
Brodie, "LICOS, a primordial costimulatory ligand?", Current Biology, 2000, pp. 333-336, vol. 10.
Carreno, "The B7 Family of Ligands and Its Receptors: New Pathways for Costimulation and Inhibition of Immune Responses", Annu. Rev. Immunol., 2002, pp. 29-53, vol. 20.
Chambers, et al., "CTLA-4-Mediated Inhibition in Regulation of T Cell Responses: Mechanisms and Manipulation in Tumor Immunotherapy", Annu. Rev. Immunol., 2001, pp. 565-594, vol. 19.
Chanbers, "Thymocyte development is normal in CTLA-4-deficient mice", PNAS, 1997, pp. 9296-9301, vol. 94.
Chapoval, "B7-H3: A costimulatory molecule for T cell activation and IFN-γ production", Nature Immunology, 2001, pp. 269-274, vol. 2, No. 3.
Chen, "Co-Inhibitory Molecules of the B7-CD28 Family in the Control of T-Cell Immunity", Nature Review of Immunology, 2004, pp. 336-347, vol. 4.
Cheung, "Evolutionarily divergent herpesviruses modulate T cell activation by targeting the herpesvirus entry mediator cosignaling pathway", PNAS, 2005, pp. 13218-13223, vol. 102, No. 37.
Compaan, "Attenuating Lymphocyte Activity The Crystal Structure of the BTLA-HVEM Complex", Journal of Biological Chemistry, 2005, pp. 39553-39561, vol. 280, No. 47.
Connolly, "Structure-Based Analysis of the Herpes Simplex Virus Glycoprotein D Binding Site Present on Herpesvirus Entry Mediator HveA (HVEM)", Journal of Virology, 2002, pp. 10894-10904, vol. 76, No. 21.
Croft, "Co-Stimulatory members of the TNFR family: keys to effective T-cell immunity?", Nature Reviews, 2003, pp. 609-620, vol. 3.
Coyle, "The expanding B7 superfamily: Increasing complexity in costimulatory signals regulating T cell function", Nature Immunology, 2001, pp. 203-209, vol. 2, No. 3.
Damle, "Costimulation of T Lymphocytes with Intergrin Ligands Intercellular Adhesion Molecule-1 or Vascular Cell Adhesion Molecule-1 Induces Functional Expression of CTLA-4, a Second Receptor for B7", Journal of Immunology, 1994, pp. 2666-2697, vol. 152.
Dong, "B7-H1, a third member of the B7 family, co-stimulates T-cell proliferation and interleukin-10 secretion", Nature Medicine, 1999, pp. 1365-1369, vol. 5, No. 12.
Freeman, "Engagement of the PD-1 Immunoinhibitory Receptor by a Novel B7 Family Member Leads to Negative Regulation of Lymphocyte Activation", J. Exp. Med., 2000, pp. 1027-1034, vol. 192, No. 7.
Granger, "LIGHT-HVEM signaling and the regulation of T cell-mediated immunity", Cytokine and Growth Factor Reviews, 2003, pp. 289-296, vol. 14.
Hsu, "ATAR, a Novel Tumor Necrosis Factor Receptor Family Member, Signals through FRAF2 and FRAF5", The Journal of Biological Chemistry, 1997, pp. 13471-13474, vol. 272, No. 21.
Hurchla, "B and T Lymphocyte Attenuator Exhibits Structural and Expression Polymorphisms and Is Highly Induced in Anergic CD4+ T Cells", The Journal of Immunology, 2005, pp. 3377-3385, vol. 174.
Kearney, "Antigen-Dependent Clonal Expansion of a Trace Population of Antigen-Specific CD4+ T Cells In Vivo Is Dependent on CD28 Costimulation and Inhibited by CTLA-4I", The Journal of Immunology, 1995, pp. 1032-1036, vol. 155.
Krummel, "CD28 and CTLA-4 Have Opposing Effects on the Response of T cells to Stimulation", J. Exp. Med., 1995, pp. 459-465, vol. 182.
Kwon, "A Newly Identified Member of the Tumor Necrosis Factor Receptor Superfamily with a Wide Tissue Distribution and Involvement in Lymphocyte Activation", The Journal of Biological Chemistry, 1997, pp. 14272-14276, vol. 272, No. 22.
Latchman, "PD-L2 is a second ligand for PD-1 and inhibits T cell activation", Nature Immunology, 2001, pp. 261-268, vol. 2, No. 3.
Liang, "The right place at the right time: novel B7 family members regulate effector T cell responses", Current Opinion in Immunology, 2002, pp. 384-390, vol. 14.
Ling, "Cutting Edge: Identification of GL50, a Novel B7-Like Protein That Functionally Binds to ICOS Receptor", Journal of Immunology, 2000, pp. 1653-1657, vol. 164.
Mauri, "LIGHT, a New Member of the TNF Superfamily and Lymphotoxin α Are Ligands for Herpesvirus Entry Mediator", Immunity, 1998, pp. 21-30, vol. 8.
Montgomery, "Herpes Simplex Virus-1 Entry into Cells Mediated by a Novel Member of the TNF/NGF Receptor Family", Cell, 1996, pp. 427-436, vol. 87.
Nishimura, "PD-1: an inhibitory immunoreceptor involved in peripheral tolerance", Trends in Immunology, 2001, pp. 265-268, vol. 22, No. 5.
Peach, "Complementarity Determining Region 1 (CDR1)- and CDR3-analogous Regions in CTLA-4 and CD28 Determine the Binding to B7-1", J. Exp. Med., 1994, pp. 2049-2056, vol. 180.
Sarrias, "The three HveA receptor ligands, gD, LT-α and LIGHT bind to distinct sites on HveA", Molecular Immunology, 2000. pp. 665-673, vol. 37.
Scheu, "Targeted Disruption of LIGHT Causes Defects in Costimulatory T Cell Activation and Reveals Cooperation with Lymphotoxin β in Mesenteric Lymph Node Genesis", J. Exp. Med., 2002, pp. 1613-1624, vol. 195, No. 12.
Sedy, "B and T lymphocyte attenuator regulates T cell activation through interaction with herpesvirus entry mediator", Nature Immunology, 2005, pp. 90-98, vol. 6, No. 1.
Sotomayor, "In vivo blockade of CTLA-4 enhances the priming of responsive T cells but fails to prevent the induction of tumor antigen-specific tolerance", PNAS, 1999, pp. 11476-11481, vol. 96.
Sun, "Characterization of Mouse and Human B7-H3 Genes", The Journal of Immunology, 2002, pp. 6294-6297, vol. 168, No. 12.
Sussman, "Activation of T Lymphocytes for the Adoptive Immunotherapy of Cancer", Annals of Surgical Oncology, 1994, pp. 296-306, vol. 1, No. 4.
Swallow, "B7h, a Novel Costimulatory Homolog of B7.1 and B7.2, Is Induced by TNF α", Immunity, 1999, pp. 423-432, vol. 11.
Tao, "Differential Effects of B and T Lymphocyte Attenuator and Programmed Death-1 on Acceptance of Partially versus Fully MHC-Mismatched Cardiac Allografts1", The Journal of Immunology, 2005, pp. 5774-5782, vol. 175.
Tseng, "B7-DC, a New Dendritic Cell Molecule with Potent Costimulatory Properties for T Cells", J. Exp. Med., 2001, pp. 839-845, vol. 193, No. 7.
Wang, "Costimulation of T cells by B7-H2, a B7-like molecule that binds ICOS", Blood, 2000, pp. 2808-2813, vol. 96.
Watanabe, "BTLA is a lymphocyte inhibitory receptor with similarities to CTLA-4 and PD-1", Nature Immunology, 2003, pp. 670-679, vol. 4, No. 7.
Whitbeck, "Glycoprotein D of Herpes Simplex Virus (HSV) Binds Directly to HVEM, a Member of the Tumor Necrosis Factor Receptor Superfamily and a Mediator of HSV Entry", Journal of Virology, 1997, pp. 6083-6093, vol. 71, No. 8.
Yang, "Enhanced Induction of Antitumor T-Cell Responses by Cytotoxic T Lymphocyte-associated Molecule-4 Blockade: The

(56) References Cited

OTHER PUBLICATIONS

Effect Is Manifested Only at the Restricted Tumor-bearing Stages", Cancer Research, 1997, pp. 4036-4041, vol. 57.

Yoshinaga, "T-cell co-stimulation through B7RP-1 and ICOS", Nature, 1999, pp. 827-832, vol. 402.

Zhu, "Cytotoxic T lymphocyte-associated antigen 4 (CTLA-4) blockade enhances incidence and severity of experimental autoimmune neuritis in resistant mice", Journal of Neuroimmunology, 2001, pp. 111-117, vol. 115.

International Search Report dated May 22, 2007 regarding PCT/US2005/041446.

Loyet, Proteomic Profiling of Surface Proteins on Th1 and Th2 Cells, Journal of Proteome Research, Jan. 28, 2005, pp. 400-409.

Gonzalez, A coreceptor interaction betwen the CD28 and TNF receptor family members B and T lymphocyte attenuator and herpesvirus entry mediator, PNAS, Jan. 25, 2005, pp. 1116-1121, vol. 102, No. 4.

Non-final Office action dated Mar. 1, 2010 from related U.S. Appl. No. 11/875,537, 6 pgs.

Non-final Office action dated Mar. 21, 2006 from related U.S. Appl. No. 10/600,997, 21 pgs.

Non-final Office action dated Jan. 8, 2007 from related U.S. Appl. No. 10/600,997, 8 pgs.

International Search Report dated Feb. 11, 2004 from related international application No. PCT/US2003/019614, 3 pgs.

Non-final Office action dated Mar. 22, 2010 from related U.S. Appl. No. 11/719,356, 8 pgs.

Notice of Allowance dated Jul. 19, 2007 from related U.S. Appl. No. 10/609,997, 8 pgs.

Non-final Office action dated Dec. 20, 2011 from related U.S. Appl. No. 11/875,537, 6 pgs.

Non-final Office action dated May 16, 2011 from related U.S. Appl. No. 11/875,537, 9 pgs.

Notice of Allowance dated Jun. 17, 2010 from related U.S. Appl. No. 11/875,537, 4 pgs.

Notice of Allowance dated Dec. 5, 2011 from related U.S. Appl. No. 11/719,356, 7 pgs.

Non-final Office action dated May 6, 2011 from related U.S. Appl. No. 11/719,356, 11 pgs.

Non-final office action dated Feb. 6, 2012 from related U.S. Appl. No. 13/005,346, 8 pgs.

Bodey, Failure of Cancer Vaccines: the Significant Limitations of This Approach to Immunotherapy, Anticancer Res. 20(4):2665-2676, Jul.-Aug. 2000.

Christadoss, Animal Models of Myasthenia Gravis, Clin. Immunol. 94(2):75-87, Feb. 2000.

Dudley, Cancer Regression and Autoimmunity in Patients After Clonal Repopulation with Anti-tumor Lymphocytes, Science, 268(5594):850-854, Oct. 2002.

Egen, CTLA-4: New Insights Into Its Biological Function and Use in Tumor, Nat. Immunol. 3(7):611-618, Jul. 2002.

Gao, Tumor Vaccination That Enhances Antitumor T-cell Responses Does Not Inhibit the Growth of Established Tumors Even in Combination with Interleukin-12 Treatment: the Importance of Inducing Intratumoral T-cell Migration, J. Immunother. 23(6):643-653, 2000.

Gribben, Alloatigen and Concomitant CTLA4 Signaling Induces Clonal Deletion of Alloreative T Cells: a Novel Method to Prevent GVHD, Blood 84(1):397a, 1994.

Heslop, Cytokine Gene Transfer in the Therapy of Malignancy, Bailliere Clin. Haematol. 7(1):135-151, Mar. 1994.

Leach, Enhancement of Antitumor Immunity by CTLA-4Blockade, Science 271(5256):1734-1739, Mar. 1996.

Lee, Increased Vaccine-specific T Cell Frequency After Peptide-based Vaccination Correlates with Increased Susceptibility to in vitro Stimulation But Does Not Lead to Tumor Regression, J. Immunol. 163(11):6292-6300, Dec. 1999.

Lewis, Growth Regulation of Human Breast and Ovarian Tumor Cells by Heregulin: Evidence of the Requirement of ErbB2 as a Critical Component in Mediating Herequlin Responsiveness, Cancer Res. 56:1457-1465, Mar. 1996.

Pardoll, Tumor Reactive T Cells Get a Boost, Nat. Biotechnol. 20(12):1207-1208, Dec. 2002.

Timmerman, Dendritic Cell Vaccines for Cancer Immunotherapy, Annu. Rev. Med. 50:507-529, 1999.

Triozzi, Clinical and Immunologic Effects of a Synthetic B-human Chorionic Gonadotropin Vaccine, Int. J. Oncol. 5:1447-1453, 1994.

Wallack, Active Specific Immunotherapy with Vaccinia Melanoma Oncolysate, Immunity 1(5):405-413, Aug. 1994.

Wang, Costimulation of T Cells by B7-H2, a B7-like Molecule That Binds ICOS, Blood 96(8):2808-2813, Oct. 2000.

Zaks, Immunization with a Peptide Epitope (p. 369-377) from HER-2/neu Leads to Peptide-specific Cytotoxic T Lymphocytes That Fail to Recognize HER-2/neu+ Tumors, Cancer Res. 58:4902-4908, Nov. 1998.

Attwood, The Babel of Bioinformatics, Science, 290:471-473, Oct. 2000.

Promega pGEM-T and pGEM-T Easy Vector Systems Technical Manual, Dec. 2005, 2 pgs.

Watanabe, BTLA is a Lymphocyte Inhibitory Receptor with Similarities to CTLA-4 and PD-1, Nature Immunology, 4 (7), 10 pgs, Jul. 2003.

Arceci, The Potential for Antitumor Vaccination in Acute Myelogenous Leukemia, J. Mol. Med. 76:80-93, 1998.

Notice of Allowance dated Apr. 24, 2013 from related U.S. Appl. No. 13/645,748; 6 pages.

Notice of Allowance dated May 28, 2013 from related U.S. Appl. No. 12/977,562; 6 pages.

* cited by examiner

MOUSE B7x PROTEIN SEQUENCE

MASLGQIIFWSIINIIIILAGAIALIIGFGISGKHFITVTTFTSAGNIGEDGTLSCTFEPDIKLNGIVIQWL

KEGIKGLVHEFKEGKDDLSQQHEMFRGRTAVFADQWVGNASLRLKNVQLTDAGTYTCYIRTS

KGKGNANLEYKTGAFSMPEINVDYNASSESLRCEAPRWFPQPTVAWASQVDQGANFSEVSNT

SFELNSENVTMKVVSVLYNVTINNTYSCMIENDIAKATGDIKVTDSEVKRRSQLQLLNSGPSPCV

FSSAFAAGWALLSLSCCLMLR

HUMAN B7x PROTEIN SEQUENCE

MASLGQILFWSIISIIIILAGAIALIIGFGISGRHSITVTTVASAGNIGEDGILSCTFEPDIKLSDIVIQWLKEG

VLGLVHEFKEGKDELSEQDEMFRGRTAVFADQVIVGNASLRLKNVQLTDAGTYKCYIITSKGKGNANL

EYKTGAFSMPEVNVDYNASSETLRCEAPRWFPQPTVVWASQVDQGANFSEVSNTSFELNSENVTM

KVVSVLYNVTINNTYSCMIENDIAKATGDIKVTESEIKRRSHLQLLNSKASLCVSSFFAISWALLPLSPYL

FIG. 1

MOUSE B7x NUCLEIC ACID SEQUENCE

ATGGCTTCCTTGGGGCAGATCATCTTTTGGAGTATTATTAACATCATCATCATCCTGGCTGGGGC

CATCGCACTCATCATTGGCTTTGGCATTTCAGGCAAGCACTTCATCACGGTCACGACCTTCACCT

CAGCTGGAAACATTGGAGAGGACGGGACCCTGAGCTGCACTTTTGAACCTGACATCAAACTCAA

CGGCATCGTCATCCAGTGGCTGAAAGAAGGCATCAAAGGTTTGGTCCACGAGTTCAAAGAAGGC

AAAGACGACCTCTCACAGCAGCATGAGATGTTCAGAGGCCGCACAGCAGTGTTTGCTGATCAGG

TGGTAGTTGGCAATGCTTCCCTGAGACTGAAAAACGTGCAGCTCACGGATGCTGGCACCTACAC

ATGTTACATCCGCACCTCAAAAGGCAAAGGGAATGCAAACCTAGAGTATAAGACCGGAGCCTTC

AGTATGCCAGAGATAAATGTGGACTATAATGCCAGTTCAGAGAGTTTACGCTGCGAGGCTCCTC

GGTGGTTCCCCCAGCCCACAGTGGCCTGGGCATCTCAAGTCGACCAAGGAGCCAACTTCTCAG

AAGTCTCGAACACCAGCTTTGAGTTGAACTCTGAGAATGTGACCATGAAGGTCGTATCTGTGCTC

TACAATGTCACAATCAACAACACATACTCCTGTATGATTGAAAATGACATTGCCAAAGCCACTGG

GGACATCAAAGTGACAGATTCAGAGGTCAAAAGGCGGAGTCAGCTGCAGCTGCTCAACTCCGG

GCCTTCCCCGTGTGTTTTTCTTCTGCCTTTGCGGCTGGCTGGGCGCTCCTATCTCTCTCCTGTT

GCCTGATGCTAAGATGA

FIG. 2

HUMAN B7x NUCLEIC ACID SEQUENCE

ATGGCTTCCCTGGGGCAGATCCTCTTCTGGAGCATAATTAGCATCATCATTATTCTGGCTGGAGC

AATTGCACTCATCATTGGCTTTGGTATTTCAGGGAGACACTCCATCACAGTCACTACTGTCGCCT

CAGCTGGGAACATTGGGGAGGATGGAATCCTGAGCTGCACIIIIGAACCTGACATCAAACTTTCT

GATATCGTGATACAATGGCTGAAGGAAGGTGTTTTAGGCTTGGTCCATGAGTTCAAAGAAGGCAA

AGATGAGCTGTCGGAGCAGGATGAAATGTTCAGAGGCCGGACAGCAGTGTTTGCTGATCAAGTG

ATAGTTGGCAATGCCTCTTTGCGGCTGAAAAACGTGCAACTCACAGATGCTGGCACCTACAAATG

TTATATCATCACTTCTAAAGGCAAGGGGAATGCTAACCTTGAGTATAAAACTGGAGCCTTCAGCA

TGCCGGAAGTGAATGTGGACTATAATGCCAGCTCAGAGACCTTGCGGTGTGAGGCTCCCCGATG

GTTCCCCCAGCCCACAGTGGTCTGGGCATCCCAAGTTGACCAGGGAGCCAACTTCTCGGAAGTC

TCCAATACCAGCTTTGAGCTGAACTCTGAGAATGTGACCATGAAGGTTGTGTCTGTGCTCTACAA

TGTTACGATCAACAACACATACTCCTGTATGATTGAAAATGACATTGCCAAAGCAACAGGGGATA

TCAAAGTGACAGAATCGGAGATCAAAAGGCGGAGTCACCTACAGCTGCTAAACTCAAAGGCTTC

TCTGTGTGTCTCTTCTTTCTTTGCCATCAGCTGGGCACTTCTGCCTCTCAGCCCTTACCTGATGCT

AAAATAA

FIG. 3

```
B7x    1 MASLGQI IFWSI INI I I I LAGAI ALI IGFGI-SGKH
B7.1   1 MACNCQLMQDTP-----LLKFPCPRLILLFVLLIRL
B7.2   1 MDPRCTMG----------LAILIFVTVLL------I
B7h    1 MQLKCPCFVSLGT--RQPVWKKLHVSSGFFSGLGLF
PD-L1  1 MRIFAGII---------FTACCHLLRA------F
PD-L2  1 MLLLLPILN--------LSLQLHPVAAL------F
B7-H3  1 MLRGWGGPSVGVCV-RTALGVLCLCLTGA------V
```

```
                                              *
FITVT------TFTSAGNIGEDGTLSCTF--EPDIKL  64
SQVSS-----DVDEQLSKSVKDKVLLPCRYN-SPHEDE 63
SDAVS------VETQAYFNGTAYLPCPFTKAQNISL   50
LLLLSSLCAASAETEVGAMVGSNVVLSCIDPHRRHFNL 72
TITAP-------KDLYVVEYGSNVTMECRFPVERELDL 50
TVTAP-------KEVYTVDGSSVSLECDFDRRECTEL  52
EVQVS------EDPVVALVDTDATLRCSFSPEPGFSL  60
```

```
B7x   65 NGIVIQWLKEG----IKGLVHEFKEGKDDLSQQHEM
B7.1  64 SEDRIYWQKHD-------KVVLSVIAGKLKVWPEYKN
B7.2  51 SELVVFWQDQQ------KLVLYEHYLG--TEKLDSVN
B7h   73 SGLYVYWQIENPEVSVTYYLPYKSPG-INVDSSYKN
PD-L1 51 LALVVYWEKED----EQVIQFVAGEE--DLKPQHSN
PD-L2 53 EGIRASLQK-----------VEN--DTSLQ-SE
B7-H3 61 AQLNLIWQLTD----TKQLVHSFTEGR-DQGSAYSN
```

```
                                                  *
FRGRTAVFADQVVVGNASLRLKNVQLTDAGTYTCYIRT 134
---RTLYDNTTY----SLIILGLVLSDRGTYSCVVQK 123
---AKYLGRTSFDRNNWTLRLHNVQIKDMGSYDCFIQK 114
---RGHLSLDSMKQGNFSLYLKNVTPQDTQEFTCRVFM 142
FRGRASLPKDQLLKGNAALQITDVKLQDAGVYCCIISY 118
---RATLLEEQLPLGKALFHIPSVQVRDSGQYRCLVIC 106
---RTALFPDLLVQGNASLRLQRVRVTDEGSYTCFVSI 126
```

Signal peptide

| | | | |
|---|---|---|---|
| human B7x | 1 MASLGQI LFWSI I | S | I I LAGATALI I GEGI SGRHS | TVT TVASGNI | 48 |
| mouse B7x | 1 MASLGQI I FWSI I | N | I I LAGAI ALI I GFGI SGKHF | LTVT T TSAGNI | 48 |

IgV-like domain

| | | | |
|---|---|---|---|
| human B7x | 49 GEDGI LSCTFEPDIKLSD | I | VIQWLKEGV LGLVHEFKEGKDELS | EQ DEM | 96 |
| mouse B7x | 49 GEDGT LSCTFEPDIKL NG | I | VIQWLKEGI KGLVHEFKEGKDDLS | QQ HEM | 96 |

| | | | |
|---|---|---|---|
| human B7x | 97 FRGRTAVFADQVI VGNASLRLKNVQLTDAGTYKCYI | TSKGKGNANLE | 144 |
| mouse B7x | 97 FRGRTAVFADQV VVGNASLRLKNVQLTDAGTY T CYI R TSKGKGNANLE | | 144 |

IgC-like domain

| | | | |
|---|---|---|---|
| human B7x | 145 YKI GAESMPE VNVDYNASSET LRCEAPHWF PQPTVVWASQVDQGANFS | 192 |
| mouse B7x | 145 YKTGAFSMPE I NVDYNASSES LRCEAPRWF PQPTVAWASQVDQGANFS | 192 |

| | | | |
|---|---|---|---|
| human B7x | 193 EVSNTSFELNSENVTMKVVSVLYNVTI NNTYSCMI ENDI AKATGDI KV | 240 |
| mouse B7x | 193 EVSNI SFELNSENVI MKVVSVLYNI I NNI YSCMI ENDI AKAI GDI KV | 240 |

Transmembrane | Cytoplasmic

| | | | |
|---|---|---|---|
| human B7x | 241 ESEI KRRS H QLLNSKA SL CV- SS F FAI SWALL PL S PYLMLK | 282 |
| mouse B7x | 241 DSEVKRRS Q QLLNSNI SGP SP CVFSS A AGWALL SL S CCLMLR | 283 |

FIG. 5

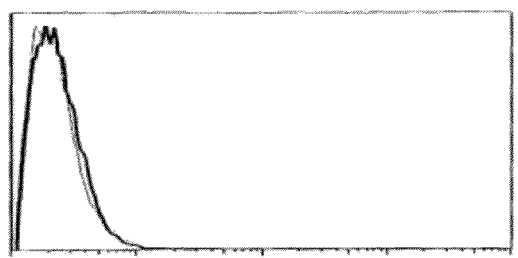 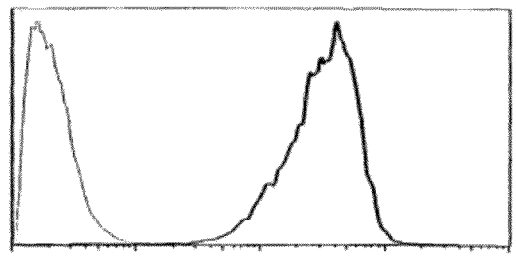
B7x-Ig                              Anti-CD28
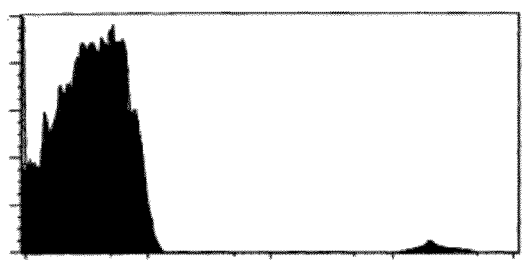 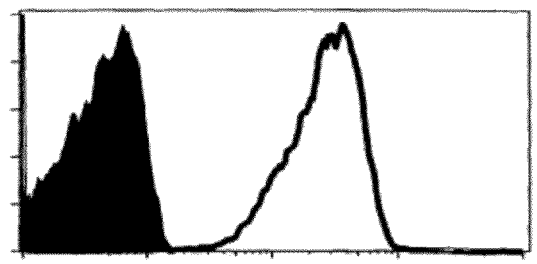
B7x-Ig                              Anti-ICOS
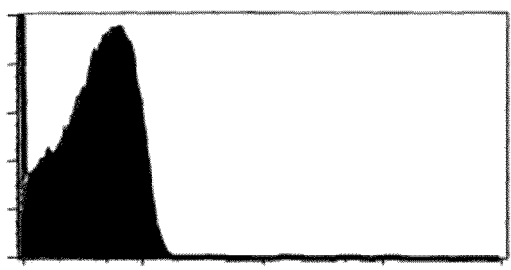 
B7x-Ig                              Anti-PD-1
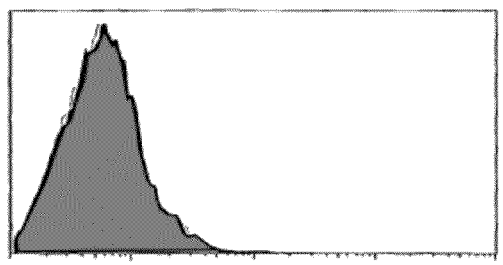 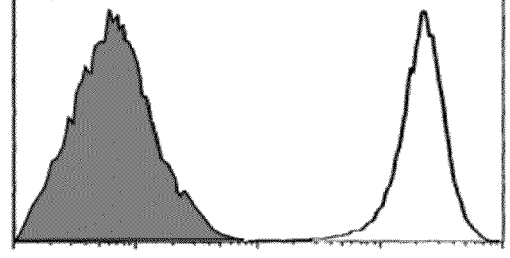
B7x-Ig                              Anti-CTLA-4
FIG. 12

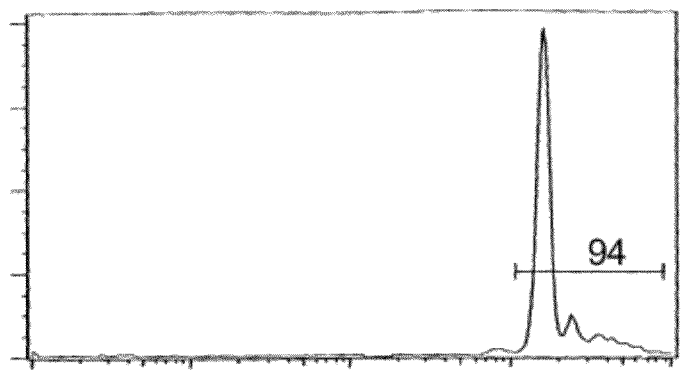
GFP/CHO
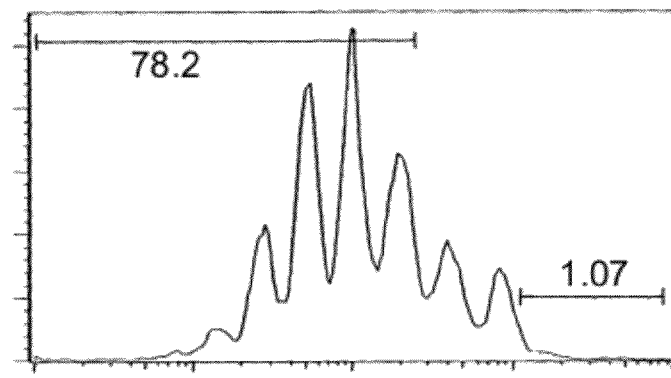
GFP/CHO + anti-CD3
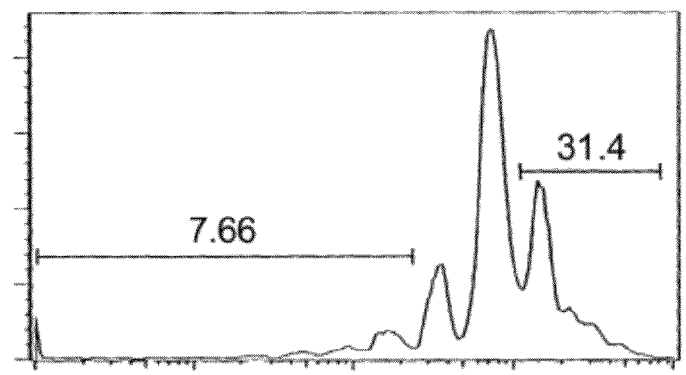
B7x/CHO + anti-CD3
FIG. 17

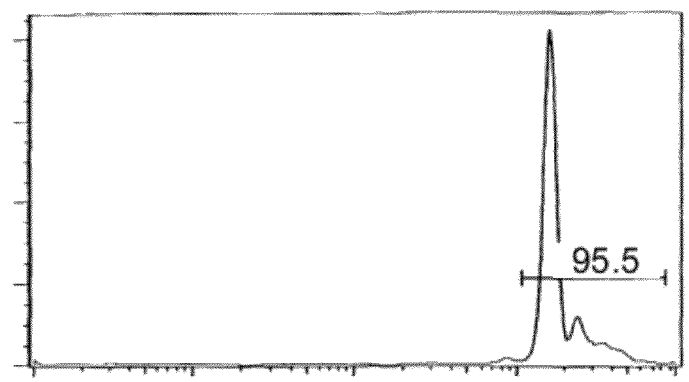
GFP/CHO
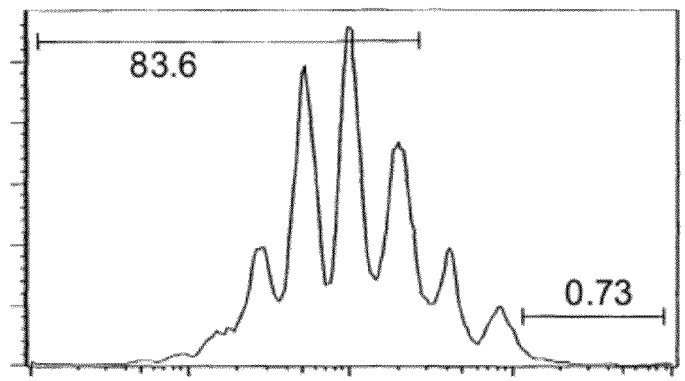
GFP/CHO + anti-CD3
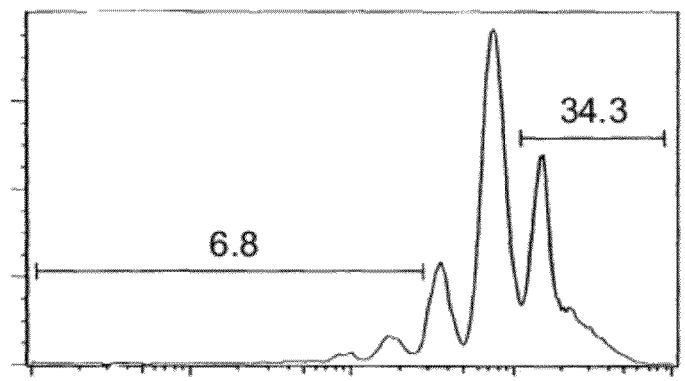
B7x/CHO + anti-CD3
FIG. 18

```
mouse BTLA  1  MKTVPAMLGTPRLFREFFIL·HLGLWSILCEKATKRNDEE
human BTLA     MKTLPAMLGTGKLFWVFFLIPYLDIWNI·······HGKES 40  CEVQLNIKRNSKHSAWTGELFKIECPVKYCVHRPNVTWCK
               CDVQLYIKRQSEHSILAGDPFELECPVKYCANRPHVTWCK 80  HNGTIWVPLEVGPQLYTSWEENRSVPVFVLHFKPIHLSDN
               LNGTTCVKLEDR·Q··TSWKEEKNISFFILHFEPVLPNDN 120  GSYSCSTNFNSQVINSHSVTIHVRERTQNSSEHPLITVSD
               GSYRCSANFQSNLIESHSTTLYVTDVKSAS··········

160  IPDATNASGPSTMEERPGRTWLLYTLLPLGALLLLL·ACV
               ········ERPSKDEMAS·RPWLLYSLLPLGGLPLLITTCF

199  CLLCFLKRIQGKEKKPSDLAGRDTNLVD········IPASS
               CLFCCLRRHQGKQNELSDTAGREINLVDAHLKSEQTEAST

232  RTNHQALPSQTGIYDNDPWSS··MQDESELTISLQSERNN
               RQNSQVLLSETGIYDNDPDLCFRMQEGSEVYSNPCLEENK

270  QGIVYASLNHCVIGRNPRQENNMQEAPTEYASICVRS
               EGIVYASLNHSVIGLNSRLARNVKEAPTEYASICVRS
```

FIG. 19

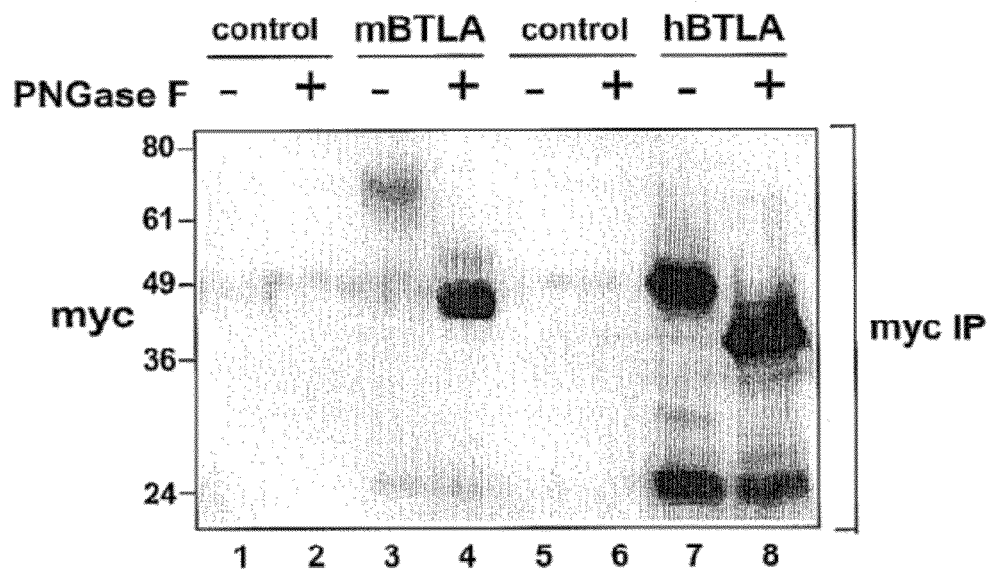
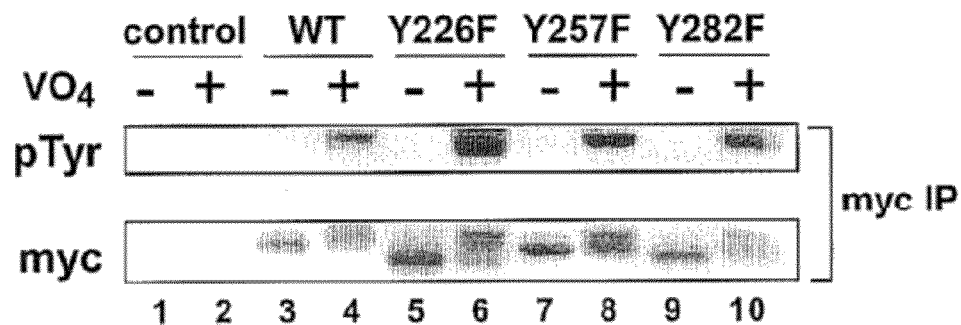
FIG. 23

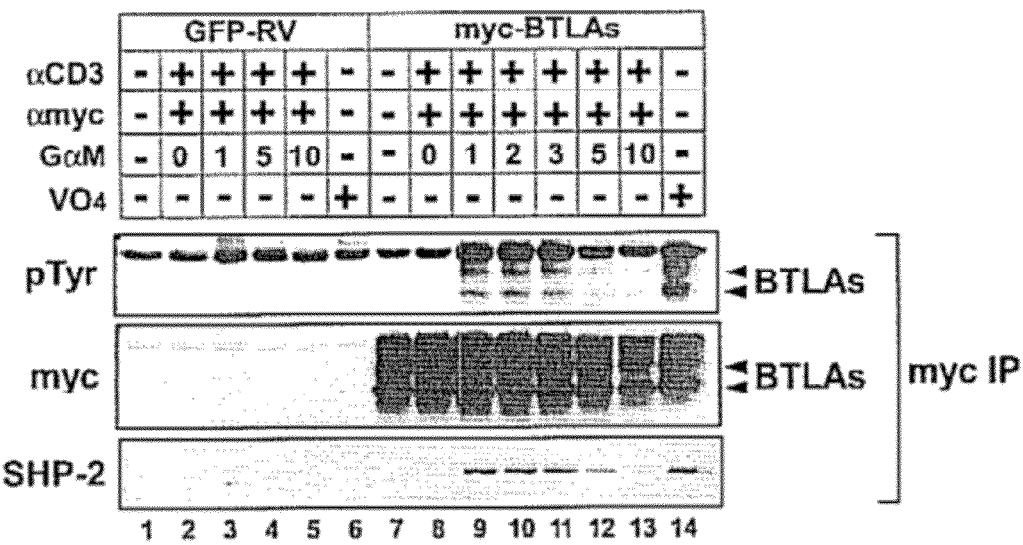
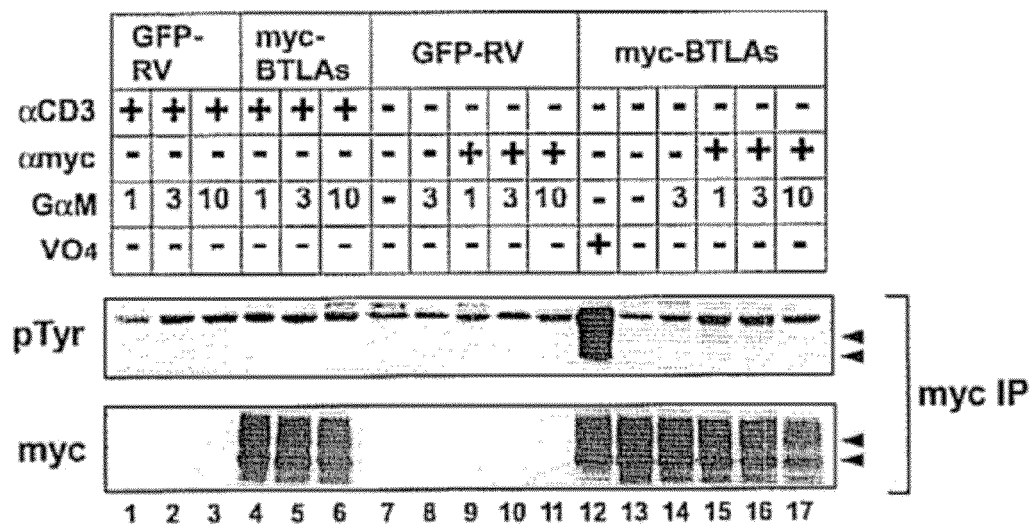
FIG. 24

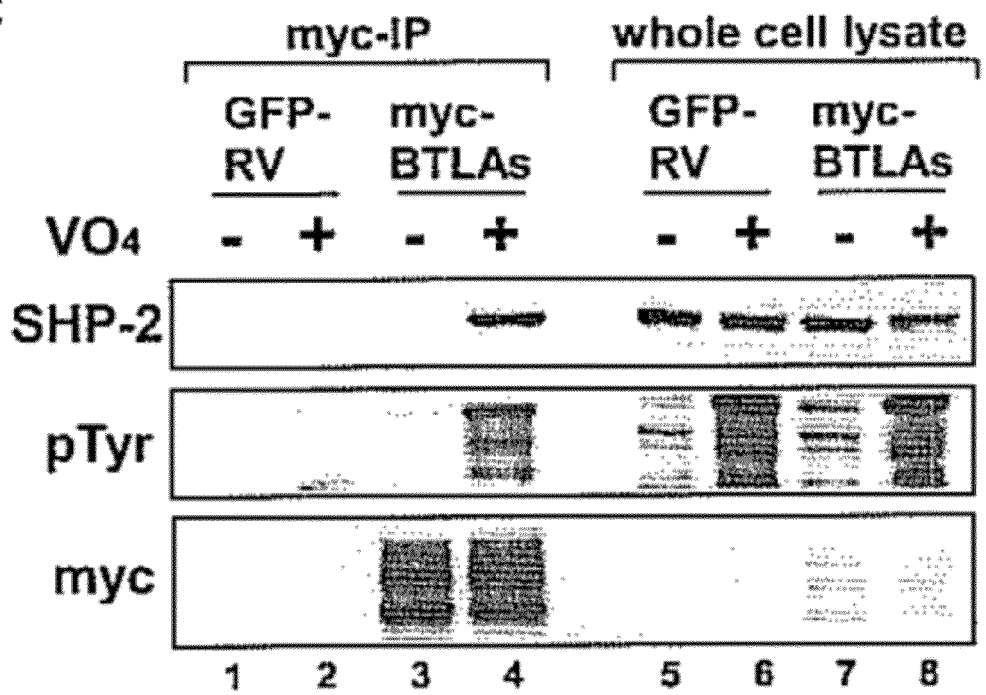
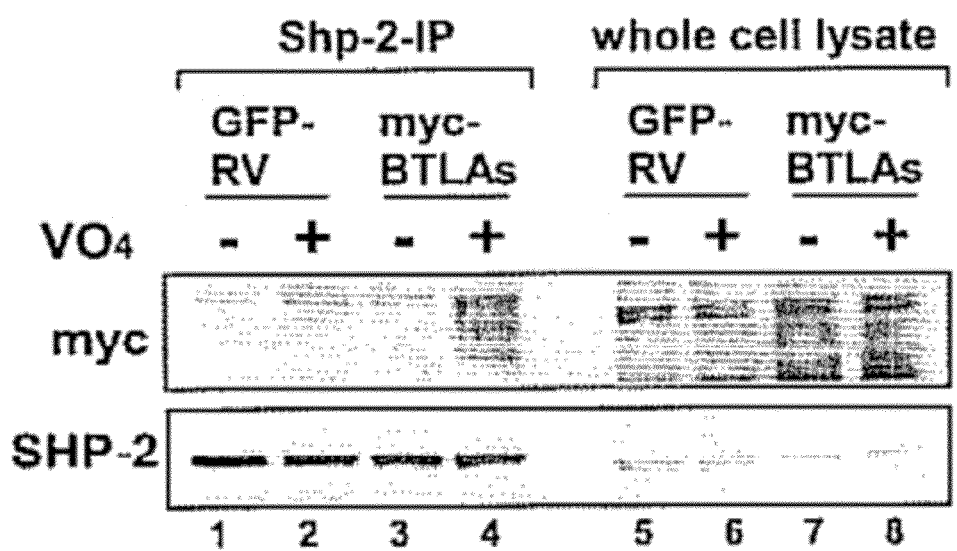
FIG. 24

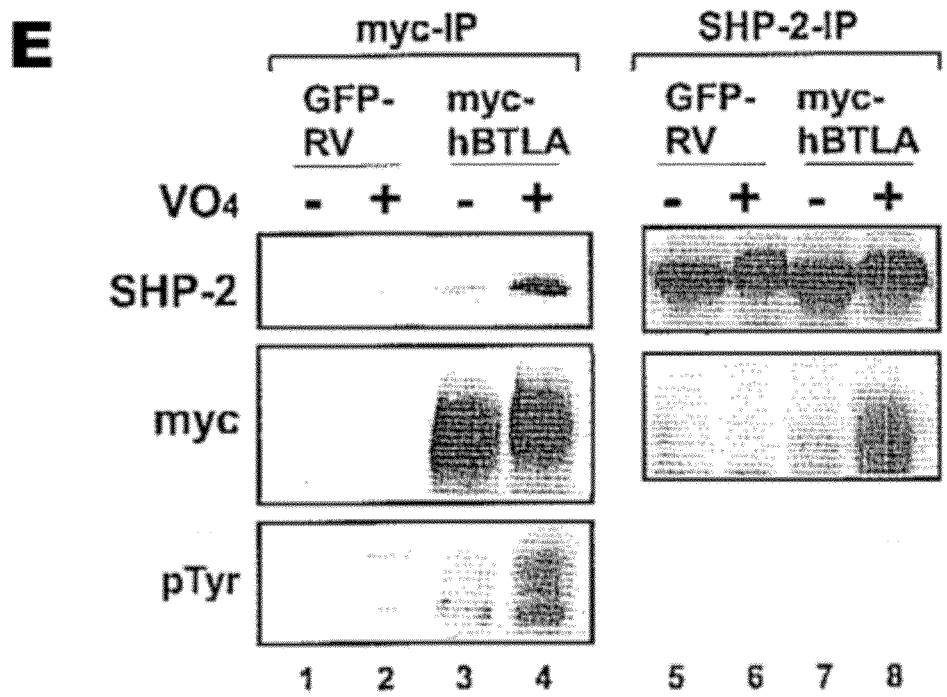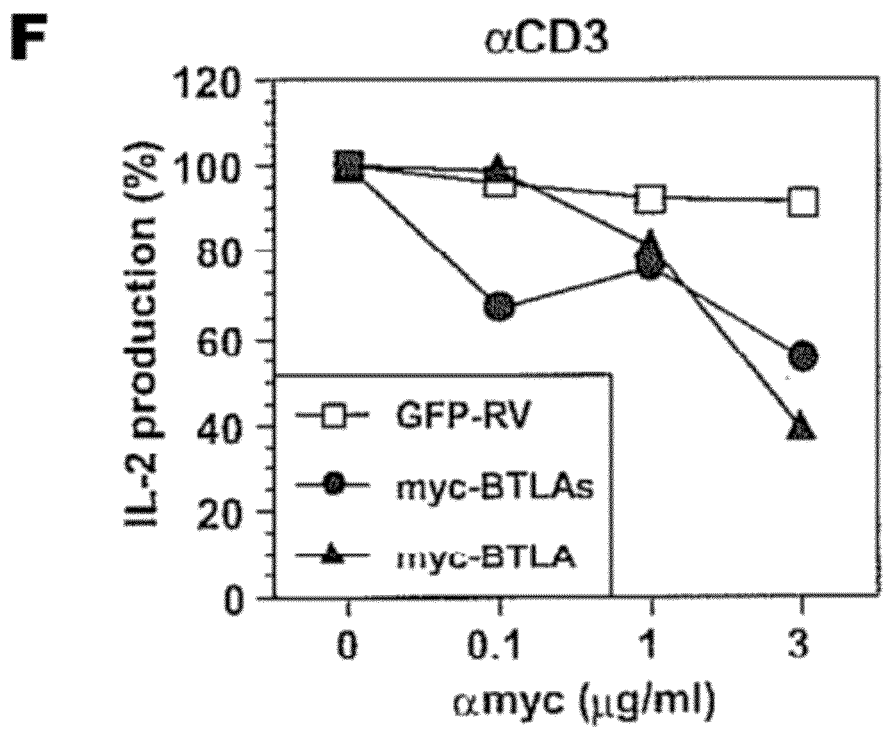
FIG. 24

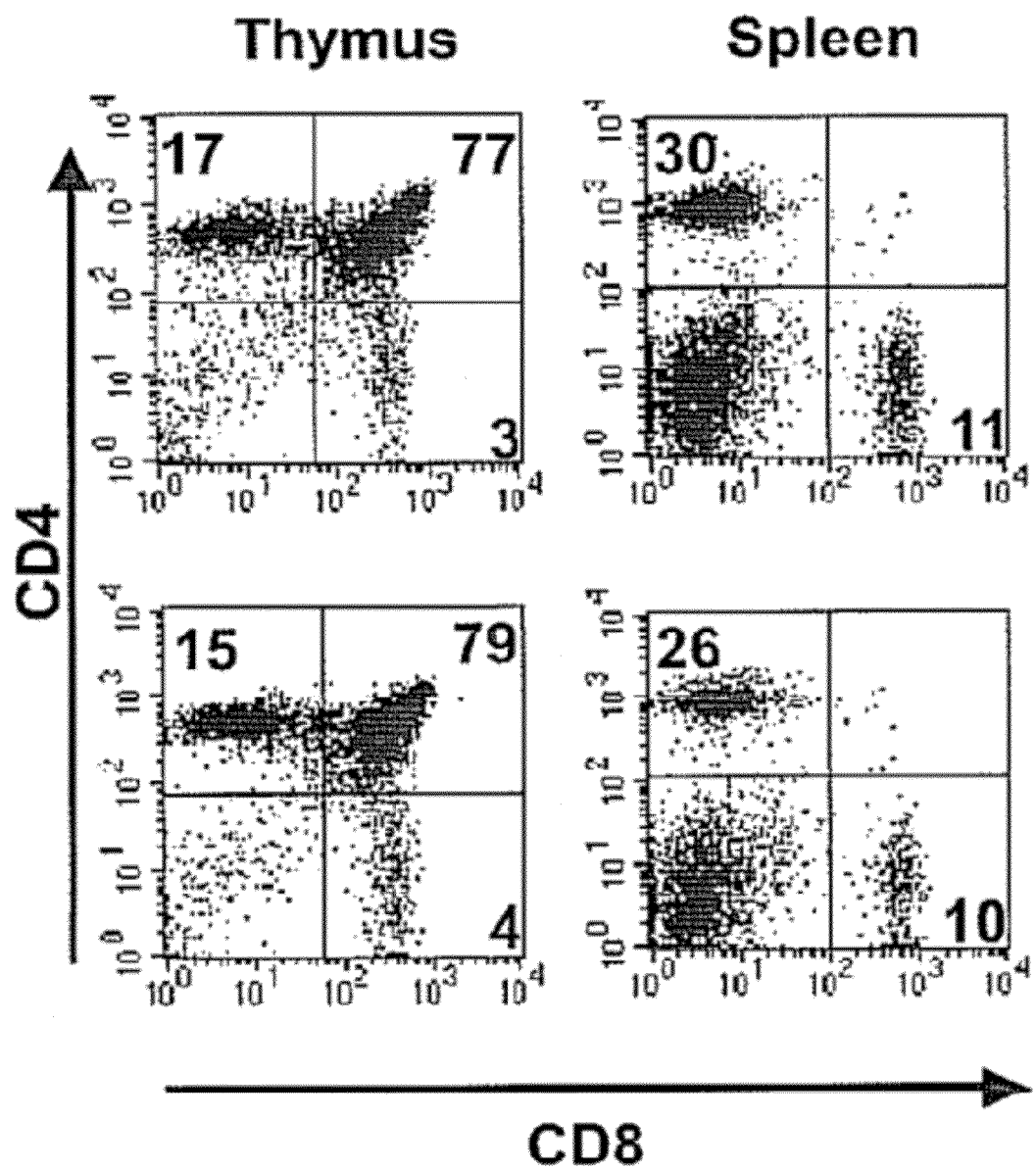
FIG. 27A(1)

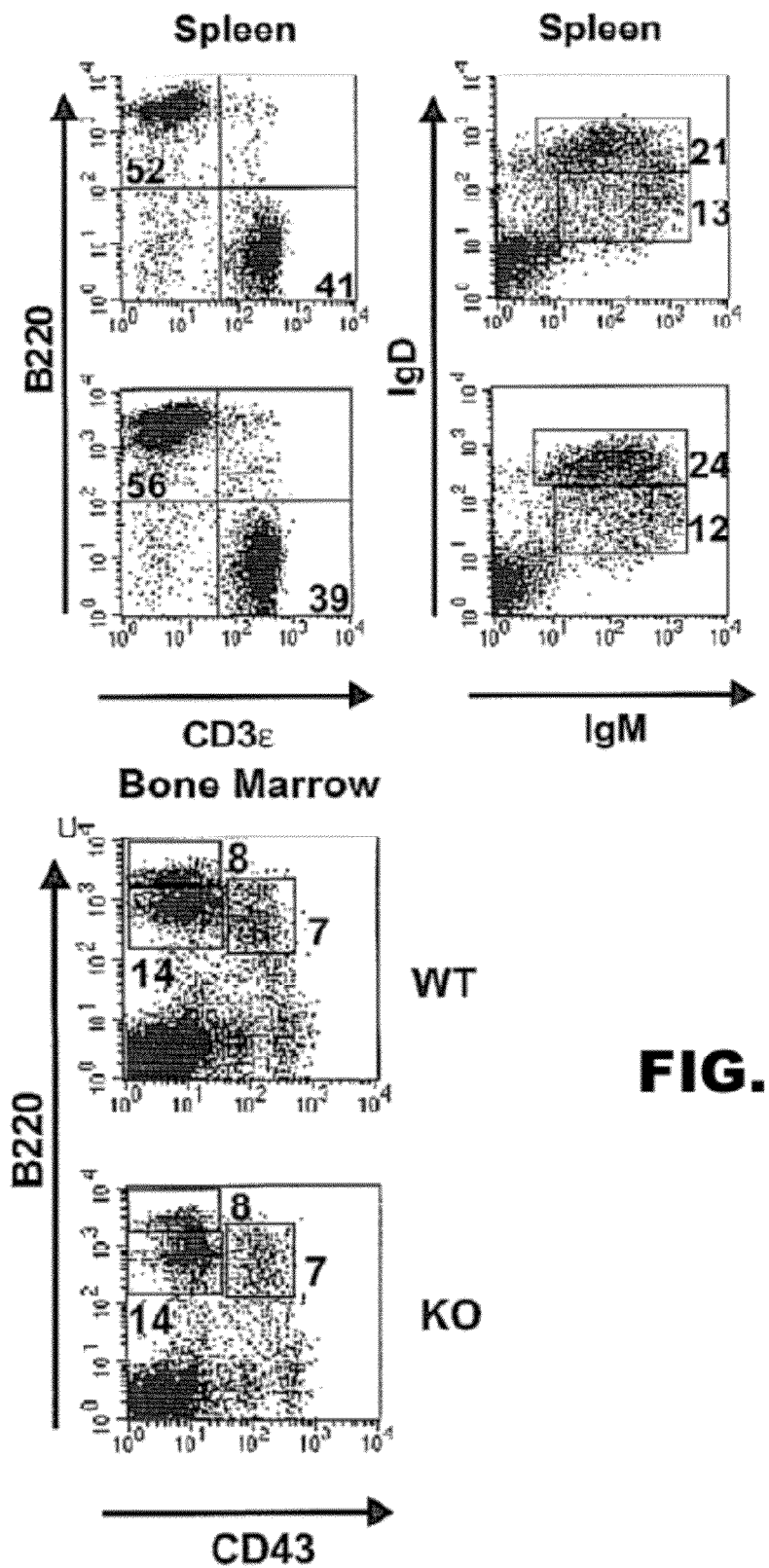
FIG. 27A(2)

HUMAN BTLA PROTEIN SEQUENCE

```
  1  mktlpamlgt gklfwvffli pyldiwnihg kescdvqlyi krqsehsila
 51  gdpfelecpv kycanrphvt wcklngttcv kledrqtswk eeknisffil
101  hfepmlpndn gsyrcsanfq snlieshstt lyvtdvkgas erpskdevas
151  rpwllysllp lgglpllitt wfclfcclrr hqgkqnelsd tagreinlvd
201  ahlkseqtea strqnsqvll seagiydndp dlcfrmqegs evcsnpclee
251  nkpgivyasl nhsviglnsr larnvkeapt eyasicvrs
```

HUMAN BTLA NUCLEIC ACID SEQUENCE

```
  1  atgaagacat tgcctgccat gcttggaact gggaaattat tttgggtctt cttcttaatc
 61  ccatatctgg acatctggaa catccatggg aaagaatcat gtgatgtaca gctttatata
121  aagagacaat ctgaacactc catcttagca ggagatccct ttgaactaga atgccctgtg
181  aaatactgtg caacaggcc tcatgtgact tggtgcaagc tcaatggaac aacatgtgta
241  aaacttgaag atagacaaac aagttggaag gaagagaaga acatttcatt tttcattcta
301  cattttgaac caatgcttcc taatgacaat gggtcatacc gctgttctgc aaattttcag
361  tctaatctca ttgaaagcca ctcaacaact ctttatgtga cagatgtaaa aggtgcctca
421  gaacgaccct ccaaggacga agtggcaagc agaccctggc tcctgtatag tttacttcct
481  ttggggggat tgcctctact catcactacc tggttctgcc tgttctgctg cctgagaagg
541  caccaaggaa agcaaaatga actctctgac acagcaggaa gggaaattaa tctggttgat
601  gctcaccta agagcgagca aacagaagca agcaccaggc aaaattccca agtactgcta
661  tcagaagctg gaatttatga taatgaccct gacctttgtt tcaggatgca ggaagggtct
721  gaagtttgtt ctaatccatg cctggaagaa aacaaaccag gcattgttta tgcttccctg
781  aaccattctg tcattggact gaactcaaga ctggcaagaa atgtaaaaga agcaccaaca
841  gaatatgcat ccatatgtgt gaggagttaa
```

FIG. 28

MOUSE BTLA PROTEIN SEQUENCE

```
1   mktvpamlgt prlfreffil hlglwsilce katkrndeec evqlnikrns khsawtgelf
61  kiecpvkycv hrpnvtwckh ngtiwvplev gpqlytswee nrsvpvfvlh fkpihlsdng
121 syscstnfns qvinshsvti hvrertqnss ehplitvsdi pdatnasgps tmeerpgrtw
181 llytllplga lllllacvcl lcflkriqgk ekkpsdlagr dtnlvdipas srtnhqalps
241 gtgiydndpw ssmqdeselt islqsernnq givyaslnhc vigrnprqen nmqeapteya
301 sicvrs
```

MOUSE BTLA NUCLEIC ACID SEQUENCE

```
1   atgaagacag tgcctgccat gcttgggact cctcggttat ttagggaatt cttcatcctc
61  catctgggcc tctggagcat cctttgtgag aaagctacta agaggaatga tgaagagtgt
121 gaagtgcaac ttaatattaa gaggaattcc aaacactctg cctggacagg agagttattt
181 aaaattgaat gtcctgtgaa atactgtgtt catagaccta atgtgacttg gtgtaagcac
241 aatggaacaa tctgggtacc ccttgaagtt ggtcctcagc tatacactag ttgggaagaa
301 aatcgatcag ttccggtttt tgttctccat tttaaaccaa tacatctcag tgataacggg
361 tcgtatagct gttctacaaa cttcaattct caagttatta atagccattc agtaaccatc
421 catgtgagag aaaggactca aaactcttca gaacacccac taataacagt atctgacatc
481 ccagatgcca ccaatgcctc aggaccatcc accatggaag agaggccagg caggacttgg
541 ctgctttaca ccttgcttcc tttgggggca ttgcttctgc tcttgcctg tgtctgcctg
601 ctctgctttc tgaaaaggat ccagggaaaa gaaaagaagc cttctgactt ggcaggaagg
661 gacactaacc tggttgatat tccagccagt tccaggacaa tcaccaagc actgccatca
721 ggaactggaa tttatgataa tgatccctgg tctagcatgc aggatgaatc tgaattgaca
781 attagcttgc aatcagagag aaacaaccag ggcattgttt atgcttcttt gaaccattgt
841 gttattggaa ggaatccaag acaggaaaac aacatgcagg aggcacccac agaatatgca
901 tccatttgtg tgagaagtta a
```

FIG. 29

|  | (1) | 1 10 20 30 40 57 |
|---|---|---|
| 129 SvJ | (1) | GATGAAGAGTGTGAAGTGCAACTTAATATTAAGAGGAATTCCAAACACTCTGCCTGG |
| MRL/lpr (bc) | (1) | GATGAAGAGTGTGAAGTGCAACTTAATATTAAGAGGAATTCCAAACACTCTGCCTGG |
| C57Bl/6 | (1) | GATGAAGAGTGTCCAGTGCAACTTACTATTACGAGGAATTCCAAACAGTCTGCCAGG |
| Balb/c | (1) | GATGAAGAGTGTGAAGTGCAACTTAATATTAAGAGGAATTCCAAACACTCTGCCTGG |
| SWR | (1) | GATGAAGAGTGTGAAGTGCAACTTAATATTAAGAGGAATTCCAAACACTCTGCCTGG |
| NZB/BinJ | (1) | GATGAAGAGTGTGAAGTGCAACTTAATATTAAGAGGAATTCCAAACACTCTGCCTGG |
| NOD | (1) | GATGAAGAGTGTGAAGTGCAACTTAATATTAAGAGGAATTCCAAACACTCTGCCTGG |
| MRL/lpr | (1) | GATGAAGAGTGTGAAGTGCAACTTAATATTAAGAGGAATTCCAAACACTCTGCCTGG |
| DBA/2J | (1) | GATGAAGAGTGTGAAGTGCAACTTAATATTAAGAGGAATTCCAAACACTCTGCCTGG |
| C3H/J | (1) | GATGAAGAGTGTGAAGTGCAACTTAATATTAAGAGGAATTCCAAACACTCTGCCTGG |
| 129SvEv | (1) | GATGAAGAGTGTGAAGTGCAACTTAATATTAAGAGGAATTCCAAACACTCTGCCTGG |
| SJL.J | (1) | GATGAAGAGTGTGAAGTGCAACTTAATATTAAGAGGAATTCCAAACACTCTGCCTGG |
| Celera old | (1) | GATGAAGAGTGTGAAGTGCAACTTAATATTAAGAGGAATTCCAAACACTCTGCCTGG |
| WEHI 2 old | (1) | GATGAAGAGTGTGAAGTGCAACTTAATATTAAGAGGAATTCCAAACACTCTGCCTGG |
| Bl/6 old | (1) | GATGAAGAGTGTCCAGTGCAACTTACTATTACGAGGAATTCCAAACAGTCTGCCAGG |
| WEHI 1old | (1) | GATGAAGAGTGTGAAGTGCAACTTAATATTAAGAGGAATTCCAAACACTCTGCCTGG |
| Consensus | (1) | GATGAAGAGTGTGAAGTGCAACTTAATATTAAGAGGAATTCCAAACACTCTGCCTGG |

|  | (58) | 58 70 80 90 100 114 |
|---|---|---|
| 129 SvJ | (58) | ACAGGAGAGTTATTTAAAATTGAATGTCCTGTGAAATACTGTGTTCATAGACCTAAT |
| MRL/lpr (bc) | (58) | ACAGGAGAGTTATTTAAAATTGAATGTCCTGTGAAATACTGTGTTCATAGACCTCAT |
| C57Bl/6 | (58) | ACAGGAGAGTTATTTAAAATTCAATGTCCTGTGAAATACTGTGTTCATAGACCTAAT |
| Balb/c | (58) | ACAGGAGAGTTATTTAAAATTGAATGTCCTGTGAAATACTGTGTTCATAGACCTAAT |
| SWR | (58) | ACAGGAGAGTTATTTAAAATTGAATGTCCTGTGAAATACTGTGTTCATAGACCTCAT |
| NZB/BinJ | (58) | ACAGGAGAGTTATTTAAAATTGAATGTCCTGTGAAATACTGTGTTCATAGACCTAAT |
| NOD | (58) | ACAGGAGAGTTATTTAAAATTGAATGTCCTGTGAAATACTGTGTTCATAGACCTAAT |
| MRL/lpr | (58) | ACAGGAGAGTTATTTAAAATTGAATGTCCTGTGAAATACTGTGTTCATAGACCTCAT |
| DBA/2J | (58) | ACAGGAGAGTTATTTAAAATTGAATGTCCTGTGAAATACTGTGTTCATAGACCTCAT |
| C3H/J | (58) | ACAGGAGAGTTATTTAAAATTGAATGTCCTGTGAAATACTGTGTTCATAGACCTAAT |
| 129SvEv | (58) | ACAGGAGAGTTATTTAAAATTGAATGTCCTGTGAAATACTGTGTTCATAGACCTAAT |
| SJL.J | (58) | ACAGGAGAGTTATTTAAAATTGAATGTCCTGTGAAATACTGTGTTCATAGACCTAAT |
| Celera old | (58) | ACAGGAGAGTTATTTAAAATTGAATGTCCTGTGAAATACTGTGTTCATAGACCTAAT |
| WEHI 2 old | (58) | ACAGGAGAGTTATTTAAAATTGAATGTCCTGTGGAATACTGTGTTCATAGACCTCAT |
| Bl/6 old | (58) | ACAGGAGAGTTATTTAAAATTCAATGTCCTGTGAAATACTGTGTTCATAGACCTAAT |
| WEHI 1old | (58) | ACAGGAGAGTTATTTAAAATTGAATGTCCTGTGGAATACTGTGTTCATAGACCTCAT |
| Consensus | (58) | ACAGGAGAGTTATTTAAAATTGAATGTCCTGTGAAATACTGTGTTCATAGACCTAAT |

FIG. 30A

```
                                                                              Section 3
           (115) 115      120       130       140       150       160       171
 129 SvJ   (115) GTGACTTGGTGTAAGCACAATGGAACAATCTGGGTACCCCTTGAAGTTGGTCCTCAG
MRL/lpr(bc)(115) GTGACTTGGTGTAAGCACAATGGAACAATCTGGGTACCCCTTGAAGTTGGTCCTCAG
  C57Bl/6  (115) GTGACTTGGTGTAAGCACAATGGAACAATCTGTGTACCCCTTGAGGTTAGCCCTCAG
   Balb/c  (115) GTGACTTGGTGTAAGCACAATGGAACAATCTGGGTACCCCTTGAAGTTGGTCCTCAG
     SWR   (115) GTGACTTGGTGTAAGCACAATGGAACAATCTGGGTACCCCTTGAAGTTGGTCCTCAG
  NZB/BinJ (115) GTGACTTGGTGTAAGCACAATGGAACAATCTGGGTACCCCTTGAAGTTGGTCCTCAG
     NOD   (115) GTGACTTGGTGTAAGCACAATGGAACAATCTGGGTACCCCTTGAAGTTGGTCCTCAG
  MRL/lpr  (115) GTGACTTGGTGTAAGCACAATGGAACAATCTGGGTACCCCTTGAAGTTGGTCCTCAG
   DBA/2J  (115) GTGACTTGGTGTAAGCACAATGGAACAATCTGGGTACCCCTTGAAGTTGGTCCTCAG
    C3H/J  (115) GTGACTTGGTGTAAGCACAATGGAACAATCTGGGTACCCCTTGAAGTTGGTCCTCAG
   129SvEv (115) GTGACTTGGTGTAAGCACAATGGAACAATCTGGGTACCCCTTGAAGTTGGTCCTCAG
    SJL.J  (115) GTGACTTGGTGTAAGCACAATGGAACAATCTGGGTACCCCTTGAAGTTGGTCCTCAG
 Celera old (115) GTGACTTGGTGTAAGCACAATGGAACAATCTGGGTACCCCTTGAAGTTGGTCCTCAG
 WEHI 2 old (115) GTGACTTGGTGTAAGCACAATGGAACAATCTGGGTACCCCTTGAAGTTGGTCCTCAG
    Bl/6 old (115) GTGACTTGGTGTAAGCACAATGGAACAATCTGTGTACCCCTTGAGGTTAGCCCTCAG
  WEHI 1old (115) GTGACTTGGTGTAAGCACAATGGAACAATCTGGGTACCCCTTGAAGTTGGTCCTCAG
 Consensus (115) GTGACTTGGTGTAAGCACAATGGAACAATCTGGGTACCCCTTGAAGTTGGTCCTCAG
                                                                              Section 4
           (172) 172      180       190       200       210       228
 129 SvJ   (172) CTATACACTAGTTGGGAAGAAAATCGATCAGTTCCGGTTTTTGTTCTCCATTTTAAA
MRL/lpr(bc)(172) CTATACACTAGTTGGGAAGAAAATCGATCAGTTCCGGTTTTTGTTCTCCATTTTAAA
  C57Bl/6  (172) CTATACACTAGTTGGGAAGAAAATCAATCAGTTCCGGTTTTTGTTCTCCACTTTAAA
   Balb/c  (172) CTATACACTAGTTGGGAAGAAAATCGATCAGTTCCGGTTTTTGTTCTCCATTTTAAA
     SWR   (172) CTATACACTAGTTGGGAAGAAAATCGATCAGTTCCGGTTTTTGTTCTCCATTTTAAA
  NZB/BinJ (172) CTATACACTAGTTGGGAAGAAAATCGATCAGTTCCGGTTTTTGTTCTCCATTTTAAA
     NOD   (172) CTATACACTAGTTGGGAAGAAAATCGATCAGTTCCGGTTTTTGTTCTCCATTTTAAA
  MRL/lpr  (172) CTATACACTAGTTGGGAAGAAAATCGATCAGTTCCGGTTTTTGTTCTCCATTTTAAA
   DBA/2J  (172) CTATACACTAGTTGGGAAGAAAATCGATCAGTTCCGGTTTTTGTTCTCCATTTTAAA
    C3H/J  (172) CTATACACTAGTTGGGAAGAAAATCGATCAGTTCCGGTTTTTGTTCTCCATTTTAAA
   129SvEv (172) CTATACACTAGTTGGGAAGAAAATCGATCAGTTCCGGTTTTTGTTCTCCATTTTAAA
    SJL.J  (172) CTATACACTAGTTGGGAAGAAAATCGATCAGTTCCGGTTTTTGTTCTCCATTTTAAA
 Celera old (172) CTATACACTAGTTGGGAAGAAAATCGATCAGTTCCGGTTTTTGTTCTCCATTTTAAA
 WEHI 2 old (172) CTATACACTAGTTGGGAAGAAAATCGATCAGTTCCGGTTTTTGTTCTCCATTTTAAA
    Bl/6 old (172) CTATACACTAGTTGGGAAGAAAATCAATCAGTTCCGGTTTTTGTTCTCCACTTTAAA
  WEHI 1old (172) CTATACACTAGTTGGGAAGAAAATCGATCAGTTCCGGTTTTTGTTCTCCATTTTAAA
 Consensus (172) CTATACACTAGTTGGGAAGAAAATCGATCAGTTCCGGTTTTTGTTCTCCATTTTAAA
```

FIG. 30B

```
                                                                    Section 5
              (229) 229      240       250       260       270       285
    129 SvJ  (229) CCAATACATCTCAGTGATAACGGGTCGTATAGCTGTTCTACAAACTTCAATTCTCAA
MRL/lpr (bc) (229) CCAATACATCTCAGTGATAACGGGTCGTATAGCTGTTCTACAAACTTCAATTCTCAA
    C57Bl/6  (229) CCAATACATCTCAGTGATAATGGGTCGTATAGCTGTTCTACAAACTTCAATTCTCAA
     Balb/c  (229) CCAATACATCTCAGTGATAACGGGTCGTATAGCTGTTCTACAAACTTCAATTCTCAA
        SWR  (229) CCAATACATCTCAGTGATAACGGGTCGTATAGCTGTTCTACAAACTTCAATTCTCAA
    NZB/BinJ (229) CCAATACATCTCAGTGATAACGGGTCGTATAGCTGTTCTACAAACTTCAATTCTCAA
        NOD  (229) CCAATACATCTCAGTGATAACGGGTCGTATAGCTGTTCTACAAACTTCAATTCTCAA
    MRL/lpr  (229) CCAATACATCTCAGTGATAACGGGTCGTATAGCTGTTCTACAAACTTCAATTCTCAA
     DBA/2J  (229) CCAATACATCTCAGTGATAACGGGTCGTATAGCTGTTCTACAAACTTCAATTCTCAA
      C3H/J  (229) CCAATACATCTCAGTGATAACGGGTCGTATAGCTGTTCTACAAACTTCAATTCTCAA
    129SvEv  (229) CCAATACATCTCAGTGATAACGGGTCGTATAGCTGTTCTACAAACTTCAATTCTCAA
       SJLJ  (229) CCAATACATCTCAGTGATAACGGGTCGTATAGCTGTTCTACAAACTTCAATTCTCAA
  Celera old (229) CCAATACATCTCAGTGATAACGGGTCGTATAGCTGTTCTACAAACTTCAATTCTCAA
  WEHI 2 old (229) CCAATACATCTCAGTGATAACGGGTCGTATAGCTGTTCTACAAACTTCAATTCTCAA
     Bl/6 old(229) CCAATACATCTCAGTGATAATGGGTCGTATAGCTGTTCTACAAACTTCAATTCTCAA
  WEHI 1old  (229) CCAATACATCTCAGTGATAACGGGTCGTATAGCTGTTCTACAAACTTCAATTCTCAA
   Consensus (229) CCAATACATCTCAGTGATAACGGGTCGTATAGCTGTTCTACAAACTTCAATTCTCAA
                                                                    Section 6
              (286) 286       300       310       322
    129 SvJ  (286) GTTATTAATAGCCATTCAGTAACCATCCATGTGAGAG
MRL/lpr (bc) (286) GTTATTAATAGCCATTCAGTAACCATCCATGTGAGAG
    C57Bl/6  (286) GTTATTAATAGCCATTCAGTAACCATCCATGTGACAG
     Balb/c  (286) GTTATTAATAGCCATTCAGTAACCATCCATGTGAGAG
        SWR  (286) GTTATTAATAGCCATTCAGTAACCATCCATGTGAGAG
    NZB/BinJ (286) GTTATTAATAGCCATTCAGTAACCATCCATGTGAGAG
        NOD  (286) GTTATTAATAGCCATTCAGTAACCATCCATGTGAGAG
    MRL/lpr  (286) GTTATTAATAGCCATTCAGTAACCATCCATGTGAGAG
     DBA/2J  (286) GTTATTAATAGCCATTCAGTAACCATCCATGTGAGAG
      C3H/J  (286) GTTATTAATAGCCATTCAGTAACCATCCATGTGAGAG
    129SvEv  (286) GTTATTAATAGCCATTCAGTAACCATCCATGTGAGAG
       SJLJ  (286) GTTATTAATAGCCATTCAGTAACCATCCATGTGAGAG
  Celera old (286) GTTATTAATAGCCATTCAGTAACCATCCATGTGAGAG
  WEHI 2 old (286) GTTATTAATAGCCATTCAGTAACCATCCATGTGAGAG
     Bl/6 old(286) GTTATTAATAGCCATTCAGTAACCATCCATGTGACAG
  WEHI 1old  (286) GTTATTAATAGCCATTCAGTAACCATCCATGTGAGAG
   Consensus (286) GTTATTAATAGCCATTCAGTAACCATCCATGTGAGAG
```

FIG. 30C

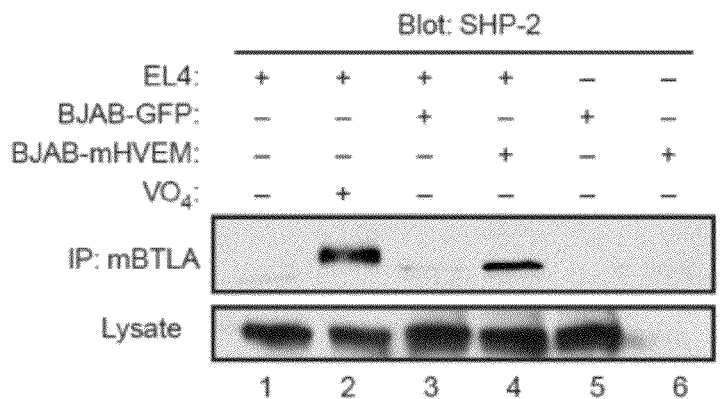
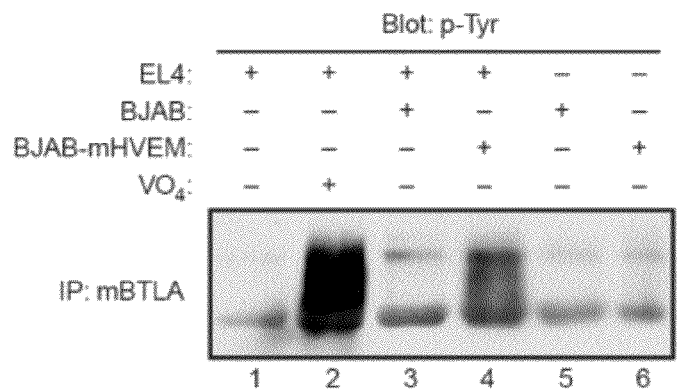
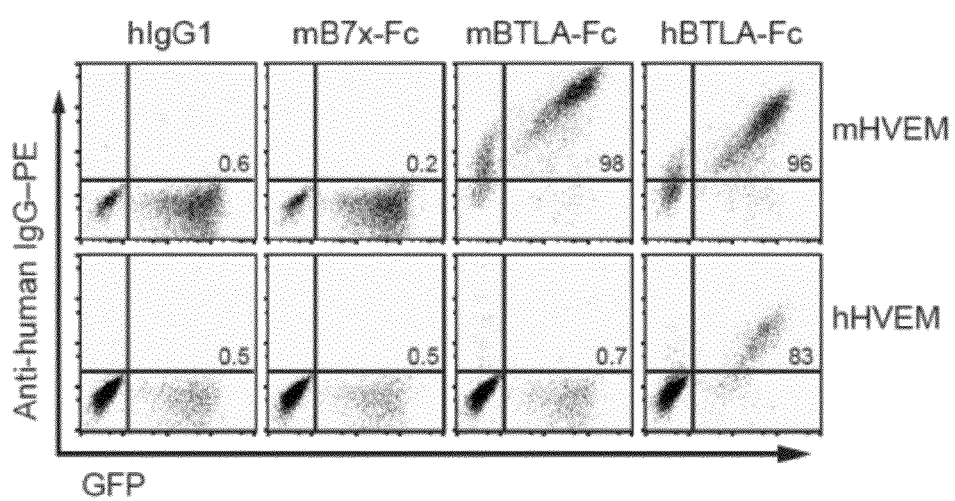
FIG. 36

A

```
BALB/c*    LEECEVQLHIKRNSKHSAWTGELFKIECPVKYCVHRPNVTWCKHNGTIRVPLEVG
MLR/Lpr^L  DEECEVQLNIKRNSKHSAWTGELFKIECPVKYCVHRPHVTWCKHNGTIRVPLEVG
C57BL/6^c  DEECPVQLTITRNSKQSARTGELFKIQCPVKYCVHRPNVTWCKHNGTICVPLEVS
Consensus  DEEC*VQL*I*RNSK*SA*TGELFKI*CPVKYCVHRP#VTWCKHNGTI*VPLEV*

BALB/c*    PQLYTSWEENRSVPVFVLHFKPIHLSDNGSYSCSTNFNSQVINSHSVTIHVR
MLR/Lpr^L  PQLYTSWEENRSVPVFVLHFKPIHLSDNGSYSCSTNFNSQVINSHSVTIHVR
C57BL/6^c  PQLYTSWEENQSVPVFVLHFKPIHLSDNGSYSCSTNFNSQVINSHSVTIHVT
Consensus  PQLYTSWEEN*SVPVFVLHFKPIHLSDNGSYSCSTNFNSQVINSHSVTIHV*
```

B

| BALB/c-like | | MLR/Lpr-like | | C57BL/6-like | |
|---|---|---|---|---|---|
| 129SvEv | 129Sv/J | AKR | SWR | B10.PL | MOLC/Rk |
| CBA/J | C3H/J | CALB/Rk | DBA/2J | MOLD/Rk | MOLE/Rk |
| SLJ/J | NZB/BinJ | | | MOLF/Ei | MOLG/Dn |
| NZW | NOD | | | CAST/Ei | CASA/Rk |
| BxSB | | | | | |

FIG. 40

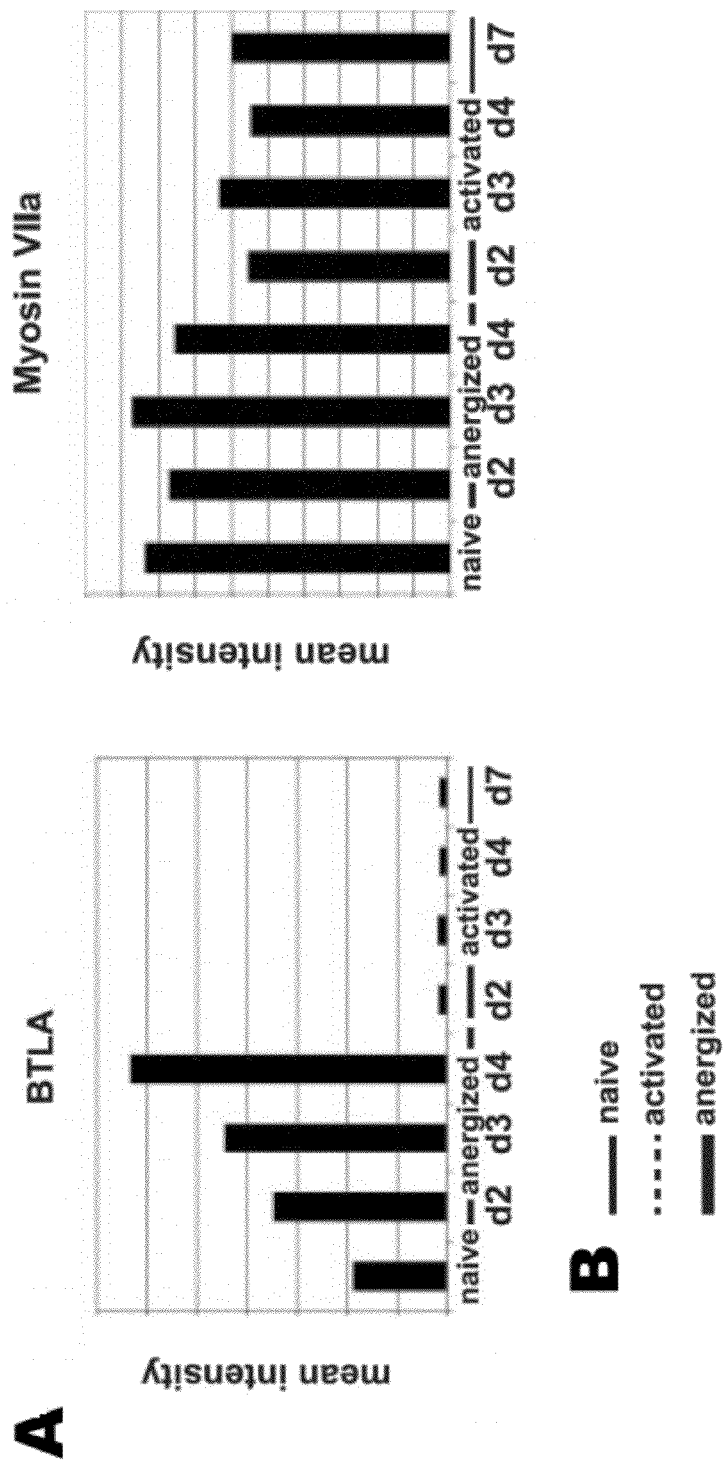
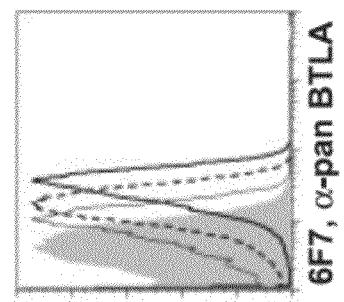
FIG. 46

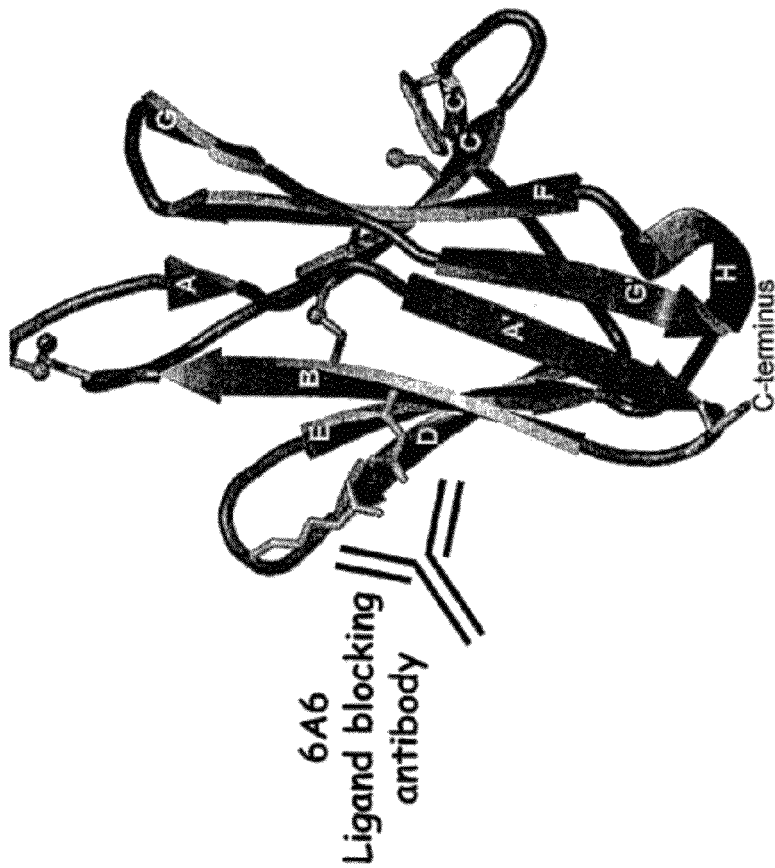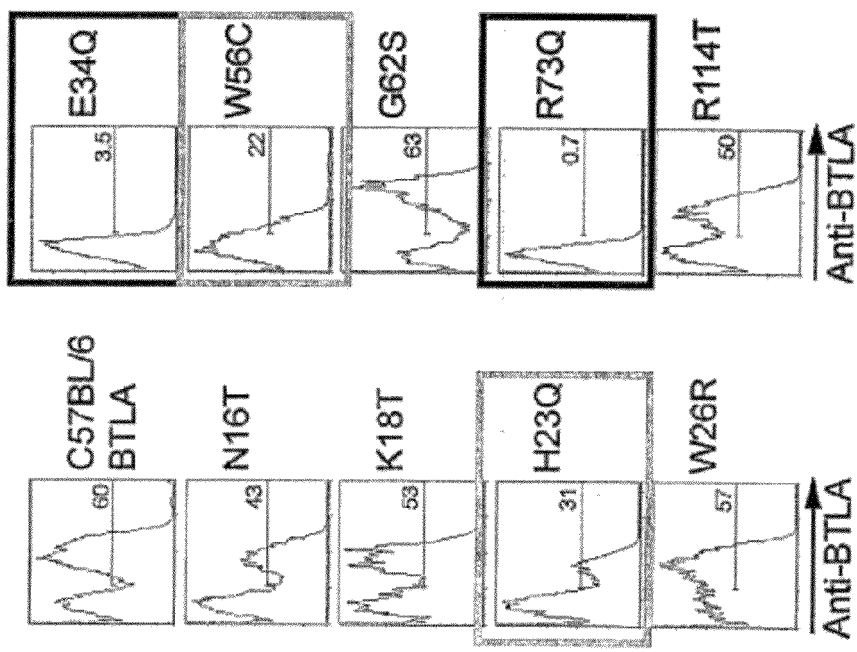
FIG. 55

BTLA SEQUENCE FROM GENBANK ACCESSION NO. AAP44003.1

```
1    mktlpamlgt gklfwvffli pyldiwnihg kescdvqlyi krqsehsila
51   gdpfelecpv kycanrphvt wcklngttcv kledrqtswk eeknisffil
101  hfepmlpndn gsyrcsanfq snlieshstt lyvtdvkgas erpskdevas
151  rpwllysllp lgglpllitt wfclfcclrr hqgkqnelsd tagreinlvd
201  ahlkseqtea strqnsqvll seagiydndp dlcfrmqegs evcsnpclee
251  nkpgivyasl nhsviglnsr larnvkeapt eyasicvrs
```

FIG. 56

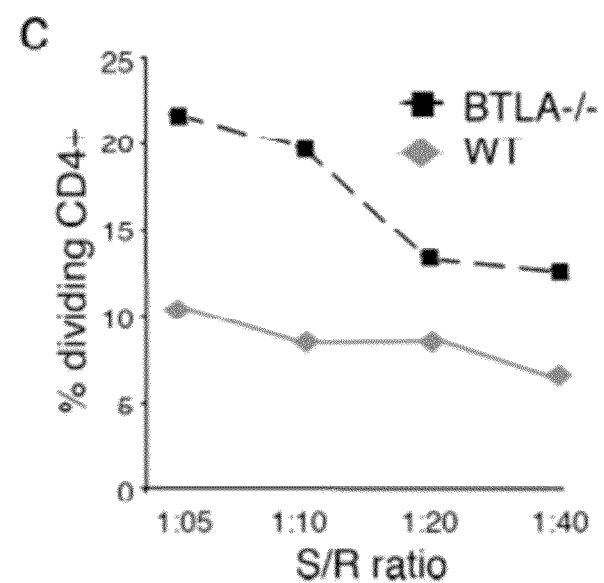
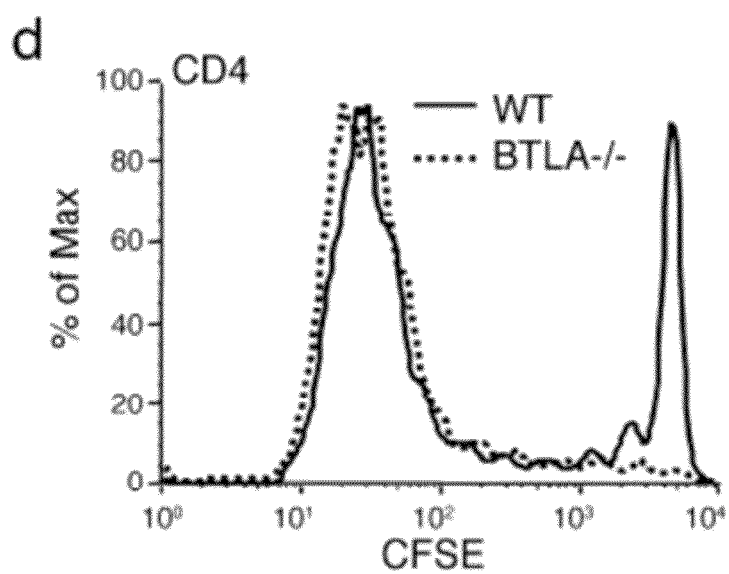
FIG. 62

SEQUENCE LISTING

```
<160> NUMBER OF SEQ ID NOS: 102

<210> SEQ ID NO 1
<211> LENGTH: 283
<212> TYPE: PRT
<213> ORGANISM: Mus musculus

<400> SEQUENCE: 1

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
                20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240
```

```
Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Ala Ala Gly Trp Ala
            260                 265                 270

Leu Leu Ser Leu Ser Cys Cys Leu Met Leu Arg
            275                 280

<210> SEQ ID NO 2
<211> LENGTH: 282
<212> TYPE: PRT
<213> ORGANISM: Homo sapiens

<400> SEQUENCE: 2

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
            275                 280

<210> SEQ ID NO 3
<211> LENGTH: 852
<212> TYPE: DNA
<213> ORGANISM: Mus musculus

<400> SEQUENCE: 3
```

| atggcttcct tggggcagat catcttttgg agtattatta acatcatcat catcctggct | 60 |
| gggggccatcg cactcatcat tggctttggc atttcaggca agcacttcat cacggtcacg | 120 |
| accttcacct cagctggaaa cattggagag acgggaccc tgagctgcac ttttgaacct | 180 |
| gacatcaaac tcaacggcat cgtcatccag tggctgaaag aaggcatcaa aggtttggtc | 240 |
| cacgagttca agaaggcaa agacgacctc tcacagcagc atgagatgtt cagaggccgc | 300 |
| acagcagtgt ttgctgatca ggtggtagtt ggcaatgctt ccctgagact gaaaaacgtg | 360 |
| cagctcacgg atgctggcac ctacacatgt acatccgca cctcaaaagg caagggaat | 420 |
| gcaaacctag agtataagac cggagccttc agtatgccag agataaatgt ggactataat | 480 |
| gccagttcag agagtttacg ctgcgaggct cctcggtggt tcccccagcc cacagtggcc | 540 |
| tgggcatctc aagtcgacca aggagccaac ttctcagaag tctcgaacac cagctttgag | 600 |
| ttgaactctg agaatgtgac catgaaggtc gtatctgtgc tctacaatgt cacaatcaac | 660 |
| aacacatact cctgtatgat tgaaaatgac attgccaaag ccactgggga catcaaagtg | 720 |
| acagattcag aggtcaaaag gcggagtcag ctgcagctgc tcaactccgg gccttccccg | 780 |
| tgtgttttttt cttctgcctt tgcggctggc tgggcgctcc tatctctctc ctgttgcctg | 840 |
| atgctaagat ga | 852 |

<210> SEQ ID NO 4
<211> LENGTH: 849
<212> TYPE: DNA
<213> ORGANISM: Homo sapiens

<400> SEQUENCE: 4

| atggcttccc tggggcagat cctcttctgg agcataatta gcatcatcat tattctggct | 60 |
| ggagcaattg cactcatcat tggctttggt atttcaggga gacactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca aagaaggcaa agatgagctg tcggagcagg atgaaatgtt cagaggccgg | 300 |
| acagcagtgt ttgctgatca agtgatagtt ggcaatgcct ctttgcggct gaaaaacgtg | 360 |
| caactcacag atgctggcac ctacaaatgt tatatcatca cttctaaagg caagggaat | 420 |
| gctaaccttg agtataaaac tggagccttc agcatgccgg aagtgaatgt ggactataat | 480 |
| gccagctcag agaccttgcg tgtgaggct ccccgatggt tcccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacagggga tatcaaagtg | 720 |
| acagaatcgg agatcaaaag gcggagtcac ctacagctgc taaactcaaa ggcttctctg | 780 |
| tgtgtctctt ctttctttgc catcagctgg gcacttctgc ctctcagccc ttacctgatg | 840 |
| ctaaaataa | 849 |

<210> SEQ ID NO 5
<211> LENGTH: 306
<212> TYPE: PRT
<213> ORGANISM: Mus musculus

<400> SEQUENCE: 5

Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30

Thr Lys Arg Asn Asp Glu Glu Cys Glu Val Gln Leu Asn Ile Lys Arg
        35                  40                  45

Asn Ser Lys His Ser Ala Trp Thr Gly Glu Leu Phe Lys Ile Glu Cys
    50                  55                  60

Pro Val Lys Tyr Cys Val His Arg Pro Asn Val Thr Trp Cys Lys His
65                  70                  75                  80

Asn Gly Thr Ile Trp Val Pro Leu Glu Val Gly Pro Gln Leu Tyr Thr
                85                  90                  95

Ser Trp Glu Glu Asn Arg Ser Val Pro Val Phe Val Leu His Phe Lys
            100                 105                 110

Pro Ile His Leu Ser Asp Asn Gly Ser Tyr Ser Cys Ser Thr Asn Phe
        115                 120                 125

Asn Ser Gln Val Ile Asn Ser His Ser Val Thr Ile His Val Arg Glu
    130                 135                 140

Arg Thr Gln Asn Ser Ser Glu His Pro Leu Ile Thr Val Ser Asp Ile
145                 150                 155                 160

Pro Asp Ala Thr Asn Ala Ser Gly Pro Ser Thr Met Glu Glu Arg Pro
                165                 170                 175

Gly Arg Thr Trp Leu Leu Tyr Thr Leu Leu Pro Leu Gly Ala Leu Leu
            180                 185                 190

Leu Leu Leu Ala Cys Val Cys Leu Leu Cys Phe Leu Lys Arg Ile Gln
        195                 200                 205

Gly Lys Glu Lys Lys Pro Ser Asp Leu Ala Gly Arg Asp Thr Asn Leu
    210                 215                 220

Val Asp Ile Pro Ala Ser Ser Arg Thr Asn His Gln Ala Leu Pro Ser
225                 230                 235                 240

Gly Thr Gly Ile Tyr Asp Asn Asp Pro Trp Ser Ser Met Gln Asp Glu
                245                 250                 255

Ser Glu Leu Thr Ile Ser Leu Gln Ser Glu Arg Asn Asn Gln Gly Ile
            260                 265                 270

Val Tyr Ala Ser Leu Asn His Cys Val Ile Gly Arg Asn Pro Arg Gln
        275                 280                 285

Glu Asn Asn Met Gln Glu Ala Pro Thr Glu Tyr Ala Ser Ile Cys Val
    290                 295                 300

Arg Ser
305

<210> SEQ ID NO 6
<211> LENGTH: 289
<212> TYPE: PRT
<213> ORGANISM: Homo sapiens

<400> SEQUENCE: 6

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val

```
               65                  70                  75                  80
Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
            130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
            195                 200                 205

Glu Ala Ser Thr Arg Gln Asn Ser Gln Val Leu Leu Ser Glu Thr Gly
            210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
            275                 280                 285

Ser

<210> SEQ ID NO 7
<211> LENGTH: 870
<212> TYPE: DNA
<213> ORGANISM: Homo sapiens

<400> SEQUENCE: 7
atgaagacat tgcctgccat gcttggaact gggaaattat tttgggtctt cttcttaatc     60
ccatatctgg acatctggaa catccatggg aagaatcat gtgatgtaca gctttatata   120
aagagacaat ctgaacactc catcttagca ggagatccct ttgaactaga atgccctgtg   180
aaatactgtg ctaacaggcc tcatgtgact tggtgcaagc tcaatggaac acatgtgta   240
aaacttgaag atagacaaac aagttggaag gaagagaaga acatttcatt tttcattcta   300
cattttgaac caatgcttcc taatgacaat gggtcatacc gctgttctgc aaattttcag   360
tctaatctca ttgaaagcca ctcaacaact ctttatgtga cagatgtaaa aggtgcctca   420
gaacgaccct ccaaggacga agtggcaagc agaccctggc tcctgtatag tttacttcct   480
ttgggggat tgcctctact catcactacc tggttctgcc tgttctgctg cctgagaagg   540
caccaaggaa agcaaaatga actctctgac acagcaggaa gggaaattaa tctggttgat   600
gctcacctta gagcgagca acagaagca agcaccaggc aaaattccca agtactgcta   660
tcagaagctg gaatttatga taatgaccct gaccttttgt tcaggatgca ggaagggtct   720
gaagtttgtt ctaatccatg cctggaagaa acaaaccag gcattgttta tgcttccctg   780
aaccattctg tcattggact gaactcaaga ctggcaagaa atgtaaaaga agcaccaaca   840
```

```
gaatatgcat ccatatgtgt gaggagttaa                                          870
```

<210> SEQ ID NO 8
<211> LENGTH: 289
<212> TYPE: PRT
<213> ORGANISM: Homo sapiens

<400> SEQUENCE: 8

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Met Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Gly Ala Ser Glu Arg Pro Ser
    130                 135                 140

Lys Asp Glu Val Ala Ser Arg Pro Trp Leu Leu Tyr Ser Leu Leu Pro
145                 150                 155                 160

Leu Gly Gly Leu Pro Leu Leu Ile Thr Thr Trp Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Ala Gly
    210                 215                 220

Ile Tyr Asp Asn Asp Pro Asp Leu Cys Phe Arg Met Gln Glu Gly Ser
225                 230                 235                 240

Glu Val Cys Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285

Ser
```

<210> SEQ ID NO 9
<211> LENGTH: 921
<212> TYPE: DNA
<213> ORGANISM: Mus musculus

<400> SEQUENCE: 9

```
atgaagacag tgcctgccat gcttgggact cctcggttat ttagggaatt cttcatcctc    60
catctgggcc tctggagcat cctttgtgag aaagctacta agaggaatga tgaagagtgt   120
gaagtgcaac ttaatattaa gaggaattcc aaacactctg cctggacagg agagttattt   180
```

-continued

```
aaaattgaat gtcctgtgaa atactgtgtt catagaccta atgtgacttg gtgtaagcac    240
aatggaacaa tctgggtacc ccttgaagtt ggtcctcagc tatacactag ttgggaagaa    300
aatcgatcag ttccggtttt tgttctccat tttaaaccaa tacatctcag tgataacggg    360
tcgtatagct gttctacaaa cttcaattct caagttatta atagccattc agtaaccatc    420
catgtgagag aaaggactca aaactcttca gaacacccac taataacagt atctgacatc    480
ccagatgcca ccaatgcctc aggaccatcc accatggaag agaggccagg caggacttgg    540
ctgctttaca ccttgcttcc tttgggggca ttgcttctgc tccttgcctg tgtctgcctg    600
ctctgctttc tgaaaaggat ccaagggaaa gaaaagaagc cttctgactt ggcaggaagg    660
gacactaacc tggttgatat tccagccagt tccaggacaa atcaccaagc actgccatca    720
ggaactggaa tttatgataa tgatccctgg tctagcatgc aggatgaatc tgaattgaca    780
attagcttgc aatcagagag aaacaaccag gcattgttt atgcttcttt gaaccattgt    840
gttattggaa ggaatccaag acaggaaaac aacatgcagg aggcacccac agaatatgca    900
tccatttgtg tgagaagtta a                                              921
```

<210> SEQ ID NO 10
<211> LENGTH: 306
<212> TYPE: PRT
<213> ORGANISM: Mus musculus

<400> SEQUENCE: 10

```
Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
                20                  25                  30

Thr Lys Arg Asn Asp Glu Glu Cys Glu Val Gln Leu Asn Ile Lys Arg
            35                  40                  45

Asn Ser Lys His Ser Ala Trp Thr Gly Glu Leu Phe Lys Ile Glu Cys
        50                  55                  60

Pro Val Lys Tyr Cys Val His Arg Pro Asn Val Thr Trp Cys Lys His
65                  70                  75                  80

Asn Gly Thr Ile Trp Val Pro Leu Glu Val Gly Pro Gln Leu Tyr Thr
                85                  90                  95

Ser Trp Glu Glu Asn Arg Ser Val Pro Val Phe Val Leu His Phe Lys
                100                 105                 110

Pro Ile His Leu Ser Asp Asn Gly Ser Tyr Ser Cys Ser Thr Asn Phe
            115                 120                 125

Asn Ser Gln Val Ile Asn Ser His Ser Val Thr Ile His Val Arg Glu
        130                 135                 140

Arg Thr Gln Asn Ser Glu His Pro Leu Ile Thr Val Ser Asp Ile
145                 150                 155                 160

Pro Asp Ala Thr Asn Ala Ser Gly Pro Ser Thr Met Glu Glu Arg Pro
                165                 170                 175

Gly Arg Thr Trp Leu Leu Tyr Thr Leu Leu Pro Leu Gly Ala Leu Leu
            180                 185                 190

Leu Leu Leu Ala Cys Val Cys Leu Leu Cys Phe Leu Lys Arg Ile Gln
        195                 200                 205

Gly Lys Glu Lys Lys Pro Ser Asp Leu Ala Gly Arg Asp Thr Asn Leu
    210                 215                 220

Val Asp Ile Pro Ala Ser Ser Arg Thr Asn His Gln Ala Leu Pro Ser
225                 230                 235                 240
```

Gly Thr Gly Ile Tyr Asp Asn Asp Pro Trp Ser Ser Met Gln Asp Glu
                245                 250                 255

Ser Glu Leu Thr Ile Ser Leu Gln Ser Glu Arg Asn Asn Gln Gly Ile
            260                 265                 270

Val Tyr Ala Ser Leu Asn His Cys Val Ile Gly Arg Asn Pro Arg Gln
        275                 280                 285

Glu Asn Asn Met Gln Glu Ala Pro Thr Glu Tyr Ala Ser Ile Cys Val
    290                 295                 300

Arg Ser
305

<210> SEQ ID NO 11
<211> LENGTH: 322
<212> TYPE: DNA
<213> ORGANISM: Mus musculus

<400> SEQUENCE: 11
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 12
<211> LENGTH: 322
<212> TYPE: DNA
<213> ORGANISM: Mus musculus

<400> SEQUENCE: 12
gatgaagagt gtgaagtgca acttaatatt aagaggaatt ccaaacactc tgcctggaca      60
ggagagttat ttaaaattga atgtcctgtg aaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 13
<211> LENGTH: 322
<212> TYPE: DNA
<213> ORGANISM: Mus musculus

<400> SEQUENCE: 13
gatgaagagt gtccagtgca acttactatt acgaggaatt ccaaacagtc tgccaggaca      60
ggagagttat ttaaaattca atgtcctgtg aaatactgtg ttcatagacc taatgtgact     120
tggtgtaagc acaatggaac aatctgtgta ccccttgagg ttagccctca gctatacact     180
agttgggaag aaaatcaatc agttccggtt tttgttctcc actttaaacc aatacatctc     240
agtgataatg ggtcgtatag ctgttctaca aacttcaatt ctcaagttat taatagccat     300
tcagtaacca tccatgtgac ag                                              322

<210> SEQ ID NO 14
<211> LENGTH: 322

```
<212> TYPE: DNA
<213> ORGANISM: Mus musculus

<400> SEQUENCE: 14
gatgaagagt gtgaagtgca acttaatatt aagaggaatt ccaaacactc tgcctggaca        60
ggagagttat ttaaaattga atgtcctgtg aaatactgtg ttcatagacc taatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322

<210> SEQ ID NO 15
<211> LENGTH: 322
<212> TYPE: DNA
<213> ORGANISM: Mus musculus

<400> SEQUENCE: 15
gatgaagagt gtgaagtgca acttaatatt aagaggaatt ccaaacactc tgcctggaca        60
ggagagttat ttaaaattga atgtcctgtg aaatactgtg ttcatagacc tcatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322

<210> SEQ ID NO 16
<211> LENGTH: 322
<212> TYPE: DNA
<213> ORGANISM: Mus musculus

<400> SEQUENCE: 16
gatgaagagt gtgaagtgca acttaatatt aagaggaatt ccaaacactc tgcctggaca        60
ggagagttat ttaaaattga atgtcctgtg aaatactgtg ttcatagacc taatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322

<210> SEQ ID NO 17
<211> LENGTH: 322
<212> TYPE: DNA
<213> ORGANISM: Mus musculus

<400> SEQUENCE: 17
gatgaagagt gtgaagtgca acttaatatt aagaggaatt ccaaacactc tgcctggaca        60
ggagagttat ttaaaattga atgtcctgtg aaatactgtg ttcatagacc taatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322

<210> SEQ ID NO 18
```

<211> LENGTH: 322
<212> TYPE: DNA
<213> ORGANISM: Mus musculus

<400> SEQUENCE: 18

| | | |
|---|---|---|
| gatgaagagt gtgaagtgca acttaatatt aagaggaatt ccaaacactc tgcctggaca | 60 |
| ggagagttat ttaaaattga atgtcctgtg aaatactgtg ttcatagacc tcatgtgact | 120 |
| tggtgtaagc acaatggaac aatctgggta ccccttgaag ttggtcctca gctatacact | 180 |
| agttgggaag aaaatcgatc agttccggtt tttgttctcc attttaaacc aatacatctc | 240 |
| agtgataacg ggtcgtatag ctgttctaca aacttcaatt ctcaagttat taatagccat | 300 |
| tcagtaacca tccatgtgag ag | 322 |

<210> SEQ ID NO 19
<211> LENGTH: 322
<212> TYPE: DNA
<213> ORGANISM: Mus musculus

<400> SEQUENCE: 19

| | | |
|---|---|---|
| gatgaagagt gtgaagtgca acttaatatt aagaggaatt ccaaacactc tgcctggaca | 60 |
| ggagagttat ttaaaattga atgtcctgtg aaatactgtg ttcatagacc tcatgtgact | 120 |
| tggtgtaagc acaatggaac aatctgggta ccccttgaag ttggtcctca gctatacact | 180 |
| agttgggaag aaaatcgatc agttccggtt tttgttctcc attttaaacc aatacatctc | 240 |
| agtgataacg ggtcgtatag ctgttctaca aacttcaatt ctcaagttat taatagccat | 300 |
| tcagtaacca tccatgtgag ag | 322 |

<210> SEQ ID NO 20
<211> LENGTH: 322
<212> TYPE: DNA
<213> ORGANISM: Mus musculus

<400> SEQUENCE: 20

| | | |
|---|---|---|
| gatgaagagt gtgaagtgca acttaatatt aagaggaatt ccaaacactc tgcctggaca | 60 |
| ggagagttat ttaaaattga atgtcctgtg aaatactgtg ttcatagacc taatgtgact | 120 |
| tggtgtaagc acaatggaac aatctgggta ccccttgaag ttggtcctca gctatacact | 180 |
| agttgggaag aaaatcgatc agttccggtt tttgttctcc attttaaacc aatacatctc | 240 |
| agtgataacg ggtcgtatag ctgttctaca aacttcaatt ctcaagttat taatagccat | 300 |
| tcagtaacca tccatgtgag ag | 322 |

<210> SEQ ID NO 21
<211> LENGTH: 322
<212> TYPE: DNA
<213> ORGANISM: Mus musculus

<400> SEQUENCE: 21

| | | |
|---|---|---|
| gatgaagagt gtgaagtgca acttaatatt aagaggaatt ccaaacactc tgcctggaca | 60 |
| ggagagttat ttaaaattga atgtcctgtg aaatactgtg ttcatagacc taatgtgact | 120 |
| tggtgtaagc acaatggaac aatctgggta ccccttgaag ttggtcctca gctatacact | 180 |
| agttgggaag aaaatcgatc agttccggtt tttgttctcc attttaaacc aatacatctc | 240 |
| agtgataacg ggtcgtatag ctgttctaca aacttcaatt ctcaagttat taatagccat | 300 |
| tcagtaacca tccatgtgag ag | 322 |

<210> SEQ ID NO 22
<211> LENGTH: 322
<212> TYPE: DNA
<213> ORGANISM: Mus musculus

<400> SEQUENCE: 22

```
gatgaagagt gtgaagtgca acttaatatt aagaggaatt ccaaacactc tgcctggaca        60
ggagagttat ttaaaattga atgtcctgtg aaatactgtg ttcatagacc taatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322
```

<210> SEQ ID NO 23
<211> LENGTH: 322
<212> TYPE: DNA
<213> ORGANISM: Mus musculus

<400> SEQUENCE: 23

```
gatgaagagt gtgaagtgca acttaatatt aagaggaatt ccaaacactc tgcctggaca        60
ggagagttat ttaaaattga atgtcctgtg aaatactgtg ttcatagacc taatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322
```

<210> SEQ ID NO 24
<211> LENGTH: 322
<212> TYPE: DNA
<213> ORGANISM: Mus musculus

<400> SEQUENCE: 24

```
gatgaagagt gtgaagtgca acttaatatt aagaggaatt ccaaacactc tgcctggaca        60
ggagagttat ttaaaattga atgtcctgtg gaatactgtg ttcatagacc tcatgtgact       120
tggtgtaagc acaatggaac aatctgggta ccccttgaag ttggtcctca gctatacact       180
agttgggaag aaaatcgatc agttccggtt tttgttctcc attttaaacc aatacatctc       240
agtgataacg ggtcgtatag ctgttctaca aacttcaatt ctcaagttat taatagccat       300
tcagtaacca tccatgtgag ag                                                322
```

<210> SEQ ID NO 25
<211> LENGTH: 322
<212> TYPE: DNA
<213> ORGANISM: Mus musculus

<400> SEQUENCE: 25

```
gatgaagagt gtccagtgca acttactatt acgaggaatt ccaaacagtc tgccaggaca        60
ggagagttat ttaaaattca atgtcctgtg aaatactgtg ttcatagacc taatgtgact       120
tggtgtaagc acaatggaac aatctgtgta ccccttgagg ttagccctca gctatacact       180
agttgggaag aaaatcgatc agttccggtt tttgttctcc attttaaacc aatacatctc       240
agtgataatg ggtcgtatag ctgttctaca aacttcaatt ctcaagttat taatagccat       300
tcagtaacca tccatgtgac ag                                                322
```

<210> SEQ ID NO 26
<211> LENGTH: 322
<212> TYPE: DNA
<213> ORGANISM: Mus musculus

<400> SEQUENCE: 26

| | | |
|---|---|---|
| gatgaagagt gtgaagtgca acttaatatt aagaggaatt ccaaacactc tgcctggaca | 60 | |
| ggagagttat ttaaaattga atgtcctgtg gaatactgtg ttcatagacc tcatgtgact | 120 | |
| tggtgtaagc acaatggaac aatctgggta ccccttgaag ttggtcctca gctatacact | 180 | |
| agttgggaag aaaatcgatc agttccggtt tttgttctcc attttaaacc aatacatctc | 240 | |
| agtgataacg ggtcgtatag ctgttctaca aacttcaatt ctcaagttat taatagccat | 300 | |
| tcagtaacca tccatgtgag ag | 322 | |

<210> SEQ ID NO 27
<211> LENGTH: 322
<212> TYPE: DNA
<213> ORGANISM: Mus musculus

<400> SEQUENCE: 27

| | | |
|---|---|---|
| gatgaagagt gtgaagtgca acttaatatt aagaggaatt ccaaacactc tgcctggaca | 60 | |
| ggagagttat ttaaaattga atgtcctgtg aaatactgtg ttcatagacc taatgtgact | 120 | |
| tggtgtaagc acaatggaac aatctgggta ccccttgaag ttggtcctca gctatacact | 180 | |
| agttgggaag aaaatcgatc agttccggtt tttgttctcc attttaaacc aatacatctc | 240 | |
| agtgataacg ggtcgtatag ctgttctaca aacttcaatt ctcaagttat taatagccat | 300 | |
| tcagtaacca tccatgtgag ag | 322 | |

<210> SEQ ID NO 28
<211> LENGTH: 26
<212> TYPE: DNA
<213> ORGANISM: Homo sapiens

<400> SEQUENCE: 28
agctctgaag atctctaggg aggaag    26

<210> SEQ ID NO 29
<211> LENGTH: 32
<212> TYPE: DNA
<213> ORGANISM: Homo sapiens

<400> SEQUENCE: 29
catgctcgag gaaggtccag acagaggtat tg    32

<210> SEQ ID NO 30
<211> LENGTH: 29
<212> TYPE: DNA
<213> ORGANISM: Homo sapiens

<400> SEQUENCE: 30
gttcagatcc aaggatgctc cagaggccc    29

<210> SEQ ID NO 31
<211> LENGTH: 32
<212> TYPE: DNA
<213> ORGANISM: Homo sapiens

<400> SEQUENCE: 31
gagcatcctt ggatctgaac aaaagctgat ta    32

```
<210> SEQ ID NO 32
<211> LENGTH: 29
<212> TYPE: DNA
<213> ORGANISM: Homo sapiens

<400> SEQUENCE: 32
ctttctcaca gagctcgtac aggtcctct                                    29

<210> SEQ ID NO 33
<211> LENGTH: 31
<212> TYPE: DNA
<213> ORGANISM: Homo sapiens

<400> SEQUENCE: 33
gtacgagctc tgtgagaaag ctactaagag g                                 31

<210> SEQ ID NO 34
<211> LENGTH: 30
<212> TYPE: DNA
<213> ORGANISM: Homo sapiens

<400> SEQUENCE: 34
tgatattcca taaacctgcc actgagccag                                   30

<210> SEQ ID NO 35
<211> LENGTH: 33
<212> TYPE: DNA
<213> ORGANISM: Homo sapiens

<400> SEQUENCE: 35
tggcaggttt atggaatatc aaccaggtta gtg                               33

<210> SEQ ID NO 36
<211> LENGTH: 31
<212> TYPE: DNA
<213> ORGANISM: Homo sapiens

<400> SEQUENCE: 36
gcttttgttc acttctcaca caaatggatg c                                 31

<210> SEQ ID NO 37
<211> LENGTH: 30
<212> TYPE: DNA
<213> ORGANISM: Homo sapiens

<400> SEQUENCE: 37
tgaggagtga acaaaagctg attagcgaag                                   30

<210> SEQ ID NO 38
<211> LENGTH: 27
<212> TYPE: DNA
<213> ORGANISM: Homo sapiens

<400> SEQUENCE: 38
ccgctcgagc tcctacaggt cctcttc                                      27

<210> SEQ ID NO 39
<211> LENGTH: 30
<212> TYPE: DNA
<213> ORGANISM: Homo sapiens

<400> SEQUENCE: 39
```

```
gaagatctgc aggaaatgaa gacattgcct                                    30

<210> SEQ ID NO 40
<211> LENGTH: 35
<212> TYPE: DNA
<213> ORGANISM: Homo sapiens

<400> SEQUENCE: 40
tcagcttttg ttccccatgg atgttccaga tgtcc                              35

<210> SEQ ID NO 41
<211> LENGTH: 34
<212> TYPE: DNA
<213> ORGANISM: Homo sapiens

<400> SEQUENCE: 41
catccatggg gaacaaaagc tgattagcga agag                               34

<210> SEQ ID NO 42
<211> LENGTH: 35
<212> TYPE: DNA
<213> ORGANISM: Homo sapiens

<400> SEQUENCE: 42
cacatgattc tttcaggtcc tcttcgctaa tcagc                              35

<210> SEQ ID NO 43
<211> LENGTH: 35
<212> TYPE: DNA
<213> ORGANISM: Homo sapiens

<400> SEQUENCE: 43
gaggacctga aagaatcatg tgatgtacag cttta                              35

<210> SEQ ID NO 44
<211> LENGTH: 32
<212> TYPE: DNA
<213> ORGANISM: Homo sapiens

<400> SEQUENCE: 44
ccgctcgagt tggagtcaga aacagactta ac                                 32

<210> SEQ ID NO 45
<211> LENGTH: 30
<212> TYPE: DNA
<213> ORGANISM: Homo sapiens

<400> SEQUENCE: 45
tgaggagtga acaaaagctg attagcgaag                                    30

<210> SEQ ID NO 46
<211> LENGTH: 30
<212> TYPE: DNA
<213> ORGANISM: Homo sapiens

<400> SEQUENCE: 46
tgaggagtga acaaaagctg attagcgaag                                    30

<210> SEQ ID NO 47
<211> LENGTH: 35
<212> TYPE: DNA
<213> ORGANISM: Homo sapiens

<400> SEQUENCE: 47
```

```
gaaactggaa tttatgataa tgaccctgac ctttg                                    35

<210> SEQ ID NO 48
<211> LENGTH: 35
<212> TYPE: DNA
<213> ORGANISM: Homo sapiens

<400> SEQUENCE: 48
gggtcattat caaaaattcc agtttctgat agcag                                    35

<210> SEQ ID NO 49
<211> LENGTH: 35
<212> TYPE: DNA
<213> ORGANISM: Homo sapiens

<400> SEQUENCE: 49
accaggcatt gtttatgctt ccctgaacca ttctg                                    35

<210> SEQ ID NO 50
<211> LENGTH: 28
<212> TYPE: DNA
<213> ORGANISM: Homo sapiens

<400> SEQUENCE: 50
agggaagcaa aaacaatgcc tggtttgt                                            28

<210> SEQ ID NO 51
<211> LENGTH: 33
<212> TYPE: DNA
<213> ORGANISM: Homo sapiens

<400> SEQUENCE: 51
gcaccaacag aatatgcatc catatgtgtg agg                                      33

<210> SEQ ID NO 52
<211> LENGTH: 33
<212> TYPE: DNA
<213> ORGANISM: Homo sapiens

<400> SEQUENCE: 52
atatggatgc aaattctgtt ggtgcttctt tta                                      33

<210> SEQ ID NO 53
<211> LENGTH: 20
<212> TYPE: DNA
<213> ORGANISM: Homo sapiens

<400> SEQUENCE: 53
tttggcctaa gatgctgcta                                                     20

<210> SEQ ID NO 54
<211> LENGTH: 20
<212> TYPE: DNA
<213> ORGANISM: Homo sapiens

<400> SEQUENCE: 54
cacagattgg gtacgacatg                                                     20

<210> SEQ ID NO 55
<211> LENGTH: 24
<212> TYPE: DNA
<213> ORGANISM: Homo sapiens
```

<400> SEQUENCE: 55 tttttccatca ctgatatgtg cagg        24

<210> SEQ ID NO 56
<211> LENGTH: 22
<212> TYPE: DNA
<213> ORGANISM: Homo sapiens

<400> SEQUENCE: 56
ggtccctgtt ggagtcagaa ac        22

<210> SEQ ID NO 57
<211> LENGTH: 306
<212> TYPE: PRT
<213> ORGANISM: Mus musculus

<400> SEQUENCE: 57

```
Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300
```

Phe Leu
305

<210> SEQ ID NO 58
<211> LENGTH: 309
<212> TYPE: PRT
<213> ORGANISM: Mus musculus

<400> SEQUENCE: 58

Met Asp Pro Arg Cys Thr Met Gly Leu Ala Ile Leu Ile Phe Val Thr
1               5                   10                  15

Val Leu Leu Ile Ser Asp Ala Val Ser Val Glu Thr Gln Ala Tyr Phe
            20                  25                  30

Asn Gly Thr Ala Tyr Leu Pro Cys Pro Phe Thr Lys Ala Gln Asn Ile
        35                  40                  45

Ser Leu Ser Glu Leu Val Val Phe Trp Gln Asp Gln Gln Lys Leu Val
    50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125

Glu Leu Ser Val Ile Ala Asn Phe Ser Glu Pro Glu Ile Lys Leu Asp
    130                 135                 140

Gln Asn Val Thr Gly Asn Ser Gly Ile Asn Leu Thr Cys Met Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205

Val Trp His Met Thr Val Val Cys Val Leu Glu Thr Glu Ser Met Lys
    210                 215                 220

Ile Ser Ser Lys Pro Leu Asn Phe Thr Gln Glu Phe Pro Ser Ala Gln
225                 230                 235                 240

Thr Tyr Trp Lys Glu Ile Thr Ala Ser Val Thr Val Ala Leu Leu Leu
                245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
        275                 280                 285

Arg Glu Thr Ile Asn Leu Lys Glu Leu Glu Pro Gln Ile Ala Ser Ala
    290                 295                 300

Lys Pro Asn Ala Glu
305

<210> SEQ ID NO 59
<211> LENGTH: 323
<212> TYPE: PRT
<213> ORGANISM: Mus musculus

<400> SEQUENCE: 59

```
Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30

Leu Phe Leu Leu Leu Leu Ser Ser Leu Cys Ala Ala Ser Ala Glu Thr
            35                  40                  45

Glu Val Gly Ala Met Val Gly Ser Asn Val Val Leu Ser Cys Ile Asp
50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
                100                 105                 110

Leu Asp Ser Met Lys Gln Gly Asn Phe Ser Leu Tyr Leu Lys Asn Val
                115                 120                 125

Thr Pro Gln Asp Thr Gln Glu Phe Thr Cys Arg Val Phe Met Asn Thr
                130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
                180                 185                 190

Glu Pro Asn Leu Tyr Trp Ile Asn Thr Thr Asp Asn Ser Leu Ile Asp
                195                 200                 205

Thr Ala Leu Gln Asn Asn Thr Val Tyr Leu Asn Lys Leu Gly Leu Tyr
                210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
                260                 265                 270

Thr His Asn Asn Glu Leu Lys Val Leu Val Pro Val Leu Ala Val Leu
                275                 280                 285

Ala Ala Ala Ala Phe Val Ser Phe Ile Ile Tyr Arg Arg Thr Arg Pro
                290                 295                 300

His Arg Ser Tyr Thr Gly Pro Lys Thr Val Gln Leu Glu Leu Thr Asp
305                 310                 315                 320

His Ala Asn

<210> SEQ ID NO 60
<211> LENGTH: 290
<212> TYPE: PRT
<213> ORGANISM: Mus musculus

<400> SEQUENCE: 60

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
            35                  40                  45
```

```
Asp Leu Leu Ala Leu Val Val Tyr Trp Glu Lys Glu Asp Glu Gln Val
 50                  55                  60

Ile Gln Phe Val Ala Gly Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290

<210> SEQ ID NO 61
<211> LENGTH: 247
<212> TYPE: PRT
<213> ORGANISM: Mus musculus

<400> SEQUENCE: 61

Met Leu Leu Leu Leu Pro Ile Leu Asn Leu Ser Leu Gln Leu His Pro
 1                5                  10                  15

Val Ala Ala Leu Phe Thr Val Thr Ala Pro Lys Glu Val Tyr Thr Val
                 20                  25                  30

Asp Val Gly Ser Ser Val Ser Leu Glu Cys Asp Phe Asp Arg Arg Glu
             35                  40                  45

Cys Thr Glu Leu Glu Gly Ile Arg Ala Ser Leu Gln Lys Val Glu Asn
         50                  55                  60

Asp Thr Ser Leu Gln Ser Glu Arg Ala Thr Leu Leu Glu Glu Gln Leu
 65                  70                  75                  80

Pro Leu Gly Lys Ala Leu Phe His Ile Pro Ser Val Gln Val Arg Asp
                 85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
            115                 120                 125
```

-continued

Arg Ile Leu Glu Val Pro Gly Thr Gly Glu Val Gln Leu Thr Cys Gln
130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
                180                 185                 190

Met Phe Trp Asn Ala His Met Lys Glu Leu Thr Ser Ala Ile Ile Asp
            195                 200                 205

Pro Leu Ser Arg Met Glu Pro Lys Val Pro Arg Thr Trp Pro Leu His
210                 215                 220

Val Phe Ile Pro Ala Cys Thr Ile Ala Leu Ile Phe Leu Ala Ile Val
225                 230                 235                 240

Ile Ile Gln Arg Lys Arg Ile
                245

<210> SEQ ID NO 62
<211> LENGTH: 316
<212> TYPE: PRT
<213> ORGANISM: Mus musculus

<400> SEQUENCE: 62

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
                20                  25                  30

Val Ser Glu Asp Pro Val Val Ala Leu Val Asp Thr Asp Ala Thr Leu
            35                  40                  45

Arg Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
                100                 105                 110

Arg Val Thr Asp Glu Gly Ser Tyr Thr Cys Phe Val Ser Ile Gln Asp
            115                 120                 125

Phe Asp Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
                180                 185                 190

Ser Gln Met Ala Asn Glu Arg Gly Leu Phe Asp Val His Ser Val Leu
            195                 200                 205

Arg Val Val Leu Gly Ala Asn Gly Thr Tyr Ser Cys Leu Val Arg Asn
        210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser

```
                245                 250                 255
Val Cys Leu Val Val Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Asp Gly Glu Gly Ser Lys Thr Ala Leu Arg Pro Leu Lys Pro
    290                 295                 300

Ser Glu Asn Lys Glu Asp Asp Gly Gln Glu Ile Ala
305                 310                 315

<210> SEQ ID NO 63
<211> LENGTH: 305
<212> TYPE: PRT
<213> ORGANISM: Mus musculus

<400> SEQUENCE: 63

Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30

Thr Lys Arg Asn Asp Glu Glu Cys Pro Val Gln Leu Thr Ile Thr Arg
        35                  40                  45

Asn Ser Lys Gln Ser Ala Arg Thr Gly Glu Leu Phe Lys Ile Gln Cys
    50                  55                  60

Pro Val Lys Tyr Cys Val His Arg Pro Asn Val Thr Trp Cys Lys His
65                  70                  75                  80

Asn Gly Thr Ile Cys Val Pro Leu Glu Val Ser Pro Gln Leu Tyr Thr
                85                  90                  95

Ser Trp Glu Glu Asn Gln Ser Val Pro Val Phe Val Leu His Phe Lys
            100                 105                 110

Pro Ile His Leu Ser Asp Asn Gly Ser Tyr Ser Cys Ser Thr Asn Phe
        115                 120                 125

Asn Ser Gln Val Ile Asn Ser His Ser Val Thr Ile His Val Thr Glu
    130                 135                 140

Arg Thr Gln Asn Ser Ser Glu His Pro Leu Ile Ile Ser Asp Ile Pro
145                 150                 155                 160

Asp Ala Thr Asn Ala Ser Gly Pro Ser Thr Met Glu Glu Arg Pro Gly
                165                 170                 175

Arg Thr Trp Leu Leu Tyr Thr Leu Leu Pro Leu Gly Ala Leu Leu Leu
            180                 185                 190

Leu Leu Ala Cys Val Cys Leu Leu Cys Phe Leu Lys Arg Ile Gln Gly
        195                 200                 205

Lys Glu Lys Lys Pro Ser Asp Leu Ala Gly Arg Asp Thr Asn Leu Val
    210                 215                 220

Asp Ile Pro Ala Ser Ser Arg Thr Asn His Gln Ala Leu Pro Ser Gly
225                 230                 235                 240

Thr Gly Ile Tyr Asp Asn Asp Pro Trp Ser Ser Met Gln Asp Glu Ser
                245                 250                 255

Glu Leu Thr Ile Ser Leu Gln Ser Glu Arg Asn Asn Gln Gly Ile Val
            260                 265                 270

Tyr Ala Ser Leu Asn His Cys Val Ile Gly Arg Asn Pro Arg Gln Glu
        275                 280                 285

Asn Asn Met Gln Glu Ala Pro Thr Glu Tyr Ala Ser Ile Cys Val Arg
    290                 295                 300
```

Ser
305

<210> SEQ ID NO 64
<211> LENGTH: 289
<212> TYPE: PRT
<213> ORGANISM: Homo sapiens

<400> SEQUENCE: 64

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Met Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Gly Ala Ser Glu Arg Pro Ser
    130                 135                 140

Lys Asp Glu Val Ala Ser Arg Pro Trp Leu Leu Tyr Ser Leu Leu Pro
145                 150                 155                 160

Leu Gly Gly Leu Pro Leu Leu Ile Thr Thr Trp Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Ala Gly
    210                 215                 220

Ile Tyr Asp Asn Asp Pro Asp Leu Cys Phe Arg Met Gln Glu Gly Ser
225                 230                 235                 240

Glu Val Cys Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 65
<211> LENGTH: 107
<212> TYPE: PRT
<213> ORGANISM: Mus musculus

<400> SEQUENCE: 65

Asp Glu Glu Cys Glu Val Gln Leu Asn Ile Lys Arg Asn Ser Lys His
1               5                   10                  15

Ser Ala Trp Thr Gly Glu Leu Phe Lys Ile Glu Cys Pro Val Lys Tyr

```
                20                  25                  30
Cys Val His Arg Pro Asn Val Thr Trp Cys Lys His Asn Gly Thr Ile
            35                  40                  45
Trp Val Pro Leu Glu Val Gly Pro Gln Leu Tyr Thr Ser Trp Glu Glu
        50                  55                  60
Asn Arg Ser Val Pro Val Phe Val Leu His Phe Lys Pro Ile His Leu
65                  70                  75                  80
Ser Asp Asn Gly Ser Tyr Ser Cys Ser Thr Trp Phe Trp Ser Gln Val
                85                  90                  95
Ile Asn Ser His Ser Val Thr Ile His Val Arg
                100                 105

<210> SEQ ID NO 66
<211> LENGTH: 107
<212> TYPE: PRT
<213> ORGANISM: Mus musculus

<400> SEQUENCE: 66

Asp Glu Glu Cys Glu Val Gln Leu Asn Ile Lys Arg Asn Ser Lys His
1               5                   10                  15
Ser Ala Trp Thr Gly Glu Leu Phe Lys Ile Glu Cys Pro Val Lys Tyr
                20                  25                  30
Cys Val His Arg Pro His Val Thr Trp Cys Lys His Asn Gly Thr Ile
            35                  40                  45
Trp Val Pro Leu Glu Val Gly Pro Gln Leu Tyr Thr Ser Trp Glu Glu
        50                  55                  60
Asn Arg Ser Val Pro Val Phe Val Leu His Phe Lys Pro Ile His Leu
65                  70                  75                  80
Ser Asp Asn Gly Ser Tyr Ser Cys Ser Thr Trp Phe Trp Ser Gln Val
                85                  90                  95
Ile Trp Ser His Ser Val Thr Ile His Val Arg
                100                 105

<210> SEQ ID NO 67
<211> LENGTH: 107
<212> TYPE: PRT
<213> ORGANISM: Mus musculus

<400> SEQUENCE: 67

Asp Glu Glu Cys Pro Val Gln Leu Thr Ile Thr Arg Asn Ser Lys Gln
1               5                   10                  15
Ser Ala Arg Thr Gly Glu Leu Phe Lys Ile Gln Cys Pro Val Lys Tyr
                20                  25                  30
Cys Val His Arg Pro Asn Val Thr Trp Cys Lys His Asn Gly Thr Ile
            35                  40                  45
Cys Val Pro Leu Glu Val Ser Pro Gln Leu Tyr Thr Ser Trp Glu Glu
        50                  55                  60
Asn Gln Ser Val Pro Val Phe Val Leu His Phe Lys Pro Ile His Leu
65                  70                  75                  80
Ser Asp Asn Gly Ser Tyr Ser Cys Ser Thr Asn Phe Asn Ser Gln Val
                85                  90                  95
Ile Trp Ser His Ser Val Thr Ile His Val Thr
                100                 105

<210> SEQ ID NO 68
<211> LENGTH: 283
<212> TYPE: PRT
```

<213> ORGANISM: Homo sapiens

<400> SEQUENCE: 68

```
Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280
```

<210> SEQ ID NO 69
<211> LENGTH: 276
<212> TYPE: PRT
<213> ORGANISM: Mus musculus

<400> SEQUENCE: 69

```
Met Glu Pro Leu Pro Gly Trp Gly Ser Ala Pro Trp Ser Gln Ala Pro
1               5                   10                  15

Thr Asp Asn Thr Phe Arg Leu Val Pro Cys Val Phe Leu Leu Asn Leu
            20                  25                  30

Leu Gln Arg Ile Ser Ala Gln Pro Ser Cys Arg Gln Glu Phe Leu
        35                  40                  45

Val Gly Asp Glu Cys Cys Pro Met Cys Asn Pro Gly Tyr His Val Lys
    50                  55                  60

Gln Val Cys Ser Glu His Thr Gly Thr Val Cys Ala Pro Cys Pro Pro
```

```
                65                  70                  75                  80
Gln Thr Tyr Thr Ala His Ala Asn Gly Leu Ser Lys Cys Leu Pro Cys
                85                  90                  95

Gly Val Cys Asp Pro Asp Met Gly Leu Leu Thr Trp Gln Glu Cys Ser
            100                 105                 110

Ser Trp Lys Asp Thr Val Cys Arg Cys Ile Pro Gly Tyr Phe Cys Glu
        115                 120                 125

Asn Gln Asp Gly Ser His Cys Ser Thr Cys Leu Gln His Thr Thr Cys
    130                 135                 140

Pro Pro Gly Gln Arg Val Glu Lys Arg Gly Thr His Asp Gln Asp Thr
145                 150                 155                 160

Val Cys Ala Asp Cys Leu Thr Gly Thr Phe Ser Gly Gly Thr Gln
                165                 170                 175

Glu Glu Cys Leu Pro Trp Thr Asn Cys Ser Ala Phe Gln Gln Glu Val
            180                 185                 190

Arg Arg Gly Thr Asn Ser Thr Asp Thr Thr Cys Ser Ser Gln Val Val
        195                 200                 205

Tyr Tyr Val Val Ser Ile Leu Leu Pro Leu Val Ile Val Gly Val Gly
    210                 215                 220

Ile Ala Gly Phe Leu Ile Cys Thr Arg Arg His Leu His Thr Ser Ser
225                 230                 235                 240

Val Ala Lys Glu Leu Glu Pro Phe Gln Gln Glu Gln Gln Glu Asn Thr
                245                 250                 255

Ile Arg Phe Pro Val Thr Glu Val Gly Phe Ala Glu Thr Glu Glu Glu
            260                 265                 270

Thr Ala Ser Asn
        275

<210> SEQ ID NO 70
<211> LENGTH: 21
<212> TYPE: DNA
<213> ORGANISM: Mus musculus

<400> SEQUENCE: 70
atggtccttc taagagtgaa c                                              21

<210> SEQ ID NO 71
<211> LENGTH: 21
<212> TYPE: DNA
<213> ORGANISM: Mus musculus

<400> SEQUENCE: 71
atagatggtc tggggtagat c                                              21

<210> SEQ ID NO 72
<211> LENGTH: 19
<212> TYPE: DNA
<213> ORGANISM: Mus musculus

<400> SEQUENCE: 72
caggctcctt cctcacagc                                                 19

<210> SEQ ID NO 73
<211> LENGTH: 19
<212> TYPE: DNA
<213> ORGANISM: Mus musculus

<400> SEQUENCE: 73
```

```
ctaagaggtc tctgggcag                                                    19

<210> SEQ ID NO 74
<211> LENGTH: 30
<212> TYPE: DNA
<213> ORGANISM: Artificial
<220> FEATURE:
<223> OTHER INFORMATION: PRIMER

<400> SEQUENCE: 74
catgccatgg agaaagctac taagaggaat                                        30

<210> SEQ ID NO 75
<211> LENGTH: 29
<212> TYPE: DNA
<213> ORGANISM: Artificial
<220> FEATURE:
<223> OTHER INFORMATION: PRIMER

<400> SEQUENCE: 75
cgggatcctg aagagttttg agtcctttc                                         29

<210> SEQ ID NO 76
<211> LENGTH: 17
<212> TYPE: PRT
<213> ORGANISM: Artificial
<220> FEATURE:
<223> OTHER INFORMATION: PRIMER

<400> SEQUENCE: 76

Gly Gly Gly Leu Asn Asp Ile Phe Glu Ala Gln Lys Ile Glu Trp His
1               5                   10                  15
Glu

<210> SEQ ID NO 77
<211> LENGTH: 26
<212> TYPE: DNA
<213> ORGANISM: Artificial
<220> FEATURE:
<223> OTHER INFORMATION: PRIMER

<400> SEQUENCE: 77
agctctgaag atctctaggg aggaag                                            26

<210> SEQ ID NO 78
<211> LENGTH: 31
<212> TYPE: DNA
<213> ORGANISM: Artificial
<220> FEATURE:
<223> OTHER INFORMATION: PRIMER

<400> SEQUENCE: 78
ccttgctcac acttctcaca caaatggatg c                                      31

<210> SEQ ID NO 79
<211> LENGTH: 29
<212> TYPE: DNA
<213> ORGANISM: Artificial
<220> FEATURE:
<223> OTHER INFORMATION: PRIMER

<400> SEQUENCE: 79
tgtgagaagt gtgagcaagg gcgaggagc                                         29

<210> SEQ ID NO 80
```

```
<211> LENGTH: 32
<212> TYPE: DNA
<213> ORGANISM: Artificial
<220> FEATURE:
<223> OTHER INFORMATION: PRIMER

<400> SEQUENCE: 80
acgcgtcgac ttacttgtac agctcgtcca tg                                    32

<210> SEQ ID NO 81
<211> LENGTH: 30
<212> TYPE: DNA
<213> ORGANISM: Artificial
<220> FEATURE:
<223> OTHER INFORMATION: PRIMER

<400> SEQUENCE: 81
gttgatattc cagtgagcaa gggcgaggag                                       30

<210> SEQ ID NO 82
<211> LENGTH: 31
<212> TYPE: DNA
<213> ORGANISM: Artificial
<220> FEATURE:
<223> OTHER INFORMATION: PRIMER

<400> SEQUENCE: 82
cttgctcact ggaatatcaa ccaggttagt g                                     31

<210> SEQ ID NO 83
<211> LENGTH: 30
<212> TYPE: DNA
<213> ORGANISM: Artificial
<220> FEATURE:
<223> OTHER INFORMATION: PRIMER

<400> SEQUENCE: 83
ggaattccat atgcagccaa gtcctgcctg                                       30

<210> SEQ ID NO 84
<211> LENGTH: 29
<212> TYPE: DNA
<213> ORGANISM: Artificial
<220> FEATURE:
<223> OTHER INFORMATION: PRIMER

<400> SEQUENCE: 84
catgctagcg agaaagctac taagaggaa                                        29

<210> SEQ ID NO 85
<211> LENGTH: 35
<212> TYPE: DNA
<213> ORGANISM: Artificial
<220> FEATURE:
<223> OTHER INFORMATION: PRIMER

<400> SEQUENCE: 85
cagtgcaact taatattacg aggaattcca aacag                                 35

<210> SEQ ID NO 86
<211> LENGTH: 31
<212> TYPE: DNA
<213> ORGANISM: Artificial
<220> FEATURE:
<223> OTHER INFORMATION: PRIMER

<400> SEQUENCE: 86
```
ctcgtaatat taagttgcac tggacactct t                              31

<210> SEQ ID NO 87
<211> LENGTH: 36
<212> TYPE: DNA
<213> ORGANISM: Artificial
<220> FEATURE:
<223> OTHER INFORMATION: PRIMER

<400> SEQUENCE: 87
gcaacttact attaagagga attccaaaca gtctgc                        36

<210> SEQ ID NO 88
<211> LENGTH: 31
<212> TYPE: DNA
<213> ORGANISM: Artificial
<220> FEATURE:
<223> OTHER INFORMATION: PRIMER

<400> SEQUENCE: 88
aattcctctt aatagtaagt tgcactggac a                              31

<210> SEQ ID NO 89
<211> LENGTH: 32
<212> TYPE: DNA
<213> ORGANISM: Artificial
<220> FEATURE:
<223> OTHER INFORMATION: PRIMER

<400> SEQUENCE: 89
gaatcccaaa cactctgcca ggacaggaga gt                             32

<210> SEQ ID NO 90
<211> LENGTH: 31
<212> TYPE: DNA
<213> ORGANISM: Artificial
<220> FEATURE:
<223> OTHER INFORMATION: PRIMER

<400> SEQUENCE: 90
ctggcagagt gtttggaatt cctcgtaata g                              31

<210> SEQ ID NO 91
<211> LENGTH: 34
<212> TYPE: DNA
<213> ORGANISM: Artificial
<220> FEATURE:
<223> OTHER INFORMATION: PRIMER

<400> SEQUENCE: 91
acagtctgcc tggacaggag agttatttaa aatt                           34

<210> SEQ ID NO 92
<211> LENGTH: 30
<212> TYPE: DNA
<213> ORGANISM: Artificial
<220> FEATURE:
<223> OTHER INFORMATION: PRIMER

<400> SEQUENCE: 92
tcctgtccag gcagactgtt ttgaattcct                                30

<210> SEQ ID NO 93
<211> LENGTH: 38
<212> TYPE: DNA

```
<213> ORGANISM: Artificial
<220> FEATURE:
<223> OTHER INFORMATION: PRIMER

<400> SEQUENCE: 93
gagttattta aaattgaatg tcctgtgaaa tactgtgt                                38

<210> SEQ ID NO 94
<211> LENGTH: 32
<212> TYPE: DNA
<213> ORGANISM: Artificial
<220> FEATURE:
<223> OTHER INFORMATION: PRIMER

<400> SEQUENCE: 94
aggacattca attttaaata actctcctgt cc                                      32

<210> SEQ ID NO 95
<211> LENGTH: 33
<212> TYPE: DNA
<213> ORGANISM: Artificial
<220> FEATURE:
<223> OTHER INFORMATION: PRIMER

<400> SEQUENCE: 95
atggaacaat ctgggtaccc cttgaggtta gcc                                     33

<210> SEQ ID NO 96
<211> LENGTH: 29
<212> TYPE: DNA
<213> ORGANISM: Artificial
<220> FEATURE:
<223> OTHER INFORMATION: PRIMER

<400> SEQUENCE: 96
gggtacccag attgttccat tgtgcttac                                          29

<210> SEQ ID NO 97
<211> LENGTH: 28
<212> TYPE: DNA
<213> ORGANISM: Artificial
<220> FEATURE:
<223> OTHER INFORMATION: PRIMER

<400> SEQUENCE: 97
ttgaggttgg cccgcagcta tacactag                                           28

<210> SEQ ID NO 98
<211> LENGTH: 30
<212> TYPE: DNA
<213> ORGANISM: Artificial
<220> FEATURE:
<223> OTHER INFORMATION: PRIMER

<400> SEQUENCE: 98
gctgcgggcc aacctcaagg ggtacacaga                                         30

<210> SEQ ID NO 99
<211> LENGTH: 36
<212> TYPE: DNA
<213> ORGANISM: Artificial
<220> FEATURE:
<223> OTHER INFORMATION: PRIMER

<400> SEQUENCE: 99
ttgggaagaa aatcgatcag ttccggtttt tgttct                                  36
```

```
<210> SEQ ID NO 100
<211> LENGTH: 30
<212> TYPE: DNA
<213> ORGANISM: Artificial
<220> FEATURE:
<223> OTHER INFORMATION: PRIMER

<400> SEQUENCE: 100
aactgatcga ttttcttccc aactagtgta                                   30

<210> SEQ ID NO 101
<211> LENGTH: 33
<212> TYPE: DNA
<213> ORGANISM: Artificial
<220> FEATURE:
<223> OTHER INFORMATION: PRIMER

<400> SEQUENCE: 101
atccatgtga gagaaaggac tcaaaactct tca                               33

<210> SEQ ID NO 102
<211> LENGTH: 33
<212> TYPE: DNA
<213> ORGANISM: Artificial
<220> FEATURE:
<223> OTHER INFORMATION: PRIMER

<400> SEQUENCE: 102
agtcctttct ctcacatgga tggttactga atg                               33
```

US 9,045,562 B2

COMPOSITIONS AND METHODS FOR MODULATING LYMPHOCYTE ACTIVITY

CROSS REFERENCE TO RELATED APPLICATIONS

This application is a continuation of U.S. application Ser. No. 12/977,562, filed Dec. 23, 2010, which is a continuation in part of U.S. application Ser. No. 11/875,537, filed Oct. 19, 2007, which is a divisional of U.S. application Ser. No. 10/600,997, filed Jun. 20, 2003, now U.S. Pat. No. 7,304,149, which claims priority to U.S. Provisional Patent Application Ser. No. 60/390,653, filed Jun. 20, 2002, and to U.S. Provisional Patent Application Ser. No. 60/438,593, filed Jan. 6, 2003, and U.S. application Ser. No. 12/977,562, filed Dec. 23, 2010, is a continuation in part of U.S. application Ser. No. 11/719,356, filed Dec. 12, 2007, which is a US National of PCT/US2005/041446, filed Nov. 15, 2005, which claims priority to U.S. Provisional Patent Application Ser. No. 60/628,474, filed Nov. 15, 2004, the disclosures of each of which are expressly incorporated herein, in their entirety, by reference.

FIELD OF THE INVENTION

The present invention relates to immunomodulatory compositions and methods, and in particular, to novel lymphocyte regulatory molecules as well as compositions and methods exploiting the same for therapeutic, diagnostic and research purposes.

BACKGROUND OF THE INVENTION

Positive and negative costimulatory signals play critical roles in the modulation of T cell activity, and the molecules that mediate these signals have proven to be effective targets for immunomodulatory agents. Positive costimulation, in addition to T cell receptor (TCR) engagement, is required for optimal activation of naïve T cells, whereas negative costimulation is believed to be required for the acquisition of immunologic tolerance to self, as well as the termination of effector T cell functions. Upon interaction with B7.1 or B7.2 on the surface of antigen-presenting cells (APC), CD28, the prototypic T cell costimulatory molecule, emits signals that promote T cell proliferation and differentiation in response to TCR engagement, while the CD28 homologue cytotoxic T lymphocyte antigen-4 (CTLA-4) mediates inhibition of T cell proliferation and effector functions (Chambers et al., Ann. Rev. Immunol., 19:565-594, 2001; Egen et al., Nature Immunol., 3:611-618, 2002).

Agents capable of modulating positive and negative costimulatory signals are highly desirable for use in the modulation of adaptive immune responses. Many autoimmune disorders are known to involve autoreactive T cells and autoantibodies. Agents that are capable of inhibiting the activation of lymphocytes that are specific for self antigens are desirable. Similarly, under certain conditions it is desirable to inhibit normal immune responses to antigen. For example, the suppression of normal immune responses in a patient receiving a transplant is desirable, and agents that exhibit such immunosuppressive activity are highly desirable.

Conversely, many cancer immunotherapies, such as adoptive immunotherapy, expand tumor-specific T cell populations and direct them to attack and kill tumor cells (Dudley et al., Science 298:850-854, 2002; Pardoll, Nature Biotech., 20:1207-1208, 2002; Egen et al., Nature Immunol., 3:611-618, 2002). Agents capable of augmenting tumor attack are highly desirable.

In addition, immune responses to many different antigens (e.g., microbial antigens or tumor antigens), while detectable, are frequently of insufficient magnitude to afford protection against a disease process. Agents capable of promoting and/or prolonging the activation (delaying termination) of lymphocytes that are specific for such antigens are highly desirable.

Costimulatory signals, particularly positive costimulatory signals, also play a role in the modulation of B cell activity. For example, B cell activation and the survival of germinal center B cells require T cell-derived signals in addition to stimulation by antigen. CD40 ligand present on the surface of helper T cells interacts with CD40 on the surface of B cells and provides such a positive costimulatory signal to B cells.

Herpes virus entry mediator ("HVEM"), a member of the TNF/NGF receptor family, is another positive costimulatory receptor that additionally mediates the entry of herpes simplex virus (HSV) into cells (Montgomery et al., Cell. 1996 Nov. 1; 87(3):427-36). Anti-HVEM antibodies and a soluble hybrid protein containing the HVEM ectodomain have been shown to inhibit such HVEM-dependent viral entry. HSV-1 glycoprotein D (gD), a structural component of the HSV envelope, binds to HVEM to facilitate viral entry (Whitbeck et al., J. Virol. 1997 August; 71(8):6083-93). HVEM binds two cellular ligands, secreted lymphotoxin alpha and LIGHT (Mauri et al., Immunity. 1998 January; 8(1):21-30). HSV-1 gD inhibits the interaction of HVEM with LIGHT. Additionally, targeted disruption of LIGHT causes immunomodulatory defects (Scheu et al., J. Exp. Med., 195:1613-1624, 2002). Additionally, a phage-derived peptide BP-2 reportedly binds to HVEM and can compete with HSV-1 gD (Carfi et al., Mol. Cell. 8:169-179, 2001; Sarrias et al., Mol. Immunol., 37:665-673, 2000).

SUMMARY OF THE INVENTION

One aspect of the present invention encompasses an antibody capable of specifically binding to a protein having an amino acid sequence set forth in SEQ ID NO:8, wherein the antibody is capable of reducing binding of a BTLA protein to an HVEM protein.

Another aspect of the invention encompass an antibody capable of specifically binding to a protein having an amino acid sequence set forth in SEQ ID NO:8, wherein the antibody is capable of reducing binding of a BTLA Ig domain to an HVEM CRD1 domain.

Yet another aspect of the invention encompasses an anti-BTLA antibody capable of specifically binding to a BTLA protein, wherein the antibody is capable of reducing binding of the BTLA protein to an HVEM protein.

Still another aspect of the invention encompasses an antibody capable of specifically binding to a protein having at least about 95% identity to the amino acid sequence set forth in SEQ ID NO:8, wherein the antibody is capable of reducing binding of a BTLA protein to an HVEM protein.

A further aspect of the invention encompasses an antibody capable of specifically binding to a protein having at least about 95% identity to the amino acid sequence set forth in SEQ ID NO:8, wherein the antibody is capable of reducing binding of a BTLA Ig domain to an HVEM CRD1 domain.

Yet a further aspect of the invention encompasses an antibody capable of specifically binding to a protein having an amino acid sequence set forth in SEQ ID NO:6, wherein the antibody is capable of reducing binding of a BTLA protein to an HVEM protein.

Still a further aspect of the invention encompasses an antibody capable of specifically binding to a protein having an amino acid sequence set forth in SEQ ID NO:6, wherein the antibody is capable of reducing binding of a BTLA Ig domain to an HVEM CRD1 domain.

Other aspects and iterations of the invention are described more thoroughly below.

BRIEF DESCRIPTION OF THE FIGURES

FIG. 1 shows the amino acid sequences of mouse B7x protein (SEQ ID NO: 1) and human B7x protein (SEQ ID NO: 2).

FIG. 2 shows the nucleotide sequence of mouse B7x nucleic acid (SEQ ID NO:3) encoding mouse B7x protein.

FIG. 3 shows the nucleotide sequence of human B7x nucleic acid (SEQ ID NO:4) encoding human B7x protein.

FIG. 4 shows amino acid sequence alignment of B7x with other mouse B7 family members obtained using the ClustalW with BLOSUM Series of MacVector 7.0. Conserved cysteine residues are marked with an asterisk. Identical amino acids are highlighted in black and similar residues in gray shading (SEQ ID NOS:57-62).

FIG. 5 shows a comparison of human B7x with mouse B7x. Predicted signal peptide, Ig V-like and C-like domains, the transmembrane region and cytoplasmic tail for B7x are indicated. Identical amino acids are highlighted in black and similar residues in gray shading. The potential N-glycosylation sites are arrowed.

FIG. 12 shows 293 cells (shaded histograms), and transfected 293 cells expressing CD28, ICOS, or PD-1 (open histograms), and DT320 cells expressing CTLA-4 (open histograms), stained with B7xIg fusion protein or control antibody (anti-CD28, anti-ICOS, anti-PD-1, anti-CTLA-4).

FIG. 17 is a series of plots showing flow cytometry analysis of CD4+ T cells. Cells were labeled with CSFE and stimulated with or without plate-bound anti-CD3 (0.25 mg/ml) and CHO transfectants expressing GFP or B7x. Percentages refer to fraction of cells in the non-dividing peak or divided more than two times.

FIG. 18 is a series of plots showing flow cytometry analysis flow cytometry analysis of CD8+ T cells. Cells were labeled with CSFE and stimulated with or without plate-bound anti-CD3 (0.25 mg/ml) and CHO transfectants expressing GFP or B7x. Percentages refer to fraction of cells in the non-dividing peak or divided more than two times.

FIG. 19 shows the amino acid sequences of a mouse BTLA protein (SEQ ID NO: 5) and a human BTLA protein (SEQ ID NO: 6). The mouse and human sequences are aligned, and spaces are shown as (●) for optimal comparison. The signal peptide and the transmembrane region are underlined. Potential N-linked glycosylation sites (−) and cysteine residues (●) predicted to participate in Ig domain disulfide bonding are indicated with markings above the residues. The conserved sequences around putative tyrosine-based signaling motifs are boxed.

FIG. 28 shows the sequences of human BTLA nucleic acid (SEQ ID NO:7) and encoded human BTLA protein (SEQ ID NO:8). The nucleic acid and amino acid sequences are found at Genbank accession numbers AY293286.1 and AAP44003.1, respectively.

FIG. 29 shows the sequences of mouse BTLA nucleic acid (SEQ ID NO:9) and encoded mouse BTLA protein (SEQ ID NO:10). The nucleic acid and amino acid sequences are found at Genbank accession numbers AY293285.1 and AAP44002.1, respectively.

FIG. 30 (A-C) shows the BTLA allelic variation between a number of mouse strains (SEQ ID NOS: 11-27, from top to bottom).

FIG. 40 Polymorphisms in the BTLA Ig domain. (A), Exon 2 of BTLA, comprising the Ig domain, was amplified by PCR from genomic DNA of the indicated mouse strains and sequenced. The amino acid alignment of the Ig domains of BALB/c (SEQ ID NO: 65), MLR/lpr (SEQ ID NO: 66), and C57BL/6 (SEQ ID NO: 67) BTLA is shown, starting with the aspartic acid (D) residue that corresponds to residue 37 of the entire BTLA protein. The last line of the alignment shows a consensus sequence (bottom), with differences between BALB/c and MLR/lpr (#) and differences between BALB/c and C57BL/6 (*) shown. (B), Strains sharing identical alleles of BTLA are grouped together under the index headings of BALB/c, MLR/lpr, and C57BL/6.

FIG. 55 6A6 binds to amino acid residues E34 and R73 of BTLA. Antibody interactions are most affected by E34Q and R73Q mutations, and slightly affected by H23Q and W56C mutations. E34 and R73 are E63 and R102 in full length protein.

FIG. 56 shows the amino acid sequence of human BTLA, also found at Genbank Accession No. AAP44003.1 (SEQ ID NO: 64).

DETAILED DESCRIPTION OF THE INVENTION

Figure 6:
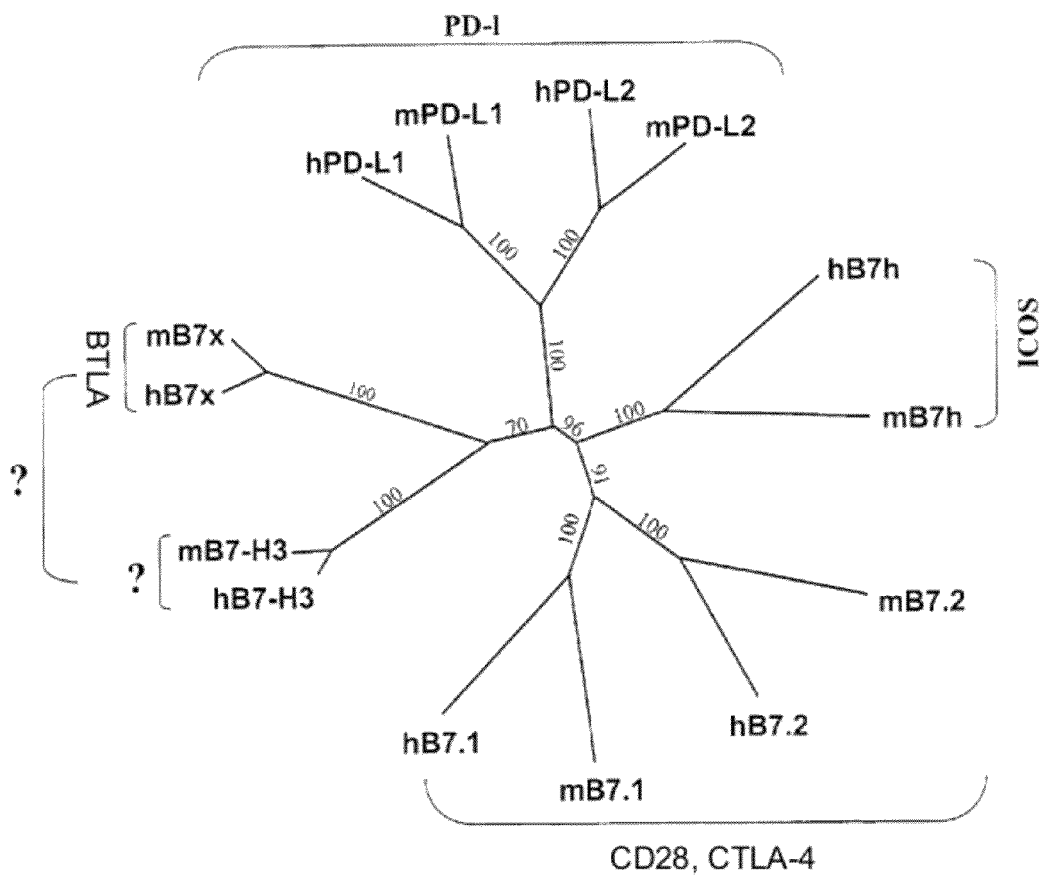
FIG. 6 shows a phylogenetic tree of the B7 family from mouse and human generated by PAUP (4.0b10) using sequence alignment by removal of significant inserts and trimming C- and N-terminal extensions. All branches of the tree were supported by Bootstrap confidence values of >50% after 100 replicates. Numbers show the percentage of bootstrap support for each Glade.

A negative costimulatory receptor analogous to CTLA-4 was herein identified on B cells and T cells. B and T lymphocyte attenuator (BTLA) is an immunoglobulin domain-containing glycoprotein with a Grb2 binding site, an immunoreceptor tyrosine-based inhibitory motif (ITIM), and an immunoreceptor tyrosine-based switch motif (ITSM). Partial BTLA sequences were disclosed previously (WO 99/40100 and WO 02/07294) though the complete sequence, distribution, and function of BTLA was not reported. Additionally, the partial BTLA sequences disclosed were asserted to correspond to secreted proteins rather than a functional receptor on the surface of lymphocytes.

BTLA acts as a negative regulator of both B and T lymphocyte activity. Crosslinking BTLA with antigen receptors induces its tyrosine phosphorylation and association with the Src homology domain 2 (SH2)-containing protein tyrosine phosphatases SHP-1 and SHP-2, and attenuates production of interleukin 2 (IL-2). BTLA-deficient T cells show increased proliferation, and BTLA-deficient mice have increased specific antibody responses and enhanced sensitivity to experimental autoimmune encephalomyelitis.

Based on indirect evidence, the ligand for BTLA was previously asserted to be B7x. However, as disclosed herein, B7x does not bind to BTLA. The identification of BTLA's cognate ligand thus remains highly desirable for an understanding of BTLA function, and for diagnostic and therapeutic purposes.

Hence, the present disclosure is directed to the identification and characterization of BTLA, a novel down-regulatory lymphocytic receptor. As shown herein, BTLA is expressed in both B and T cells and exhibits dynamic expression, with very low expression levels in naïve B and T cells, rapid induction upon stimulation of cells with antigen, and increased expression in activated B and T cells. Moreover, there is a high level of BTLA expression in Th1 cells and a much lower level in Th2 cells following Th polarization. The present invention further demonstrates that stimulation of BTLA (e.g., via the interaction of HVEM and BTLA) inhibits T cell activity, and that loss of BTLA function leads to T cell hyperactivation. Thus, as disclosed herein, BTLA represents a novel negative regulatory receptor for both B and T lymphocytes, and plays a role in controlling inflammatory responses and autoimmunity.

The present disclosure is also directed to the characterization of B7x, a new member of the B7 family the expression of which is not limited to lymphoid tissue. As shown herein, B7x is expressed in cells of non-hematopoietic origin, as well as in cells of the hematopoietic lineage, and is highly expressed in a variety of tumor cells. The present invention further demonstrates for the first time that B7x is capable of inhibiting immune-responses, and in particular, both B and T cell responses, via an interaction with BTLA. The present invention further identifies the role of B7x in the maintenance of immunological self-tolerance and the inhibition of autoimmunity. The present invention also identifies the role of B7x in promoting the survival of tumor cells by inhibiting T cell activation.

The present disclosure also establishes that Herpes virus entry mediator (HVEM) is the cognate ligand of BTLA. HVEM belongs to the TNF receptor family of proteins and is itself a costimulatory receptor expressed on naive T cells. HVEM is also expressed to a lesser extent on dendritic cells, resting B cells, and macrophages. HVEM has four extracellular cysteine-rich domains (CRDs) and interacts with two known TNF family members, LIGHT and lymphotoxin alpha (LTα), through CRD2 and CRD3. For further discussion of HVEM, see for example Granger et al., Cytokine Growth Factor Rev., 14:289-96, 2003; and Croft, Nat. Rev. Immunol., 3:609-620, 2003. As disclosed herein, HVEM directly binds to BTLA and stimulates BTLA activity. As further disclosed herein, HVEM binding to BTLA can reduce the activation of BTLA expressing lymphocytes, as well as decrease the effector activity of BTLA expressing lymphocytes.

The present disclosure also establishes that B7x does not directly bind to BTLA and does not directly modulate BTLA activity. B7x is expressed in a wide variety of normal and cancer cells, and was previously reported to be a ligand for BTLA based on indirect evidence. It was postulated that the interaction of B7x with BTLA inhibited both B and T cell responses, and was a means by which B7x-expressing tumor tissue inhibited the activity of tumor-specific T cells. It was further posited that B7x expressed on non-tumor non-lymphoid tissue served to maintain immunological tolerance to self antigens.

Stemming from the discovery of the HVEM-BTLA interaction, in one aspect, the present invention provides BTLA antibodies, sometimes referred to herein as BTLA blocking antibodies. A BTLA antibody of the invention is capable of specifically binding to a BTLA protein and is capable of reducing the binding of the BTLA protein to an HVEM protein. Especially preferred are BTLA antibodies that specifically bind to a region of the BTLA Ig domain, which region binds to the HVEM CRD1 domain. Such a BTLA antibody is capable of binding to a fragment of the BTLA Ig domain, which fragment is capable of binding to an HVEM CRD1 domain.

Aberrant BTLA activity, for example, as a result of aberrant BTLA/HVEM interaction, aberrant BTLA/B7x interaction, or aberrant BTLA, HVEM or B7x expression, can promote diseases associated with T cell activity. As noted above, a high level of B7x expression on tumor cells facilitates the inhibition of T cell activation by tumor cells, and tumor cell survival. Conversely, a low level of B7x expression on non-lymphoid tissue can render the tissue susceptible to attack by autoreactive T and B cells, and predisposes a subject to autoimmune disease. Similarly, an increased level of BTLA expression in lymphocytes, or increased effective activity, can sensitize lymphocytes to inhibitory costimulation, making them less responsive to antigen, suppressing the immune system, and potentiating the growth of tumor tissue. Conversely, a decreased level of BTLA expression in lymphocytes, or decreased effective activity, can make lymphocytes refractive to particular inhibitory costimulation signals, such as those of B7x, and lead to a hyperimmune state characterized by a predisposition to autoimmune disease.

In accordance with the foregoing, the present invention provides methods and compositions for modulating immune responses.

In one embodiment, bioactive agents and methods for increasing and/or up-regulating B and T cell activity are provided. In a preferred embodiment, such bioactive agents comprise antagonists of BTLA-mediated signaling. In a particularly preferred embodiment, such bioactive agents comprise blocking agents as described herein, and in a specific embodiment, such blocking agents are capable of interfering with the interaction of BTLA and B7x or BTLA and HVEM. In a further embodiment, adjuvant compositions are provided utilizing BTLA, HVEM, and/or B7x blocking agents and other antagonists of BTLA-mediated signaling.

In an alternative embodiment, bioactive agents and methods for inhibiting and/or down-regulating B and T cell activity are provided. In a preferred embodiment, such bioactive agents comprise agonists of BTLA-mediated signaling. In a particularly preferred embodiment, such bioactive agents comprise mimicking agents as described herein, and in a specific embodiment, such mimicking agents are capable of replacing and/or augmenting the interaction of BTLA and B7x or the interaction of BTLA and HVEM. In a further embodiment, immunosuppressive compositions are provided utilizing BTLA, HVEM, and/or B7x mimicking agents and other agonists of BTLA-mediated signaling.

In a further embodiment, methods and compositions for modulating immunoglobulin production by B cells is provided.

The methods and compositions described herein will find advantageous use in immunotherapy, including, e.g., autoimmunity, immune suppression, cancer immunotherapy and immune adjuvants.

(I) B7x and BTLA Nucleic Acids and Proteins

Murine B7x encodes a 283 amino acid protein and shares varying degrees of identity with mouse B7.1 (13%), B7.2 (13%), B7h (14%), PD-L1 (20%), PD-L2 (16%) and B7-H3 (24%).

Two human epithelial cell cDNAs encoding a polypeptide (previously called hypothetical protein FLJ22418) having similarity to mouse B7x were identified, and two EST clones (GenBank accession nos. BF680206 and AI799522) corresponding to the same human nucleotide sequence have been identified.

Human B7x encodes a 282 amino acid protein and has 87% amino acid identity with mouse B7x. Notably, this is much higher than the 40-46% identity between human and mouse B7.1 or B7.2.

B7x protein is a type I transmembrane protein that belongs to the immunoglobulin (Ig) superfamily. It has a signal peptide in its N-terminus, single extracellular IgV- and IgC-like domains, a transmembrane region and a very short cytoplasmic stub of only 1 amino acid. The absence of a heptad structure and B30.2 domains distinguishes B7x from the butyrophilins and myelin oligodendrocyte glycoproteins.

Numerous potential N-linked glycosylation sites are present in the extracellular portion of B7x. Like other members of the B7 family, B7x has four conserved cysteine residues that are likely involved in the formation of IgV- and IgC-like domains.

In both mouse and human, B7x genes are located on different chromosomes from the other known B7 family members. Mouse B7x consists of 6 exons occupying 70.15 kb in the F3 region of chromosome while human B7x is of similar size and organization in the p12/13.1 region of chromosome 1. A phylogenetic comparison of the seven known members of the B7 family from human and mouse was performed using PAUP. This analysis suggests that the extended B7 family can be divided into 3 groups: group I including B7.1, B7.2 and B7h, group II consisting of PD-L1 and PD-L2, and group III containing B7x and B7-H3.

The BTLA protein comprises a signal sequence, an extracellular V-like Ig domain, a transmembrane region, and an intracellular domain of approximately 100 amino acids that comprises several motifs implicated in signal transduction. Notably, three tyrosine residues within the cytoplasmic domain are contained within sequence motifs that are conserved between mouse and human and are implicated in signal transduction. Particularly, conserved tyrosine residues are found within a Grb2 interaction site and within two ITIM sequences.

In one aspect, the present invention provides nucleic acids encoding B7x proteins, and B7x proteins so encoded, which are capable of modulating T cell activation.

In one aspect, the present invention provides nucleic acids encoding BTLA proteins, and BTLA proteins so encoded, which are capable of modulating T cell activation.

The B7x and BTLA proteins of the present invention may be identified in several ways. "Protein" in this sense includes proteins, polypeptides, and peptides. Included among BTLA proteins are protein fragments, extracellular fragments being particularly preferred, which possess at least one activity of the BTLA protein set forth by SEQ ID NO:8 or 10, and/or at least one epitope of the BTLA protein set forth by SEQ ID NO:8 or 10. Included among B7x proteins are protein fragments, extracellular fragments being particularly preferred, which possess at least one activity of the B7x protein set forth by SEQ ID NO:1 or 2 and/or at least one epitope of the BTLA protein set forth by SEQ ID NO:1 or 2.

A B7x protein may be identified by amino acid sequence identity or similarity to the amino acid sequences set forth in SEQ ID NO:1 or 2.

A B7x protein may be identified by its ability to bind to the surface of T cells, preferably activated CD4+ and/or activated CD8+ T cells. A B7x protein may also be identified by its ability to bind to B cells expressing BTLA. Generally, a B7x protein may be identified by its ability to bind to B or T cells expressing BTLA.

A B7x protein may be identified by its ability to bind to a BTLA protein described herein.

A B7x protein may be identified by its ability to modulate T-lymphocyte activation, preferably Th1 activation. More preferably, a B7x protein may be identified by its ability to bind to BTLA expressed on a T cell and to thereby inhibit T cell activation.

A B7x protein may be identified by its elevated expression in tumor cells.

A BTLA protein may be identified by amino acid sequence identity or similarity to the amino acid sequences set forth in SEQ ID NO:8 or 10.

A BTLA protein may be identified by its ability to bind to the surface of tumor cells expressing B7x.

A BTLA protein may be identified by its ability to bind to a B7x protein described herein.

A BTLA protein may be identified by its expression in Tc and Th cells, and its elevated expression in polarized Th1 cells.

A BTLA protein may be identified by its ability to modulate T cell activation, preferably CD4+ and CD8+ T cell activation, when expressed in the T cell, and upon binding to ligand. Preferably, the ligand is B7x, a fragment thereof, or a fusion protein comprising B7x, or a fragment thereof.

B7x and BTLA proteins may initially be identified by sequence identity or similarity to the sequences set forth in the figures, as further described below. In a preferred embodiment, B7x and BTLA proteins have sequence identity or similarity to the sequences and one or more B7x and BTLA bioactivities, respectively. Such sequence identity or similarity can be based upon the overall sequence.

In a preferred embodiment, B7x proteins provided herein comprise an amino acid sequence having at least about 80%, more preferably at least about 85%, more preferably at least about 90%, more preferably at least about 95%, more preferably at least about 98% identity to the amino acid sequence set forth in SEQ ID NO:1 or 2. In a preferred embodiment, the B7x protein comprises the amino acid sequence set forth in SEQ ID NO:1 or 2.

In a preferred embodiment, BTLA proteins provided herein comprise an amino acid sequence having at least about 80%, more preferably at least about 85%, more preferably at least about 90%, more preferably at least about 95%, more preferably at least about 98% identity to the amino acid sequences set forth in SEQ ID NO:6, or 8, or 10. In a preferred embodiment, the BTLA protein comprises the amino acid sequence set forth in SEQ ID NO:6, or 8, or 10.

In a preferred embodiment, a B7x protein provided herein comprises an extracellular domain as shown in FIG. 5. In a preferred embodiment, the B7x protein comprises an IgV-like domain and an IgC-like domain.

In another preferred embodiment, a B7x protein provided herein comprises an extracellular domain and a transmembrane domain as shown in FIG. 5. In a preferred embodiment, the B7x protein comprises an IgV-like domain and an IgC-like domain, and a transmembrane domain.

In a preferred embodiment, a B7x protein provided herein comprises a cytoplasmic domain as shown in FIG. 5.

In a preferred embodiment, a B7x protein provided herein comprises a cytoplasmic domain and a transmembrane domain as shown in FIG. 5.

In a preferred embodiment, a B7x protein provided herein comprises an extracellular domain, a transmembrane domain, and a cytoplasmic domain as shown in FIG. 5.

In a preferred embodiment, the invention provides B7x protein extracellular fragments that are capable of interacting with BTLA but incapable of activating BTLA-mediated signaling. In another preferred embodiment, the invention provides B7x protein extracellular fragments that are capable of interacting with BTLA and capable of activating BTLA-mediated signaling.

The present invention also provides BTLA proteins.

In a preferred embodiment, a BTLA protein provided herein comprises a signal sequence, an extracellular Ig domain, a transmembrane region, and an intracellular domain of approximately 100 amino acids that comprises three tyrosine residues within a Grb2 interaction site and two ITIM sequences.

In another preferred embodiment, a BTLA protein provided herein comprises an extracellular Ig domain, a transmembrane region, and an intracellular domain of approximately 100 amino acids that comprises three tyrosine residues within a Grb2 interaction site and two ITIM sequences.

Figure 21:
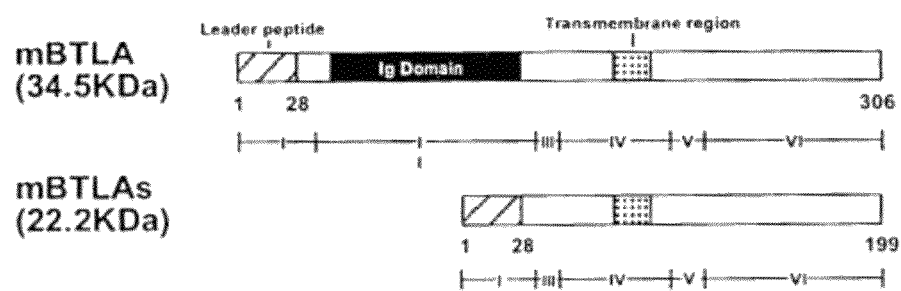
FIG. 21 shows the predicted structural regions of BTLA. Full length murine BTLA (MBTLA) and a minor splice variant (BTLAs) lacking exon 2 and deleting the Ig domain, are shown. Roman numerals shown below the figure indicate the exon from which the predicted region is derived. In parentheses is indicated the theoretical molecular weight of the predicted protein before addition of further modifications.

In another preferred embodiment, a BTLA protein provided herein comprises an extracellular Ig domain, as shown in FIG. 21.

In a preferred embodiment, the invention provides BTLA protein fragments comprising a V-like Ig domain, wherein the Ig-like domain comprises an amino acid sequence having at least about 70% identity to residues 43-134, more preferably 47-133, more preferably 51-117 of the amino acid sequence set forth in SEQ ID NO:8.

In an especially preferred embodiment, the invention provides BTLA protein fragments comprising a V-like Ig domain, wherein the Ig-like domain comprises the amino acid sequence of residues 43-134, more preferably 47-133, more preferably 51-117 of the amino acid sequence set forth in SEQ ID NO:8.

In a preferred embodiment, the invention provides BTLA protein fragments comprising a V-like Ig domain, wherein the Ig-like domain comprises an amino acid sequence having at least about 70% identity to residues 57-142, more preferably residues 57-124 of the amino acid sequence set forth at SEQ ID NO:10.

In an especially preferred embodiment, the invention provides BTLA protein fragments comprising a V-like Ig domain, wherein the Ig-like domain comprises the amino acid sequence of residues 57-142, more preferably residues 57-124 of the amino acid sequence set forth at SEQ ID NO:10.

In a preferred embodiment, the invention provides BTLA protein extracellular fragments having at least about 70% identity to a portion of the extracellular domain of BTLA protein set forth by SEQ ID NO:8, particularly to a portion (at least about 20 amino acids) of the sequence from about residue 31 to about residue 153 in SEQ ID NO:8.

In an especially preferred embodiment, the invention provides BTLA protein extracellular fragments comprising at least about a 20 amino acid sequence from about residue 31 to about residue 153 in SEQ ID NO:8.

In a preferred embodiment, the invention provides BTLA protein extracellular fragments having at least about 70% identity to a portion of the extracellular domain of BTLA protein set forth by SEQ ID NO:8, particularly to a portion (at least about 20 amino acids) of the sequence from about residue 30 to about residue 181 in SEQ ID NO:10.

In an especially preferred embodiment, the invention provides BTLA protein extracellular fragments comprising at least about a 20 amino acid sequence from about residue 30 to about residue 181 in SEQ ID NO:10.

In a preferred embodiment, a BTLA protein provided herein comprises a signal sequence and an extracellular V-like Ig domain, as shown in FIG. 21.

In another preferred embodiment, a BTLA protein provided herein comprises an extracellular V-like Ig domain and a transmembrane region, as shown in FIG. 21.

In another preferred embodiment, a BTLA protein provided herein comprises a signal sequence, an extracellular V-like Ig domain and a transmembrane region, as shown in FIG. 21.

In another preferred embodiment, a BTLA protein provided herein comprises an intracellular domain of approximately 100 amino acids, which further comprises a Grb2 interaction site and two ITIM sequences, as shown in FIG. 21.

In another preferred embodiment, a BTLA protein provided herein comprises a transmembrane region and an intracellular domain of approximately 100 amino acids, which further comprises a Grb2 interaction site and two ITIM sequences, as shown in FIG. 21.

Figure 20:
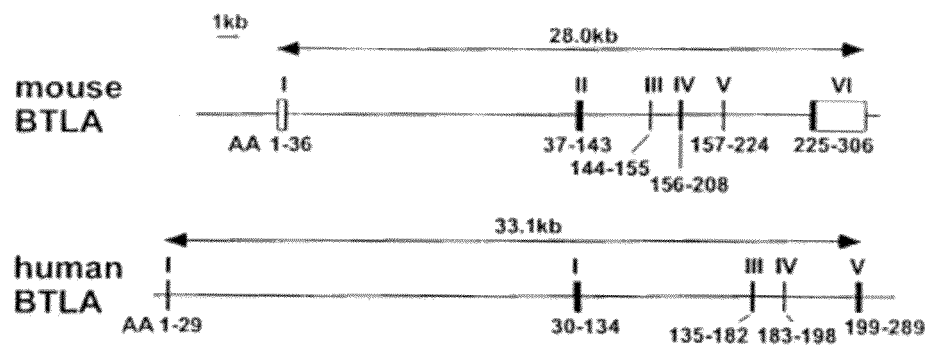
FIG. 20 shows the exon/intron organization of mouse and human BTLA genes. Filled boxes indicate coding sequence within exons, and unfilled boxes indicate 3' and 5' untranslated regions. The amino acid number encoded by each exon is indicated below.

In a highly preferred embodiment, a BTLA protein provided herein lacks the amino acid sequence encoded by exon 2 shown in FIG. 20, and accordingly lacks the Ig domain depicted in FIG. 19. In a preferred embodiment, such a BTLA protein possesses BTLA protein function.

Fragments are included in the definition of B7x and BTLA proteins herein.

In a preferred embodiment, a B7x protein provided herein consist essentially of an extracellular domain as shown in FIG. 5. In a preferred embodiment, the B7x protein consists essentially of an IgV-like domain and an IgC-like domain.

In another preferred embodiment, a B7x protein provided herein consists essentially of an extracellular domain and a transmembrane domain as shown in FIG. 5. In a preferred embodiment, the B7x protein consists essentially of an IgV-like domain and an IgC-like domain, and a transmembrane domain.

In a preferred embodiment, a B7x protein provided herein consists essentially of a cytoplasmic domain as shown in FIG. 5.

In a preferred embodiment, a B7x protein provided herein consists essentially of a cytoplasmic domain and a transmembrane domain as shown in FIG. 5.

BTLA protein fragments are also provided.

In a preferred embodiment, a BTLA protein provided herein consists essentially of an extracellular V-like Ig domain, as shown in FIG. 21.

In a preferred embodiment, a BTLA protein provided herein consists essentially of a signal sequence and an extracellular V-like Ig domain, as shown in FIG. 21.

In another preferred embodiment, a BTLA protein provided herein consists essentially of an extracellular V-like Ig domain and a transmembrane region, as shown in FIG. 21.

In another preferred embodiment, a BTLA protein provided herein consists essentially of a signal sequence, an extracellular V-like Ig domain and a transmembrane region, as shown in FIG. 21.

In another preferred embodiment, a BTLA protein provided herein consists essentially of an intracellular domain of approximately 100 amino acids, which further comprises a Grb2 interaction site and two ITIM sequences, as shown in FIG. 21.

In another preferred embodiment, a BTLA protein provided herein consists essentially of a transmembrane region and an intracellular domain of approximately 100 amino acids, which further comprises a Grb2 interaction site and two ITIM sequences, as shown in FIG. 21.

As used herein, peptide refers to at least two covalently attached amino acids, which includes proteins, polypeptides, and oligopeptides. The protein may be made up of naturally occurring amino acids and peptide bonds, or synthetic peptidomimetic structures. Thus, "amino acid" or "peptide residue" as used herein means both naturally occurring and synthetic amino acids. For example, homo-phenylalanine, citrulline, and norleucine are considered amino acids for the purposes of the invention. "Amino acids" also includes imino residues such as proline and hydroxyproline. The side chains may be either the D- or L-configuration, or combinations thereof. Although the bond between each amino acid is typically an amide or peptide bond, it is to be understood that peptide also includes analogs of peptides in which one or more peptide linkages are replaced with other than an amide or peptide linkage, such as a substituted amide linkage, an isostere of an amide linkage, or a peptide or amide mimetic linkage (See™, for example, Spatola, "Peptide Backbone Modifications," in Chemistry and Biochemistry of Amino Acids Peptides and Proteins, Weinstein, Ed., Marcel Dekker, New York (1983); Son et al., J. Med. Chem. 36:3039-3049 (1993); and Ripka and Rich, Curr. Opin. Chem. Biol. 2:441-452 (1998)).

Typically, peptides will generally be less than about 100 amino acids, less that about 50 amino acids, or less than about 20 amino acids.

A peptide herein is typically an isolated or purified peptide. As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The phrase "substantially free of chemical precursors or other chemicals" includes preparations of the peptide in which it is separated from chemical precursors or other chemicals that are involved in its synthesis. Preparations of a peptide are substantially free of precursors in preparation having less than about 30% (by dry weight) chemical precursors or other chemicals, less than about 20% chemical precursors or other chemicals, less than about 10% chemical precursors or other chemicals, or less than about 5% chemical precursors or other chemicals.

The peptides of this invention can be made by chemical synthesis methods which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Peptides can be synthesized using the automated Merrifield techniques of solid phase synthesis with the aNH2 protected by either t-Boc or Fmoc chemistry using side chain protected amino acids on, for example, an Applied Biosystems Peptide Synthesizer Model 430A or 431.

After complete assembly of the desired peptide, the resin is treated according to standard procedures to cleave the peptide from the resin and deblock the functional groups on the amino acid side chains. The free peptide is purified, for example by HPLC, and characterized biochemically, for example, by amino acid analysis, mass spectrometry, and/or by sequencing. Purification and characterization methods for peptides are well known to those of ordinary skill in the art.

Longer synthetic peptides can be synthesized by well-known recombinant DNA techniques. Many standard manuals on molecular cloning technology provide detailed protocols to produce the peptides of the invention by expression of recombinant DNA and RNA. To construct a gene encoding a peptide of this invention, the amino acid sequence is reverse translated into a nucleic acid sequence, preferably using optimized codon usage for the organism in which the gene will be expressed. Next, a gene encoding the peptide is made, typically by synthesizing overlapping oligonucleotides which encode the peptide and necessary regulatory elements. The synthetic gene is assembled and inserted into the desired expression vector. Nucleic acids which comprise sequences that encode the peptides of this invention are also provided. The synthetic gene is inserted into a suitable cloning vector and recombinants are obtained and characterized. The peptide is then expressed under conditions appropriate for the selected expression system and host. The peptide is purified and characterized by standard methods.

Recombinant techniques that are well known in the art may be used to combine BTLA or B7x protein fragments disclosed herein with other moieties for a variety of purposes, as further discussed below. These processes involve the manipulation of nucleic acids encoding BTLA and B7x proteins disclosed herein.

In one aspect, the present invention provides B7x nucleic acids, including B7x nucleic acids encoding B7x proteins.

In another aspect, the present invention provides BTLA nucleic acids, including BTLA nucleic acids encoding B7x proteins.

By "nucleic acid" or oligonucleotide or grammatical equivalents herein means at least two nucleotides covalently linked together. A nucleic acid of the present invention will generally contain phosphodiester bonds, although in some cases, as outlined herein, particularly with respect to antisense nucleic acids or probes, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), 0-methylphosphoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et at., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

With respect to nucleic acids that encode B7x and BTLA proteins, it will be appreciated by those in the art, that due to the degeneracy of the genetic code, an extremely large number of nucleic acids may be made, all of which encode the B7x and BTLA proteins of the present invention. Thus, having identified a particular amino acid sequence, those skilled in the art could make any number of different nucleic acids, by simply modifying the sequence of one or more codons in a way which does not change the amino acid sequence of the B7x or BTLA protein.

Included among B7x nucleic acids are allelic variants. A B7x allelic variant refers to one of several possible naturally occurring alternate forms of the B7x gene occupying a given locus on a chromosome of an organism or a population of organisms. The existence of naturally occurring alternate forms is referred to as polymorphism. B7x nucleic acids also include splice variants. B7x splice variant refers to a nucleic acid, usually RNA, which is generated by alternative processing of intron sequences in an B7x RNA transcript to produce alternate B7x proteins.

Included among BTLA nucleic acids are allelic variants. A BTLA allelic variant refers to one of several possible naturally occurring alternate forms of the BTLA gene occupying a given locus on a chromosome of an organism or a population of organisms. The existence of naturally occurring alternate forms is referred to as polymorphism. As disclosed herein, BTLA polymorphism has been observed in mice. BTLA nucleic acids also include splice variants. BTLA splice variant refers to a nucleic acid, usually RNA, which is generated by alternative processing of intron sequences in an BTLA RNA transcript to produce alternate BTLA proteins. As disclosed herein, presumed alternatively spliced forms of BTLA have been identified.

In a preferred embodiment, the present invention provides B7x nucleic acids encoding B7x proteins, which comprise a nucleotide sequence having at least about 80%, more preferably at least about 85%, more preferably at least about 90%, more preferably at least about 95%, most preferably at least about 98% identity to the nucleotide sequence set forth in FIG. 2 or FIG. 3.

In another preferred embodiment, the present invention provides B7x nucleic acids encoding B7x proteins, which comprise a nucleotide sequence encoding an amino acid sequence having at least about 80%, more preferably at least about 85%, more preferably at least about 90%, more preferably at least about 95%, most preferably at least about 98% identity to one of the amino acid sequence set forth in FIG. 1.

In a preferred embodiment, the present invention provides B7x nucleic acids encoding a B7x protein, which nucleic acids are about 1.9, 3.5, or 8.2 kb in size.

In another preferred embodiment, the present invention provides B7x nucleic acids encoding a B7x protein, which nucleic acids are about 3.2 kb in size.

In another preferred embodiment the present invention provides BTLA nucleic acids encoding BTLA proteins, which comprise a nucleotide sequence encoding an amino acid sequence having at least about 80%, more preferably at least about 85%, more preferably at least about 90%, more preferably at least about 95%, most preferably at least about 98% identity to one of the amino acid sequences set forth in FIG. 19.

In another preferred embodiment, the present invention provides BTLA nucleic acids encoding BTLA proteins that lack the protein sequence encoded by exon 2, and consequently lack the Ig domain depicted in FIG. 21.

In a preferred embodiment, the present invention provides B7x nucleic acids encoding B7x protein fragments described herein.

In another preferred embodiment, the present invention provides BTLA nucleic acids encoding BTLA protein fragments described herein.

In some embodiments, B7x and BTLA nucleic acids are determined through hybridization studies. Thus, for example, nucleic acids which hybridize under high stringency conditions to the nucleotide sequences set forth in the figures, or to those which encode the amino acid sequences set forth in the figures, or complements thereof, or fragments thereof or their complements, are considered B7x or BTLA nucleic acids. High stringency conditions are known in the art; see for example Sambrook et al., Molecular Cloning, A Laboratory Manual, 3rd edition, 2001, Cold Spring Harbor Press, Cold Spring Harbor, N.Y.; and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In other embodiments, less stringent hybridization conditions are used; for example, moderate or low stringency conditions may be used, as are known in the art; see Sambrook et al., Molecular Cloning, A Laboratory Manual, 3rd edition, 2001, Cold Spring Harbor Press, Cold Spring Harbor, N.Y.; and Tijssen, supra.

Also provided herein are B7x antisense nucleic acids which will hybridize under high stringency conditions to a B7x nucleic acid. In a preferred embodiment, the B7x antisense nucleic acid inhibits expression of B7x protein. In a preferred embodiment, the B7x antisense nucleic acid inhibits B7x protein activity.

Also provided herein are BTLA antisense nucleic acids which will hybridize under high stringency conditions to a BTLA nucleic acid encoding a BTLA protein. In a preferred embodiment, the BTLA antisense nucleic acid inhibits expression of BTLA protein. In a preferred embodiment, the BTLA antisense nucleic acid inhibits BTLA protein activity.

As is known in the art, a number of different programs can be used to identify whether a protein or nucleic acid has sequence identity or similarity to a known sequence. For a detailed discussion, see D. Mount, Bioinformatics, Cold Spring Harbor Press, Cold Spring Harbor, N.Y., 2001, ISBN 0-87969-608-7. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps. Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits. A percent amino acid sequence identity value is determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the protein sequences set forth in the figures, it is understood that in one embodiment, the percentage of sequence identity will be determined based on the number of identical amino acids in relation to the total number of amino acids. Thus, for example, the percent sequence identity of sequences shorter than those shown in the figures will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of 0, which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

In a similar manner, percent (%) nucleic acid sequence identity is defined as the percentage of nucleotide residues in a candidate sequence that are identical with the nucleotide residues in the B7x nucleic acid set forth in FIG. 2 or 4, or a BTLA nucleic acid sequence encoding a BTLA amino acid sequence set forth in FIG. 19. A preferred method utilizes the BLASTN module of WU-BLAST-2 set to the default parameters, with overlap span and overlap fraction set to 1 and 0.125, respectively.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

B7x and BTLA proteins of the present invention may be shorter or longer than the amino acid sequences set forth in the figures, or encoded by the nucleic acid sequences set forth in the figures.

In one embodiment herein, fragments of B7x proteins are considered B7x proteins if a) they share at least one antigenic epitope; b) have at least the indicated sequence identity; c) and preferably have B7x protein activity as further defined herein.

Similarly, fragments of BTLA proteins are considered BTLA proteins if a) they share at least one antigenic epitope; b) have at least the indicated sequence identity; c) and preferably have BTLA protein activity as further defined herein.

The nucleic acids of the present invention may also be shorter or longer than those shown in the figures, or those encoding the amino acid sequences shown in the figures. In some cases, where a sequence is used diagnostically, that is, when the presence or absence of a B7x or a BTLA nucleic acid is determined, only the indicated sequence identity is required. The nucleic acid fragments provided herein include nucleic acids consisting essentially of portions of the sequences provided herein that have not been exactly identified previously; fragments having sequences with the indicated sequence identity to that portion not previously identified are also provided in an embodiment herein.

In addition, as is more fully outlined below, B7x and BTLA proteins can be made that are longer than those depicted in the figures, for example, by the addition of epitope or purification tags, the addition of other fusion sequences, or the elucidation of additional coding and non-coding sequences. As described below, the fusion of a B7x or BTLA protein to a fluorescent protein, such as Blue Fluorescent Protein (BFP) or Green Fluorescent Protein (GFP), is preferred in one embodiment. In a highly preferred embodiment, a B7x or BTLA protein, or fragment thereof, is fused to the constant region of an immunoglobulin, thereby creating a B7x-Ig or BTLA-Ig fusion protein.

The B7x and BTLA proteins and nucleic acids of the present invention are preferably recombinant. As used herein and further defined below, nucleic acid may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the figures also include the complement of the sequence.

By the term recombinant nucleic acid herein is meant nucleic acid, originally formed in vitro, in general, by the manipulation of nucleic acid by endonucleases, in a form not normally found in nature. Thus an isolated B7x or BTLA nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a recombinant protein is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a B7x and BTLA proteins from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag, or amino acid substitutions, insertions and deletions, as discussed below.

An isolated polypeptide refers to a polypeptide of the invention that (1) has been separated from at least about 50% of polynucleotide, lipid, carbohydrate, or other material with which it is naturally found when isolated from a source cell, (2) is not linked (by covalent or noncovalent interaction) to all or a portion of a polypeptide to which the isolated polypeptide is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

In a preferred embodiment, the present invention provides B7x protein variants. In another preferred embodiment, the invention provides BTLA protein variants. These variants fall into one or more of three classes: substitutional, insertional or deletional variants. These variants ordinarily are prepared by site specific mutagenesis of nucleotides in the DNA encoding a B7x or BTLA protein, using cassette or PCR mutagenesis or other techniques well known in the art, to produce DNA encoding the variant, and thereafter expressing the DNA in recombinant cell culture as outlined above. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies B7x or BTLA proteins. The variants typically exhibit the same qualitative biological activity as the naturally occurring analogue, although variants can also be selected which have modified characteristics, as will be more fully outlined below.

In an especially preferred embodiment, the invention provides B7x variants that exhibit an elevated B7x bioactivity as compared to the activity of B7x proteins set forth in FIG. 1.

In another especially preferred embodiment, the invention provides BTLA variants that exhibit an elevated BTLA bioactivity as compared to the activity of BTLA proteins set forth in FIG. 19.

While the site or region for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence are well known, for example, M13 primer mutagenesis and PCR mutagenesis. Screening of the mutants may be done using assays that measure B7x or BTLA activity, as described herein.

In an especially preferred embodiment, B7x variant proteins are screened for their ability to modulate T-lymphocyte activation as described herein.

In another especially preferred embodiment, B7x variant proteins are screened for their ability to bind BTLA protein.

In another especially preferred embodiment, BTLA variant proteins are screened for their ability to modulate T cell activation as described herein.

In another especially preferred embodiment, BTLA variant proteins are screened for their ability to bind B7x protein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the B7x protein are desired, substitutions are generally made in accordance with the following chart:

CHART 1

| Original residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |

CHART 1-continued

| Original residue | Exemplary Substitutions |
| --- | --- |
| Ile | Leu, Val |
| Leu | Ile, Val |
| Lys | Arg, Gln Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the B7x and BTLA proteins as needed. The variant may be designed such that the biological activity of the B7x or BTLA protein is altered. For example, glycosylation sites may be altered or removed.

Covalent modifications of BTLA and B7x polypeptides are included within the scope of this invention. One type of covalent modification includes reacting targeted amino acid residues of a B7x or BTLA polypeptide with an organic derivatizing agent that is capable of reacting with selected side chains or the N- or C-terminal residues of the polypeptide. Derivatization with bifunctional agents is useful, for instance, for crosslinking B7x or BTLA to a water-insoluble support matrix or surface for use in a method for purifying anti-B7x or anti-BTLA antibodies, or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional inidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of B7x and BTLA polypeptides included within the scope of this invention comprises altering the native glycosylation pattern of the polypeptide. Altering the native glycosylation pattern is intended for purposes herein to mean deleting one or more carbohydrate moieties found in the native sequence of B7x or BTLA polypeptide, and/or adding one or more glycosylation sites that are not present in the native sequence.

Addition of glycosylation sites to B7x or BTLA polypeptides may be accomplished by altering the amino acid sequence thereof. The alteration may be made, for example, by the addition of, or substitution by, one or more serine or threonine residues to the native polypeptide sequence (for 0-linked glycosylation sites). The B7x or BTLA amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on the B7x or BTLA polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on a B7x or BTLA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of B7x and BTLA protein contemplated by the invention comprises linking the polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

B7x and BTLA polypeptides of the present invention may also be modified in a way to form chimeric molecules comprising a B7x or BTLA polypeptide fused to another, heterologous polypeptide or amino acid sequence. In one embodiment, such a chimeric molecule comprises a fusion of a B7x or BTLA polypeptide with a tag polypeptide which provides an epitope to which an anti-tag antibody can selectively bind. In a preferred embodiment, such a tag is the "flag tag" described below. The epitope tag is generally placed at the amino- or carboxyl-terminus of the B7x or BTLA polypeptide. The presence of such epitope-tagged forms of polypeptide can be detected using an antibody against the tag. Also, provision of the epitope tag enables the B7x or BTLA polypeptide to be readily purified by affinity purification using an anti-tag antibody or another type of affinity matrix that binds to the epitope tag. In an alternative embodiment, the chimeric molecule may comprise a fusion of a B7x or BTLA polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnoloov, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

In some embodiments herein, B7x or BTLA protein family members and B7x or BTLA proteins from other organisms are cloned and expressed as outlined below. Thus, probe or degenerate polymerase chain reaction (PCR) primer sequences may be used to find other related B7x and BTLA proteins from humans or other organisms. As will be appreciated by those in the art, particularly useful probe and/or PCR primer sequences include the unique areas of B7x and BTLA nucleic acid sequences. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant B7x and BTLA nucleic acids can be further used as probes to identify and isolate other B7x and BTLA nucleic acids. They can also be used as precursor nucleic acids to make modified or variant nucleic acids and proteins.

Using the nucleic acids of the present invention, a variety of expression vectors are made. The expression vectors may be either self-replicating extrachromosomal vectors or vectors which integrate into a host genome. Generally, these expression vectors include transcriptional and translational regulatory nucleic acid operably linked to a nucleic acid encoding a B7x or BTLA protein. The term control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the B7x or BTLA protein; for example, transcriptional and translational regulatory nucleic acid sequences from Bacillus are preferably used to express protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

B7x and BTLA proteins of the present invention may be produced by culturing a host cell transformed with an expression vector containing a B7x or BTLA nucleic acid encoding a B7x or BTLA protein, respectively, under the appropriate conditions to induce or cause expression of the protein. The conditions appropriate for B7x or BTLA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are Drosophila melangaster cells, Saccharomyces cerevisiae and other yeasts, E. coli, Bacillus subtilis, SF9 cells, C129 cells, 293 cells, Neurospora, BHK, CHO, COS, and HeLa cells, fibroblasts, Schwanoma cell lines, immortalized mammalian myeloid and lymphoid cell lines such as Jurkat and BJAB cells.

In a preferred embodiment, B7x and BTLA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for B7x or BTLA into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, B7x and BTLA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of B7x or BTLA into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the B7x or BTLA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In some embodiments, B7x or BTLA proteins are produced in insect cells. Expression vectors for the transformation of insect cells, and in particular, baculovirus-based expression vectors, are well known in the art.

In a preferred embodiment, a B7x or BTLA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

Preferred promoter sequences for expression in yeast include the inducible GAL1,10 promoter, the promoters from alcohol dehydrogenase, enolase, glucokinase, glucose-6-phosphate isomerase, glyceraldehyde-1-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

B7x and BTLA proteins may also be made as fusion proteins, using techniques well known in the art. Thus, for example, for the creation of monoclonal antibodies, if the desired epitope is small, the B7x or BTLA protein may be fused to a carrier protein to form an immunogen. Alternatively, the B7x or BTLA protein may be made as a fusion protein to increase expression, or for other reasons. For example, when the B7x or BTLA protein is a peptide, the nucleic acid encoding the peptide may be linked to other nucleic acid for expression purposes. Similarly, B7x and BTLA proteins of the invention can be linked to protein labels, such as green fluorescent protein (GFP), red fluorescent protein (RFP), blue fluorescent protein (BFP), yellow fluorescent protein (YFP), etc.

In some embodiments, the B7x or BTLA nucleic acids, and/or proteins, and/or antibodies of the invention are labeled. By labeled herein is meant that a compound has at least one element, isotope or chemical compound attached to enable the detection of the compound. In general, labels fall into four classes: a) isotopic labels, which may be radioactive or heavy isotopes; b) immune labels, which may be antibodies or antigens; c) colored or fluorescent dyes; d) magnetic moieties. The labels may be incorporated into the compound at any position.

In a preferred embodiment, a B7x or BTLA protein is purified or isolated after expression. B7x and BTLA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the B7x protein may be purified using a standard anti-B7x antibody column.

Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the B7x or BTLA protein. In some instances no purification will be necessary.

Once expressed, and purified if necessary, the B7x and BTLA proteins and nucleic acids are also useful in a number of applications.

The nucleotide sequences (or their complement) encoding BTLA and B7x proteins have various applications in the art of molecular biology, including uses as hybridization probes, in chromosome and gene mapping and in the generation of anti-sense RNA and DNA. These nucleic acids are also useful for the preparation of B7x and BTLA proteins by the recombinant techniques described herein.

The full-length native sequence of the B7x or BTLA gene, or portions thereof, may be used as a hybridization probe for a cDNA library to isolate other genes (for example, allelic variants or species variants) which have a desired sequence identity to the B7x or BTLA nucleic acids. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the B7x gene using the known DNA sequence to synthesize a selected probe of about 40 bases. Hybridization probes may be labeled by a variety of labels, including radionucleotides such as 32P or 35S, or enzymatic labels such as alkaline phosphatase coupled to the probe via avidin/biotin coupling systems. Labeled probes having a sequence complementary to that of the B7x gene of the present invention can be used to screen libraries of human cDNA, genomic DNA or mRNA to determine which members of such libraries the probe hybridizes.

Nucleotide sequences encoding a B7x of BTLA protein can also be used to construct hybridization probes for mapping genes that encode B7x or BTLA proteins, and for the genetic analysis of individuals with B7x- or BTLA-related genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode B7x or BTLA protein or modified forms thereof can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a B7x protein can be used to clone genomic DNA encoding a B7x protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009.

Alternatively, non-human homologues of the B7x or BTLA protein can be used to construct a "knock out" animal which has a defective or altered gene encoding either B7x or BTLA protein as a result of homologous recombination between the endogenous gene and an altered genomic DNA encoding B7x or BTLA, which is introduced into an embryonic cell of the animal. For example, cDNA encoding a B7x protein can be used to clone genomic DNA encoding a B7x protein in accordance with established techniques. A portion of the genomic DNA encoding a B7x protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the B7x protein.

It is understood that the models described herein can be varied. For example, "knock-in" models can be formed, or the models can be cell-based rather than animal models.

(II) Fusion Proteins

Variant polypeptides of the present invention may also be fused to another, heterologous polypeptide or amino acid sequence to form a chimera. In some embodiments, fusion proteins comprise fusion partners comprising labels (e.g. autofluorescent proteins, survival and/or selection proteins), stability and/or purification sequences, toxins, or any other protein sequences of use. Additional fusion partners are described below. In some instances, the fusion partner is not a protein.

In another embodiment, a polypeptide of the invention is fused with human serum albumin to improve pharmacokinetics.

In a further embodiment, a polypeptide of the invention is fused to a cytotoxic agent. In this method, the polypeptide of the invention acts to target the cytotoxic agent to cells, resulting in a reduction in the number of afflicted cells. Cytotoxic agents include, but are not limited to, diphtheria A chain, exotoxin A chain, ricin A chain, abrin A chain, curcin, crotin, phenomycin, enomycin and the like, as well as radiochemicals.

Peptide Tags

Various tag polypeptides and their respective antibodies are well known in the art. Epitope tags may be placed at the amino- or carboxyl-terminus of a polypeptide of the invention to enable antibody detection. Also, the epitope tag enables a polypeptide of the invention to be readily purified by affinity purification. Examples of peptide tags include, but are not limited to, poly-histidine (poly-His) or poly-histidine-glycine (poly-His-Gly) tags; the flu HA tag polypeptide [Field et al., Mol. Cell. Biol. 8:2159-2165 (1988)]; the c-myc tag [Evan et al., Molecular and Cellular Biology, 5:3610-3616 (1985)]; the Herpes Simplex virus glycoprotein D (gD) tag [Paborsky et al., Protein Engineering, 3(6):547-553 (1990)1 the Flag-peptide [Hopp et al., BioTechnology 6:1204-1210 (1988)]; the KT3 epitope peptide [Martin et al., Science 255:192-194 (1992)]; tubulin epitope peptide [Skinner et al., J. Biol. Chem. 266:15163-15166 (1991)]; and the T7 gene 10 protein peptide tag [Lutz-Freyermuth et al., Proc. Natl. Acad. Sci. U.S.A. 87:6393-6397 (1990)].

Labels

In one embodiment, a polypeptide of the invention is modified by the addition of one or more labels. For example, labels that may be used are well known in the art and include but are not limited to biotin, tag and fluorescent labels (e.g. fluorescein). These labels may be used in various assays as are also well known in the art to achieve characterization.

(III) Antibodies

BTLA, HVEM and B7x proteins and fragments thereof, HVEM CRD1 domain peptides, BTLA Ig domain peptides, BTLA fusion proteins, B7x fusion proteins, and HVEM fusion proteins may be used to generate anti-BTLA and anti-B7x antibodies of the invention.

The terms "antibody" and "antibodies" as used herein include both monoclonal and polyclonal antibodies as well as antibody fragments, as are known in the art, including Fab, F(ab)2, single chain antibodies (Fv for example), chimeric antibodies, humanized antibodies, etc., either produced by the modification of whole antibodies or those synthesized de novo using recombinant DNA technologies, as described in more detail herein. Antibody fragments include those portions of the antibody that bind to an epitope on the BTLA or B7x polypeptides. Antibody fragments include those portions of the antibody that bind to an HVEM CRD1 domain or a BTLA Ig domain.

Preferably, when a B7x, BTLA or HVEM protein fragment is to be used as an immunogen to generate antibodies, the fragment must share at least one epitope or determinant with the full length protein, particularly an HVEM CRD1 domain or a BTLA Ig domain. By epitope or determinant herein is meant a portion of a protein which will generate and/or bind an antibody. Thus, in most instances, antibodies made to a smaller or truncated B7x, BTLA or HVEM protein will be able to bind to the corresponding full length protein. In a preferred embodiment, the epitope is unique; that is, antibodies generated to a unique epitope show little or no cross-reactivity.

In one embodiment, the invention provides antagonistic BTLA antibodies that are capable of reducing, including eliminating, one or more biological functions of the BTLA protein expressed at the surface of a cell. That is, the addition of anti-BTLA antibodies (polyclonal, or preferably monoclonal) to BTLA proteins (or cells comprising BTLA proteins) may reduce or eliminate at least one BTLA protein activity. BTLA activity includes but is not limited to the inhibition of lymphocyte activation; phosphorylation of tyrosine residues in the Grb2 binding site, the ITIM, or the ITSM; binding to SHP-1 and/or SHP-2; and activation of SHP-1 and/or SHP-2. The reduction of BTLA activity is observed in the presence of BTLA agonist (eg. HVEM on the surface of a second cell) which stimulates BTLA activity in the absence of an antagonistic BTLA antibody. In a preferred embodiment, such an antagonistic BTLA antibody interferes with the binding of HVEM on the surface of one cell to BTLA on the surface of a second cell. Generally, at least a 25% decrease in activity is preferred, with at least about 50% being particularly preferred and about a 95-100% decrease being especially preferred. These antibodies are also sometimes referred to herein as function-blocking antibodies or, more generally, as blocking agents. In a particularly preferred embodiment, such an antibody has the ability to modulate lymphocyte activity and, still more preferably, to increase and/or up-regulate such activity by inhibiting negative BTLA-mediated signaling. Further, such antibodies have the ability to modulate immunoglobulin production by B cells expressing BTLA, and more preferably, to increase immunoglobulin production.

In an alternative embodiment, the invention provides agonistic BTLA antibodies that increase or potentiate one or more biological functions of the BTLA protein expressed at the surface of a cell (a function-activating antibody), and/or mimics the natural binding interaction of B7x of HVEM with BTLA (more generally, a "mimicking agent"). That is, the addition of an agonistic BTLA antibody (polyclonal, or preferably monoclonal) to a cell expressing BTLA at its surface will increase or potentiate at least one BTLA activity. BTLA activity includes but is not limited to the inhibition of lymphocyte activation; phosphorylation of tyrosine residues in the Grb2 binding site, the ITIM, or the ITSM; binding to SHP-1 and/or SHP-2; and activation of SHP-1 and/or SHP-2.

In a preferred embodiment, the agonistic BTLA antibodies are function-activating antibodies. Such antibodies have the ability to decrease B and T lymphocyte activation by increasing BTLA activity in lymphocytes. Further, such antibodies have the ability to modulate immunoglobulin production by B cells expressing BTLA, and more particularly, to decrease immunoglobulin production. Further, such an antibody may have the ability to modulate immunoglobulin production by B cells expressing BTLA, and more preferably, to decrease immunoglobulin production.

The anti-BTLA antibodies of the invention bind to BTLA proteins. In a preferred embodiment, the BTLA antibody of the invention specifically binds to the BTLA Ig domain of a BTLA protein. By "specifically bind" herein is meant that the antibodies bind to the protein with a binding constant in the range of at least $10^{-4}$-$10^{-6}$ $M^{-1}$, with a preferred range being $10^{-7}$-$10^{-9}$ $M^{-1}$.

The present invention provides antibodies that specifically bind to naturally occurring human BTLA and/or murine BTLA proteins. In a preferred embodiment, the present invention provides a monoclonal anti-BTLA antibody that specifically binds to murine and/or human BTLA proteins and in particular to one or more epitopes in the extracellular domains of such proteins. In an especially preferred embodiment, the monoclonal antibody provided is capable of inhibiting BTLA-mediated signaling, e.g., by interfering with the natural interaction of HVEM and BTLA.

The BTLA proteins bound by BTLA antibodies may be human BTLA proteins, murine BTLA proteins, or other, preferably mammalian, BTLA proteins. In a preferred embodiment, the BTLA protein is a human BTLA protein.

The murine BTLA gene is polymorphic, and variations in sequence within the Ig domain that binds to murine HVEM are described herein in the figures. Despite their sequence variation, the murine BTLA Ig domains are each capable of binding to murine HVEM, and a number of BTLA blocking antibodies are capable of binding to multiple isoforms of murine BTLA.

The human BTLA gene is also polymorphic, as disclosed in U.S. application Ser. No. 10/600,997, expressly incorporated herein in its entirety by reference. As disclosed herein, human HVEM is capable of binding to human BTLA. It is within the skill of the artisan to determine if alternative alleles of human BTLA are capable of binding to HVEM. As used herein, the term "BTLA" includes any human isoform of BTLA that is capable of binding to HVEM.

In a preferred embodiment, the present invention provides monoclonal BTLA antibodies that specifically bind to murine and/or human BTLA proteins.

In one embodiment, the invention provides antagonistic HVEM antibodies that are capable of reducing, including eliminating, the ability of HVEM protein when expressed at the surface of a cell to increase BTLA activity in a second cell expressing BTLA at its surface. BTLA activity includes but is not limited to the inhibition of lymphocyte activation; phosphorylation of tyrosine residues in the Grb2 binding site, the ITIM, or the ITSM; binding to SHP-1 and/or SHP-2; and activation of SHP-1 and/or SHP-2. In a preferred embodiment, such an antagonistic HVEM antibody interferes with the binding of HVEM on the surface of one cell to BTLA on the surface of a second cell.

Generally, at least a 25% decrease in activity is preferred, with at least about 50% being particularly preferred and about a 95-100% decrease being especially preferred.

Such antibodies have the ability to increase B and T lymphocyte activation by decreasing BTLA activity in lymphocytes. Further, such antibodies have the ability to modulate immunoglobulin production by B cells expressing BTLA, and more particularly, to increase immunoglobulin production.

The HVEM antibodies of the invention specifically bind to HVEM CRD1 domains. By "specifically bind" herein is meant that the antibodies bind to the protein with a binding constant in the range of at least $10^{-4}$-$10^{-6}$ M$^{-1}$, with a preferred range being 10-7-10-9

The HVEM proteins bound by HVEM antibodies may be human HVEM proteins, murine HVEM proteins, or other, preferably mammalian, HVEM proteins.

HVEM protein sequences and encoding nucleic acid sequences are well known in the art. For example, see Montgomery et al., Cell, 87: 427-436, 1996; Kwon et al., Journal of Biological Chemistry, 272:14272-14276, 1997; Hsu et al., Journal of Biological Chemistry 272:13471-13474, 1997.

Stemming from the discovery of the HVEM-BTLA interaction, in one aspect, the present invention provides BTLA antibodies, sometimes referred to herein as BTLA blocking antibodies. A BTLA antibody of the invention is capable of specifically binding to a BTLA protein and is capable of reducing the binding of the BTLA protein to an HVEM protein. Especially preferred are BTLA antibodies that specifically bind to a region of the BTLA Ig domain, which region binds to the HVEM CRD1 domain. Such a BTLA antibody is capable of binding to a fragment of the BTLA Ig domain, which fragment is capable of binding to an HVEM CRD1 domain.

In one embodiment, a BTLA antibody is capable of binding to a mouse BTLA Ig domain.

In one embodiment, a BTLA antibody is capable of binding to a mouse BTLA Ig domain in a human BTLA tetramer.

In one embodiment, a BTLA antibody is capable of binding to a human BTLA Ig domain.

In one embodiment, a BTLA antibody is capable of binding to a human BTLA Ig domain in a human BTLA tetramer.

In one embodiment, a BTLA antibody is capable of binding toward the DEBA face of the Ig fold of BTLA. The phrase "DEBA face" refers to the regions of the BTLA molecule composed of the beta strands labelled "D", "E", "B", and "A" strands.

See, for example, structure of BTLA ectodomain deposited at NCB! by C. A. Nelson, D. H. Fremont, Midwest Center For Structural & Genomics (Mcsg), 26 Aug. 4. See also Compaan et al., J Biol. Chem. 2005 Sep. 16, Epub manuscript M507629200.

In one embodiment, a BTLA antibody is capable of binding an epitope of BTLA that is capable of binding to an antibody selected from the group consisting of '6A6', '6F7', '6G3', '6H6', '8F4', and '3F9.D12'.

In one embodiment, a BTLA antibody is capable of competing with an antibody selected from the group consisting of '6A6', '6F7', '6G3', '6H6', '8F4', and '3F9.D12' for binding to BTLA.

In one embodiment, a BTLA antibody is capable of binding to an epitope of BTLA that is homologous to an epitope capable of binding an antibody selected from the group consisting of '6A6', '6F7', '6G3', '6H6', '8F4', and '3F9.D12'.

In one embodiment, a BTLA antibody is capable of binding to an epitope comprising one or more residues selected from the group consisting of R55, Q63, Q 102, and C85 of murine C57BL/6 BTLA (SEQ ID NO: 63).

In one embodiment, a BTLA antibody is capable of binding to an epitope comprising one or more residues selected from the group consisting of the residues in a BTLA protein corresponding to the residues V42, Q43, L44, R55, Q63, Q102, and C85 of murine C57BL/6 BTLA (SEQ ID NO: 63).

In one embodiment, a BTLA antibody is capable of binding to an epitope comprising one or more residues selected from the group consisting of the residues in human BTLA corresponding to the residues V42, Q43, L44, R55, Q63, Q102, and C85 of murine C57BL/6 BTLA (SEQ ID NO: 63).

In one embodiment, a BTLA antibody is capable of binding to an epitope comprising one or more residues selected from the group consisting of V36, Q37, L38, L49, E57, C79, K93, and S96 in the human BTLA sequence set forth at Genbank accession no. AAP44003.1 (SEQ ID NO: 64).

In one embodiment, a BTLA antibody is capable of binding to an epitope comprising one or more residues in a human BTLA corresponding to residues from the group consisting of V36, Q37, L38, L49, E57, C79, K93, and S96 in the human BTLA sequence set forth at Genbank accession no. AAP44003.1 (SEQ ID NO: 64).

In one embodiment, a BTLA antibody is capable of binding to a polypeptide having at least about 80%, more preferably 85%, more preferably 90%, more preferably 95% identity to the amino acid sequence set forth by residues 37-47, 39-49, 41-49, 50-60, 58-68, 80-90, 97-107, 50-90, 55-85, 58-90, 63-85, 80-107, 85-102, 127-137, 55-102, 50-107, and 41-137 of murine Bl/6 BTLA (SEQ ID NO: 63).

In one embodiment, a BTLA antibody is capable of binding to a polypeptide selected from the group consisting of the amino acid sequences set forth by residues 37-47, 39-49, 41-49, 50-60, 58-68, 80-90, 97-107, 50-90, 55-85, 58-90, 63-85, 80-107, 85-102, 127-137, 55-102, 50107, and 41-137 of murine C57BL/6 BTLA (SEQ ID NO: 63).

In one embodiment, a BTLA antibody is capable of binding to a polypeptide having at least about 80%, more preferably 85%, more preferably 90%, more preferably 95% identity to the amino acid sequence set forth by residues 31-41, 32-42, 35-43, 44-54, 52-62, 74-84, 88-98, 44-84, 49-79, 52-84, 57-79, 74-98, 79-93, 118-128, 49-93, 44-98, 35-98, and 35-128 of the human BTLA isoform found at Genbank accession no. AAP44003.1 (SEQ ID NO: 64).

In one embodiment, a BTLA antibody is capable of binding to a polypeptide selected from the group consisting of the amino acid sequences set forth by residues 31-41, 32-42, 35-43, 44-54, 52-62, 74-84, 88-98, 44-84, 49-79, 52-84, 57-79, 74-98, 79-93, 118-128, 49-93, 44-98, 35-98, and 35-128 of the human BTLA isoform found at Genbank accession no. AAP44003.1 (SEQ ID NO: 64).

In one embodiment, a BTLA antibody is selected from the group consisting of '6A6', '6F7', '6G3', '6H6', '8F4', and '3F9.D12'.

In one embodiment, a BTLA antibody is capable of competing with CMV UL144 for binding to BTLA.

In one embodiment, the invention provides BTLA antibodies which are monoclonal antibodies.

In one embodiment, the invention provides BTLA antibodies which are human antibodies.

In one aspect, the invention provides a hybridoma that produces a BTLA antibody disclosed herein.

In one aspect, the invention provides BTLA antibodies that are capable of modulating BTLA activity.

In one embodiment, the invention provides BTLA antibodies that are antagonistic BTLA antibodies, which are capable of reducing BTLA activity. Such antibodies are capable of reducing the activation of BTLA by HVEM. Preferably, such antagonistic BTLA antibodies are also capable of reducing the activation of BTLA by another ligand which binds to the HVEM binding region of BTLA, such as UL144. The UL144 open reading frame in human cytomegalovirus (CMV) encodes a homologue of the herpesvirus entry mediator, HVEM, a member of the tumor necrosis factor receptor superfamily (Lurain et al., J. Virol. 1999 December; 73(12): 10040-50).

In another embodiment, the invention provides BTLA antibodies that are agonistic BTLA antibodies, which are capable of increasing BTLA activity. Such antibodies are capable of increasing BTLA activity in a cell having BTLA on its surface.

In one aspect, the invention provides HVEM antibodies, sometimes referred to herein as HVEM blocking antibodies. An HVEM antibody specifically binds to an HVEM protein and is capable of reducing the binding of the HVEM protein to a BTLA protein. Especially preferred are HVEM antibodies that specifically bind to a region of the HVEM CRD1 domain that binds to the BTLA Ig domain. Such an HVEM antibody is capable of binding to a fragment of the HVEM CRD1 domain, which fragment is capable of binding to a BTLA Ig domain. Preferred HVEM antibodies do not bind to the HVEM CRD2 or HVEM CRD3 domains, though antibodies binding to the CRD2 and/or CRD3 domains in addition to the CRD1 domain may be used in the methods herein.

In one embodiment, the invention provides HVEM antibodies which are monoclonal antibodies.

In one aspect, the invention provides a hybridoma that produces a HVEM antibody disclosed herein.

In one embodiment, the invention provides HVEM antibodies which are human antibodies.

In one aspect, the invention provides HVEM antibodies that are capable of modulating BTLA activity.

In a preferred embodiment, the invention provides HVEM antibodies that are antagonistic HVEM antibodies, which are capable of reducing the ability of HVEM to activate BTLA on the surface of a cell.

In another embodiment, the invention provides HVEM antibodies that are agonistic HVEM antibodies, which are capable of binding to HVEM and stimulating HVEM activity in a cell, thereby mimicking BTLA. HVEM activity in this sense includes increased NF-kB activity and increased AP-1 activity.

In one embodiment, the invention provides HVEM antibodies that do not inhibit the binding of HVEM to LIGHT or LTα.

In one embodiment, the invention provides HVEM antibodies that additionally reduce the binding of HSV-1 glycoprotein D to HVEM.

In another embodiment, the invention provides anti-B7x antibodies. In preferred embodiments, the anti-B7x antibodies are capable of reducing or eliminating one or more biological functions of the B7x polypeptide described herein. That is, the addition of anti-B7x antibodies (polyclonal, or preferably monoclonal) to B7x proteins (or cells comprising B7x proteins) may reduce or eliminate at least one B7x protein activity. Generally, at least a 25% decrease in activity is preferred, with at least about 50% being particularly preferred and about a 95-100% decrease being especially preferred. These antibodies are sometimes referred to herein as function-blocking antibodies or, more generally, blocking agents. Preferably, such an antibody has the ability to modulate lymphocyte activity, and more preferably, to increase and/or up-regulate lymphocyte activity by interfering with the functional interaction of BTLA and B7x. Further, such an antibody may have the ability to modulate immunoglobulin production by B cells expressing BTLA, and more preferably, to increase immunoglobulin production.

In an alternative embodiment, the invention provides an anti-B7x antibody that increases or potentiates the activity of B7x (a function-activating antibody).

The anti-B7x antibodies of the invention bind to B7x proteins. In a preferred embodiment, the antibodies specifically bind to B7x proteins. By "specifically bind" herein is meant that the antibodies bind to the protein with a binding constant in the range of at least $10^{-4}$-$10^{-6}$ M$^{-1}$, with a preferred range being $10^{-7}$-$10^{-6}$ M$^{-1}$.

The present invention provides antibodies that specifically bind to naturally occurring human B7x and/or murine B7x proteins. In a preferred embodiment, the present invention provides a monoclonal anti-B7x antibody that specifically binds to murine and/or human B7x protein. In an especially preferred embodiment, the monoclonal antibody provided is capable of interfering with the natural interaction of B7x and BTLA and inhibiting BTLA-mediated signaling The term "antibody", as used herein, includes immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The phrase "complementary determining region" (CDR) includes the region of an antibody molecule which comprises the antigen binding site.

The antibody may be an IgG such as IgG1, IgG2, IgG3 or IgG4; or IgM, IgA, IgE or IgD isotype. The constant domain of the antibody heavy chain may be selected depending upon the effector function desired. The light chain constant domain may be a kappa or lambda constant domain.

The term "antibody" as used herein also encompasses antibody fragments, and in particular, fragments that retain the ability to specifically bind to an antigen (e.g., the extracellular domain of B7x, the HVEM CRD1 domains or the BTLA Ig domain). It has been shown that the antigen-binding function of an antibody can be performed by fragments of a full-length antibody. Examples of such binding fragments include (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antibody." Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or fragment thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab').sub.2 fragments, can be prepared from whole antibodies using conventional techniques, such as papain or pepsin digestion, respectively, of whole antibodies. Moreover, antibodies, antibody fragments and immunoadhesion molecules can be obtained using standard recombinant DNA techniques, as described herein.

Antibodies may be polyclonal or monoclonal; xenogeneic, allogeneic, or syngeneic; or modified forms thereof, e.g. humanized, chimeric, etc. Preferably, antibodies of the invention bind specifically or substantially specifically to HVEM, B7x and/or BTLA. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition typically displays a single binding affinity for a particular antigen with which it immunoreacts.

The antibodies described herein may be humanized antibodies, e.g., antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. Such humanized antibodies may also include antibodies in which CDR sequences derived from the germline of another mammalian species, such as a mouse, have been grafted onto human framework sequences.

As used herein, the term "extracellular domain of B7x" includes a portion of the B7x peptide which, in the cell-associated form, is extracellular. A B7x extracellular domain includes the portion of a B7x polypeptide involved in its interaction with BTLA. Similarly, the term "extracellular domain of BTLA" includes a portion of the BTLA peptide which, in the cell-associated form, is extracellular. A BTLA extracellular domain includes the portion of a BTLA polypeptide involved in its interaction with B7x.

Preferably, the anti-BTLA antibodies of the invention bind to naturally occurring forms of BTLA, but are substantially unreactive, e.g., have background binding to unrelated molecules. More preferably, such antibodies may also be specific for BTLA and substantially unreactive with other co-stimulatory T cell receptors, e.g. CTLA-4, CD28 and PD-1. Similarly, the anti-B7x antibodies of the invention preferably bind to naturally occurring forms of B7x, but are substantially unreactive, e.g., have background binding to unrelated, non-B7 molecules. In a particularly preferred embodiment such antibodies may also be specific for B7x and substantially unreactive with related B7 molecules, e.g. B7.1 or B7.2.

In addition, antibodies specific for naturally occurring HVEM, B7x or BTLA peptides may or may not bind to mutant forms of such peptides. In one embodiment, mutations in the amino acid sequence of a naturally occurring HVEM, B7x or BTLA peptide result in modulation of the binding (e.g., either increased or decreased binding) of the antibody to the HVEM, B7x or BTLA peptide, respectively. Antibodies to HVEM, B7x and BTLA peptides can be readily screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified HVEM, B7x or BTLA protein, or alternatively may use cells that express HVEM, B7x or BTLA, e.g. cells transfected with an expression construct for HVEM, B7x or BTLA.

As is well known in the art, HVEM, B7x and BTLA polypeptides from a variety of species, whether in soluble form or membrane bound, can be used as immunogens to induce the formation of anti-HVEM, anti-B7x and anti-BTLA antibodies, respectively. A variety of techniques for the preparation of such antibodies, whether polyclonal, monoclonal or humanized, are well know to the skilled artisan and do not require recitation herein. A concise summary of such techniques with reference to the preparation of antibodies to known B7 antigens is provided in U.S. Patent Publication No. US 2002/0071839, the entire disclosure of which is expressly incorporated herein by reference.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce antibodies having fully human sequences.

Human Antibodies

Introduction of human immunoglobulin (Ig) loci into mice in which the endogenous Ig genes have been inactivated provides an ideal source for production of fully human monoclonal antibodies (Mabs). Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as cancer, which may require repeated antibody administrations.

Mouse strains have been engineered with large fragments of the human Ig loci and to produce human antibodies in the absence of mouse antibodies.

See Green et al. Nature Genetics 7:13-21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Further reported work involved the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. Nature Genetics 15:146-156 (1997), Green and Jakobovits J. Exp. Med. 188:483-495 (1998), the disclosures of which are hereby incorporated by reference.

Such approaches are further discussed and delineated in European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In an alternative approach, others have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a p constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625, 126, 5,633,425, 5,661,016, 5,770,429, 5,789,650, and 5,814, 318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al., Nucleic Acids Research 20:62876295 (1992); Chen et al. International Immunology 5:647-656 (1993); Tuaillon et al., Proc. Natl. Acad. Sci. USA 90:3720-3724 (1993); Choi et al., Nature Genetics 4:117-123 (1993); Lonberg et al., Nature 368:856-859 (1994); Taylor et al., International Immunology 6:579-59.1 (1994); Tuaillon et al., J. Immunol. 154:6453-6465 (1995); Fishwild et al., Nature Biotech. 14:845-851 (1996); the disclosures of which are hereby incorporated by reference in their entirety.

(IV) Bioactive Agents

It will be appreciated by those skilled in the art that it is within their skill to generate bioactive agents and screen for their activity by following standard techniques. In a preferred embodiment, the B7x, HVEM, and/or BTLA proteins, nucleic acids, variants, modified proteins, cells and/or transgenics containing the said nucleic acids or proteins are used in screening assays. Identification of the B7x, HVEM, and/or BTLA proteins provided herein permits the design of drug screening assays for compounds that bind B7x, HVEM, and/ or BTLA proteins, interfere with B7x, HVEM, and/or BTLA protein binding, or modulate B7x, HVEM, and/or BTLA activity.

The assays described herein preferably utilize human B7x, human BTLA proteins, and human HVEM, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease.

In some embodiments, the methods comprise combining a B7x protein and a candidate bioactive agent, and determining the binding of the candidate agent to the B7x protein. In other embodiments, further discussed below, binding interference or bioactivity is determined.

In preferred embodiments, the methods comprise combining a BTLA protein and a candidate bioactive agent, and determining the binding of the candidate agent to the BTLA protein. In other embodiments, further discussed below, binding interference or bioactivity is determined.

In other preferred embodiments, the methods comprise combining an Ig domain of a BTLA protein, or an HVEM binding portion thereof, with a candidate bioactive agent, and determining the binding of the candidate agent to the BTLA domain. In another preferred embodiment, the methods involve combining an HVEM CRD1 domain, or a BTLA binding portion thereof, with a candidate agent, and determining the binding of the candidate agent to the HVEM domain.

The term "candidate bioactive agent" or "exogenous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind B7x protein, e.g. BTLA, may be used, and vice-versa. In addition, positive controls, i.e. the use of agents known to bind BTLA or HVEM may be used.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides, e.g., peptidomimetics. Peptidomimetics can be made as described, e.g., in WO 98/56401

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are organic chemical moieties or small molecule chemical compositions, a wide variety of which are available in the literature.

In one aspect, the invention provides BTLA-HVEM antagonists. A BTLA-HVEM antagonist may be any of a wide variety of bioactive agents capable of reducing the activation of BTLA by HVEM. In a preferred embodiment, a BTLA-HVEM antagonist is capable of reducing the binding of an HVEM CRD1 domain to a BTLA Ig domain. While many BTLA-HVEM antagonists are capable of binding to BTLA, such a BTLA-HVEM antagonist does not increase BTLA activity in a cell expressing BTLA on its surface.

Preferred BTLA-HVEM antagonists are capable of reducing BTLA activity in a cell having BTLA on its surface. In a preferred embodiment, the cell is a lymphocyte, a T cell, a CD4+ T cell, a TH1 cell, a CD8f T cell, a B cell, a plasma cell, a macrophage, or an NK cell.

Suitable bioactive agents include BTLA antibodies and HVEM antibodies (e.g., monoclonal, polyclonal, single chain, and/or bispecific antibodies as well as Fab and F(ab)2 fragments, variants and derivatives thereof). Suitable bioactive agents also include fragments and truncated forms of BTLA and HVEM proteins, fusion proteins, and the like, for example, soluble proteins and polypeptides comprising or consisting essentially of a BTLA Ig domain fragment capable of binding an HVEM CRD1 domain; soluble proteins and polypeptides comprising or consisting essentially of an HVEM CRD1 domain or fragment thereof capable of binding a BTLA Ig domain; a BTLA Ig domain peptide, a CRD1 domain peptide. Suitable bioactive agents also include small molecule chemical compositions.

In one embodiment, the invention provides a BTLA-HVEM antagonist capable of reducing the binding of a BTLA protein to an HVEM protein, wherein the antagonist does not comprise an HVEM CRD2 domain, an HVEM CRD3 domain, or both, and wherein the antagonist does not bind to an HVEM CRD2 domain or an HVEM CRD3 domain, with the proviso that the antagonist is not an HSV-1 glycoprotein D, a phage-derived peptide BP-2, or a soluble protein comprising a complete BTLA Ig domain capable of binding said HVEM protein.

In the methods herein, glycoprotein D and phage-derived peptide BP-2, as well as HVEM-¬ binding fragments thereof, and fusion proteins comprising the same, may be used as BTLA-HVEM antagonists.

Preferred BTLA-HVEM antagonists are capable of binding to a BTLA Ig domain and are capable of reducing the binding of the BTLA Ig domain to an HVEM CRD1 domain. Especially preferred are BTLA-HVEM antagonists capable of binding to a region of the BTLA Ig domain that binds to the HVEM CRD1 domain. Such a BTLA-HVEM antagonist is capable of binding to a fragment of the BTLA Ig domain, which fragment is capable of binding to an HVEM CRD1 domain.

In one embodiment, a BTLA-HVEM antagonist binds an epitope of BTLA that is capable of binding to an antibody selected from the group consisting of '6A6', '6F7', '6G3', '6H6', '8F4', and '3F9.D12'.

In one embodiment, a BTLA-HVEM antagonist is capable of competing with an antibody selected from the group consisting of '6A6', '6F7', '6G3', '6H6', '8F4', and '3F9.D12' for binding to BTLA.

In one embodiment, a BTLA-HVEM antagonist binds to an epitope of BTLA that is homologous to an epitope capable of binding an antibody selected from the group consisting of '6A6', '6F7', '6G3', '6H6', '8F4', and '3F9.D12'.

In one embodiment, a BTLA-HVEM antagonist is capable of binding to an epitope comprising one or more residues selected from the group consisting of V42, Q43, L44, R55, Q63, Q102, and C85 of murine C57BL/6 BTLA (SEQ ID NO: 63).

In one embodiment, a BTLA-HVEM antagonist is capable of binding to an epitope comprising one or more residues selected from the group consisting of the residues in a BTLA protein corresponding to the residues V42, Q43, L44, R55, Q63, Q102, and C85 of murine C57BL/6 BTLA (SEQ ID NO: 63).

In one embodiment, a BTLA-HVEM antagonist is capable of binding to an epitope comprising one or more residues selected from the group consisting of the residues in human BTLA corresponding to the residues V42, Q43, L44, R55, Q63, Q102, and C85 of murine C57BL/6 BTLA (SEQ ID NO: 63).

In one embodiment, a BTLA-HVEM antagonist is capable of binding to an epitope comprising one or more residues selected from the group consisting of V36, Q37, L38, L49, E57, C79, K93, and S96 in the human BTLA sequence set forth at Genbank accession no. AAP44003.1 (SEQ ID NO: 64).

In one embodiment, a BTLA-HVEM antagonist is capable of binding to an epitope comprising one or more residues of human BTLA corresponding to residues from the group consisting of V36, Q37, L38, L49, E57, C79, K93, and S96 in the human BTLA sequence set forth at Genbank accession no. AAP44003.1 (SEQ ID NO: 64).

In one embodiment, a BTLA-HVEM antagonist is capable of binding to a polypeptide having at least about 80%, more preferably 85%, more preferably 90%, more preferably 95% identity to the amino acid sequence set forth by residues 37-47, 39-49, 41-49, 50-60, 58-68, 80 90, 97-107, 50-90, 55-85, 58-90, 63-85, 80-107, 85-102, 127-137, 55-102, 50-107, and 41-137 of murine C57BL/6 BTLA (SEQ ID NO: 63).

In one embodiment, a BTLA-HVEM antagonist is capable of binding to a polypeptide selected from the group consisting of the amino acid sequences set forth by residues 37-47, 39 49, 41-49, 50-60, 58-68, 80-90, 97-107, 50-90, 55-85, 58-90, 63-85, 80-107, 85-102, 127-137, 55-102, 50-107, and 41-137 of murine C57BL/6 BTLA (SEQ ID NO: 63).

In one embodiment, a BTLA-HVEM antagonist is capable of binding to a polypeptide having at least about 80%, more preferably 85%, more preferably 90%, more preferably 95% identity to the amino acid sequence set forth by residues 31-41, 32-42, 35-43, 44-54, 52-62, 74 84, 88-98, 44-84, 49-79, 52-84, 57-79, 74-98, 79-93, 118-128, 49-93, 44-98, 35-98, and 35-128 of the human BTLA isoform found at Genbank accession no. AAP44003.1 (SEQ ID NO: 64).

In one embodiment, a BTLA-HVEM antagonist is capable of binding to a polypeptide selected from the group consisting of the amino acid sequences set forth by residues 31-41, 32 42, 35-43, 44-54, 52-62, 74-84, 88-98, 44-84, 49-79, 52-84, 57-79, 74-98, 79-93, 118-128, 4993, 44-98, 35-98, and 35-128 of the human BTLA isoform found at Genbank accession no. AAP44003.1 (SEQ ID NO: 64).

In one embodiment, a BTLA-HVEM antagonist is capable of competing with CMV UL144 for binding to BTLA.

In one embodiment, a BTLA-HVEM antagonist is capable of competing with HSV-1 glycoprotein D for binding to HVEM.

In one embodiment, a BTLA-HVEM antagonist is a BTLA antibody.

In one embodiment, a BTLA-HVEM antagonist is an HVEM antibody.

In one aspect, the invention provides BTLA-HVEM antagonists that comprise a BTLA Ig domain fragment capable of binding an HVEM CRD1 domain. In another aspect, the invention provides BTLA-HVEM antagonists that consist essentially of a BTLA Ig domain fragment capable of binding an HVEM CRD1 domain.

Accordingly, in a preferred embodiment, the invention provides BTLA-HVEM antagonists that are BTLA fusion proteins which are capable of binding to an HVEM CRD1 domain and reducing the binding of the HVEM CRD1 domain to a BTLA Ig domain. Preferred BTLA fusion proteins do not bind to the CRD2 or CRD3 domains of HVEM. Preferred BTLA fusion proteins can compete with an HVEM antibody disclosed herein for binding to an HVEM CRD1 domain. Preferred BTLA fusion proteins do not comprise an entire BTLA Ig domain.

In another preferred embodiment, the invention provides BTLA-HVEM antagonists that are BTLA protein fragments which are capable of binding to the CRD1 domain of HVEM and reducing the binding of the HVEM CRD1 domain to a BTLA Ig domain. Preferred BTLA protein fragments do not bind to the CRD2 or CRD3 domains of HVEM. In a preferred embodiment, a BTLA protein fragment consists essentially of a BTLA Ig domain fragment that is capable of binding to an HVEM CRD1 domain. Preferred BTLA protein fragments can compete with an HVEM antibody disclosed herein for binding to an HVEM CRD1 domain.

In one aspect, the invention provides BTLA-HVEM antagonists that comprise an HVEM CRD1 domain or fragment thereof capable of binding to a BTLA Ig domain. In another aspect, the invention provides BTLA-HVEM antagonists that consist essentially of an HVEM CRD1 domain or fragment thereof capable of binding to a BTLA Ig domain.

Accordingly, in a preferred embodiment, the invention provides BTLA-HVEM antagonists that are HVEM fusion proteins which are capable of binding to a BTLA Ig domain and reducing the binding of the BTLA Ig domain to an HVEM CRD1 domain. Such HVEM fusion proteins lack an HVEM CRD2 and/or CRD3 domain. Preferred HVEM fusion proteins can compete with a BTLA antibody disclosed herein for binding to a BTLA Ig domain.

In another preferred embodiment, the invention provides BTLA-HVEM antagonists that are HVEM protein fragments which are capable of binding to a BTLA Ig domain and reducing the binding of the BTLA Ig domain to an HVEM CRD1 domain. Such HVEM protein fragments lack an HVEM CRD2 and/or CRD3 domain. In a preferred embodiment, an HVEM protein fragment consists essentially of an HVEM CRD1 domain or fragment thereof which is capable of binding to a BTLA Ig domain. Preferred HVEM protein fragments can compete with a BTLA antibody disclosed herein for binding to a BTLA Ig domain.

In one embodiment, the invention provides fusion proteins that comprise an Fc region of an immunoglobulin.

In one embodiment, for use in the methods herein, HSV-1 glycoprotein D may be used as a BTLA-HVEM antagonist.

In one embodiment, a BTLA-HVEM antagonist is capable of reducing tyrosine phosphorylation on the intracellular domain of BTLA protein in a cell having BTLA protein on its surface.

In one embodiment, a BTLA-HVEM antagonist is capable of reducing association of BTLA protein with SHP-2, PI3K, or Grb2 in a cell having BTLA protein on its surface.

In one embodiment, a BTLA-HVEM antagonist is capable of increasing proliferation of a cell having BTLA protein on its surface.

In one embodiment, a BTLA-HVEM antagonist is capable of increasing IL-2 production by a cell having BTLA protein on its surface.

In one embodiment, a BTLA-HVEM antagonist is capable of increasing or prolonging antibody production by a cell having said BTLA protein on its surface.

In one embodiment, a BTLA-HVEM antagonist is capable of increasing or prolonging the cytotoxicity of a cell having said BTLA protein on its surface.

In one aspect, the invention provides BTLA-HVEM agonists. A BTLA-HVEM agonist may be any of a wide variety of bioactive agents capable of activating BTLA and thereby mimicking the activity of HVEM.

Preferred BTLA-HVEM agonists are capable of increasing BTLA activity in a cell having BTLA on its surface. In a preferred embodiment, the cell is a lymphocyte, a T cell, a CD4+ T cell, a TH1 cell, a CD8+ T cell, a B cell, a plasma cell, a macrophage, or an NK cell.

Suitable bioactive agents include BTLA antibodies (e.g., monoclonal, polyclonal, single chain, and/or bispecific antibodies as well as Fab and F(ab)2 fragments, variants and derivatives thereof). Suitable bioactive agents also include fragments and truncated forms of HVEM proteins, fusion proteins, and the like, such as soluble proteins and polypeptides comprising or consisting essentially of an HVEM CRD1 domain or fragment thereof capable of binding to a BTLA Ig domain and increasing BTLA activity, and lacking a CRD2 and/or CRD3 domain. Suitable bioactive agents also include small molecule chemical compositions.

In one embodiment, the invention provides a BTLA-HVEM agonist capable of binding to BTLA protein and increasing BTLA activity, wherein the agonist does not comprise an HVEM CRD2 domain, an HVEM CRD3 domain, or both, with the proviso that the agonist is not a human CMV UL144 protein.

In one embodiment, for use in the methods herein, CMV UL144, BTLA-binding fragments thereof, and fusion proteins comprising the same, may be used as a BTLA-HVEM agonist. Further regarding UL144, see Cheung et al., PNAS 102:13218-13223, 2005.

Preferred BTLA-HVEM agonists bind to a BTLA Ig domain and are capable of reducing the binding of the BTLA Ig domain to an HVEM CRD1 domain, and mimicking the stimulation of BTLA by HVEM. Especially preferred are BTLA-HVEM agonists are capable of binding to a region of the BTLA Ig domain that binds to the HVEM CRD1 domain.

In one embodiment, a BTLA-HVEM agonist binds an epitope of BTLA that is capable of binding to an antibody selected from the group consisting of '6A6', '6F7', '6G3', '6H6', '8F4', and '3F9.D12'.

In one embodiment, a BTLA-HVEM agonist is capable of competing with an antibody selected from the group consisting of '6A6', '6F7', '6G3', '6H6', '8F4', and '3F9.D12' for binding to BTLA.

In one embodiment, a BTLA-HVEM agonist binds to an epitope of BTLA that is homologous to an epitope capable of binding an antibody selected from the group consisting of '6A6', '6F7', '6G3', '6H6', '8F4', and '3F9.D12'.

In one embodiment, a BTLA-HVEM agonist is capable of binding to an epitope comprising one or more residues selected from the group consisting of V42, Q43, L44, R55, Q63, Q102, and C85 of murine C57BL/6 BTLA (SEQ ID NO: 63).

In one embodiment, a BTLA-HVEM agonist is capable of binding to an epitope comprising one or more residues selected from the group consisting of the residues in a BTLA protein corresponding to the residues V42, Q43, L44, R55, Q63, Q102, and C85 of murine C57BL/6 BTLA (SEQ ID NO: 63).

In one embodiment, a BTLA-HVEM agonist is capable of binding to an epitope comprising one or more residues selected from the group consisting of the residues in human BTLA corresponding to the residues V42, Q43, L44, R55, Q63, Q102, and C85 of murine C57BL/6 BTLA (SEQ ID NO: 63).

In one embodiment, a BTLA-HVEM agonist is capable of binding to an epitope comprising one or more residues selected from the group consisting of V36, Q37, L38, L49, E57, C79, K93, and S96 in the human BTLA sequence set forth at Genbank accession no. AAP44003.1 (SEQ ID NO: 64).

In one embodiment, a BTLA-HVEM agonist is capable of binding to an epitope comprising one or more residues in human BTLA corresponding to residues from the group consisting of V36, Q37, L38, L49, E57, C79, K93, and S96 in the human BTLA sequence set forth at Genbank accession no. AAP44003.1 (SEQ ID NO: 64).

In one embodiment, a BTLA-HVEM agonist is capable of binding to a polypeptide having at least about 80%, more preferably 85%, more preferably 90%, more preferably 95% identity to the amino acid sequence set forth by residues 37-47, 39-49, 41-49, 50-60, 58-68, 80 90, 97-107, 50-90, 55-85, 58-90, 63-85, 80-107, 85-102, 127-137, 55-102, 50-107, and 41-137 of murine C57BL/6 BTLA (SEQ ID NO: 63).

In one embodiment, a BTLA-HVEM agonist is capable of binding to a polypeptide selected from the group consisting of the amino acid sequences set forth by residues 37-47, 39 49, 41-49, 50-60, 58-68, 80-90, 97-107, 50-90, 55-85, 58-90, 63-85, 80-107, 85-102, 127-137, 55-102, 50-107, and 41-137 of murine C57BL/6 BTLA (SEQ ID NO: 63).

In one embodiment, a BTLA-HVEM agonist is capable of binding to a polypeptide having at least about 80%, more preferably 85%, more preferably 90%, more preferably 95% identity to the amino acid sequence set forth by residues 31-41, 32-42, 35-43, 44-54, 52-62, 74 84, 88-98, 44-84, 49-79, 52-84, 57-79, 74-98, 79-93, 118-128, 49-93, 44-98, 35-98, and 35-128 of the human BTLA isoform found at Genbank accession no. AAP44003.1 (SEQ ID NO: 64).

In one embodiment, a BTLA-HVEM agonist is capable of binding to a polypeptide selected from the group consisting of the amino acid sequences set forth by residues 31-41, 32 42, 35-43, 44-54, 52-62, 74-84, 88-98, 44-84, 49-79, 52-84, 57-79, 74-98, 79-93, 118-128, 4993, 44-98, 35-98, and 35-128 of the human BTLA isoform found at Genbank accession no. AAP44003.1 (SEQ ID NO: 64).

In one embodiment, a BTLA-HVEM agonist is capable of competing with CMV UL144 for binding to BTLA.

In one embodiment, a BTLA-HVEM agonist is a BTLA antibody.

In one aspect, the invention provides BTLA-HVEM agonists that comprise an HVEM CRD1 domain or fragment thereof capable of binding to a BTLA Ig domain and stimulating BTLA activity. In another aspect, the invention provides BTLA-HVEM agonists that consist essentially of an HVEM CRD1 domain or fragment thereof capable of binding to a BTLA Ig domain and stimulating BTLA activity.

Accordingly, in a preferred embodiment, the invention provides BTLA-HVEM agonists that are agonistic HVEM fusion proteins which are capable of binding to a BTLA Ig domain, reducing the binding of the BTLA Ig domain to an HVEM CRD1 domain, and stimulating BTLA activity. Such agonistic HVEM fusion proteins lack an HVEM CRD2 and/or CRD3 domain. Preferred agonistic HVEM fusion proteins can compete with a BTLA antibody disclosed herein for binding to a BTLA Ig domain.

In another preferred embodiment, the invention provides BTLA-HVEM agonists that are agonistic HVEM protein fragments which are capable of binding to a BTLA Ig domain, reducing the binding of the BTLA Ig domain to an HVEM CRD1 domain, and stimulating BTLA activity. Such agonistic HVEM protein fragments lack an HVEM CRD2 and/or CRD3 domain. In a preferred embodiment, an agonistic HVEM protein fragment consists essentially of an HVEM CRD1 domain of fragment thereof which is capable of binding to a BTLA Ig domain and stimulating BTLA activity. Preferred agonistic HVEM protein fragments can compete with a BTLA antibody disclosed herein for binding to a BTLA Ig domain.

In one embodiment, a BTLA-HVEM agonist is capable of increasing tyrosine phosphorylation on the intracellular domain of BTLA protein in a cell having BTLA protein on its surface.

In one embodiment, a BTLA-HVEM agonist is capable of increasing association of BTLA protein with SHP-2, PI3K, or Grb2 in a cell having BTLA protein on its surface.

In one embodiment, a BTLA-HVEM agonist is capable of decreasing proliferation of a cell having BTLA protein on its surface.

In one embodiment, a BTLA-HVEM agonist is capable of decreasing IL-2 production by a cell having BTLA protein on its surface.

In one embodiment, a BTLA-HVEM agonist is capable of decreasing antibody production by a cell having said BTLA protein on its surface.

In one embodiment, a BTLA-HVEM antagonist is capable of decreasing the cytotoxicity of a cell having said BTLA protein on its surface.

(V) Additional Therapeutic Agents

In a further embodiment, the bioactive agents disclosed herein may be advantageously combined with one or more additional therapeutic agents.

In one aspect, the antagonists and blocking agents described herein can be administered in combination with additional immune response stimulating agents such as, e.g., cytokines as well as various antigens and vaccine preparations including tumor antigens and tumor vaccines. In preferred embodiments, such cytokines stimulate antigen presenting cells, e.g., GM-CSF, M-CSF, G-CSF, IL-3, IL-12, etc. Additional proteins and/or cytokines known to enhance T cell proliferation and secretion, such as IL-2, IL-2, B7, anti-CD3 and anti-CD28 can be employed simultaneously or sequentially with the blocking agents to augment the immune response. The subject therapy may also be combined with the transfection or transduction of tumor cells with genes encoding for various cytokines or cell surface receptors, as is known in the art. See, e.g. Ogasawara et al. (1993) Cancer Res. 53:3561-8 and Townsend et al. (1993) Science 259:368-370.

In another aspect, the agonists and mimicking agents as described herein can be administered in combination with other immunosuppressive agents, e.g., antibodies against other immune cell surface markers (e.g., CD40) or against cytokines, other fusion proteins, e.g., CTLA4Ig, or other immunosuppressive drugs (e.g., cyclosporin A, FK506-like compounds, rapamycin compounds, or steroids).

It is further contemplated that the subject compositions and methods may be synergistically combined with immunotherapies based on modulation of other positive and negative costimulatory pathways, and with CTLA-4 modulation in particular. For example, BTLA-HVEM antagonists may be advantageously combined with CTLA-4 blocking agents as described in U.S. Pat. Nos. 5,855,887; 5,811,097; and 6,051,227, and International Publication WO 00/32231. Such CTLA-4 blocking agents inhibit T cell down-regulation mediated by CTLA-4 interaction with B7 family members B71 and B72 expressed on lymphoid and dendritic cells. Similarly, BTLA-HVEM agonists may be advantageously combined with CTLA-4 mimicking agents such as CTLA-4Ig, which has already found clinical use as an immunosuppressive agent.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds suitable for use in the invention, as well as other methods in which Rapamycin has been administered are known in the art (See, e.g. WO 95/22972, WO 95/16691, WO 95/04738, U.S. Pat. Nos. 6,015,809; 5,989,591; U.S. Pat. Nos. 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506 like compounds include, for example, those described in WO 00/01385. Preferably, the language "rapamycin compound" as used herein does not include FK506-like compounds.

Another preferred embodiment of candidate nucleic acids are double stranded RNA capable of inducing RNA interference or RNAi (Bosher, J. M. et al. (2000) Nat. Cell Biol. 2: E31-36). Introducing double stranded RNA can trigger specific degradation of homologous RNA sequences, generally within the region of identity of the dsRNA (Zamore, P. D. et. al. (1997) Cell 101: 25-33). This provides a basis for silencing expression of genes, thus permitting a method for altering the phenotype of cells.

The dsRNA may comprise synthetic RNA made either by known chemical synthetic methods or by in vitro transcription of nucleic acid templates carrying promoters (e.g., T7 or SP6 promoters). Alternatively, the dsRNAs are expressed in vivo, preferably by expression of palindromic fusion nucleic acids, that allow facile formation of dsRNA in the form of a hairpin when expressed in the cell. The double strand regions of the iRNA are generally about 10-500 basepairs or more, preferably 15-200 basepairs, and most preferably 20-100 basepairs.

(VI) Methods

The disclosure provides methods for modulating BTLA activity which involve the use of BTLA-HVEM agonists BTLA-B7x agonists, BTLA-HVEM antagonists or BTLA-B7x antagomists described herein.

In one aspect, the invention provides methods for decreasing BTLA activity, comprising contacting BTLA or HVEM with a BTLA-HVEM antagonist.

In a preferred embodiment, the method comprises contacting a cell having BTLA on its surface with a BTLA-HVEM antagonist, wherein the cell is capable of contacting HVEM protein in the absence of the BTLA-HVEM antagonist. In one embodiment, the methods involve use of a BTLA antibody.

In a preferred embodiment, the cells having BTLA on their surface are lymphocytes, NK cells, or macrophages.

In another embodiment, the method comprises contacting HVEM protein with a BTLA-HVEM antagonist, wherein the HVEM protein is capable of contacting a cell having BTLA on its surface in the absence of the BTLA-HVEM antagonist. In one embodiment, the methods involve use of an HVEM antibody.

In a preferred embodiment, the HVEM protein is on the surface of a dendritic cell or a lymphocyte.

In another embodiment, the invention provides methods for decreasing BTLA activation by a BTLA ligand that is capable of competing with HVEM for binding to BTLA, which comprise the use of a BTLA-HVEM antagonist. In one embodiment, the BTLA ligand is CMV UL144.

In one aspect, the invention provides methods for increasing BTLA activity comprising contacting a cell having BTLA on its surface with a BTLA-HVEM agonist. In one embodiment, the methods involve use of a BTLA antibody.

In a preferred embodiment, the cells having BTLA on their surface are lymphocytes, NK cells, or macrophages.

In one aspect, the invention provides methods for modulating lymphocyte activation which involve the use of BTLA-HVEM agonists or BTLA-HVEM antagonists described herein.

In one aspect, the invention provides methods for increasing lymphocyte activation. In one embodiment, the methods comprise contacting a lymphocyte having BTLA on its surface with a BTLA¬HVEM antagonist, wherein the lymphocyte is capable of contacting HVEM protein in the absence of the BTLA-HVEM antagonist. In one embodiment, the methods involve use of a BTLA antibody.

In one embodiment, the methods involve contacting HVEM protein with a BTLA-HVEM antagonist, wherein the HVEM protein is capable of contacting a lymphocyte having BTLA on its surface in the absence of the BTLA-HVEM antagonist.

In one embodiment, the methods involve use of a HVEM antibody.

In a preferred embodiment, a lymphocyte in which activation is increased is selected from the group consisting of naïve T cells, CM+ T cells, CD4+ T cells, TH1 cells, naive B cells, and plasma cells.

In another embodiment, the invention provides methods for decreasing lymphocyte activation, comprising contacting a lymphocyte having BTLA on its surface with a BTLA-HVEM agonist. In one embodiment, the Methods involve use of a BTLA antibody.

In a preferred embodiment, a lymphocyte in which activation is decreased is selected from the group consisting of naïve T cells, CD8+ T cells, CD4+ T cells, TH1 cells, naive B cells, and plasma cells.

In one aspect, the invention provides methods for modulating lymphocyte effector activity.

In one aspect, the invention provides methods for decreasing lymphocyte effector activity, comprising contacting a lymphocyte having BTLA on its surface with a BTLA-HVEM agonist. In one embodiment, the methods involve the use of a BTLA antibody. Decreasing lymphocyte effector activity includes promoting the termination of effector activity, i.e., shortening the duration of effector activity.

In one aspect, the invention provides methods for increasing and/or prolonging lymphocyte effector activity, comprising contacting a lymphocyte having BTLA on its surface with a BTLA-HVEM antagonist. In one embodiment, the methods involve the use of a BTLA antibody. In another embodiment, the methods involve contacting an HVEM protein with a BTLA-HVEM antagonist. Prolonging effector activity includes delaying the termination of effector activity.

In another aspect, the invention provides methods for modulating an immune response to an antigen, which involve the use of BTLA-HVEM agonists or BTLA-HVEM antagonists described herein.

In one aspect, the invention provides methods for increasing an immune response to an antigen, comprising contacting a lymphocyte having BTLA on its surface with a BTLA-HVEM antagonist, wherein the lymphocyte has specificity for the antigen, and wherein the lymphocyte is capable of contacting HVEM protein in the absence of the BTLA-HVEM antagonist. In one embodiment, the methods involve use of a BTLA antibody.

In another embodiment, the methods comprise contacting HVEM protein with a BTLA-HVEM antagonist, wherein the HVEM protein is capable of contacting a lymphocyte having BTLA on its surface in the absence of the BTLA-HVEM antagonist, wherein the lymphocyte has specificity for the antigen. In one embodiment, the methods involve use of a HVEM antibody.

In a preferred embodiment, the antigen is a cancer cell antigen.

In another preferred embodiment, the antigen is a viral antigen.

In another preferred embodiment, the antigen is presented by a pathogen.

In another preferred embodiment, the antigen is provided by a vaccine.

In a preferred embodiment, the lymphocyte having BTLA on its surface and specificity for the antigen is contacted with a BTLA-HVEM antagonist in vivo.

In a preferred embodiment, the HVEM protein is contacted with a BTLA-HVEM antagonist in vivo.

In a preferred embodiment, the lymphocyte having specificity for the antigen is selected from the group consisting of naïve T cells, CD8+ T cells, CD4+ T cells, TH1 cells, naive B cells, and plasma cells.

In one embodiment, the methods further comprise administering antigen to a patient receiving the BTLA-HVEM antagonist.

In one embodiment, the methods further comprise administering a bioactive agent that increases a positive costimulatory signal to a patient receiving the BTLA-HVEM antagonist.

In one embodiment, the methods further comprise administering a bioactive agent that decreases a negative costimulatory signal to a patient receiving the BTLA-HVEM antagonist. For example, it is contemplated that use of a BTLA-HVEM antagonist will be synergistic in combination with agents capable of providing CTLA-4 blockade as described in U.S. Pat. Nos. 5,855,887; 5,811,097; and 6,051,227, and International Publication WO 00/32231, the disclosures of which are expressly incorporated herein by reference.

In one embodiment, the invention provides methods for increasing an immune reaction against a tumor in a patient, comprising contacting a lymphocyte having BTLA on its surface with a BTLA-HVEM antagonist, wherein the lymphocyte has specificity for a cancer cell antigen associated with the tumor and is capable of contacting HVEM protein. In one embodiment, the methods involve use of a BTLA antibody.

In another embodiment, the methods comprise contacting HVEM protein with a BTLA-HVEM antagonist, wherein the HVEM protein is capable of contacting a lymphocyte having BTLA on its surface, and wherein the lymphocyte has specificity for a cancer cell antigen associated with the tumor. In one embodiment, the methods involve use of a HVEM antibody.

In a preferred embodiment, the methods further comprise administering a cancer cell antigen to the patient.

In a preferred embodiment, the methods further comprise administering a bioactive agent that increases a positive costimulatory signal.

In a preferred embodiment, the methods further comprise administering a bioactive agent that decreases a negative costimulatory signal to the cancer patient. For example, it is contemplated that use of a BTLA-HVEM antagonist will be synergistic in combination with agents capable of providing CTLA-4 blockade as described in U.S. Pat. Nos. 5,855,887; 5,811,097; and 6,051,227, and International Publication WO 00/32231.

In a preferred embodiment, the lymphocyte having BTLA on its surface and specificity for the cancer cell antigen is contacted with a BTLA-HVEM antagonist in vivo.

In a preferred embodiment, the HVEM protein is contacted with a BTLA-HVEM antagonist in vivo.

In a preferred embodiment, the lymphocyte having specificity for the cancer cell antigen is selected from the group consisting of naïve T cells, CD8+ T cells, CD4+ T cells, 'TH1 cells, naive B cells, and plasma cells.

In one aspect, the invention provides methods for inhibiting tumor growth, comprising administering to a patient a therapeutically effective amount of a BTLA-HVEM antagonist.

In a preferred embodiment, the methods further comprise administering a cancer cell antigen to the patient.

In a preferred embodiment, the methods further comprise administering a bioactive agent that increases a positive costimulatory signal.

In a preferred embodiment, the methods further comprise administering a bioactive agent that decreases a negative costimulatory signal to the cancer patient. For example, it is contemplated that use of a BTLA-HVEM antagonist will be synergistic in combination with agents capable of providing CTLA-4 blockade as described in U.S. Pat. Nos. 5,855,887; 5,811,097; and 6,051,227, and International Publication WO 00/32231.

In one aspect, the invention provides methods for treating cancer, comprising administering to a patient a therapeutically effective amount of a BTLA-HVEM antagonist.

In a preferred embodiment, the methods further comprise administering a cancer cell antigen to the patient.

In a preferred embodiment, the methods further comprise administering a bioactive agent that increases a positive costimulatory signal.

In a preferred embodiment, the methods further comprise administering a bioactive agent that decreases a negative costimulatory signal to the cancer patient. For example, it is contemplated that use of a BTLA-HVEM antagonist will be synergistic in combination with agents capable of providing CTLA-4 blockade as described in U.S. Pat. Nos. 5,855,887; 5,811,097; and 6,051,227, and International Publication WO 00/32231.

In one aspect, the invention provides methods for reducing an immune response to an antigen, comprising contacting a lymphocyte having BTLA on its surface with a BTLA-HVEM agonist, wherein the lymphocyte has specificity for the antigen. In one embodiment, the methods involve use of a BTLA antibody.

In a preferred embodiment, the antigen is a graft cell antigen.

In another preferred embodiment, the antigen is a self antigen.

In another preferred embodiment, the lymphocyte having specificity for the antigen is selected from the group consisting of naïve T cells, CD8+ T cells, CD4+ T cells, TH1 cells, naive B cells, and plasma cells.

In one embodiment, the methods further comprise administering a bioactive agent that decreases a positive costimulatory signal to the patient.

In one embodiment, the methods further comprise administering an immunosuppressant to the patient.

In one embodiment, the methods further comprise administering a bioactive agent that increases a negative costimulatory signal to the patient.

In one embodiment, the invention provides methods for reducing an immune reaction against a graft in a patient, comprising contacting a lymphocyte having BTLA on its surface with a BTLA HVEM agonist, wherein the lymphocyte has specificity for a graft cell antigen. In one embodiment, the BTLA-HVEM agonist is a BTLA antibody.

In another preferred embodiment, the lymphocyte having specificity for the antigen is selected from the group consisting of naïve T cells, CD8 T cells, CD4+ T cells, TH1 cells, naive B cells, and plasma cells.

In one embodiment, the methods further comprise administering a bioactive agent that decreases a positive costimulatory signal to the patient.

In one embodiment, the methods further comprise administering an immunosuppressant to the patient.

In one embodiment, the methods further comprise administering a bioactive agent that increases a negative costimulatory signal to the patient.

In one aspect, the invention provides methods for reducing rejection of a graft by a patient, comprising administering to the patient a therapeutically effective amount of a BTLA-HVEM agonist.

In one embodiment, the methods further comprise administering a bioactive agent that decreases a positive costimulatory signal to the patient.

In one embodiment, the methods further comprise administering an immunosuppressant to the patient.

In one embodiment, the methods further comprise administering a bioactive agent that increases a negative costimulatory signal to the patient.

In one aspect, the invention provides methods for prolonging the survival of a graft in a patient, comprising administering to the patient a therapeutically effective amount of a BTLA-HVEM agonist.

In one embodiment, the methods further comprise administering a bioactive agent that decreases a positive costimulatory signal to the patient.

In one embodiment, the methods further comprise administering an immunosuppressant to the patient.

In one embodiment, the methods further comprise administering a bioactive agent that increases a negative costimulatory signal to the patient.

In one aspect, the invention provides methods for reducing a graft versus host response in a patient, comprising administering to the patient a therapeutically effective amount of a BTLA-HVEM antagonist.

In one embodiment, the methods further comprise administering a bioactive agent that increases a positive costimulatory signal to the patient.

In one embodiment, the methods further comprise administering a bioactive agent that decreases a negative costimulatory signal to the patient. For example, it is contemplated that use of a BTLA-HVEM antagonist will be synergistic in combination with agents capable of activating CTLA-4 as described in U.S. Pat. Nos. 5,855,887; 5,811,097; and 6,051,227, and International Publication WO 00/32231.

In one aspect, the invention provides methods for treating a patient having an autoimmune disease, comprising administering to the patient a therapeutically effective amount of a BTLA-HVEM agonist.

In one embodiment, the autoimmune disease is selected from the group consisting of Rheumatoid arthritis, type 1 diabetes, autoimmune thyroiditis, and Lupus.

In one embodiment, the methods further comprise administering a bioactive agent that decreases a positive costimulatory signal to the patient.

In one embodiment, the methods further comprise administering an immunosuppressant to the patient.

In one embodiment, the methods further comprise administering a bioactive agent that increases a negative costimulatory signal to the patient.

In one aspect, the invention provides methods for treating a patient having an allergic reaction, comprising administering to the patient a therapeutically effective amount of a BTLA-HVEM agonist.

In one aspect, the invention provides methods for preventing a patient from having an allergic reaction, comprising administering to the patient a therapeutically effective amount of a BTLA-HVEM agonist.

In one aspect, the invention provides methods for reducing an allergic reaction in a patient, comprising administering to the patient a therapeutically effective amount of a BTLA-HVEM agonist.

In one aspect, the invention provides methods for reducing an asthmatic response in a patient, comprising administering to the patient a therapeutically effective amount of a BTLA-HVEM agonist.

In one aspect, the invention provides methods for enhancing recovery from an asthmatic response in a patient, comprising administering to the patient a therapeutically effective amount of a BTLA-HVEM agonist.

In one aspect, the invention provides methods for treating asthma, comprising administering to an asthma patient a therapeutically effective amount of a BTLA-HVEM agonist.

In one aspect, the invention provides methods for reducing an inflammatory reaction in a patient, comprising administering to the patient a therapeutically effective amount of a BTLA-HVEM agonist.

In one aspect, the invention provides methods for reducing the interaction of cell having BTLA on its surface and a second cell having HVEM on its surface. The methods involve the use of a BTLA-HVEM antagonist or a BTLA-HVEM agonist. In a preferred embodiment, the methods involve use of a BTLA antibody or a HVEM antibody. In a preferred embodiment, the cell having BTLA on its surface is selected from the group consisting of naïve T cells, CD8+ T cells, CD4+ T cells, TH1 cells, naive B cells, and plasma cells.

In one aspect, the invention provides methods for modulating memory cell formation, comprising contacting a lymphocyte exposed to antigen with a BTLA-HVEM agonist or antagonist. In a preferred embodiment, the methods involve the use of a BTLA antibody.

In one aspect, the invention provides methods for modulating tolerance of self antigen, comprising contacting a lymphocyte exposed to self antigen with a BTLA-HVEM agonist or antagonist. In a preferred embodiment, the methods involve the use of a BTLA antibody.

Also provided are adjuvant compositions comprising at least one of the BTLA-HVEM antagonists described herein.

Also provided are immunosuppressant compositions comprising at least one of the BTLA-HVEM agonists described herein.

In another aspect, the present invention provides methods of screening for BTLA-HVEM agonists and BTLA-HVEM antagonists, which agonists and antagonists find therapeutic uses for the modulation of immune reactions.

The invention further contemplates the use of the aforementioned polypeptides in immunoassays.

The invention further contemplates the use of the aforementioned polypeptides as immunogens for the production of antibodies.

Gene Therapy

In a further aspect, the present invention provides compositions and methods for gene therapy.

Nucleic acids encoding HVEM, B7x or BTLA polypeptides, as well as genetic antagonists or agonists of HVEM, BTLA or B7x, may be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene marking and gene therapy protocols see Anderson et al., Science 256, 808-813 (1992).

Diagnostic Uses

Mutations, deletions, duplications, and/or rearrangements that decrease B7x expression and/or activity lead to a loss of signaling that normally inhibits T cell activation. These may be germline or somatic changes. The functional consequence of this loss of inhibition is a hyperimmune state, characterized by autoimmune disease. Particularly affected are those tissues that harbor cells with the mutation and that show high levels of B7x expression normally, such as kidney, placenta, liver, lung and heart. The clinical manifestations of such B7x mutations may include autoimmune disorders such as e.g., diabetes, pre-eclampsia, rheumatoid arthritis, multiple sclerosis, and the like.

Similarly, mutations, deletions, duplications, and/or rearrangements that decrease BTLA expression and/or activity lead to a loss of signaling that normally inhibits T cell activation. These may be germline or somatic changes. The functional consequence of this loss of inhibition is a hyperimmune state, characterized by autoimmune disease. Particularly affected are tissues that harbor antigens with which the affected T cells react, and that show high levels of B7x expression normally, such as kidney, placenta, liver, lung and heart. The clinical manifestations of such BTLA mutations may include autoimmune disorders.

In a preferred embodiment, the invention provides methods of diagnosing an autoimmune predisposition and/or disease. The methods involve measuring the expression and/or activity of HVEM, BTLA and/or B7x.

Mutations, deletions, duplications, and/or rearrangements that increase B7x expression and/or activity lead to an increase in signaling that normally inhibits T cell activation. These may be germline or somatic changes. The functional consequence of this increase in inhibitory signaling is a hypoimmune state, characterized by undesired cell growth and undesired cell survival.

As identified herein, B7x is highly expressed in a number of tumor cells. The high level of B7x expression allows such tumor cells to inhibit a T cell immune response that would otherwise be mounted against the tumor tissue.

Similarly, mutations, deletions, duplications, and/or rearrangements that increase BTLA expression and/or activity lead to an increase in signaling that normally inhibits T cell activation. These may be germline or somatic changes. The functional consequence of this increase in inhibitory signaling is a hypoimmune state, characterized by undesired cell growth, undesired cell survival, and increased susceptibility to disease caused by pathogens.

In one embodiment, the present invention provides methods of diagnosing a predisposition to cancer, or the existence or recurrence of cancer. The methods involve measuring the expression and/or activity of HVEM, BTLA and/or B7x, either generally or in a tissue-specific fashion.

Modulation of Immune Responses

The present invention provides methods for modulating lymphocyte activity and immune responses to antigens using BTLA-HVEM antagonists, BTLA-HVEM agonists, BTLA-B7x antagonists, and BTLA-B7x agonists described herein. The methods are useful for modulating the activity of, for example, naïve T cells, CD8+ Tc cells, CD4+ cells, TH1 cells, and B cells.

Surprisingly, also demonstrated herein is the expression of BTLA on activated B cells and its ability to inhibit B cell activity. B cells from mice lacking BTLA function exhibit increased responses to stimulation with anti-IgM, and BTLA deficient mice exhibit a three-fold increase in the amount of specific IgG1, IgG2a, and IgG2b isotypes as compared with control littermates. These observations are the first evidence of an inhibitory B cell activity for BTLA, which enables the use of agents that are capable of modulating BTLA activity to modulate B cell activity and antibody production. Accordingly, the invention also provides compositions and methods for modulating B cell activity and antibody production, which involve the use of agents capable of modulating BTLA activity.

Included among the preferred bioactive agents are B7x antibodies (anti-B7x antibodies), HVEM antibodies (anti-HVEM antibodies), BTLA antibodies (anti-BTLA antibodies), B7x fusion proteins, HVEM fusion proteins, BTLA fusion proteins, B7x proteins and fragments, HVEM proteins and fragments, BTLA proteins and fragments, peptides, and small molecule chemical compositions. Agonists of BTLA-mediated signaling, such as B7x proteins, B7x fusion proteins, and function activating anti-BTLA antibodies, may be used to stimulate BTLA and inhibit T and B cell activity. Conversely, antagonists of BTLA-mediated signaling, such as BTLA-Ig fusion proteins, function blocking anti-BTLA antibodies, function blocking anti-HVEM antibodies, and anti-B7x antibodies, may be used to inhibit BTLA-mediated signaling, thereby preventing the attenuation of T and B cell activity mediated by BTLA signaling and, preferably, increasing T and B cell activity.

The anti-B7x antibodies provided herein specifically bind to B7x protein, and in particular, to one or more epitopes present in the extracellular domain of B7x identified above. The anti-BTLA antibodies provided herein specifically bind to BTLA protein, and in particular, to one or more epitopes present in the extracellular domain of BTLA identified above. The anti-HVEM antibodies provided herein specifically bind to HVEM protein, and in particular, to one or more epitopes present in the extracellular domain of HVEM identified above. Preferably, these antibodies effectively inhibit or interfere with the natural interaction between HVEM or B7x with BTLA.

By inhibiting the interaction of BTLA and B7x, anti-B7x antibodies are used in a preferred embodiment to inhibit the suppression and/or attenuation of lymphocyte activity mediated by BTLA signaling.

Blocking anti-BTLA antibodies and anti-HVEM antibodies are used in a preferred embodiment to inhibit the suppression and/or attenuation of lymphocyte activity mediated by BTLA signaling. In an alternative embodiment, a function activating anti-BTLA antibody or anti-HVEM antibody is used to stimulate BTLA and promote the suppression and/or attenuation of lymphocyte activity mediated by BTLA signaling.

The present invention provides methods of screening for bioactive agents capable of modulating the natural interaction between B7x and BTLA or HVEM and BTLA. In a preferred embodiment, the methods involve providing a B7x protein, a BTLA protein, and a candidate agent, and determining the binding of B7x to BTLA in the presence of the candidate agent. Agents that interfere with the binding of BTLA to B7x find use as antagonists of the natural interaction of BTLA-expressing and B7x-expressing cells. Accordingly, such agents find use as modulators of T cell activation. In some cases, an agent may mimic the action of B7x towards BTLA, or the action of BTLA towards B7x. In another preferred embodiment, the methods involve providing a HVEM protein, a BTLA protein, and a candidate agent, and determining the binding of HVEM to BTLA in the presence of the candidate agent. Agents that interfere with the binding of BTLA to HVEM find use as antagonists of the natural function of BTLA. Accordingly, such agents find use as modulators of T cell activation. In some cases, an agent may mimic the action of HVEM towards BTLA, or the action of BTLA towards HVEM.

BTLA-HVEM or B7x-BTLA antagonists are used alone or in combination with other therapeutic agents to reduce the negative costimulatory signals emitted by BTLA, and to reduce the suppression and/or attenuation of lymphocyte activity mediated by BTLA signaling.

BTLA-HVEM or B7x-BTLA agonists are used are used alone or in combination with other therapeutic agents to increase negative costimulatory signals emitted by BTLA, thereby increasing the suppression and/or attenuation of lymphocyte activity mediated by BTLA signaling.

In a preferred embodiment, the methods comprise contacting a lymphocyte expressing BTLA on its surface, or a second cell expressing HVEM on its surface, or both, with a BTLA-HVEM antagonist, wherein the lymphocyte and second cell are able to contact each other such that BTLA on the lymphocyte can bind to HVEM on the second cell, and wherein the BTLA-HVEM antagonist reduces the activation of BTLA on the lymphocyte by HVEM on the second cell.

In another preferred embodiment, the methods comprise contacting a lymphocyte expressing BTLA on its surface with a BTLA-HVEM agonist, such that the BTLA-HVEM agonist increases BTLA activity in the lymphocyte.

In one aspect, the present invention provides a medicament for the treatment of diseases associated with lymphocyte activity.

Antigens

As described herein, the compositions and methods provided herein find use in modulating lymphocyte activity in response to antigenic stimulation. Such antigenic stimulation can come from tumor-associated antigens, pathogen antigens and autoantigens. Antigenic stimulation caused by tumor-associated antigens and pathogen antigens may be a result of on-going malignancy or infection, and/or may be a result of vaccine antigens.

A wide variety of antigens may find use in conjunction with the compositions and formulations of the present invention. In particular, the adjuvant compositions provided herein may be advantageously combined with antigenic stimulation from tumor-associated antigens or pathogen antigens to increase lymphocyte activity against the corresponding tumor or pathogen. Generally, suitable antigens may be derived from proteins, peptides, polypeptides, lipids, glycolipids, carbohydrates and DNA found in the subject tumor or pathogen.

Tumor-associated antigens finding utility herein include both mutated and non-mutated molecules which may be indicative of a single tumor type, shared among several types of tumors, and/or exclusively expressed or over-expressed in tumor cells in comparison with normal cells. In addition to proteins and glycoproteins, tumor-specific patterns of expression of carbohydrates, gangliosides, glycolipids and mucins have also been documented.

Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and HER-2/neu and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject compositions and methods may find advantageous use in conjunction with conventional chemotherapy and/or radiation therapy.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously utilized in conjunction with the compositions and methods provided herein. It is estimated that close to 16% of the worldwide incidence of cancer can be attributed to infectious pathogens, and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLV1 (adult T cell leukemia), oncogenic human papilloma viruses types 16, 18, 33, 45 (adult cervical cancer), and the bacterium *Helicobacter pylori* (B cell gastric lymphoma).

Also contemplated herein are pathogen antigens derived from infectious microbes such as virus, bacteria, parasites and fungi and fragments thereof, in order to increase lymphocyte activity in response to active infection or improve the efficacy of prophylactic vaccine therapy. Examples of infectious virus include, but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis • viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria serve as antigens in vertebrate animals. Such gram positive bacteria include, but are not limited to *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of pathogens also include, but are not limited to, infectious fungi that infect mammals, and more particularly humans. Examples of infectious fingi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (i.e. protists) include *Toxoplasma gondii*.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases, the compositions and methods of the present invention are useful for treating infections of nonhuman mammals. Many vaccines for the treatment of non-human mammals are disclosed in Bennett, K. Compendium of Veterinary Products, 3rd ed. North American Compendiums, Inc., 1995.

Treatment of Autoimmune Disease

The present invention also provides compositions and methods for inhibiting autoimmune responses. In a preferred embodiment, compositions and methods for inhibiting the activity of autoreactive T and B cells that specifically recognize autoantigens are provided. Desirably, these compositions and methods may be used to inhibit killing of non-tumor cells mediated by one or more autoantigens.

In preferred embodiments, the methods for inhibiting autoimmune responses and treating autoimmune diseases, comprising administering to a patient a therapeutically effective amount of a BTLA-HVEM agonist. Without being bound by theory, administration of a therapeutically effective amount of a BTLA-HVEM agonist inhibits the activity of autoreactive T and B cells that specifically recognize autoantigens and otherwise negatively affect the physiology of cells that bear them.

In other preferred embodiments, compositions for use in the treatment of autoimmune disease comprise the agonists of BTLA-mediated signaling described herein including the above-described mimicking agents. Especially preferred agents include B7x protein fragments comprising the B7x extracellular domain, or a portion thereof; B7x-Ig fusion proteins comprising the B7x extracellular domain, or a portion thereof; function-activating anti-BTLA antibody; peptides that mimic B7x (mimetics); and small molecule chemical compositions that mimic the natural interaction of BTLA and B7x. Also preferred are compositions capable of binding to both BTLA and TCR, either in a cross-linking fashion or as polyclonal mixtures.

Also contemplated in the present invention are genetic approaches to autoimmune disease. Particularly, gene therapy may be used to increase the level of BTLA expression on T cells, and/or increase the level of expression of B7x on non-lymphoid cells that are subject to attack by autoreactive lymphocytes. The use of isoforms of BTLA and B7x that exhibit elevated specific activity is also contemplated, the object of each method being to potentiate signaling that is suppressive to T cell activation.

Also provided herein are methods of screening for bioactive agents that increase the level and/or activity of B7x. Further provided are methods of screening for bioactive agents that increase the level and/or activity of BTLA. Also provided are methods of screening for bioactive agents that increase the level and/or activity of HVEM. The present invention contemplates the use of such agents to treat autoimmune diseases, the object being to potentiate signaling that is suppressive to lymphocyte activity.

Autoimmune disease as used herein includes Rheumatoid arthritis, type 1 diabetes, autoimmune thyroiditis, and Lupus. Additional autoimmune diseases are described, for example, in Mackay et al., NEJM, 345:340-350, 2001.

In one aspect, the present invention provides a medicament for the treatment of autoimmune disease.

In one aspect, the present invention provides a medicament for the treatment of autoimmune disease, wherein the medicament comprises a BTLA-HVEM agonist. Also provided are methods for making a medicament useful for the treatment of autoimmune disease, which medicament comprises a BTLA-HVEM agonist.

In another aspect, the invention provides methods for preventing or reducing an allergic reaction in a patient, comprising administering to a patient a therapeutically effective amount of a BTLA-HVEM agonist.

In one aspect, the present invention provides a medicament for the treatment or prevention of allergy, wherein the medicament comprises a BTLA-HVEM agonist. Also provided are methods for making a medicament useful for the treatment or prevention of allergy, which medicament comprises a BTLA-HVEM agonist.

In one aspect, the invention provides methods for reducing the severity of an asthmatic reaction in a patient, comprising administering to a patient a therapeutically effective amount of a BTLA-HVEM antagonist.

In one aspect, the invention provides methods for shortening the duration of an asthmatic reaction in a patient, comprising administering to a patient a therapeutically effective amount of a BTLA-HVEM antagonist.

In one aspect, the invention provides methods for improving recovery from an asthmatic reaction in a patient, comprising administering to a patient a therapeutically effective amount of a BTLA-HVEM antagonist.

Treatment of Cancer

The present invention also provides compositions and methods for treating cancer. In some embodiments, the present invention provides immunotherapeutic methods for treating cancer, comprising administering to a patient a therapeutically effective amount of a BTLA-HVEM antagonist, either alone or in combination with other therapeutic compositions. In preferred embodiments, immunization is done to promote a tumor-specific T cell immune response. In this embodiment, a BTLA-HVEM antagonist is administered in combination with a tumor-associated antigen. The combination of a tumor-associated antigen and a BTLA-HVEM antagonist promotes a tumor specific T cell response, in which T cells encounter reduced negative costimulatory signals mediated by BTLA as compared to those in the absence of the BTLA-HVEM antagonist.

In other embodiments, the present invention also provides compositions and methods for treating cancer by increasing the activity of BTLA-positive lymphocytes against B7x-positive tumor cells. In a preferred embodiment, compositions and methods for increasing the T cell response to tumor-associated antigens other than B7x are provided. Desirably, these compositions and methods may be used to inhibit the growth of tumor cells capable of expressing B7x.

In other embodiments, compositions for use in the treatment of cancer are the antagonists of BTLA-mediated signaling described herein including, e.g., BTLA, HVEM or B7x blocking agents. Especially preferred agents include anti-B7x antibodies; protein fragments comprising the BTLA extracellular domain, or a portion thereof; BTLA-Ig fusion proteins comprising the BTLA extracellular domain, or a portion thereof; function-blocking anti-BTLA antibody; peptides that mimic BTLA (mimetics); and small molecule chemical compositions that interfere with the natural interaction of BTLA and B7x.

Also contemplated in the present invention are genetic approaches to the treatment of cancer. Particularly, gene therapy may be used to decrease the level of BTLA expression on T cells, and/or decrease the level of expression of B7x on tumor cells. The use of isoforms of BTLA and B7x that exhibit dominant negative activity is also contemplated, the object of each method being to inhibit signaling that is normally suppressive to T cell activation. Genetic approaches may involve the use of tissue and cell specific promoters to target expression of BTLA and/or B7x dominant negative variants, antisense nucleic acids, or small inhibitory RNAs to T cells and tumor cells, respectively. The methods may additionally involve the use of tumor-targeted viruses, or other delivery vehicles that specifically recognize tumor cells. The methods may additionally involve the use of T cell-targeted viruses, or other delivery vehicles that specifically recognize T cells.

Also provided herein are methods of screening for bioactive agents that decrease the level and/or activity of B7x. Further provided are methods of screening for bioactive agents that decrease the level and/or activity of BTLA. The present invention contemplates the use of such agents to treat cancer, the object being to inhibit signaling that normally attenuates the lymphocytic response to tumor antigens and tumor tissues.

Particularly preferred are agents that may be selectively targeted to tumor cells, and effect a decrease in B7x expression in tumor cells without reducing the level of B7x expression in non-tumor cells to deleterious levels. Highly preferred are agents that have a precursor form. These "prodrugs" are converted to their active form in the vicinity of tumor tissue typically by an enzymatic activity that is restricted in its distribution to the vicinity of the tumor.

Also highly preferred are agents that can be combined with targeting moieties that selectively deliver the agent to a tumor. These targeting moieties provide a high local concentration of the agent in the vicinity of the tumor tissue, and reduce the amount of agent that must be administered to effect the desired response.

Also contemplated in the present invention is the use of combination therapy to treat cancer, as described above.

In a preferred embodiment, immunization is done to promote a tumor-specific T cell immune response. In this embodiment, a bioactive agent that inhibits BTLA activation is administered in combination with a tumor-associated antigen other than B7x. The combination of a tumor-associated antigen and a BTLA-inhibitory/B7x functional-mimetic promotes a tumor specific T cell response, in which T cells encounter a lower level of inhibition than exerted by the tumor tissue in the absence of the bioactive agent.

In one aspect, the present invention provides a medicament for the treatment of cancer.

Promote Graft Survival

The present invention also provides compositions and methods for modulating normal but undesired immune responses involving T and B cell activity. In a preferred embodiment, compositions and methods for inhibiting the host lymphocyte response to transplanted tissue and organs are provided. Desirably, these compositions and methods may be used to prolong the survival of grafted tissue.

Preferred compositions for use in the prevention of acute and/or chronic graft rejection comprise the agonists of BTLA-mediated signaling described herein including, e.g., the above-described mimicking agents. Especially preferred agents include a BTLA-HVEM agonist as described above; function-activating anti-BTLA antibodies; peptides that mimic HVEM (mimetics); peptides that mimic B7x; B7x polypeptides comprising the B7x extracellular domain, or a portion thereof; HVEM polypeptides comprising the HVEM CDR domain, or a portion thereof; B7x-Ig fusion proteins comprising the B7x extracellular domain, or a portion thereof; small molecule chemical compositions that mimic the natural interaction of BTLA and HVEM; and small molecule chemical compositions that mimic the natural interaction of BTLA and B7x.

In addition to their utility in general immunosuppressive strategies, the subject agonists of BTLA-mediated signaling described herein may also have important implications for tolerance induction in tissue and organ transplantation, by biasing the recipient T helper cell immune response away from an unfavorable Th-1-type response and towards a more favorable Th-2 type response. As demonstrated herein, BTLA is highly expressed in Th-1 type T cells in comparison with low expression in Th-2 type T cells after T cell polarization, and thus the subject agonists will preferentially attenuate the activity of Th-1 cells over Th-2 cells. Recent evidence suggests that the creation of a Th-2 type cytokine milieu can be more favorable to tolerance induction, and thus the need for life-long immunosuppressive therapy in transplant patients may be reduced or eliminated by employing the compositions and methods described herein.

In one aspect, the present invention provides a medicament for use in transplantation and immune suppression. In one embodiment, the medicament comprises a BTLA-HVEM agonist. In another embodiment, the medicament comprises a BTLA-B7x agonist. Also provided are methods for making such a medicament.

(VII) Administration of Therapeutic Compositions

The bioactive agents of the present invention are administered to subjects in a biologically compatible form suitable for pharmaceutical administration in vivo. By "biologically compatible form suitable for administration in vivo" is meant a form of the agent to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a bioactive agent as described herein can be in any pharmacological form, including a therapeutically active amount of an anti-B7x or anti-BTLA antibody alone or in combination with each other, or with an additional therapeutic agent as described herein and a pharmaceutically acceptable carrier. Administration of a therapeutically effective amount of the therapeutic compositions of the present invention is defined as an amount effective, at dosages and for periods of time necessary to achieve the desired immunotherapeutic result. For example, a therapeutically active amount of an anti-B7x or anti-BTLA antibody may vary according to factors such as the disease state, age, sex, and weight of the individual, and the ability of peptide to elicit a desired response in the individual. A dosage regime may be adjusted to provide the optimum therapeutic response. For example, several divided doses may be administered daily or the dose may be proportionally reduced as indicated by the exigencies of the therapeutic situation.

The bioactive agent (e.g., antibody) may be administered in a convenient manner such as by injection (subcutaneous, intravenous, etc.), oral administration, inhalation, transdermal application, or rectal administration. Depending on the route of administration, the bioactive agent may be coated in a material to protect the compound from the action of enzymes, acids and other natural conditions which may inactivate the compound.

To administer a bioactive agent comprising a protein, e.g. an anti-BTLA antibody, by other than parenteral administration, it may be necessary to coat the peptide with, or co-administer the antibody with, a material to prevent its inactivation. An anti-B7x or anti-BTLA antibody may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Exemplary adjuvants include alum, resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) J. Neuroimmunol 7:27).

The bioactive agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

In one embodiment, a pharmaceutical composition suitable for injectable use include sterile aqueous solutions (where water soluble) or dispersions and sterile powders for the extemporaneous preparation of sterile injectable solutions or dispersion. In all cases, the composition will preferably be sterile and fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating one or more bioactive agents, together or separately with additional immune response stimulating agents or immunosupressants, in the required amount in an appropriate solvent with one or a combination of ingredients enumerated above, as required, followed by filtered sterilization. Generally, dispersions are prepared by incorporating the bioactive agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

When a bioactive agent comprising a peptide is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary bioactive agents can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of bioactive agent calculated to produce the desired therapeutic effect in association with the required pharmaceutical carrier. The specification for the dosage unit forms of the invention are dictated by and directly dependent on (a) the unique characteristics of the bioactive agent(s) and the particular therapeutic effect to be achieved, and (b) the limitations inherent in the art of compounding such an agent for the treatment of sensitivity in individuals.

The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The toxicity and therapeutic efficacy of the bioactive agents described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography.

In one embodiment of the present invention a therapeutically effective amount of an antibody to HVEM, B7x or BTLA is administered to a subject. As defined herein, a therapeutically effective amount of antibody (i.e., an effective dosage) ranges from about 0.001 to 50 mg/kg body weight, preferably about 0.01 to 40 mg/kg body weight, more preferably about 0.1 to 30 mg/kg body weight, about 1 to 25 mg/kg, 2 to 20 mg/kg, 5 to 15 mg/kg, or 7 to 10 mg/kg body weight. The optimal dose of the antibody given may even vary in the same patient depending upon the time at which it is administered.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of assays designed to monitor transplant status (e.g., whether rejection or an immune response in the subject has occurred) as known in the art or as described herein.

In one embodiment, a pharmaceutical composition for injection could be made up to contain 1 ml sterile buffered water, and 1 to 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980), which is incorporated herein by reference. The compositions comprising the present antibodies can be administered for prophylactic and/or therapeutic treatments. In therapeutic application, compositions can be administered to a patient already suffering from a disease, in an amount sufficient to cure or at least partially arrest the disease and its complications. An amount adequate to accomplish this is defined as a "therapeutically effective dose." Amounts effective for this use will depend upon the clinical situation and the general state of the patient's own immune system. For example, doses for preventing transplant rejection may be lower than those given if the patient presents with clinical symptoms of rejection. Single or multiple administrations of the compositions can be carried out with dose levels and pattern being selected by the treating physician. In any event, the pharmaceutical formulations should provide a quantity of the bioactive agents described herein sufficient to effectively treat the patient.

Dose administration can be repeated depending upon the pharmacokinetic parameters of the dosage formulation and the route of administration used. It is also provided that certain protocols may allow for one or more agents describe herein to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The pharmaceutical compositions can be included in a container, pack, or dispenser together with instructions for administration. Kits for practice of the instant invention are also provided. For example, such a kit comprises a bioactive agent such as, e.g., an antibody reactive with HVEM, B7x or BTLA, together with a means for administering the antibody conjugate, e.g., one or more syringes. The kit can come packaged with instructions for use.

DEFINITIONS

By "BTLA signaling", "BTLA-mediated signaling", "BTLA-mediated negative signaling" and variations thereof is meant intracellular signaling in lymphocytes caused by the binding and/or activation of the BTLA receptor by its corresponding ligand(s) resulting in attenuation and/or down-regulation of lymphocyte activity. In one aspect, BTLA-mediated signaling comprises activation of SHP-1 and/or SHP-2.

"Lymphocyte activity" as used herein refers to the immunological processes of B and T cell activation, proliferation, differentiation and survival, as well as associated effector immune functions in lymphocytic cells including cytolytic activity (Tc cells), cytokine production (Th cells), antibody production (B cells), and antigen presentation (B cells). As noted above, there are numerous assays well known to the skilled artisan for detecting and/or monitoring such processes, including but not limited to the assays described in the examples provided herein.

As used herein, the phrase "interaction of BTLA and B7x" refers to direct physical interaction (e.g. binding) and/or other indirect interaction of a functional B7x molecule with a functional BTLA receptor on a lymphocyte, resulting in stimulation of the BTLA receptor and associated intracellular BTLA signaling. Similarly, the phrase "natural interaction of BTLA and B7x" refers to direct physical interaction (e.g. binding) and/or other indirect interaction of a functional and endogenously expressed B7x molecule with a functional and endogenously expressed BTLA receptor on a lymphocyte, resulting in stimulation of the BTLA receptor and associated intracellular BTLA signaling.

As used herein, "functional" means to be able to carry out normal activities, such as to recognize and 40 bind a target, or to activate intracellular signaling pathways upon stimulation.

As used herein, the term "blocking agent" includes those agents that interfere with the interaction of B7x and BTLA, and/or that interfere with the ability of B7x to inhibit lymphocyte activity, e.g., as measured by cytokine production and/or proliferation. The term "blocking agent" further includes agents that inhibit the ability of BTLA to bind a natural ligand, e.g., B7x, and/or that interfere with the ability of BTLA to inhibit T cell activity. Exemplary agents include function-blocking antibodies, as well as peptides that block the binding of B7x with BTLA but which fail to stimulate BTLA-mediated signaling in a lymphocyte (e.g., BTLA fusion proteins), peptidomimetics, small molecules, and the like. Preferred blocking agents include agents capable of inhibiting the inducible association of BTLA with SHP-1 and/or SHP-2, or the signal transduction that derives from the interaction of SHP-1 and/or SHP-2 with BTLA.

As used herein, the term "mimicking agent" includes those agents that mimic the interaction of B7x and BTLA, and/or that augment, enhance or increase the ability of B7x and/or BTLA to inhibit lymphocyte activity. Exemplary agents include function-activating antibodies, as well as peptides that augment or enhance the ability of B7x to bind to BTLA or substitute for B7x in stimulating BTLA-mediated signaling (e.g, B7x fusion proteins), peptidomimetics, small molecules, and the like.

As used herein, the term "HVEM CRD1 domain" refers to the CRD1 domain of an HVEM protein. An HVEM CRD1 domain binds to a BTLA Ig domain, and can be specifically bound by a preferred HVEM antibody disclosed herein. The HVEM CRD1 domain does not include the CRD2 or CRD3 domains of the HVEM protein. A preferred CRD1 domain is that set forth by residues 41-76 of the human HVEM protein sequence at Genbank accession no. AAB58354.1 (SEQ ID NO: 68). See Montgomery et al., Cell, 87:427-436, 1996. Other preferred CRD1 domains are those having at least about 80%, 85%, 90% or 95% identity to the sequence set forth by residues 41-76 of the human HVEM protein sequence at Genbank accession no. AAB58354.1 (SEQ ID NO: 68). Another preferred CRD1 domain is that set forth by residues 3980 of the murine HVEM protein sequence at Genbank accession no. AAQ08183.1 (SEQ ID NO: 69). Other preferred CRD 1 domains are those having at least about 80%, 85%, 90% or 95% identity to the sequence set forth by residues 39-80 of the murine HVEM protein sequence at Genbank accession no. AAQ08183.1 (SEQ ID NO: 69).

As used herein, the term "HVEM CRD1 domain peptide" refers to a peptide corresponding in sequence to a region of the CRD1 domain of HVEM, which peptide can bind to the Ig domain of BTLA. An HVEM CRD1 domain peptide is capable of reducing the binding of the HVEM CRD1 domain to the BTLA Ig domain, and is a BTLA-HVEM antagonist.

As used herein, the term "BTLA Ig domain" refers to the portion of a BTLA protein corresponding to the portion of BTLA that has been used to identify the HVEM-BTLA interaction. In particular, the BTLA Ig domain, as used herein, comprises an immunogloublin domain. Further, as compared to the BTLA sequence of C57BL/6 mouse, as found at Genbank accession no. NP 808252.1 (SEQ ID NO: 63), the BTLA Ig domain corresponds to amino acids 30-166. Further, as compared to the human BTLA sequence found at Genbank accession no. AAP44003.1 (SEQ ID NO: 64), the BTLA Ig domain corresponds to amino acids 31-149. A BTLA Ig domain binds to an HVEM CRD1 domain. Further, a fragment of a BTLA Ig domain binds to an HVEM CRD1 domain, and can be specifically bound by a preferred BTLA antibody disclosed herein. Some preferred BTLA Ig domains comprise a cysteine residue corresponding to residue C85 of the murine Bl/6 BTLA isoform (SEQ ID NO: 63), which corresponds to residue C79 of the human BTLA isoform found at Genbank accession no. AAP44003.1 (SEQ ID NO: 64).

As used herein, the term "BTLA Ig domain peptide" refers to a peptide corresponding in sequence to a region of the Ig domain of BTLA, which peptide can bind to the CRD1 domain of HVEM and is capable of reducing the binding of the BTLA Ig domain to the HVEM CRD1 domain. Such peptides are BTLA-HVEM antagonists.

As used herein, the term "HVEM blocking antibody" refers to an antibody that specifically binds to HVEM and reduces binding of HVEM to BTLA. Preferred HVEM blocking antibodies bind to the CRD1 domain, more preferably to a segment thereof that binds to the Ig domain of BTLA.

As used herein, the term "BTLA blocking antibody" refers to an antibody that specifically binds to BTLA and reduces binding BTLA to HVEM. Preferred BTLA blocking antibodies bind to the Ig domain of BTLA, preferably to a segment thereof that binds to the HVEM CRD1 domain.

As used herein, the term "BTLA-HVEM antagonist" refers to a bioactive agent capable of reducing BTLA activity in a cell having BTLA on its surface. Preferred BTLA-HVEM antagonists are capable of reducing the binding of HVEM on the surface of a cell to BTLA on the surface of the same or a second cell. In some preferred embodiments, BTLA-HVEM antagonists are capable of binding to the BTLA Ig domain. Binding of a BTLA-HVEM antagonist to BTLA on the surface of a cell does not increase BTLA activity in the cell.

As used herein, the term "BTLA-HVEM agonist" refers to a bioactive agent capable of increasing BTLA activity in a cell having BTLA on its surface, thereby mimicking the action of HVEM on BTLA. Preferred BTLA-HVEM agonists are capable of reducing the binding of HVEM on the surface of a cell to BTLA on the surface of the same or a second cell.

Both HVEM and BTLA are synthesized and inserted into the plasma membrane as transmembrane proteins, and thereby expose respective extracellular domains. The phrase "on the surface of a cell" in respect of BTLA or HVEM refers to non-soluble BTLA and HVEM protein localized at the plasma membrane.

As used herein, the term "antagonistic HVEM antibody" refers to an antibody that specifically binds to HVEM and can reduce the ability of HVEM to increase BTLA activity in a cell having BTLA on its surface.

As used herein, the term "antagonistic BTLA antibody" refers to an antibody that specifically binds to BTLA and can reduce the ability of HVEM to increase BTLA activity in a cell having BTLA on its surface. Binding of an antagonistic BTLA antibody to BTLA on the surface of a cell does not increase BTLA activity in the cell.

As used herein, the term "agonistic BTLA antibody" refers to an antibody that specifically binds to BTLA, is capable of reducing the binding of HVEM to BTLA, and increases BTLA activity in a cell having BTLA on its surface.

By "BTLA activity" and variations thereof is meant intracellular signaling and the effects thereof, caused by the binding of BTLA on the surface of a cell by a BTLA agonist, e.g., HVEM on the surface of a second cell; CMV UL144. BTLA activity includes but is not limited to inhibition of lymphocyte activation; phosphorylation of BTLA intracellular domain tyrosine residues, particularly those in the Grb2 binding site, the immunoreceptor tyrosine-based inhibitory motif (ITIM), and/or the immunoreceptor tyrosine-based switch motif (ITSM); binding of BTLA to SHP-1 and/or SHP-2; activation of SHP-1 and/or SHP-2; binding of BTLA to Grb2; and binding of BTLA to p85 of PI3K.

By "modulating BTLA activity" is meant increasing or decreasing BTLA activity, which includes completely decreasing BTLA activity such that no BTLA activity is detectable.

As used herein, the term "lymphocyte activation" refers to the processes attendant B cell and T cell activation in primary or subsequent immune responses, which processes include but are not limited to cell proliferation, differentiation, migration, and survival, as well as effector activities exhibited by B cells and T cells such as, but not limited to, cytokine production, antibody production, Fas ligand production, chemokine production, granzyme production and release, and antigen presentation. Accordingly, as used herein, modulation of lymphocyte activation includes modulation of effector function, such as modulation of the termination of effector function, etc. Numerous assays are well known to the skilled artisan for detecting and/or monitoring such processes.

As used herein, the term "immune response" includes both T and/or B cell responses, i.e., cellular and/or humoral immune responses. In one embodiment, the compositions and methods disclosed herein can be used to reduce or enhance helper T cell (Th) responses, and more preferably, Th1 cell responses. In another embodiment, the compositions and methods disclosed herein can be used to reduce or, enhance cytotoxic T cell (Tc) responses. The claimed methods can be used to reduce or enhance both primary and secondary immune responses and effector function (e.g., cytolytic activity, cytokine and antibody production, and antigen presentation). The immune response of a subject can be readily determined by the skilled artisan using methods well known in the art, for example, by assaying for antibody production, immune cell proliferation, the release of cytokines, the expression of cell surface markers, cytotoxicity, etc.

By "modulating lymphocyte activation" is meant increasing or decreasing lymphocyte activation, which includes decreasing lymphocyte activation such that no lymphocyte activation is detectable.

"Decreasing", "reducing", "inhibiting", and grammatical equivalents thereof are used interchangeably herein and refer to reductions in levels of binding, activity, etc., which include reductions to levels beyond detection, including complete inhibition. Reduced binding can be effected, for example, by competitive binding of an antagonist.

As used herein, the term "immune response" includes T and/or B cell responses, i.e., cellular and/or humoral immune responses.

By "inhibiting tumor growth" is meant maintaining or reducing the tumor burden of an animal having an extant tumor, which includes eradicating the tumor. Even though the tumor burden is maintained or reduced, cancer cell proliferation may be ongoing.

As used herein, "human antibodies" includes humanized antibodies.

It will be evident herein that the use of "BTLA", "B7x", and "HVEM" refers to BTLA protein, B7x protein, and HVEM protein in many instances.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods for Examples 1-3

Mice and Cells.

Female BALB/c mice were purchased from Jackson Laboratories (Bar Harbor, Me.) and were used at ages 6-9-weeks-old. Animals were housed in accordance with the Animal Care and Use Committee regulations at the University of California, Berkeley. All cell purifications were performed with magnetic cell sorting separation columns (Milternyi Biotec, Auburn, Calif.) with purities >95%. Macrophages were obtained from peritoneal cavity. All cells were cultured in DMEM supplemented with 10% fetal calf serum, 2 µM L-glutamine, and 100 U/ml penicillin and streptomycin (all from BioWhittaker), and 2 µM 2-mercaptoethanol (Sigma).

Production of Fusion Protein.

B7xIg was prepared by fusing the coding region of the extracellular domain of B7x to a chimeric sequence containing the CH2-CH3 domain of mouse IgG1 and a Myc-His-tag in pcDNA4 (a gift from Dr. William Sha, UC Berkeley). The construct was linearized with Bgl II and transfected into 293T cells with FuGENE 6 Transfection Reagent (Roche, Ind.). Stable transfectants were selected in 1 mg/ml of Zeocin (Invitrogen). To produce fusion protein, stable transfectants were cultured in serum-free DMEM for 72 h, the supernatant was collected and B7xIg was purified by affinity column chromatography over His-Bind resin (Novagen). The purity of the fusion protein was confirmed by SDS-PAGE and by immunoblotting with antibodies against Myc and mouse IgG.

Northern Blot Analysis.

Mouse and human multiple tissue northern blots (Clontech) were probed with cDNA fragments labeled by $^{32}$P-dCTP with Random Primed DNA Labeling kit (Roche). Mouse and human B7x probes consisted of the entire coding regions. 8-actin probes were supplied by Clontech. Blots were hybridized for 1 h at 68° C., washed twice at room temperature in 2×SSC containing 0.05% SDS, followed by 0.1×SSC containing 0.1% SDS at 50° C. and examined on an PhosphorImager.

RT-PCR, and Retrovirus Constructs.

Total RNA was isolated using TR1Reagent (Sigma). Reverse transcription was performed using oligo(dT) as the first primer and 2 µg of total RNA with Omniscript Reverse Transcriptase Kit (QIAGEN). RT-PCR was performed using HotStarTag (QIAGEN). B7x-GFP fusion protein constructs were generated using PCR to amplify the coding sequence of B7x without the stop codon and then cloned into the pEGFPN3 vector (Clontech). Following confirmation by DNA sequencing, the constructs of B7x-GFP fusion protein or GFP alone were cloned into a mouse stem cell virus (MSCV) retroviral expression vector (a generous gift from Dr. William Sha, UC Berkeley). Retrovirus was produced by transient transfection of the Pheonix-GP packaging cell line. For infection of CHO cells, retroviruses were pseudotyped with vesicular stomatitis virus G-glycoprotein. Stable clones were selected by flow cytometric single cell sorting. For experiments using B7.2 only or B7.2/B7x cotransfected cells, the transfectants were matched for B7.2 expression levels.

CHO Cell Stimulation of T Cells.

CHO cells transfected with vector were incubated with mitomycin C (50 µg/ml, Sigma) for 16 h. The cells were treated with PBS-EDTA (10 mM), washed twice, resuspended in complete DMEM and left on ice for 2 h. The cells were subsequently washed twice and resuspended in completed DMEM. Purified T cells ($10^5$/well) were incubated with mitomycin-treated CHO transfectants ($10^5$/well) in anti-CD3 (500A2)-bound-96-well plates. To analyze T cell proliferation, cultures were pulsed with 1 µCi/well of [$^3$H]thymidine for the last 16 h of a 72-h incubation.

Cytokines ELISA.

Aliquots of supernatants were collected at 48 h after initiation of cell cultures. IL-2, IL-4, IFN-γ and IL-10 were measured with monoclonal antibodies and recombinant cytokine standards from PharMingen.

Flow Cytometry.

After incubation with the anti-Fc receptor antibody 24G2 for Fc receptor-blocking, cells were stained with B7x-Ig or mouse IgG1 as a control for 45 min on ice and then stained with an anti-mouse-IgG PE-conjugate (Caltag) for 30 min. In some experiments, cells were stained with PE-conjugated anti-ICOS (eBioscience), anti-F480 (eBioscience), anti-CD4 and anti-CD8 (Caltag); or biotin-conjugate anti-B7.2 (Pharmingen), anti-CD28 (Pharmingen), anti-PD-1 (eBioscience), and then stained with PE-Streptavidin (Caltag). The cells were analyzed on an XL (Coulter Electronics, Hialeah, Fla.)

CSFE Staining and Analyses.

Purified T cells (107/ml) were washed with HBSS, labeled with 2.5 µM CSFE (Molecular Probes, Oreg.) for 10 min at 37° C., and then washed twice with cold completed DMEM. T cells were stimulated with plate-bound anti-CD3 500A2 and the indicated CHO transfectants. On day 4 of culture, cells were stained with PE-anti-CD4 or PE-anti-CD8, and analyzed by flow cytometry.

Example 1

Expression of B7x

Figure 7:
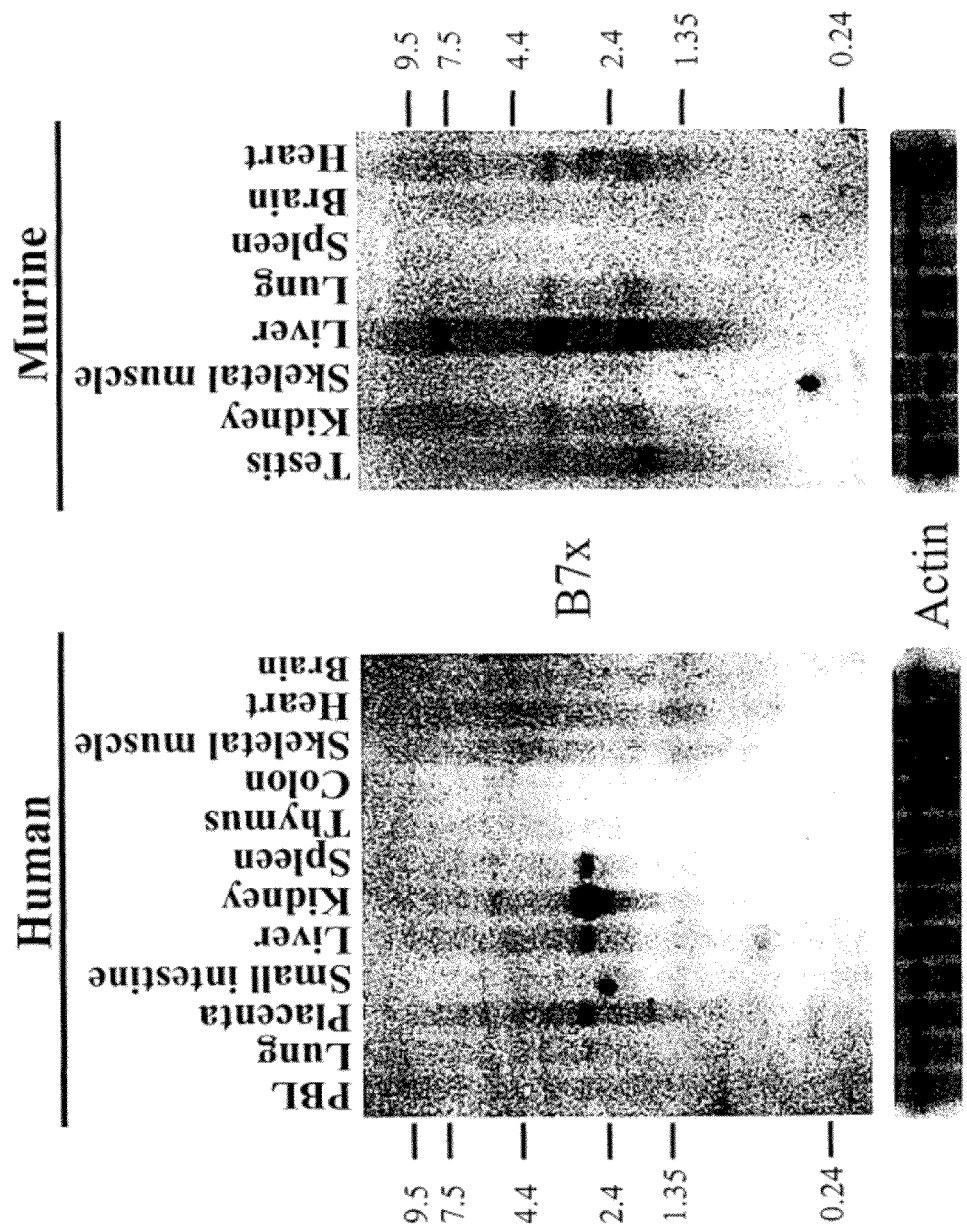
FIG. 7 shows Northern blot analysis of human poly(A) RNA (left panel) and mouse poly(A) RNA (right panel) from a variety of tissues with B7x and actin cDNA probes.
Figure 8:
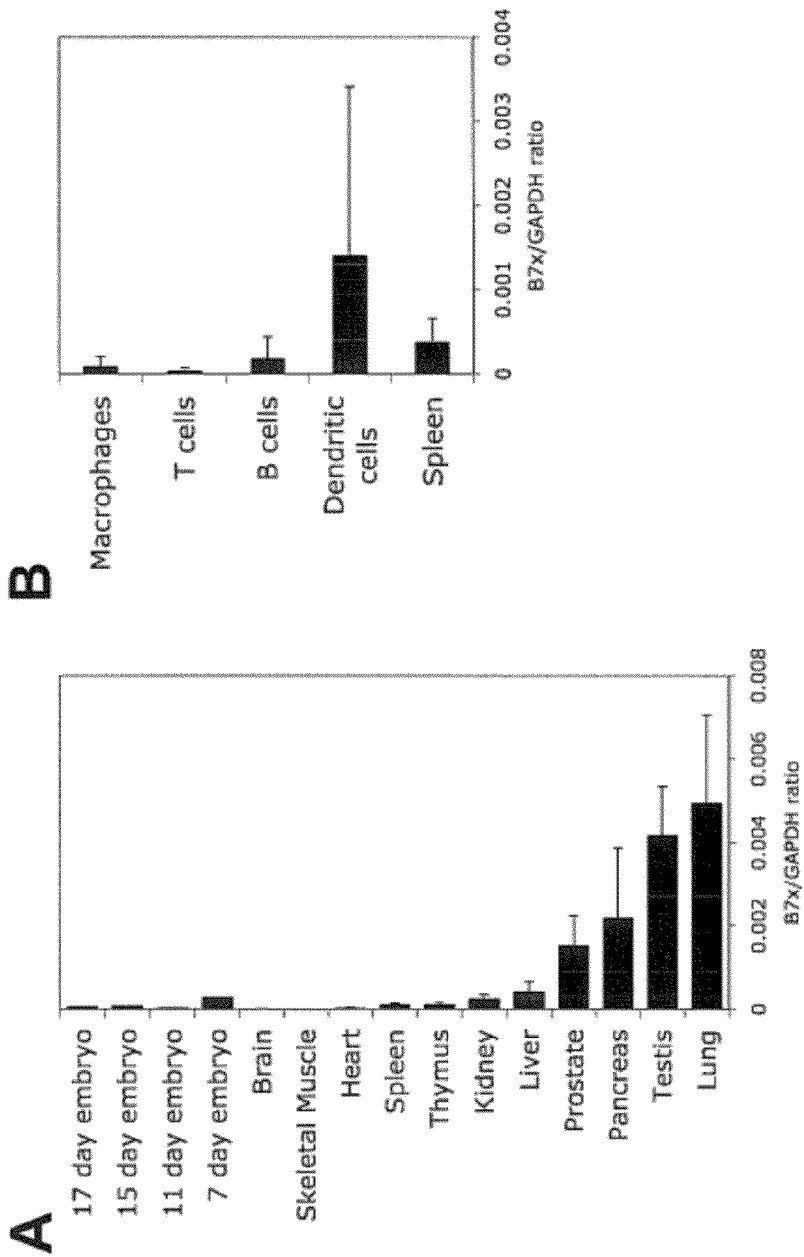
FIG. 8 shows RT-PCR analysis of B7x mRNA expression in a variety of mouse tissues and immune cells. (A) Real time PCR was performed on cDNA from multiple mouse tissues. cDNA from the Clontech Mouse MTC panel I was used as well as cDNA made from tissues dissected out of 2 C57/BL6 mice. The results shown are the average and standard deviation between the 3 mouse cDNA samples. (B) Real time PCR was performed on CD11c+ Denndritic cells, B cells and T cells that were purified from the spleen and compared to the whole spleen. Thioglycolate induced macrophages were purified by overnight adherence and removal of non-adherent cells. The results shown represents the average and standard deviation between 4-10 individual mouse samples.

The expression of B7x mRNA in human and mouse tissues was analyzed by Northern blot hybridization. Human B7x was present in a single 3.2-kb mRNA readily detectable in kidney, liver, spleen and placenta. Mouse B7x had three transcripts of 1.9, 3.5 and 8.2 kb, and was expressed significantly in liver, testis, kidney, lung and heart (FIG. 7). With RT-PCR, B7x mRNA was also detected in mouse spleen, prostate, lymph node, thymus, eye, pancreas, B cells, T cells, macrophages, and dendritic cells. (FIG. 8, and data not shown).

Figure 9:
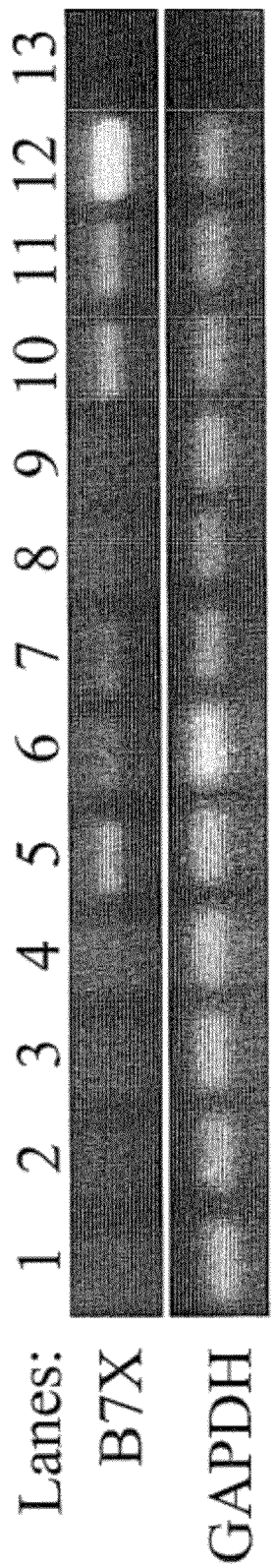
FIG. 9 shows RT-PCR analysis of B7x mRNA expression in a variety of tumor cells. Lanes: 1: EL4, 2:B16BL6, 3: B16F10, 4: Lewis lung carcinoma, 5: TRAMP C2, 6:MC38, 7: SAI/N, 8: SM1, 9: C6VL, 10: DC2.4, 11: CHO cells, 12: CHO cells transfected with B7x gene, 13: no DNA control.

Interestingly, 5 of 8 mouse B7x ESTs located in database searches had been derived from mammary tumors, and 3 of 6 human B7x ESTs originated from ovarian and uterine tumors. To determine whether expression of B7x might be a regular feature of tumors, we used Northern blot analysis to examine a panel of mouse tumors for B7x mRNA expression. Most of the tumor cell lines tested, including NB41A3 (neuroblastoma), P815 (mastocytoma), L1210 (lymphocytic leukemia), R1.1 (T lymphoma), Hepa 1-6 (hepatoma), P19 (teratocarcinoma), M-MSV-BALB/3T3 (fibroblast transformed by Moloney murine sarcoma virus), K-BALB (fibroblast transformed by Kirsten murine sarcoma virus) and RAW264.7 (macrophage tumor) expressed readily detectable B7x transcript (data not shown). In addition, RT-PCR analysis of B7x mRNA expression revealed that B7x is expressed in a variety of tumor cells (FIG. 9).

Figure 10:
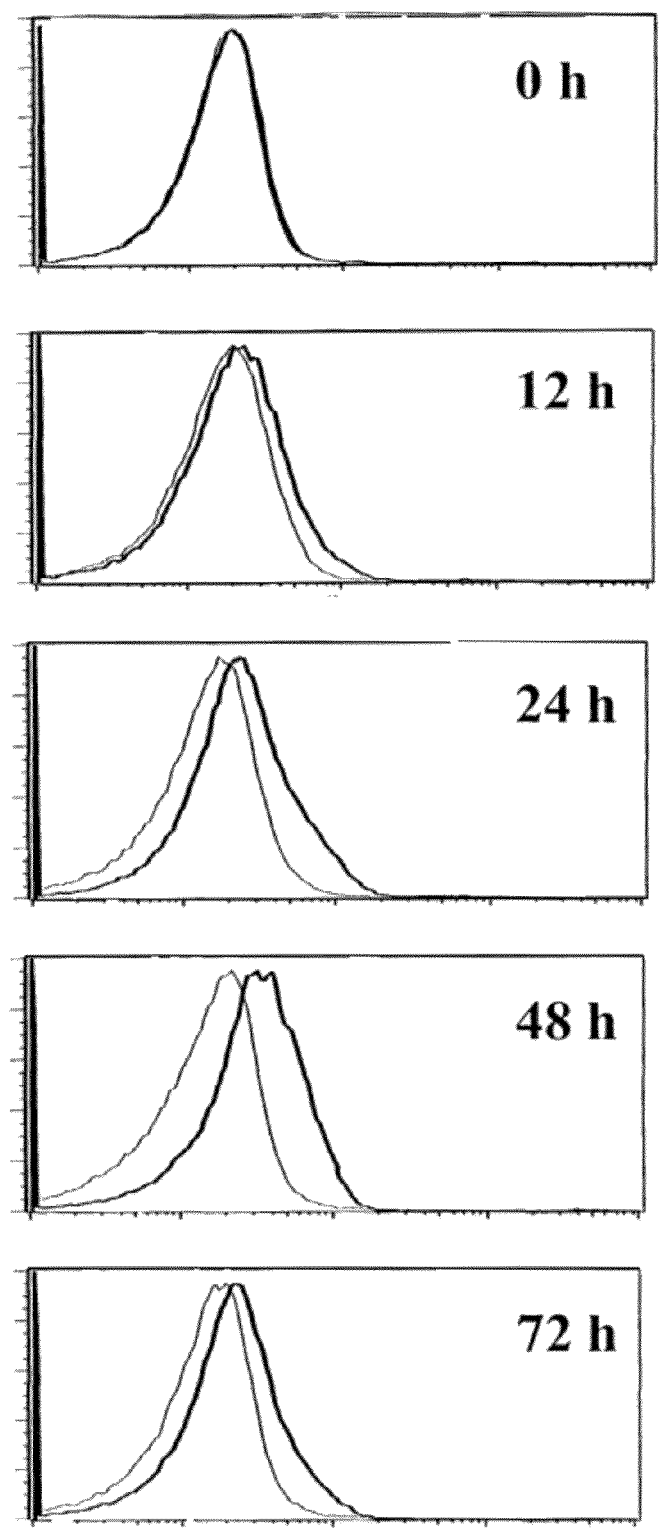
FIG. 10 shows activated CD4+ T cells stained with B7xIg fusion protein (black line) or control mouse IgG1 (gray line).
Figure 11:
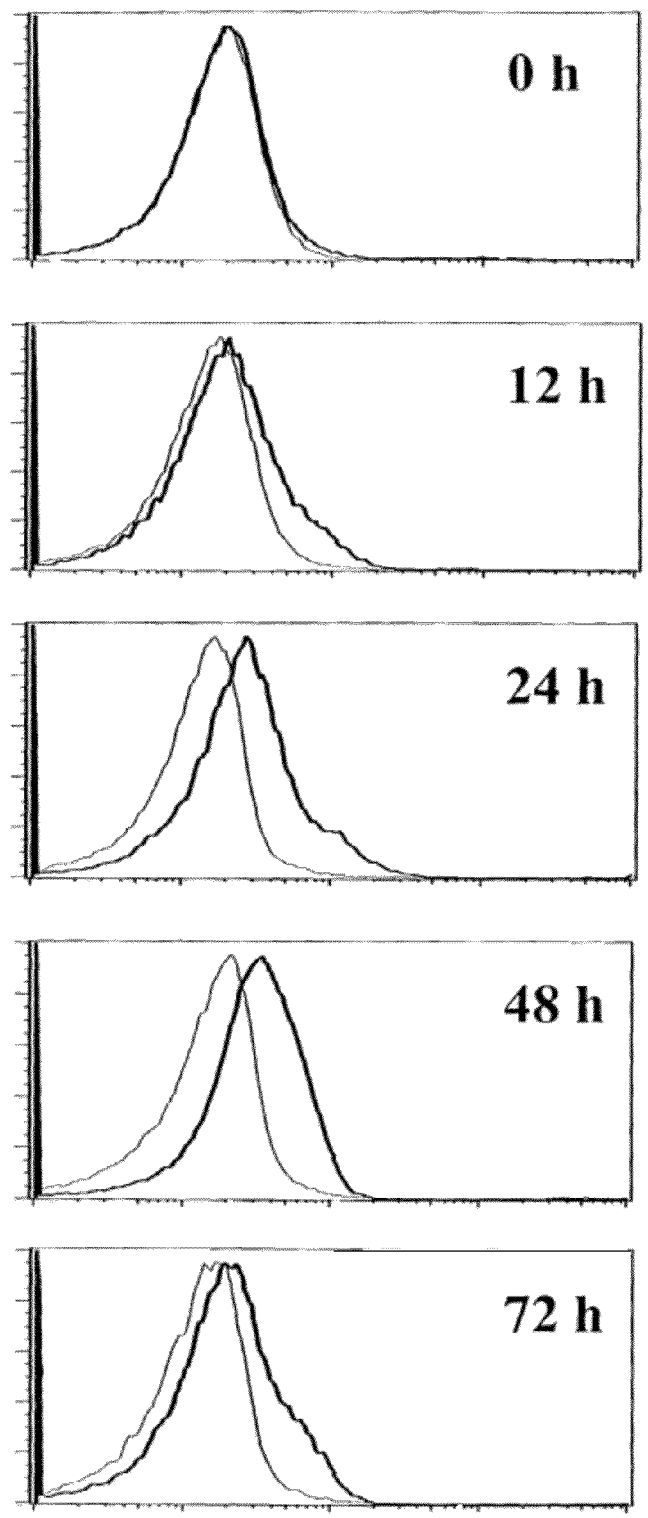
FIG. 11 shows activated CD8+ T cells stained with B7x-Ig fusion protein (black line) or control mouse IgG1 (gray line).

To determine if T cells express a B7x counterreceptor, we performed flow cytometric analyses with a B7xIg fusion protein prepared by linking the extracellular domain of B7x to the CH2-CH3 domains of mouse IgG1. Resting T cells did not bind B7x-Ig. However, stimulation of T cells with PMA (50 ng/ml) and ionomycin (1 µg/ml) resulted in rapid acquisition of B7x binding on both CD4 and CD8 T cells within 12 hours of stimulation (FIGS. 10 and 11). These results suggest that a receptor for B7x is rapidly induced on both CD4 and CD8 T cells in response to stimulation.

Having determined that T cells express a counter-receptor for B7x, we next examined the possibility that this receptor might be one of the T cell surface molecules know to bind other B7 family members. B7xIg failed to bind to transfected 293 cells expressing high levels of CD28, CTLA-4, ICOS, or PD-1 (FIG. 12). Thus, B7x binds to an activation-induced counter-receptor on T cells that is distinct from the known CD28 family members.

Example 2

B7x Inhibits T Cell Activation Processes

Figure 14:
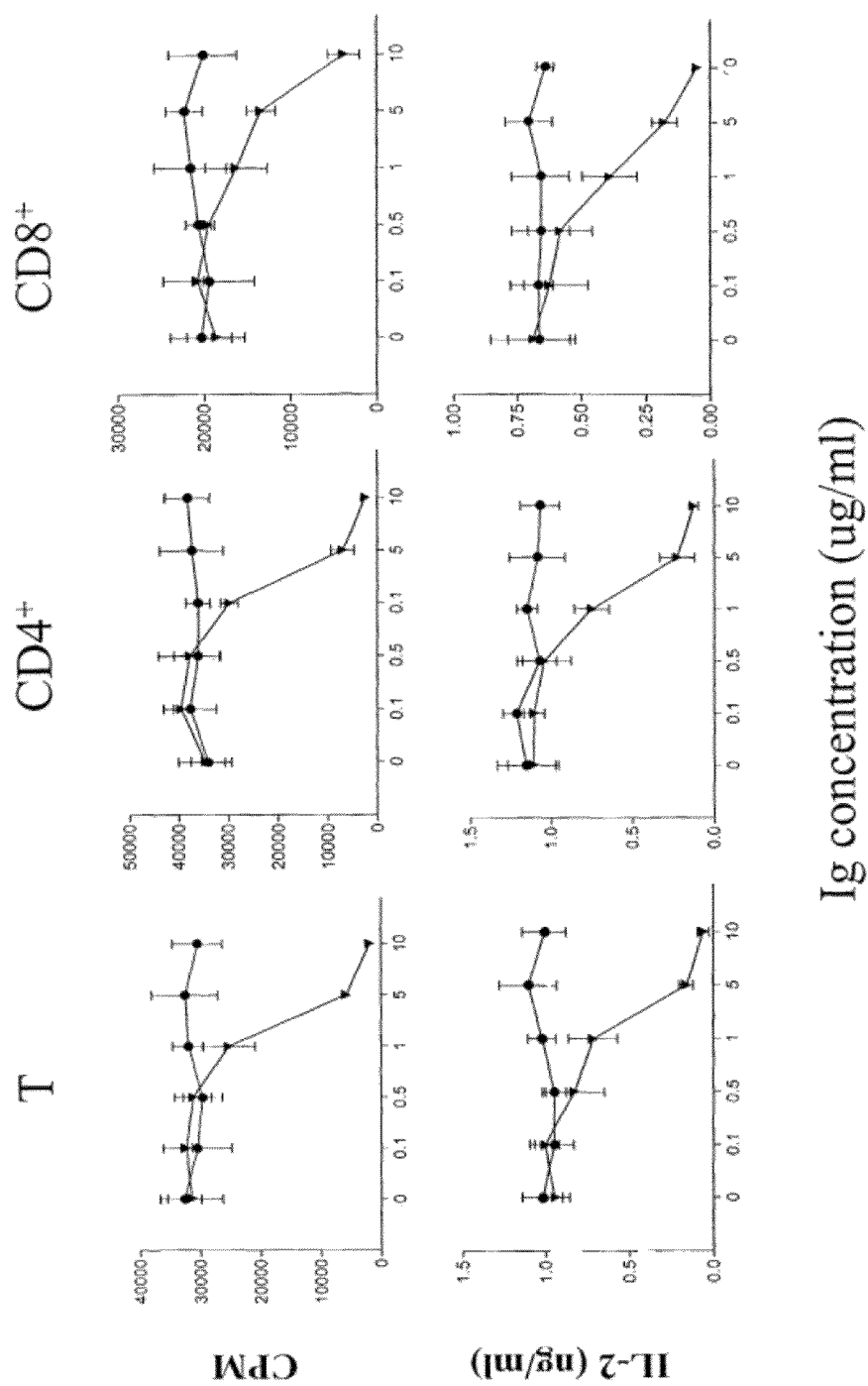
FIG. 14 is a series of graphs representing the results from experiments in which murine T cells, and T cell subsets (CD4+ and CD8+) were stimulated with plate-bound anti-CD3 and varied amounts of plate-bound B7x-Ig (▼) or control Ig (●). IL-2 production and $^{3}$H-thymidine incorporation were measured.
Figure 15:
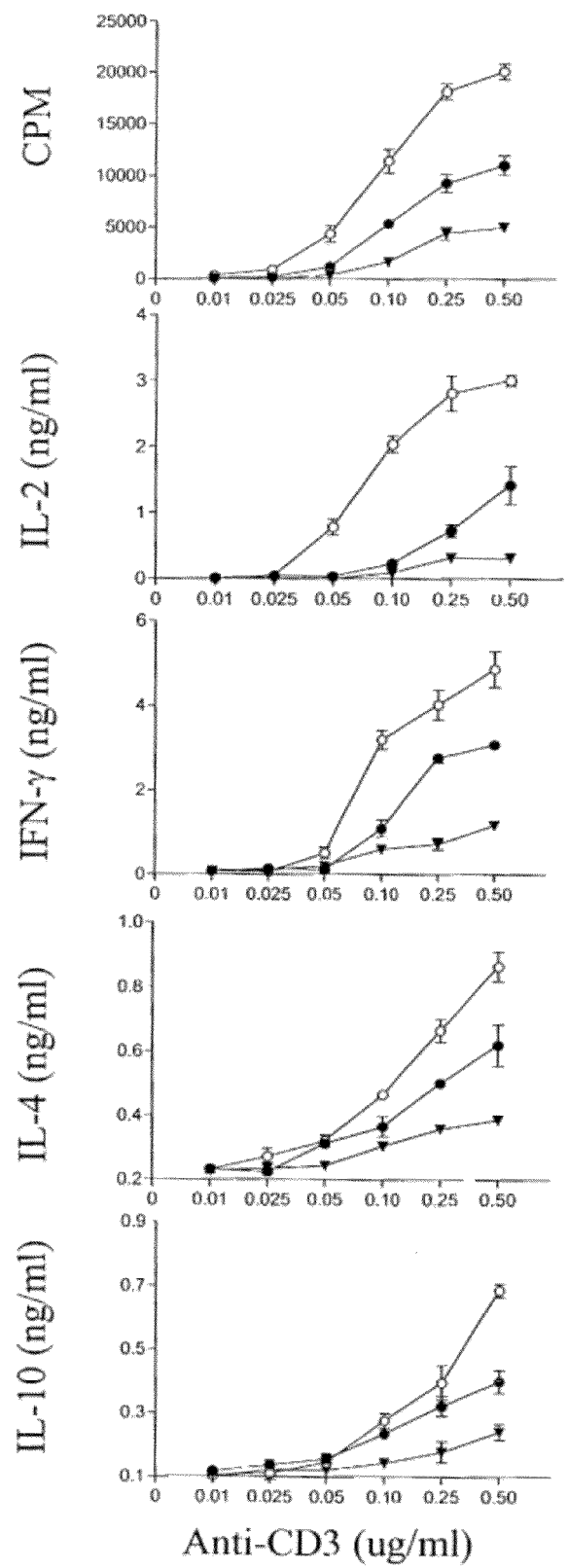
FIG. 15 is a series of graphs representing the results from experiments in which purified T cells were stimulated with varied amounts of plate-bound anti-CD3 and CHO transfectants expressing GFP (●), B7.2 (○) or B7x (▼ The production of IL-10, IL-4, IFN-.gamma., and IL-2, and the incorporation of and $^{3}$H-thymidine were measured.
Figure 16:
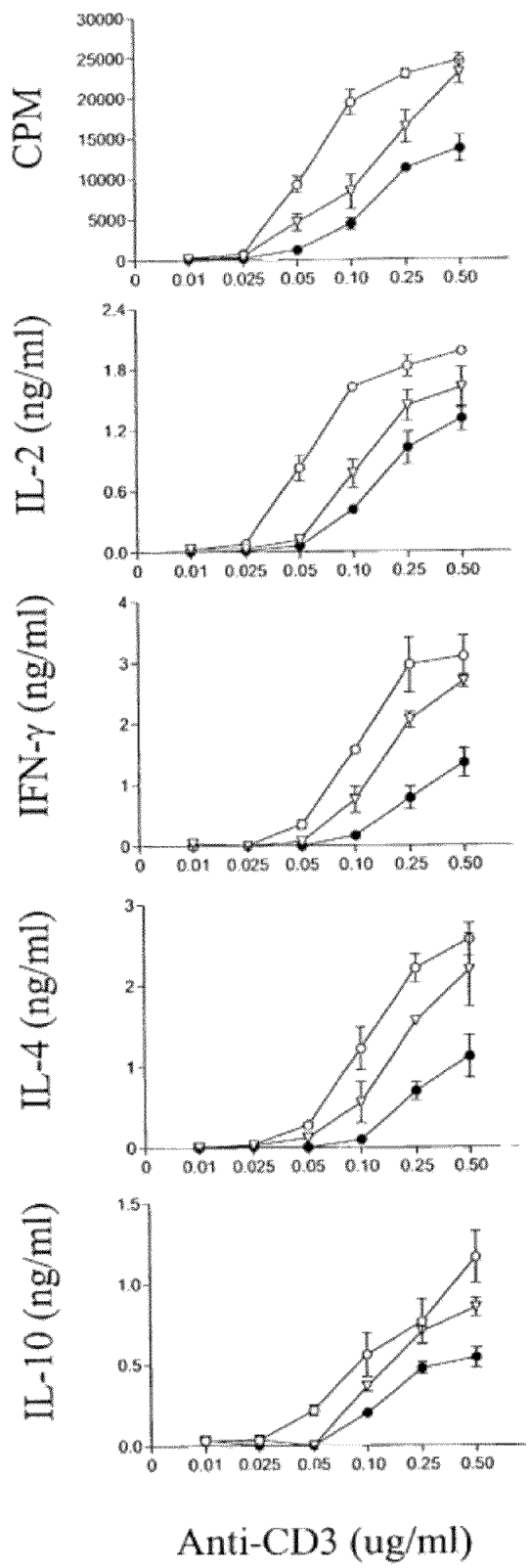
FIG. 16 is a series of graphs representing the results from experiments in which murine T cells were stimulated with varied amounts of plate-bound anti-CD3 and CHO transfectants expressing GFP (●), B7.2 (○) or B7x/B7.2 (▼). The production of IL-10, IL-4, IFN-.gamma., and IL-2, and the incorporation of and $^{3}$H-thymidine were measured.

Initial experiments used purified T cells activated with plate-bound anti-CD3 in the presence of different amounts of immobilized B7xIg. B7xIg decreased proliferation and IL-2 production in a dose-dependent fashion. Additional experiments with purified T cell subsets showed that B7xIg inhibited both CD4 and CD8 T cell responses (FIG. 14). We next employed a conventional costimulation assay. Purified T cells were activated with different amounts of plate-bound anti-CD3 in the presence of CHO transfectants expressing either GFP, B7.2 or B7x. As expected, T cells stimulated in the presence of B7.2/CHO exhibited enhanced proliferation and cytokine production compared to control GFP/CHO. In contrast, B7x/CHO significantly reduced T cell proliferation and cytokine production (FIG. 15). In order to determine the effect of B7x on T cell activation in the face of costimulation, we also used CHO cells which expressed B7.2 or coexpressed B7.2 and B7x. The presence of B7x resulted in a partial inhibition of proliferation and cytokine production by B7.2-costimulated T cells, an effect that was more pronounced at lower levels of anti-CD3 (FIG. 16). Together these results show that B7x can strongly inhibit TCR-mediated T cell proliferation and cytokine production, even in the presence of CD28-mediated costimulation.

Example 3

B7x Limits the Number and the Division Rate of T Cells that Enter Cell Cycle

Having determined that B7x has a potential counter-receptor on T cells and that the interaction of B7x with its receptor leads to a dramatic inhibition of T cell activation, we further investigated the mechanism of B7x action. T cells were labeled with carboxyfluorescein diacetate succinimidyl ester (CSFE) and stimulated with various CHO transfectants with or without plate-bound anti-CD3. Cells were harvested on day 4 and stained for CD4 and CD8 expression. B7x-mediated inhibition was determined by electronically gating on CD4+ or CD8+ T cells populations and measuring CFSE fluorescence intensity (FIGS. 17 and 18). T cells did not divide when incubated with GFP/CHO only. When stimulated with anti-CD3 and GFP/CHO, T cells went through at least 7-8 divisions, with most CD4+ and CD8+ T cells dividing more than 2 times. However, when T cells were incubated with anti-CD3 and 87x/CHO, they were limited to 3-4 divisions. Further, only about 1% of T cells did not divide when stimulated with anti-CD3, whereas 31.4% of CD4+ and 34.3% of CD8+ T cells could not divide in the presence of B7x. These differences in the number of divisions as well as the percentage of non-dividing cells indicate that the interaction of B7x and its receptor on T cells leads to decreased proliferation by limiting the number and the division rate of both CD4+ and CD8+ T cells that enter cell cycle.

Further Description of FIGS. 14-18

FIG. 14: T cells, and T cell subsets (CD4+ and CD8+) from BALB/c mice were stimulated with plate-bound anti-CD3 (0.25 mg/ml for CD4+ and total T cells; 2 ug/ml for CD8+ T cells) and plate-bound B7x-Ig (▼) or control Ig (•) (FIG. 14). IL-2 production and $^3$H-thymidine incorporation were measured. The results revealed that B7x inhibits TCR-mediated T cell responses, particularly cytokine production and proliferation. Error bars in FIG. 14 indicate standard deviation of triplicate cultures. The data presented in FIG. 14 are representative of three independent experiments.

FIG. 15: Purified T cells were stimulated with plate-bound anti-CD3 and CHO transfectants expressing GFP (•), B7.2 (O) or B7x (▼) (FIG. 15). Aliquots of supernatants were collected at 48 h after initiation of cultures and cytokines (IL-10, IL-4, IFN-γ, and IL-2) measured by ELISA, and cell proliferation was measured after 72 h with [$^3$H]thymidine incorporation. The results reveal that B7x inhibits TCR-mediated T cell responses, particularly cytokine production and proliferation. The error bars in FIG. 15 indicate standard deviation of triplicate cultures. The data in FIG. 15 are representative of five independent experiments.

FIG. 16: T cells purified from BALC/c mice were stimulated with plate-bound anti-CD3 and CHO transfectants expressing GFP (•), B7.2 (○) or B7x/B7.2 (▼). The production of IL-10, IL-4, IFN-γ, and IL-2, and the incorporation of and 3H-thymidine were measured (FIG. 16). Aliquots of supernatants were collected at 48 h after initiation of cultures and cytokines measured by ELISA. Proliferation was measured after 72 h with [31-lithymidine incorporation. The error bars in FIG. 16 indicate standard deviation of triplicate cultures. The data in FIG. 16 are representative of three independent experiments.

FIG. 17: T cells were labeled with CSFE and stimulated with or without plate-bound anti-CD3 (0.25 mg/ml) and CHO transfectants expressing GFP or B7x. On day 4, cells were harvested, stained with PE-anti-CD4 and analyzed by flow cytometry (FIG. 17). The results reveal that B7x limits the number and division rate of T cells that enter the cell cycle. Percentages in FIG. 17 refer to fraction of cells in the non-dividing peak or divided more than 2 times. The data in FIG. 17 are representative of three independent experiments. These data show that B7x limits the number and division rate of CD4+ T cells that enter the cell cycle.

FIG. 18: T cells were labeled with CSFE and stimulated with or without plate-bound anti-CD3 (0.25 mg/ml) and CHO transfectants expressing GFP or B7x. On day 4, cells were harvested, stained with PE-anti-CD8 and analyzed by flow cytometry. Percentages refer to fraction of cells in the non-dividing peak or divided more than 2 times. These data are representative of three independent experiments. These data show that B7x limits the number and division rate of CD8+ T cells that enter the cell cycle.

General Materials and Methods for Examples 4-9

Plasmid Constructions.

Myc-tagged BTLA constructs were prepared as follows. The open reading frame of mBTLAs was amplified from a colony obtained from screening a DO11.10 TH1 cDNA library with primers J10-RV1-Bgl2 (5'-AGCTCTGAA-GATCTCTAGGGAGGAAG-3') (SEQ ID NO:28) and J10-Xho1 (5'.-CATGCTCGAGGAAGGICCAGACAGAGG-TATTG-3'.) (SEQ ID NO:29). The product was digested with Bg/II and XhoI and cloned into the IRES-GFP-RV retrovirus48 at the BglII and XhoI sites to produce mBTLAs-RV. The N-terminal Myc-tagged version of mBTLAs (Myc3-mBTLAs-RV) contains a triple Myc tag inserted downstream of the signal peptide. To produce this construct, a PCR product containing the mBTLA signal sequence and 3. overhang homologous to the Myc tag was prepared with mBTLAs-RV as the template and primers J10-RV1-Bgl2 and J10-A2 (5. GTTCAGATCCAAGGATGCTCCAGAGGCCC-3.) (SEQ ID NO:30). This PCR product was annealed to a second PCR product comprising three copies of the Myc epitope with 5. and 3. overhangs homologous to the N- and C-terminal portions of BTLA, respectively, which had been amplified from the triple Myc/Bluescript template with primers J10-A3 (5. GAGCATCCTTGGATCTGAACAAAAGCTGATTA-3.) (SEQ ID NO:31) and J10-A4 (5.-CTTTCTCACA-GAGCTCGTACAGGTCCTCT-3.) (SEQ ID NO:32). The triple Myc/Bluescript template contains 'anchor' sequences 5. (GS) and 3. (YEL) to the Myc3 coding sequence, which are included in the final Myc-tagged mBTLA protein. We then amplified the two annealed pieces with primers J10-RV1-Bgl2 and J10-A4. This product was annealed to a third PCR product containing a 5. Myc homologous tail and the C-terminal portion of BTLA amplified from the template mBTLAs-RV with primers J10-A5 (5.-GTACGAGCTCTGT-GAGAAAGCTACTAAGAGG-3.) (SEQ ID NO:33) and J10-Xho1, and the full-length chimeric cDNA was amplified with primers J10-RV1-Bgl2 and J10 Xho1. The resulting product was digested with Bg/II and XhoI and ligated into the Bg/II and XhoI sites of IRES-GFP-RV to yield Myc3-mBTLAs-RV.

To produce the N-terminal Myc-tagged version of mBTLA (Myc3-mBTLARV), primers J10-RV1-Bgl2 and J10-A4 were used to amplify the signal sequence linked to the triple Myc epitope from template Myc3-mBTLAs-RV. A second PCR product was amplified with primers J10-A5 and J10 Xho1 and the template mJ11W1. The two PCR products were annealed and amplified with primers J10-RV1-Bgl2 and J10 Xho1, digested, and ligated into the retroviral vector to produce Myc3-mBTLA-RV. A further modification was made by using the Quick Change mutagenesis kit (Stratagene) to convert a cysteine downstream of the Myc tag to alanine to mimic more accurately the predicted signal sequence processing in which this cysteine would be removed (SignalP V2.0). cyt-Myc3-mBTLA-RV was generated using Quick Change mutagenesis of Myc3-mBTLA-RV with the primers mJ11 trunc top (5. TGATATTCCATAAAC CTGCCACTGAGC-CAG-3.) (SEQ ID NO:34) and mJ11 trunc bottom (5.-TG-GCAGGTTTATG GAATATCAACCAGGTTAGTG-3.) (SEQ ID NO:35). mBTLA-Myc2-RV, which expresses mBTLA with two C-terminal Myc epitopes, was generated by 'splicing by overlap extension' (SOEing) together two PCR products (generated from primers J10-RV1-Bgl2 and 3. mj11 Myc tail (5.-GCTTTTGTTCACTTCTCACA CAAATGGATGC-3.) (SEQ ID NO:36) with template mJ11W1, and primers 5. mj11 Myc tail (5. TGAGGAGT-GAACAAAAGCTGATTAGCGAAG-3.) (SEQ ID NO:37) and new 3. Xho Myc tail (5.-CCGCTCGAGTCCTACAG-GTCCTCTTC-3.) (SEQ ID NO:38) with template triple Myc/Bluescript) with primers J10-RV1-Bgl2 and new 3. XhoI Myc tail and Pfu polymerase. After digestion with BglII and XhoI, the PCR product was ligated into the retroviral expression vector Tb-lym-GFP RV49, which had been digested with BglII and XhoI, to generate mBTLA-Myc2-RV.

The N-terminal Myc-tagged version of hBTLA containing a triple Myc tag inserted downstream of the signal peptide (Myc3-hBTLA-RV) was prepared similarly. Three separate PCR products were generated using the following primers and templates: 5. Bgl2 hj11 (5'-GAAGATCTGCAGGAAAT-GAAGACATTGCCT-3'.) (SEQ ID NO:39) and 3. Myc/hj11 bottom (5' TCAGCTTTTGTTCCCCATGGATGTTCCA-GATGTCC-3') (SEQ ID NO:40) with hj11#14u; 5. hj11/Myc top (5.-CATCCATGGGGAACAAAAGCTGATTAGC-GAAGAG-3.) (SEQ ID NO:41) and 3. hj11/Myc bottom (5.-CACATGATTCTTTCAGGTCCTCT-TCGCTAATCAGC-3.) (SEQ ID NO:42) with triple Myc/Bluescript; and 5. Myc/hj11 top (5.-GAGGACCTGAAA-GAATCATGTGATGTACAGCTTTA-3.) (SEQ ID NO:43) and 3. Xho hj11 (5.-CCGCTCGAGTTGGAGTCAGAAA-CAGACTTAAC-3.) (SEQ ID NO:44) with hj11#14u. These PCR products were sequentially annealed and amplified, and cloned into tb-lym-GFP-RV, which had been digested with BglII and XhoI. hBTLA containing three carboxy-terminal Myc epitopes (hBTLA-Myc3-RV) was generated by SOEing together two PCR products (from primers 5. Bgl2 hJ11 and 3. hJ11 Myc tail (5.-TGAGGAGTGAACAAAAGCTGATT-AGCGAAG-3.) (SEQ ID NO:45) with template hJ11#14u, and primers 5. hj11 Myc tail (5.-TGAGGAGTGAA-CAAAAGCTGATTAGCGAAG-3.) (SEQ ID NO:46) and new 3. Xho Myc tail with template triple Myc/Bluescript) with primers 5. Bgl2 hJ11 and new 3. Xho Myc tail and Pfu polymerase. After digestion with Bg/II and XhoI, the PCR product was ligated into retroviral expression vector Tb-lym-GFP-RV49, which had been digested with BglII and XhoI, to generate hBTLA-Myc3-RV. Embryonic stem cells (MC50) were a gift of R. Schreiber.

Tyrosine Mutations.

Single tyrosine-to-phenylalanine mutations of hBTLA-Myc3-RV were produced using Quick Change mutagenesis and Pfu polymerase (Stratagene) with the following oligonucleotide pairs: Y226F top2 (5.-GAAACTGGAATTTAT-GATAATGACCCTGACCTTTG-3.) (SEQ ID NO:47) and Y226F bot (5.-GGGTCATTATCAAAAATTCCAGTTTCT-GATAGCAG-3.) (SEQ ID NO:48); Y257F top2 (5.-ACCAG-GCATTGTTTATGCTTCCCTGAACCATTCTG-3.) (SEQ ID NO:49) and Y257F bot (5. AGGGAAGCAAAAACAAT-GCCTGGTTTGT-3.) (SEQ ID NO:50); Y282F top2 (5.-GCACCAACAGAATATGCATCCATATGTGTGAGG-3.) (SEQ ID NO:51) and Y282F bot (5.-ATATGGATGCAAAT-TCTGTTGGTGCTTCTTTTA-3.) (SEQ ID NO:52). We produced double and triple tyrosine-to-phenylalanine mutations of hBTLA-Myc3-RV by using the oligonucleotide pair Y257F top2 and Y257F bot first with the Y226F-mutated hBTLA-Myc3-RV template to produce Y226F/Y257F and then with the Y282F-mutated template to produce Y257F/Y282F. The oligonucleotide pair Y282F top2 and Y282F bot was used with the Y226F-mutated template to produce Y226F/Y282F, and with the Y226F/Y257F-mutated template to produce Y226F/Y257F/Y282F.

Cell Culture and Expression Analysis.

Activation of DO11.10 TCR transgenic T cells and retroviral infections, northern analysis and immunoblotting were done as described. We prepared tissue and cellular RNA with the RNeasy Midi kit (Qiagen). A 20 stock of pervanadate was prepared 5 min before use by diluting 12.5 µl of 1 M NaVO4 and 4 µl of 30% $H_2O_2$ to 600 µl in distilled water. The Opteia Mouse IL-2 set (PharMingen) was used to measure for IL-2 by enzyme-linked immunosorbent assay (ELISA).

Immunoblotting and Analysis of N-Linked Glycosylation.

To analyze the glycosylation status cells ($15 \times 10^6$ per ml) were lysed in Triton X-100 lysis buffer (25 mM HEPES (pH 7.5), 0.15 M NaCl, 1% Triton (v/v), 1 mM pervanadate, 1 µg/ml of leupeptin, 1 µg/ml of pepstatin, 1 µg/ml of aprotinin and 1 mM phenyl methylsulfonyl fluoride) for 30 min at 4° C. and centrifuged at 14,000 g for 10 min. Extracts from $15 \times 10^6$ per ml cells were immunoprecipitated with 1 µg of monoclonal antibodies to Myc (clone 9E10; Santa Cruz) and 20 µl of a 1:1 slurry of protein G-Sepharose (PGS) (Pharmacia). After being washed three times in Triton lysis buffer, the pellets were boiled for 10 min in 10 µl of PNGase denaturing buffer (NEB). After centrifugation to remove PGS, eluted proteins were transferred to PCR tubes containing 1 µl of 10% Nonidet P-40 (NP-40) and 1 µl of 10. G7 buffer (NEB), divided into two 6-µl aliquots, and treated without or with 1 µl of PNGase F (NEB) for 1 h at 37° C. We boiled samples with 6 µl of 2. SDS-PAGE sample buffer and resolved them on 10% polyacrylamide gels. The proteins were transferred to nitrocellulose, blocked in 3% bovine serum albumin (BSA) in TBS-T buffer, blotted with rabbit anti-Myc (Santa Cruz) and horseradish peroxidase (HRP)-conjugated goat anti-rabbit IgG (Jackson), and analyzed by enhanced chemiluminescence (ECL). To analyze the phosphorylation status cells were treated with 1 mM pervanadate for 2 min at 37° C., placed on ice for 1 min, lysed in an equal volume of 2.1% Triton X-100 lysis buffer for 30 min and centrifuged for 10 min at 8,000 g. Extracts from $15 \times 10^6$ cells were immunoprecipitated using 1 µg of anti-Myc (clone 9E10) and PGS. Blots were first analyzed for phosphotyrosine (pTyr) using HRP-conjugated (clone 4G10, Upstate Biotechnology), and then stripped and reanalyzed using rabbit anti-Myc and HRP-conjugated goat anti-rabbit IgG.

TCR Crosslinking.

To analyze the induction of tyrosine phosphorylation and association with SHP-1 and SHP-2 on TCR crosslinking, we infected D011.10 hybridoma T cells with GFP-RV48 or Myc3-mBTLAs-RV and purified them by sorting. Cells were incubated with 4 µg/ml of hamster anti-CD3ε (clone 145-2C11, PharMingen) and 2 µg/ml of anti-Myc for 30 min at 4° C., and crosslinked with 100 µg/ml of prewarmed goat anti-mouse IgG (GaM; Caltag) for various times, as indicated. We used fluorescence-activated cell sorting (FACS) to confirm the cross-reactivity of goat anti-mouse IgG with hamster anti-CD3ε. As a positive control for phosphorylation, some cells were incubated with 1 mM pervanadate for 2 min at 37° C. Cells were lysed in RIPA buffer, and 1 ml of lysates from $25 \times 10^6$ cells were immunoprecipitated with 2 µg of anti-Myc (9E10). We used the following antibodies to analyze the immunoprecipitates: anti-pTyr (RC2OH, Transduction Laboratories), polyclonal rabbit anti-Myc (A-1 4, Santa Cruz), rabbit anti-SHP-2 (C-1 8, Santa Cruz), rabbit anti-SHP-1 antibody (C-19, Santa Cruz) and anti-Myc (9E10). To measure the effect of crosslinking on IL-2 production, 3.104 D011.10 cells expressing GFP-RV, Myc3-mBTLAs-RV or Myc3-mBTLA-RV were stimulated with 1 µg/ml of immobilized anti-CD3ε in combination with various concentrations of immobilized polyclonal rabbit anti-Myc or 50 ng/ml of PMA plus 1 µM ionomycin. Culture supernatants of triplicate cultures were collected after 24 h, and the IL-2 concentration was determined by ELISA.

FACS Analysis.

Human IgG1 and goat anti-human PE were gifts of M. Cella (Washington Univ., St. Louis, Mo., USA). The construct for the B7h-Ig fusion protein, a gift of W. Sha (Univ. California Berkeley), and the cDNA encoding the fusion protein were inserted into the GFP-RV retroviral vector, and the retrovirus was used to infect J558 cells. We purified fusion protein from infected J558 supernatant with His-Bind resin (Novagen). B7.1-Ig, B7.2-Ig, PD-L1-Ig and PD-L2-Ig fusion proteins (Fc portion; human IgG1 isotype) were obtained from R&D Systems. All analyses were done on a FACSCalibur. To measure the surface expression of BTLA, Bjab cells were infected with amphotrophic retrovirus prepared in Phoenix A packaging cells to express empty vector, Myc3-mBTLA-RV, .cyt-Myc3-mBTLA-RV and Myc3-mBTLAs-RV. Expression of the Myc epitope on GFP¬ipositive cells was assayed on a FACScalibur with rabbit anti-Myc polyclonal serum (Santa Cruz) and PE-conjugated goat $F(ab)_2$ anti-rabbit IgG (Jackson Research Laboratories).

Antibody Responses.

Eight-week-old littermate wild-type, Btla+/. and Btla./. mice on a pure 129SvEv background (n=5) were injected intraperitoneally with 100 µg of NP17-KLH (Biosearch Technologies) in alum (Pierce) on days 0 and 14. Sera was collected on day 28, and the titers of anti-NP were determined by ELISA using NP25-BSA (Biosearch Technologies) for antibody capture and the SBA Clonotyping system/HRP kit for IgG subclass-specific ELISA (Southern Biotech).

In Vitro Responses of BTLA-Deficient Lymphocytes.

T and B cells from wildtype or BTLA-deficient mice were purified by cell sorting using fluorescein isothiocyanate (FITC)-conjugated anti-CD4 (Caltag), FITC-conjugated anti-CD8α (PharMingen) or phycoerythrin (PE)-conjugated anti-B220 (PharMingen). Cells ($5 \times 10^5$ per ml) were stimulated with various concentrations of plate-bound anti-IgM (Affinipure $F(ab)_2$ fragment goat anti-mouse IgM 115-006-075, Jackson ImmunoResearch), LPS (serotype 055:B5, Sigma), concanavalin A or plate-bound anti-CD3e (PharMingen, 145-2C11). Cell proliferation was measured after 48 h by pulsing with [$^3$H]thymidine for 16 h.

Production and Interaction of B7x-Ig.

In the public databases we identified a B7 homolog, B7x, that was conserved in mouse (accession code XP_143450.2 and AAH32925.1), rat (accession code XP_227553.1) and human (accession code NP_078902.1) and was highly conserved in sequence. B7x-Ig was prepared by fusing the coding region of the extracellular domain of B7x to the CH2-CH3 domain of mouse IgG1 and a Myc-His tag in pcDNA4 (a gift of W. Sha, Univ. California Berkeley, Berkeley, Calif., USA). The construct was linearized with BglII and transfected into 293T cells with FuGENE 6 (Roche). Stable transfectants were selected in 1 mg/ml of Zeocin (Invitrogen). To obtain fusion protein, we cultured stable transfectants in serum-free Dulbecco's modified Eagle's medium for 72 h, collected the supernatant and purified B7x-Ig by affinity column chromatography over His-Bind resin (Novagen). The purity of the fusion protein was confirmed by SOS-PAGE and by immunoblotting with antibodies against Myc and mouse IgG. The following reagents were used to measure receptor and B7 ligand interactions: anti-CD4-FITC (Caltag); human IgG1 antibody (Sigma); biotinylated anti-Myc (Santa Cruz); streptavidin-PE (PharMingen); B7.1-Ig, B7.2-Ig, PD-L1-Ig and PD-L2-Ig fusion proteins (Fc portion; human IgG1 isotype; R&D Systems); goat anti-human Fcγ $F(ab)2$PE (Jackson ImmunoResearch); and anti-PD-1-PE (PharMingen).

Example 4

Identification of BTLA

In a previous Affymetrix screen, we identified an anonymous Th1-specific EST. The full-length cDNA of this EST, cloned from a murine cDNA library, predicts a protein with a signal sequence, extracellular V-like Ig domain, transmembrane region and intracellular domain of approximately 100 amino acids (FIG. 19). A homology search identified a single human gene homologue, having a similar domain structure (FIG. 19). Notably, three tyrosine residues within the cytoplasmic domain are contained within three sequence motifs that are conserved between mouse and human, the first, a potential Grb2 interaction site, and the others, ITIM, sequences (FIG. 19). In addition to BTLA, a minor alternatively spliced transcript, BTLAs, was detected by RT-PCR in mouse tissue. BTLAs lacks exon 2, and thus the Ig domain. Additionally, an alternatively spliced human BTLA transcript lacking exon 3, and thus the TM domain, and portions of the cytoplasmic and extracellular domains, was detected.

Methods for Example 4

We used an EST (aa839766) expressed by Th1, but not Th2, cells to screen a Th1 cDNA phage library made in the Lambda ZAP vector (Stratagene) and isolated a partial clone, BTLAs, that lacked an Ig domain. Full length BTLA cDNA, amplified from WEHI cell RNA by RT-PCR with primers J10-3K (5'-TTTGGCCTAAGATGCTGCTA-3') (SEQ ID NO: 53) and J10-7F (5'-CACAGATTGGGTACGACATG-3'.) (SEQ ID NO: 54), was inserted into the GEM-T Easy Vector (Promega) to produce mJ11W1. We obtained additional full-length. BTLA cDNA isolates by screening a second mouse splenocyte cDNA library (Stratagene) using the 5' region of mj11W1 as a probe. Coding sequence and intron-exon boundaries were further determined by sequencing 129SvEv strain bacterial artificial chromosome clones containing the BTLA region (Genome Systems). Some Ig domain sequence polymorphisms occur among mouse strains. Human BTLA cDNA, amplified from Ramos B lymphoma RNA by RT-PCR with primers hJ10 (5'-TTTTCCAT-CACTGATATGTGCAGG-3') (SEQ ID NO: 55) and hJ10 AS (5'-GGTCCCTGTTGGAGTCAGAAAC-3') (SEQ ID NO: 56) based on the Celera human genome assembly, was inserted into the GEM-T Easy Vector to produce hJ11#14u. The Celera database sequence predicted the human BTLA amino acid sequence set forth in FIG. 19 (SEQ ID NO:6), which differs from the BTLA sequence obtained from Ramos cells (SEQ ID NO:8) at amino acid residue 138. This is likely due to polymorphism, given the different human sources. The BTLA sequence as found in Ramos cells (SEQ ID NOs:7 and 8) was used for experiments disclosed herein.

Example 5

Figure 22:
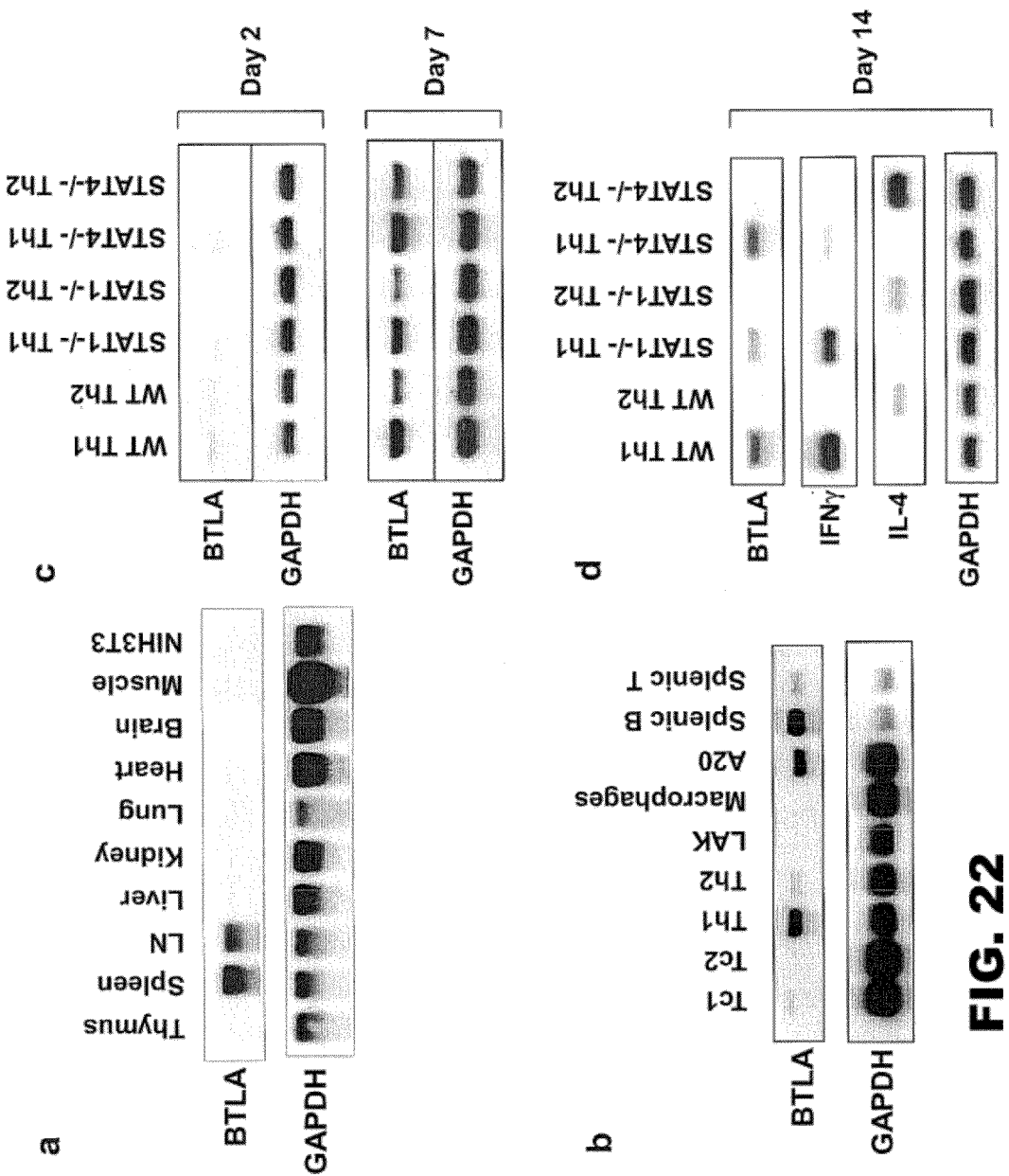
FIG. 22 shows Northern blot analyses of the expression of BTLA. 10 mg of tissue or cellular RNA, or total RNA from the indicated cells, probed with a full-length BTLA or GAPDH cDNA probe.

Expression of BTLA (FIG. 22)

BTLA is expressed strongly in spleen and lymph node tissues, but very weakly or undetectably by several somatic tissues. It is expressed by both splenic B and T cells, with slightly higher levels in the former. Further, we confirmed BTLA is expressed highly in Th1 cells and resting splenic B cells, but weakly in Th2 and Tc2 cells. The A20 B cell line, but not macrophages and LAK cells, also showed BTLA expression. BTLA is expressed weakly on day 2 after primary T cell activation with no difference between Th1 and Th2 conditions. On day 7, BTLA expression is slightly higher in Th1 than Th2 cells, and after a second 2 round of polarization, BTLA expression was much stronger in Th1 than Th2 cells, and slightly diminished in Stat1−/−, but not Stat4−/−, Th1 cells. Thus, BTLA is lymphoid specific and becomes selectively expressed on Th1 cells after full polarization.

Methods for Example 5, Further Description of FIG. 22

Northern blot analysis of an organ blot probed with a full-length BTLA or GAPDH cDNA probe against 10 mg of tissue or cellular RNA prepared with RNeasy Midi kit (QIAGEN). Northern blot analysis was also performed on blots containing total RNA from the indicated cells. Tc1 and Tc2 cells were prepared from in vitro polarized 2C21 TCR transgenic T cells, LAK cells by culturing C57/B6 splenocytes with 1000 U/ml IL-2 for 9 days, and macrophages BALB/c bone marrow derived with L-cell conditioned media and confirmed as >95% Mac-1 positive. Splenic B and T cells were purified to >98% purity by cell sorting.

Example 6

Figure 23A:
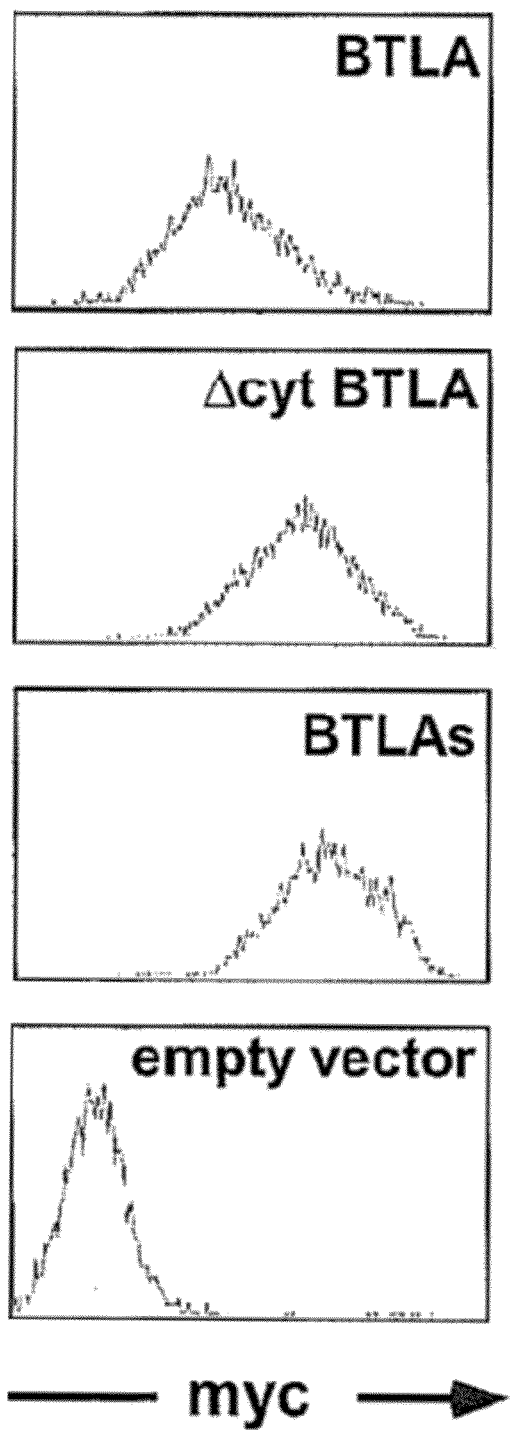
FIG. 23: BTLA is a transmembrane, glycosylated protein that is inducibly tyrosine phosphorylated. (A) FACScalibur analysis of BJAB cells infected with myc-tagged BTLA, Acyt BTLA, BTLAs and empty vector, and stained with anti-myc mAb. (B) Anti-myc Western blot. BJAB cells were infected with myc-tagged mouse BTLA or myc-tagged human BTLA, lysed, and anti-myc immunoprecipitates were treated with peptide N-glycosidase F, where indicated. (C) Anti-phosphotyrosine Western blot. BJAB cells infected with myc-tagged BTLA (WT) or single tyrosine mutant myc-tagged BTLA (Y226F, Y257F, Y282F) were incubated in the absence or presence of pervanadate (VO₄), BTLA proteins were immunoprecipitated with anti-myc, and immunoprecipitates were probed with anti-phosphotyrosine. (D) Anti-phosphotyrosine Western blot. BJAB cells infected with myc-tagged BTLA (WT) or with double or triple tyrosine mutant myc-tagged BTLA (as indicated) were incubated in the absence or presence of pervanadate (VO₄), BTLA proteins were immunoprecipitated with anti-myc, and immunoprecipitates were probed with anti-phosphotyrosine.
Figure 23D:
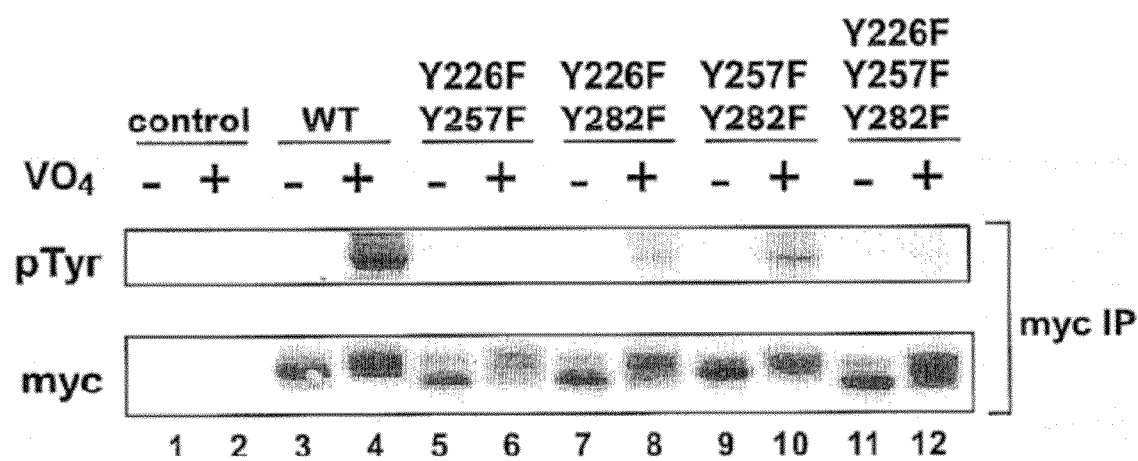

Characterization of BTLA (FIG. 23)

To test whether BTLA is a transmembrane protein, we expressed three forms of myc-epitope tagged BTLA in the BJAB cell line. Cell surface expression of wild type BTLA was detected as predicted. Notably, deleting either the cytoplasmic or Ig domain increased surface expression, suggesting roles for these domains in controlling the level of surface expression, perhaps similar to CTLA-4 surface regulation by its cytoplasmic domain.

Next we confirmed that BTLA is a glycoprotein. Peptide N-glycosidase F treatment reduced the apparent molecular weight of both human and murine BTLA, consistent with N-linked glycosylation sites predicted present between the Ig domain and transmembrane region. The apparent molecular weight of peptide N-glycosidase F treated human and murine BTLA was still higher than predicted by its core amino acid sequence, suggesting additional modifications such as O-link glycosylation. Finally, pervanadate treatment induced tyrosine phosphotyrosine of BTLA. Single phenylalanine mutations of tyrosines 226, 257 or 282 left pervanadate-induced BTLA phosphorylation intact, but the triple tyrosine mutation blocked phosphorylation completely. The Y226FIY257 double mutations severely reduced pervanadate-induced phosphorylation, suggesting tyrosine 282 is either weakly phosphorylated or requires prior phosphorylation at Y226 or Y257. In summary, BTLA is an Ig domain transmembrane glycoprotein that is inducibly tyrosine phosphorylated at conserved cytoplasmic ITIM like motifs.

Further Description of FIG. 23

(a) Transmembrane cell surface expression of BTLA. BJAB cells infected with myc-tagged BTLA, Δcyt BTLA, BTLAs and empty vector were stained with anti-myc mAb (9E10, Santa Cruz) and visualized by phycoerythrin (PE)-conjugated goat anti-mouse IgG (CALTAG). Cells were analyzed on a FACScalibur and gated for GFP+ cells.

(b) Murine and human BTLA contain N-linked oligosaccharides. BJAB cells infected with mouse BTLA or human BTLA were lysed and BTLA proteins were immunoprecipitated with anti-myc Ab (9E10, Santa Cruz). The immunoprecipitates were treated with peptide N-glycosidase F where indicated and analyzed by anti-myc Western blotting.

(c) Tyrosine phosphorylation of BTLA upon pervanadate stimulation. BJAB cells infected with WT or single tyrosine mutants were incubated in the absence or presence of pervanadate for 2 min at 37° C. Cells were lysed and BTLA proteins were immunoprecipitated with anti-myc Ab. The immunoprecipitates were first analyzed using antipTyr (RC2OH) Western blotting (top). Membrane was then stripped and incubated with rabbit anti-myc Ab (bottom).

(d) BJAB cells infected with double or triple tyrosine mutants were analyzed for tyrosine phosphorylation by pervanadate treatment. Samples were prepared similarly as described above.

Example 7

Figure 24G:
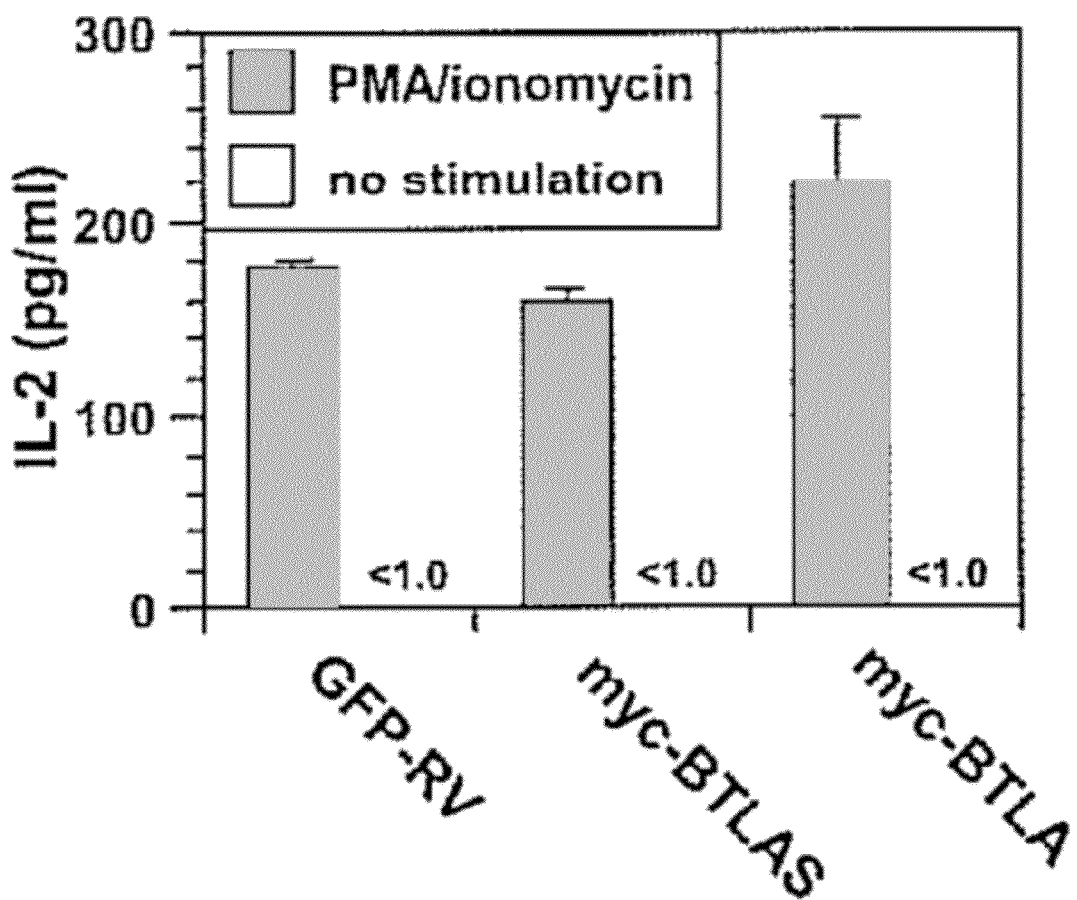
FIG. 24 Inducible association of BTLA with SHP-2. (A) Anti-phosphotyrosine and anti-SHP-2 Western blots. DO11.10 cells with empty vector (GFP-RV), or expressing BTLAs with extracellular myc epitope (myc-BTLAs). Cells were incubated with anti-CD3, anti-myc, or pervanadate as indicated. Cells were treated with goat anti-mouse IgG (GaM) for indicated time. Anti-myc immunoprecipitate was probed with anti-phosphotyrosine and anti-SHP-2 antibody. (B) Anti-phosphotyrosine Western blot. Cells and treatment as described in (A) and indicated. (C) Anti-phosphotyrosine, anti-SHP-1 and anti-SHP-2 Western blots. Cells as described in (A), incubated in the absence (−) or presence (+) of pervanadate. Anti-myc immunoprecipitates and whole cell lysates probed with anti-phosphotyrosine, anti-SHP-1, and anti-SHP-2 antibodies. (D) Anti-myc and anti-SHP-2 Western blots. Cells as described in (A), incubated in the absence (−) or presence (+) of pervanadate. Anti-SHP-2 immunoprecipitates and whole cell lysates probed with anti-myc and anti-SHP-2 antibodies. (E) Anti-myc, anti-SHP-2 and anti-phosphotyrosine Western blots. Jurkat T cells with GFP-RV, or expressing a full length human BTLA containing an N-terminal myc epitope. Cells were treated with pervanadate as indicated. Anti-myc and anti-SHP-2 immunoprecipitates were probed with anti-myc, anti-SHP-2 and anti-phosphotyrosine. (F) DO11.10 cells expressing control vector (GFP-RV), myc-BTLAs (short isoform), or myc-BTLA were stimulated with anti-CD3 plus the indicated amounts of anti-myc, and IL-2 production was determined by ELISA. (G) DO11.10 cells expressing control vector (GFP-RV), myc-BTLAs (short isoform), or myc-BTLA were stimulated with PMA plus ionomycin as indicated.

Inducible Association of BTLA with SHP-2 (FIG. 24)

Sequences surrounding Y226 suggest potential Grb2 interaction, Y257 an ITIM motif, and Y282 are similar to the ITSM motif in PD-113 and SLAM (CD150/IPO-3). To evaluate such potential interactions, we developed a system of inducible BTLA phosphorylation. An extracellular myc-tagged BTLAs was expressed stably in the D011.10 hybridoma. In similar strategy used for crosslinking PD-1 with the BCR complex, we crosslinked BTLA with the TCR using antibodies to CD3 and the myc epitope, followed by secondary crosslinking. With this approach, we detected BTLA tyrosine phosphorylation that was dependent upon secondary crosslinking and not induced with only CD3 or anti-myc antibodies alone and was specific to BTLA-transfected cell.

BTLA tyrosine phosphorylation was time dependent, appearing rapidly and optimal at 2-3 minutes, and extinguished by 10 minutes after secondary crosslinking. We surveyed various signaling molecules for co-immunoprecipitation with myc-BTLA. Notably, we found strong association with SHP-2 that occurred with the same time course as BTLA phosphorylation that was dependent upon co-crosslinking. Since SHP-2 association with BTLA was also induced by pervanadate, this condition was used to further examine SHP-2/BTLA association. Pervanadate treatment induced.

BTLA tyrosine phosphorylation, and SHP-2 was co-precipitated only with phosphorylated BTLA. In anti-SHP-2 immunoprecipitations, BTLA co-precipitates only in pervanadate treated cells, and not in untreated cells.

Finally, we confirmed this inducible SHP-2 association occurs for human BTLA. A myc-tagged human BTLA was expressed in the human T cell line Jurkat. Immunoprecipitated myc-hBTLA co-precipitated with SHP-2 only in pervanadate treated cells, and was specific to myc-hBTLA expression. Likewise, immunoprecipitation with anti-SHP-2 led to the coprecipitation of myc-BTLA only in pervanadate treated cells. Under these conditions, we did not detect specific co-immunoprecipitation of BTLA with Grb2, SHIP, or SHP-1.

Crosslinking BTLA with TCR attenuated IL-2 production in a T cell hybridoma. Myc-tagged BTLA and BTLAs was stably expressed in D011.10 hybridoma T cells. The control D011.10 hybridoma infected with GFP-RV showed anti-CD3-induced IL-2 production that was not affected by plate-bound anti-myc antibody. In contrast, IL-2 production by myc-BTLA expressing D011.10 cells showed inhibition by plate-bound anti-myc antibody that was dose-dependent. No differences in PMA/Ionomycin-induced IL-2 production were observed.

Further Description of FIG. 24

(a) Tyrosine phosphorylation of BTLA upon TCR crosslinking. D011.10 hybridoma T cells were infected with the empty retroviral vector (GFP-RV) or retrovirus expressing BTLAs containing an extracellular myc Epitope (myc-BTLAs) and infected cells purified by sorting. For crosslinking, cells were incubated (+) with 4 mg/ml of anti-CD3c (clone 145-2C11, PharMingen) (αCD3) or 2 mg/ml of anti-myc (clone 9E10, Santa Cruz) (amyc) as indicated for 30 min at 4° C. After washing, cells were treated with 100 mg/ml of pre-warmed goat anti-mouse IgG antibody (CALTAG) (GaM) for indicated time. As a positive control for phosphorylation, cells were incubated with 1 mM pervanadate for 2 min at 37° C. Cells were lysed in RIPA buffer, and 1 ml lysates of $25 \times 10^6$ cells were immunoprecipitated with 2 mg of anti-myc antibody (9E10). Immunoprecipitates were analyzed first with anti-phosphotyrosine (RC2OH, Transduction Laboratories) as described (upper panel), membranes stripped and re-probed with polyclonal rabbit anti-myc antibody (A-14, Santa Cruz) (middle panel), and finally with rabbit anti-SHP-2 antibody (C-1 8, Santa Cruz) (bottom panel). Arrowheads indicate the major glysosylated forms of BTLAs.

(b) BTLA tyrosine phosphorylation requires co-crosslinking. Cells described in (a) were treated (+) as described above, only with αCD3 or amyc antibodies, as indicated, followed by secondary GaM, and analyzed as in (a) for phosphotyrosine (pTyr) (top panel) or Myc (bottom panel).

(c) Cells described in (a) were incubated in the absence (−) or presence (+) of pervanadate for 2 min at 37° C., lysed in 1% NP-40 lysis buffer and immunoprecipitated using anti-myc antibody as in (a). Immunoprecipitates and whole cell lysates ($25 \times 10^6$) were first analyzed using antiphosphotyrosine (p-Tyr) (RC2OH) (middle panel), stripped and probed for SHP-2 (top panel, and finally for Myc as in (a).

(d) Cells described in (a) were incubated in the absence (−) or presence (+) of pervanadate for 2 min at 37° C., lysed in 1% NP-40 lysis buffer and immunoprecipitated using anti-SHP-2, and immunoprecipitates and whole cell lysates analyzed using anti-myc antibody (upper panel) stripped and re-probed for SHP-2 (lower panel).

(e) Jurkat T cells were infected with GFP-RV or with a retrovirus expressing a full length human BTLA containing an N-terminal myc epitope. Infected Jurkat T cells were sorted three times to obtain a >95% population containing high surface expression of myc-hBTLA. The indicated cells were treated (+) with pervanadate for 4 min at 37° C., lysed in 1% Triton lysis buffer, immunoprecipitated with anti-myc (9E10) (left panel) or anti-SHP-2 (Santa Cruz) (right panel), and immunoprecipitates analyzed for myc, SHP-2 and phosphotyrosine as above.

(f-g) The $3 \times 10^4$ D011.10 expressing control vector (GFP-RV), myc-BTLAs, or myc-BTLA were stimulated with 1 mg/ml immobilized anti-CD3c mAb in combination with the indicated concentrations of immobilized anti-myc antibody (9E10) (f) or 50 ng/ml PMA plus 1 mM ionomycin (g). Culture supernatants of triplicate cultures were collected at 24 hours and IL-2 concentration was determined by ELISA. In (f), IL-2 titer was normalized by the IL-2 concentration induced by αCD3 stimulation alone.

Example 8

Figure 25:
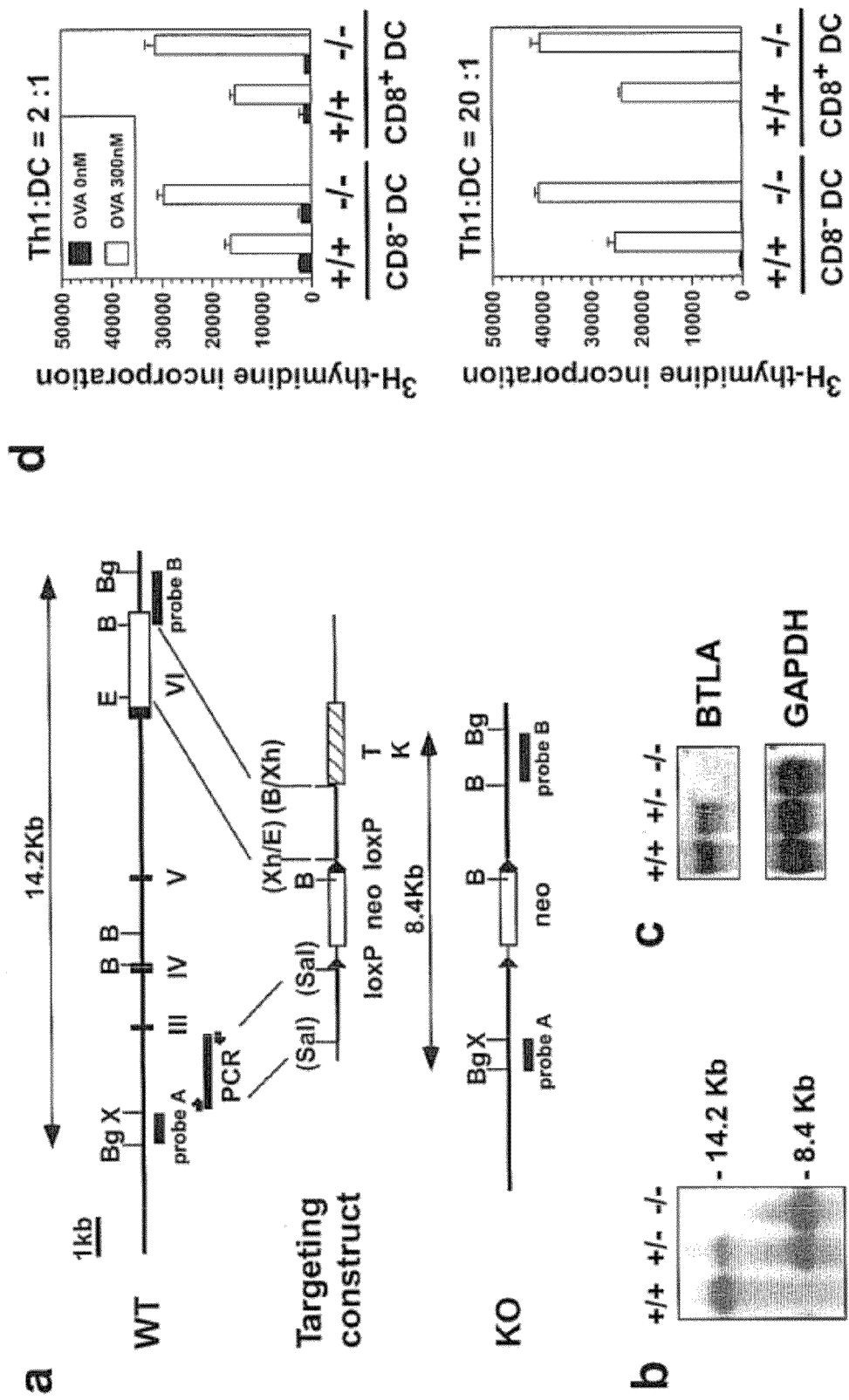
FIG. 25 (A) The scheme used to generate BTLA−/− mice. (B) Southern blot. BglII-digested tail DNA hybridized with probe B. (C) Northern blot. RNA from splenocytes probed with full length mouse BTLA cDNA probe, and GAPDH probe for control. (D) Th1 proliferation assay. Resting Th1 cells from DO01.10+/BTLA+/+(+/+) or DO11.10+/BTLA−/−(−/−) mice were incubated with CD8+ or CD8− DCs with or without OVA323-339 peptide, and [$^3$H] thymidine incorporation was measured.

Generation and Analysis of BTLA−/− Mice. (FIG. 25)

To test for an in vivo role as an inhibitory receptor, we targeted the BTLA gene to produce BTLA−/− mice. 129SvEv background BTLA−/− lacked BTLA mRNA expression in peripheral lymphocytes. No T or B cell developmental defects in thymus or bone marrow in BTLA−/− mice. We produced mixed 129/Balb/c background BTLA−/− D011.10 TCR transgenic mice for in vitro analysis of T cells. Fully polarized BTLA−/− Th1 cells showed enhanced proliferative responses in response to OVA-pulsed dendritic cells in vitro. Approximately two-fold increased proliferative responses were observed to 0.3 mM OVA peptide presented by CD8+ or CD8− CD1 Ic+ dendritic cells. After NP-KLH/alum immunization, we observed approximately three-fold increase in NP-KLH specific IgG1, IgG2a and IgG2b isotypes in BTLA−/− compared to control littermate 129/SvEv mice at 4 weeks. These results suggest BTLA ligation during T cell activation might attenuate the strength of Th1 responses.
Further Description of FIG. 25

(a) The figure shows the BTLA locus and targeting construct. Exons III through VI, encoding extracellular, transmembrane and cytoplasmic regions are indicated. BglII digestion of the germline locus generates a 14.2 kb restriction fragment hybridizes to probes A and B, and 8.4 fragment in correctly targeted clones. B, BamHI; Bg, BglII; E, EcoRI; Sal, SalI; X, XbaI; Xh, XhoI. TK, thymidine kinase gene; neo, neomycin resistance cassette.

(b) Southern analysis. BglII-digested tail DNA hybridized with probe B.

(c) Northern analysis. RNA was prepared directly from splenocytes of mice of the indicated genotype, and Northern blots hybridized to a full length mouse BTLA cDNA probe, stripped and re-probed for GAPDH.

(d) Proliferative responses of polarized Th1 cells induced by incubation with Ag-pulsed DCs. BTLA−/− mice were back-crossed onto the DO11.10 TCR background. Naïve CD4 T cells from DO11.10+ BTLA+/+ or BTLA−/− mice were activated in vitro passed biweekly in Th1 conditions. Resting Th1 cells ($5\times10^4$) were incubated with BALB/c derived CD8+ or CD8− DCs ($2.5\times10^4$ (top) or $0.25\times10^4$-(bottom)) with or without 300 nM of OVA323-339 peptide. Cell proliferation was measured by pulsing with [$^3$H] thymidine for 16 hours.
Further Description of FIG. 29

(a) Thymus, spleen and bone marrow cells from 8 week old BTLA-F/+ and BTLA−/− littermates were stained using CD4-PE, CD8-FITC, CD3ε-biotin/SA-Cychrome, B220-PE, αIgM-biotin/SA-Cychrome, αIgD-FITC and CD43-FITC (PharMingen). For splenocytes and bone marrow cells, 2.4G2 (antimouse CD16/32 Ab, PharMingen) was used to block non-specific binding of staining antibodies to Fc receptors. The percentages of the live cells in the quadrants or gates are indicated. (b) Splenocytes were stained with γδ-TCR-FITC, DX5-FITC (pan NK), Gr-1-biotin/SA-Cychrome, Mac-1-biotin/SA Cychrome, and anti-cKit-biotin/SA-Cychrome (PharMingen.) The histograms were overlayed for each marker (black line; +/+, red line; −/−). (c) Thymocytes and splenocytes from 8 weeks old BTLA+/+ and BTLA−/− littermates were counted by trypan-blue dye exclusion. The data are presented as the mean±SD of five mice.

Example 9

Figure 13A:
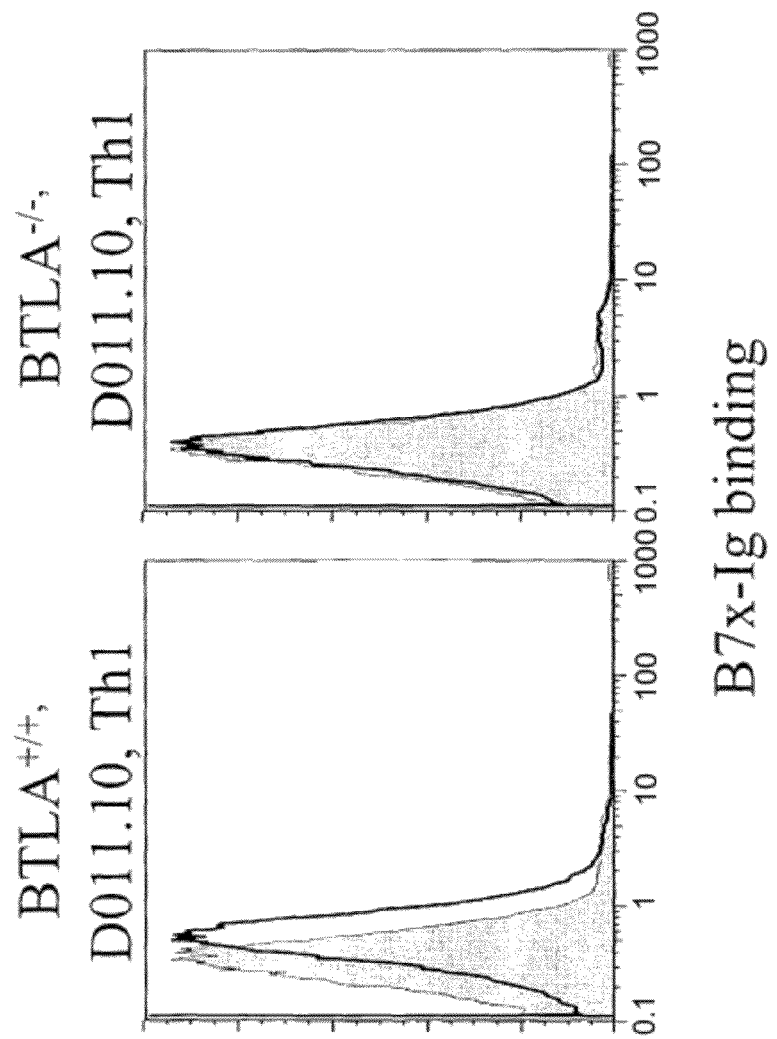
FIGS. 13A and 13B show T cells purified from wildtype and BTLA−/− mice that are stained with B7x-Ig fusion protein or B7h-Ig fusion protein as indicated.
Figure 13B:
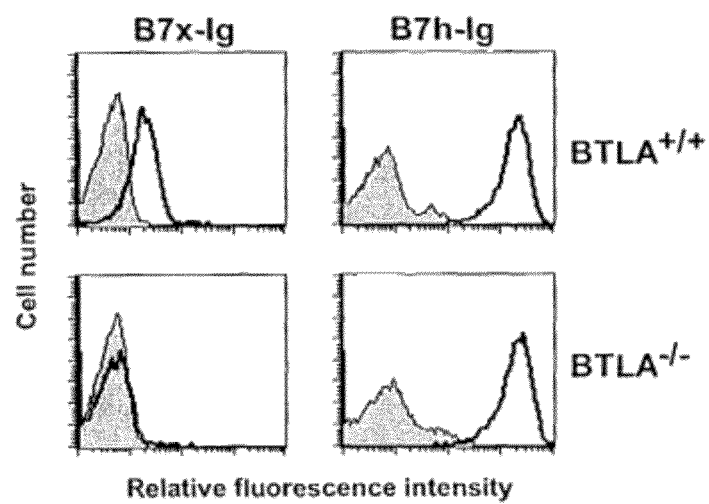

B7x Binding to Lymphocytes Requires BTLA Expression (FIG. 13)

Figure 31:
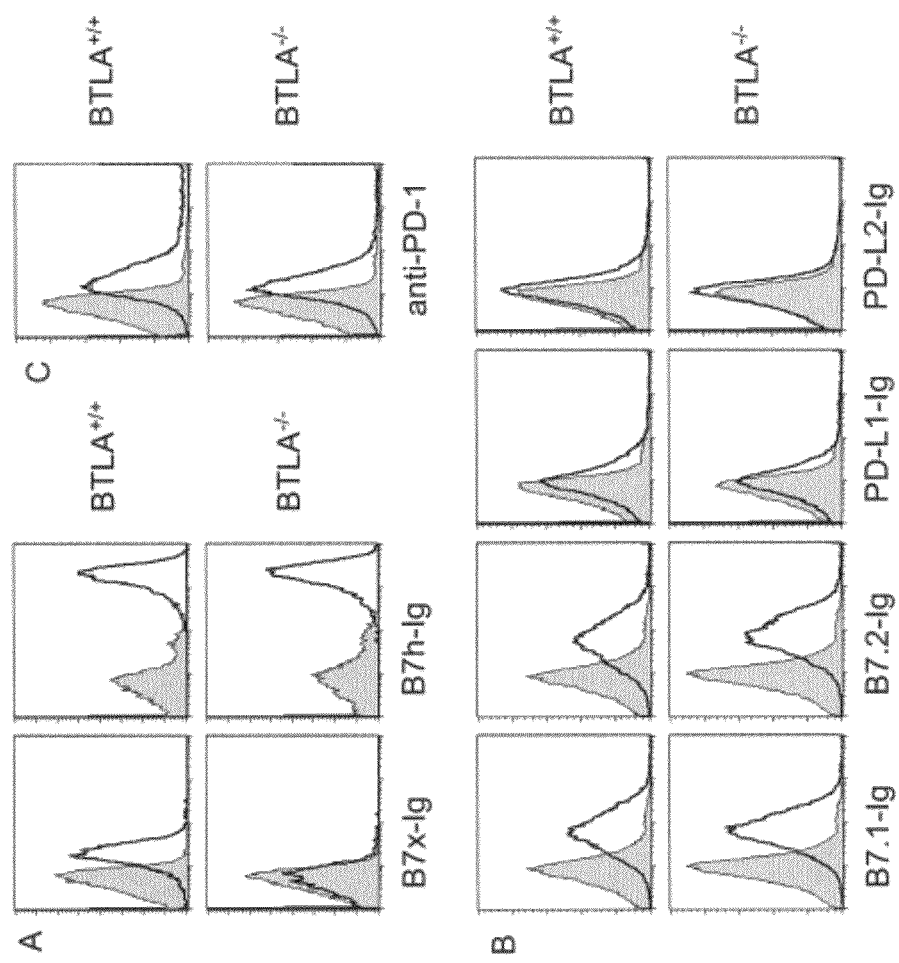
FIG. 31: BTLA interacts with an orphan B7, B7x. (A) Spleen and lymph node cells from BTLA wild-type and BTLA-deficient DO11.10+ TCR transgenic mice were collected and stimulated with 0.3 µM OVA peptide, 10 U/ml of IL-12 and neutralizing antibodies to IL-4, and assayed for Ig fusion binding after 4 d. Cells were stained with anti-CD4-FITC. Left, cells were stained with a human IgG1 antibody as a negative control (filled) or with a B7x-Ig fusion protein (open), followed by goat anti-human IgG-PE. Right, cells were unstained (filled) or stained with B7h-Ig (open), followed by biotinylated anti-Myc (murine IgG1 isotype) and streptavidin-PE. Anti-Myc was used as a negative control for the B7h-Ig fusion protein. (B, C) TH1 cell lines derived from BTLA wild-type and BTLA-deficient DO11.10+ mice were stimulated as above, collected on day 3, and assayed for binding to Ig fusion proteins. All cells were stained with anti-CD4-FITC. In B, Cells were stained with a human IgG1 antibody (filled) or with B7.1-Ig, B7.2-Ig, PD-L1-Ig and PD-L2-Ig fusion proteins (open), followed by goat anti-human Fcγ F(ab)2-PE. In c, Cells were stained with a hamster IgG2-PE as a negative control (filled) or with anti-PD-1-PE. Histograms are gated on CD4+ cells.

T cells purified from wildtype and BTLA−/− mice were stained B7x-Ig fusion protein, which revealed that BTLA is required for binding of B7x-Ig fusion protein to T cells, implicating BTLA as a counter-receptor for B7x. Additionally, as shown in FIGS. 31 (b) and (c), BTLA expression is not required for the binding of B71.11 g, B7.21 g, PD-L11g, PD-L21g and B7hIg, to Th1 cells.

Example 10

Figure 32:
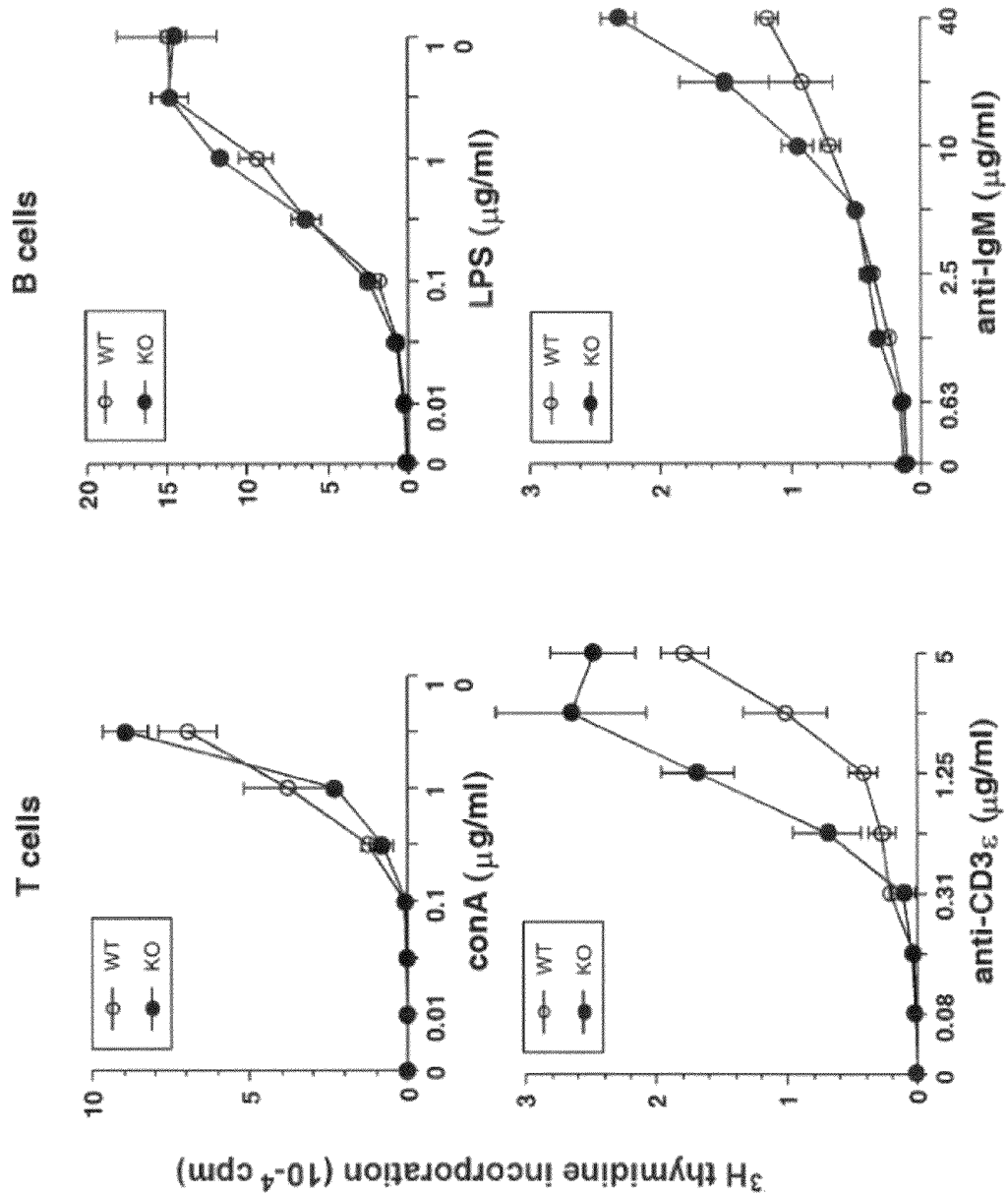
FIG. 32: In vitro responses of BTLA-deficient lymphocytes. T and B cell from wild-type (WT) or BTLA-deficient (KO) mice were purified by cell sorting using anti-CD4-FITC, anti-CD8.alpha.-FITC or anti-B220-PE. Cells were stimulated with the indicated final concentrations of plate-bound anti-IgM, LPS, concanavalin A or plate-bound anti-CD3ε. Cell proliferation was measured by pulsing with [$^3$H] thymidine for 16h.

In vitro responses of BTLA-deficient lymphocytes (FIG. 32)

T and B cell from wild-type (WT) or BTLA-deficient (KO) mice were purified by cell sorting using anti-CD4-FITC, anti-CD8α-FITC or anti-B220-PE. Cells were stimulated with the indicated final concentrations of plate-bound anti-IgM, LPS, concanavalin A or plate-bound anti-CD3. Cell proliferation was measured by pulsing with [$^3$H]thymidine for 16 h. These results support that BMA has inhibitory effect on lymphocyte responses.

Example 11

Figure 26:
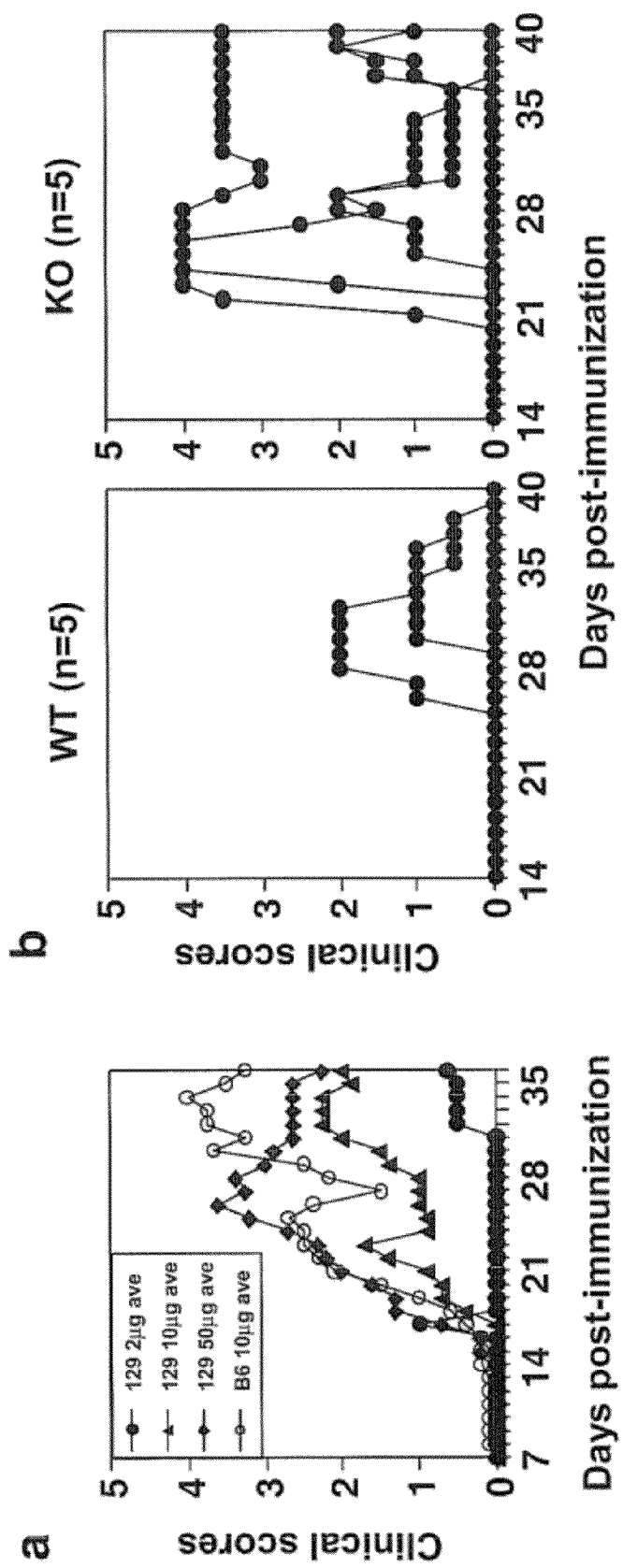
FIG. 26 Increased EAE susceptibility in BTLA−/− mice. (A) Clinical scoring of WT mice injected with 2 µg, 10.mu.g, and 50.mu.g in incomplete Freund's adjuvant. Clinical scores: score 0, normal mouse, no overt signs of disease; 1, limp tail or hind limb weakness, but not both; 2, limp tail or hind limb weakness; 3, partial hind limb paralysis; 4, complete hind limb paralysis; 5, moribund state, death by EAE, sacrifice for humane reasons). (B) Clinical scoring of WT and BTLA−/− mice injected with suboptimal dose (2 µg) of MOG peptide.
Figure 27B:
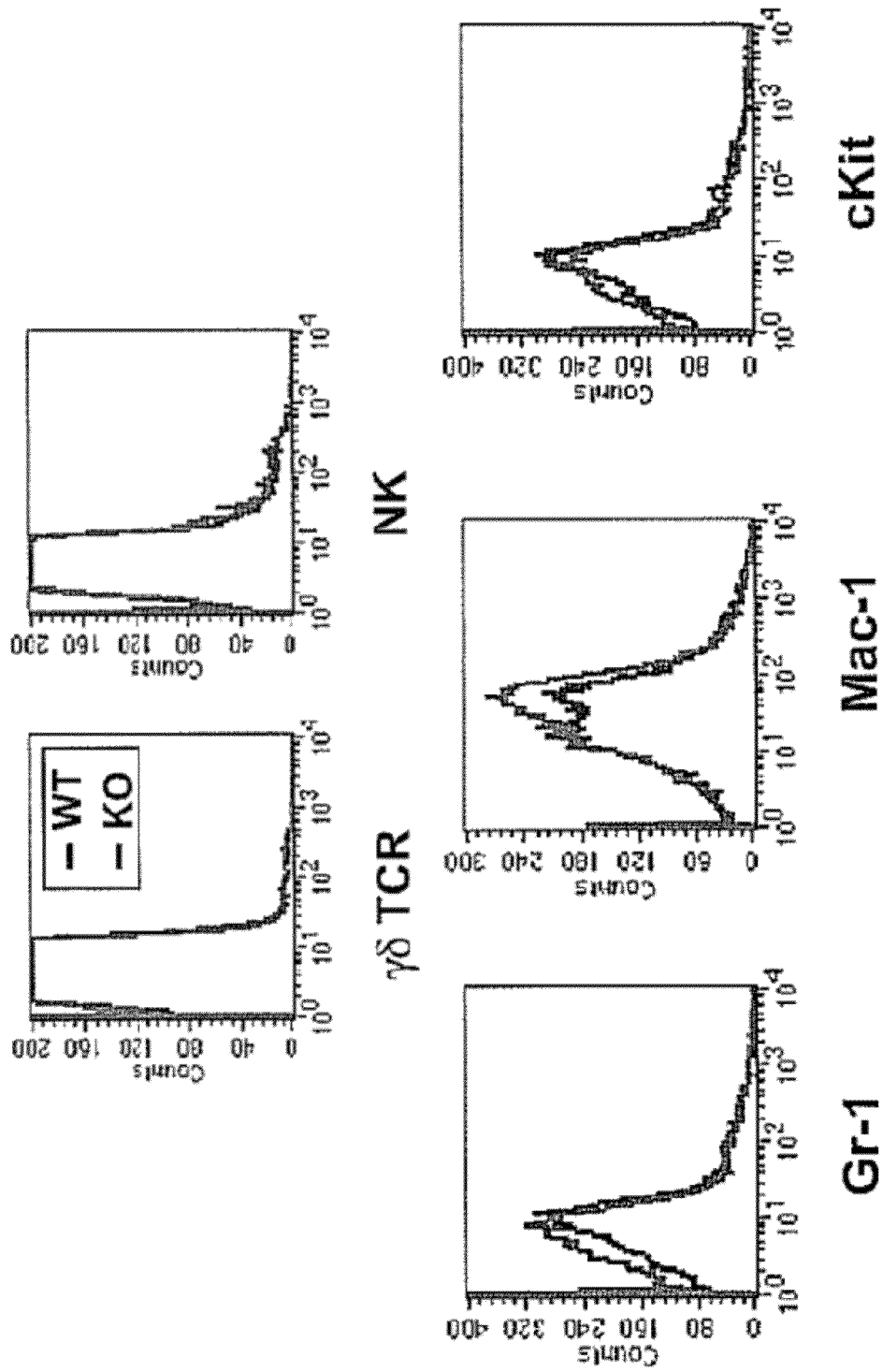
FIG. 27: Normal lymphocyte development in BTLA−/− mice (A) FACS analysis of thymus, spleen and bone marrow cells from BTLA+/+ and BTLA−/− littermates stained with CD4-PE, CD8-FITC, CD3ε-biotin/SA-Cychrome, B220-PE, αIgM-biotin/SA-Cychrome, αIgD-FITC and CD43-FITC. (B) FACS analysis of splenocytes stained γδ-TCR-FITC, DX5-FITC (pan NK), Gr-1-biotin/SA-Cychrome, Mac-1-biotin/SA-Cychrome, and anti-cKit-biotin/SA-Cychrome. Histograms overlayed for each marker (black line; +/+, red line; −/−). (C) Thymocytes and splenocytes from 8 weeks old BTLA+/+ and BTLA−/− littermates were counted by trypan-blue dye exclusion. The data are presented as the mean±SD of five mice.

Increased EAE Susceptibility in BTLA−/− mice (FIG. 26)

To test for an in vivo action of BTLA in T cells, we considered experimental allergic encephalitis (EAE). Our data suggest BTLA may be inhibitory, so we required a system that could potentially reveal enhanced T cell responses in BTLA−/− mice. Since presently we have pure 129 background BTLA−/− mice, we determined the antigen dose-titration of the MOG peptide in this background. 10 μg and 50 μg of peptide induced severe disease in 129SvEv mice, but 2 μg induced disease, which was more mild and delayed. At this antigen dose, BTLA−/− mice showed higher incidence, increased clinical score, earlier disease onset and prolonged duration compared to littermate wild type controls. Histologocial analysis supported these results (data not shown), demonstrating infiltration of the CNS in MOG-induced EAE in BTLA-deficient mice.
Further Description of FIG. 26

(a) Titration of MOG peptide in 129 SvEv mice. 129 SvEv mice were injected subcutaneously with MOG peptide at 2 μg, 10 μg, and 50 μg (n=5) in IFA and 500 μg of mycobacterium on day 0.300 ng of Pertussis toxin was injected intravenously on day 1 and 3. C57BL/6 mice were injected with 10 μg of MOG used as positive controls. Mice were monitored daily for clinical symptoms. Clinical scores: score 0, normal mouse, no overt signs of disease; 1, limp tail or hind limb weakness, but not both; 2, limp tail or hind limb weakness; 3, partial hind limb paralysis; 4, complete hind limb paralysis; 5, moribund state, death by EAE, sacrifice for humane reasons)

(b) Active induction of EAE by suboptimal dose of MOG peptide in BTLA−/− mice. 6-8 weeks old pure 129 SvEv BTLA−/− or wild type littermate control mice (n=5) were injected with 2 μg of MOG peptide as described in (a). Mean clinical scores: Wt, 0.6±0.9; BTLA−/−, 2.4±1.7. Mean peak clinical score; Wt, 1.5±0.7; BTLA−/−3.0±1.2.

For further discussion, see Watanabe N, et al., BTLA is a lymphocyte inhibitory receptor with similarities to CTLA-4 and PD-1. Published online: 8 Jun. 2003, doi:10.1038/ni944 Nat. Immunol. 2003 Jun. 8 [Epub ahead of print] PMID: 12796776, which is expressly incorporated herein by reference.

Example 12

Experimental BTLA Antibodies

Armenian hamsters and Balb/c BTLA KO mice were immunized with oxidatively refolded Bl/6 BTLA tetramer protein. The ability of antibody to block binding of BTLA tetramer to HVEM was determined.

| Clone | Isotype | Allelic Specificity | Blocking? | Applications |
|---|---|---|---|---|
| 6A6 | Hamster IoG | Bl/6 only | Yes | FACS, IP |
| 6F7 | Mouse IgG1, | Balb/c and 81/6 | Yes | FACS, IP, WB |

-continued

| Clone | Isotype | Allelic Specificity | Blocking? | Applications |
|---|---|---|---|---|
| 6G3 | Mouse IgG1, | Balb/c and BI/6 | Yes | FACS, IF |
| 6H6 | Mouse IgG1, | Balb/c and BI/6 | Weak | FACS, IP |
| 8F4 | Mouse IgG1, | Balb/c and BI/6 | Yes | FAGS, IP |
| 3F9.D12 | Mouse IgG1, | Balb/c and BI/6 | Yes | FACS, IP |
| 3F9.C6 . | Mouse IgG1, | BI/6 only | No | FAGS, IF, WB |

Yeast Display Data: The ability of antibody to bind to BTLA mutants was determined. + indicates binding.

| BI/6 BTLA Mutations | 6A6 | 3F9.C6 | 6G3 | 6F7 | 3F9.D12 |
|---|---|---|---|---|---|
| P41E | + | + | + | + | + |
| T45N | + | + | + | + | + |
| P41 E, T47K | + | + | + | + | + |
| P41 E, Q52H | + | + | + | + | + |
| P41 E, R55W | + | − | + | + | + |
| P41 E, Q63E | − | + | + | + | + |
| P41 E, C85W | +/− | + | +/− | +/− | +/− |
| P41 E, S91G | + | + | + | + | + |
| P41E, Q102R | − | + | + | + | + |
| P41 E, T143R | + | + | + | + | + |
| WEHI.2 | − | − | − | − | − |

Example 13

BTLA Ligand Binding and BTLA Activation

B7 molecules bind to MYPPPY motif on CD28 and CTLA4 within FG loop. For example, PD-L1 and PD-L2 bind to FG loop of PD-1. The FG loop of BTLA is four amino acids shorter than FG loop in CD28/CTLA4, and epitope mapping places HVEM interaction towards 'DEBA' face of Ig fold.
BTLA Binds Naive T Cells but does not Bind B7x To test for direct interactions between BTLA and B7x, we made NI H 3T3 cell lines stably expressing the extracellular domains of B7x, BTLA, and programmed death 1 (PD-1) and its ligand (PD-L1), and stained the cells with PD-1 and BTLA tetramers and with PD-L1 and B7x Fc fusion proteins. Whereas PD-1 tetramer bound to cells expressing PD-L1, as expected, the BTLA tetramer did not bind to cells expressing PD-L1 or B7x. Furthermore, our B7x-Fc fusion protein did not bind cells expressing BTLA.

Figure 33:
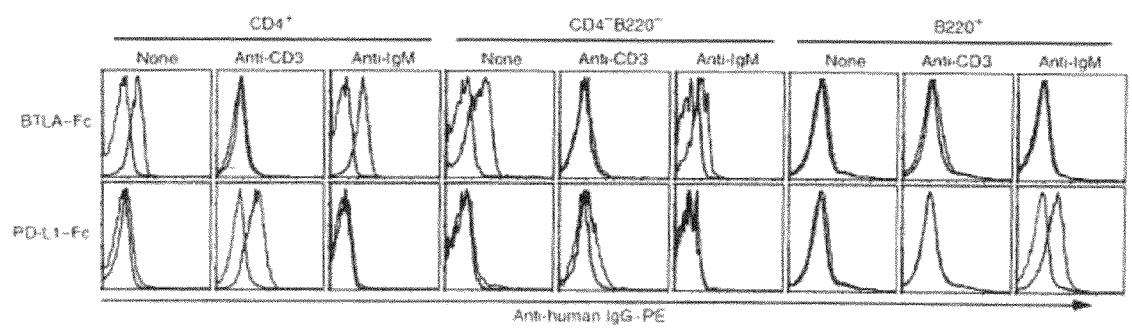
FIG. 33 BTLA recognizes a ligand on naive T cells. Splenocytes from BALB/c and C57BL/6 mice were collected and either were directly stained (None) or were activated with plate-bound 500A2 (Anti-CD3; 1:200 dilution of ascites fluid) or soluble anti-IgM (10 µg/ml) for 48 h, and then were stained with BTLA-Fc or PD-L1-Fc fusion protein (shaded histograms) followed by anti-human IgG-phycoerythrin (Anti-human IgG-PE), anti-CD4-tricolor and anti-B220-FITC. Open histograms, staining with human IgG1 isotype control in place of Fc fusion protein.
Figure 34:
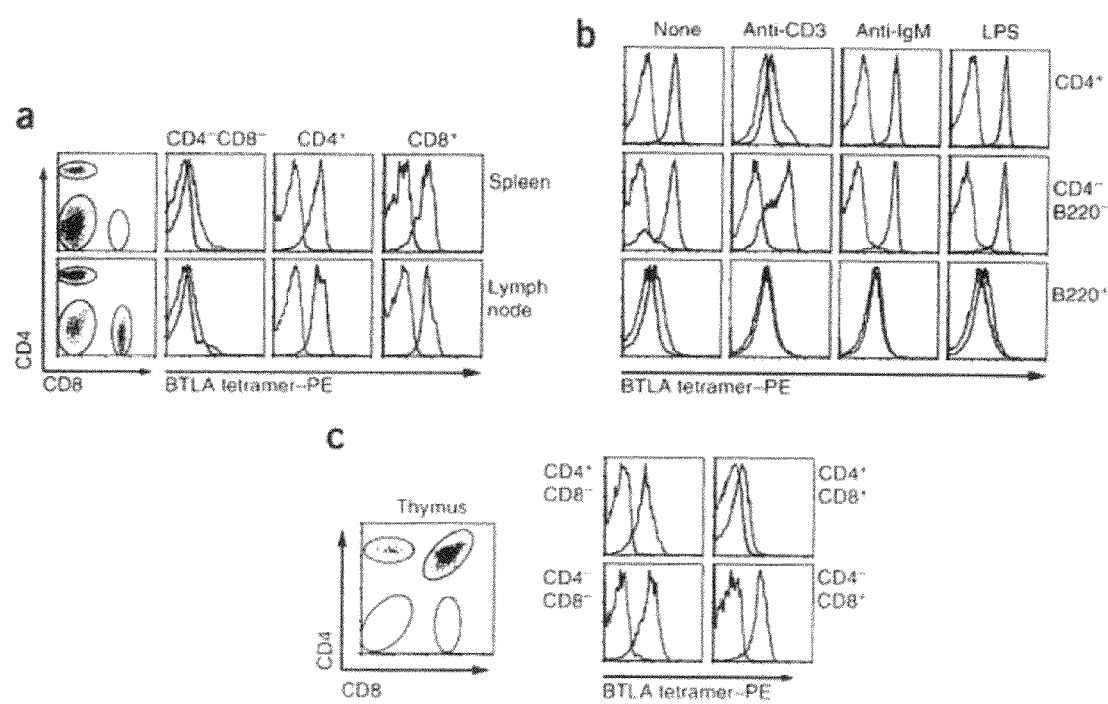
FIG. 34 BTLA tetramer staining identifies a ligand on CD4+ and CD8+ cells. (A) Splenocytes and lymph node cells from pooled C57BL/6 and BALB/c mice were stained with anti-CD8-FITC, anti-CD4-CyChrome, and either streptavidin-phycoerythrin (open histograms) or BTLA tetramer-phycoerythrin (shaded histograms). Dot plots (left) show the CD4-CD8 gates used for single-color histograms of BTLA tetramer-phycoerythrin staining (right). (B) Splenocytes from pooled C57BL/6 and BALB/c mice were left untreated or were activated 48 h with anti-CD3 or anti-IgM as described in FIG. 33 or with lipopolysaccharide (1 μg/ml) for 24 h and were stained with anti-B220-FITC, anti-CD4-CyChrome, and either streptavidin-phycoerythrin (open histograms) or BTLA tetramer-phycoerythrin (shaded histograms). (C) Thymocytes from pooled C57BL/6 and BALB/c mice were stained with anti-CD8-FITC, anti-CD4-CyChrome, and either streptavidin-phycoerythrin (open histograms) or BTLA tetramer-phycoerythrin (shaded histograms). The dot plot (left) shows the CD4/CD8 gates used for the single-color histograms of BTLA-tetramer staining.

To identify potential ligands on normal lymphocytes, we next used a BTLA-Fc fusion protein and BTLA tetramer to stain splenocytes (FIGS. 33 and 34). As a control, the PD-L1Fc fusion protein showed selective binding to activated but not resting CD4+ T cells and B220+ B cells (FIG. 33), as expected and consistent with the reported inducibility of PD-1 expression. Notably, our BTLA-Fc fusion protein showed specific binding to resting CD4+ and CD8+ T cells but not to B220+ B cells (FIG. 33). In addition, this binding was greatly reduced after T cell activation by treatment with antibody to CD3 (anti-CD3) but was not affected by B cell activation. As B7x is not reported to be expressed by naive T cells, the binding of the BTLA-Fc fusion protein to T cells is not consistent with an interaction with B7x. However, we independently confirmed that B7x was not expressed by T cells by examining the expression of B7x and several other CD28-B7 family members. B7x mRNA was most highly expressed in heart and lung but was absent from spleen, lymph node and naive CD4+ T cells. In contrast, we confirmed the expected lymphoid-specific expression pattern for several CD28– B7 family members, including ICOS, PD-1 and BTLA.

Figure 35:
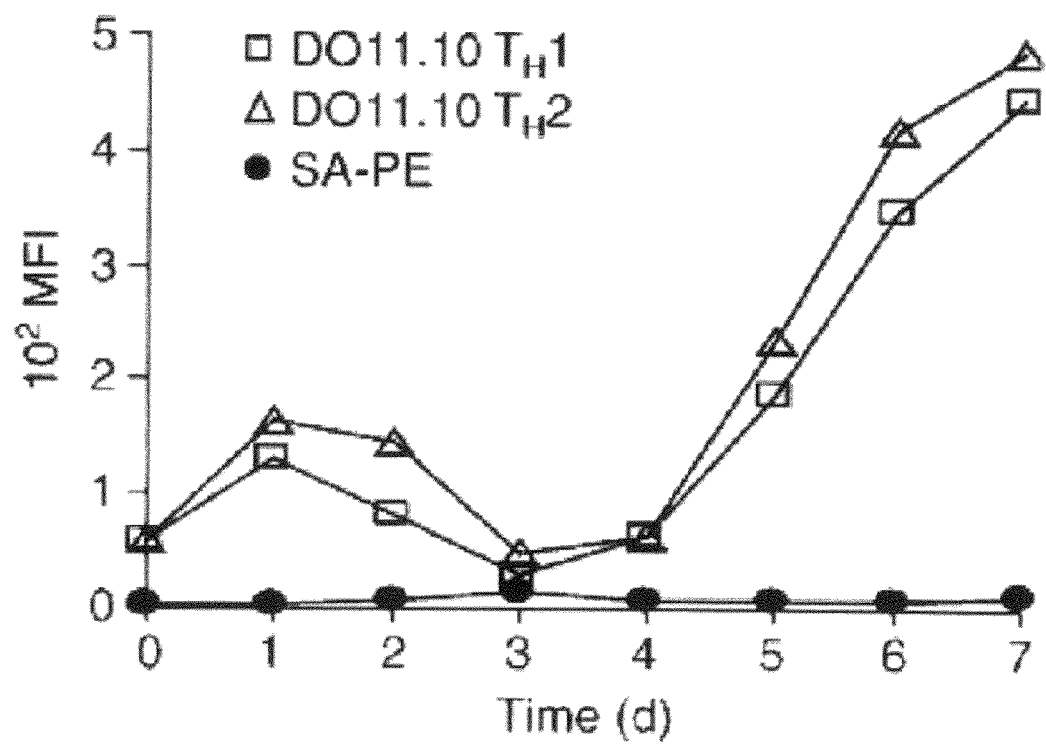
FIG. 35 BTLA ligand expression is modulated during T cell activation. DO11.10 splenocytes were stimulated with 0.3 μM OVA peptide in T helper type 1 conditions ($T_H1$; 10 Uml of IL-12 and 10 μg/ml of anti-IL-4) or T helper type 2 conditions ($T_H2$; 100 μml of IL-4 and 3 μ/m1 of anti-IL-12). Cultures were collected after activation (time, horizontal axis) and were stained with anti-CD4-FITC and BTLA tetramer-phycoerythrin. Filled circles, streptavidin-phycoerythrin (SA-PE) staining of T helper type 1 cultures without BTLA tetramer. MFI, mean fluorescence intensity.

To confirm and characterize the potential ligand on T cells identified by the BTLA-Fc fusion protein, we next analyzed the properties of BTLA tetramers binding to lymphocytes (FIG. 34). The BTLA tetramer showed strong binding to both CD4+ and CD8+ T cells obtained from both spleen and lymph nodes and bound weakly to non-T lymphocytes (FIG. 34A). Furthermore, binding to T cells was reduced after anti-CD3 stimulation (FIG. 34B), similar to our results obtained with BTLA-Fc fusion proteins (FIG. 33). In contrast, treatment of splenocytes with antiimmunoglobulin M (anti-IgM) or lipopolysaccharide did not reduce BTLA tetramer staining of CD4+ T cells. BTLA tetramers showed very slight binding to resting and activated B cells (FIG. 34B). We also examined BTLA tetramer staining in thymic subsets (FIG. 34C). BTLA tetramer staining was lowest in CD4+CD8+ (double-positive) thymocytes and showed more staining in mature CD4+ or CD8+ thymocytes and double-negative (CD4−CD8−) thymocytes, again indicating some physiological regulation of the BTLA ligand. As BTLA tetramer binding was modulated 48 h after anti-CD3 stimulation of T cells, we did a more detailed kinetic analysis using DO11.10 T cells activated in vitro with ovalbumin (OVA) peptide (FIG. 35). Again, BTLA tetramer binding was regulated during activation, initially increasing by twofold at 24 and 48 h after antigen-specific stimulation, decreasing on day 3 and day 4, and increasing again by day 7. Expression of this BTLA ligand was similar in both T helper type 1- and T helper type 2-inducing conditions. Thus, BTLA tetramers and BTLA-Fc fusion proteins have very similar binding properties to lymphocytes, and a BTLA ligand is expressed by resting T cells and undergoes regulation during thymocyte development and T cell activation.

Cloning a BTLA-Interacting Protein

Figure 36:
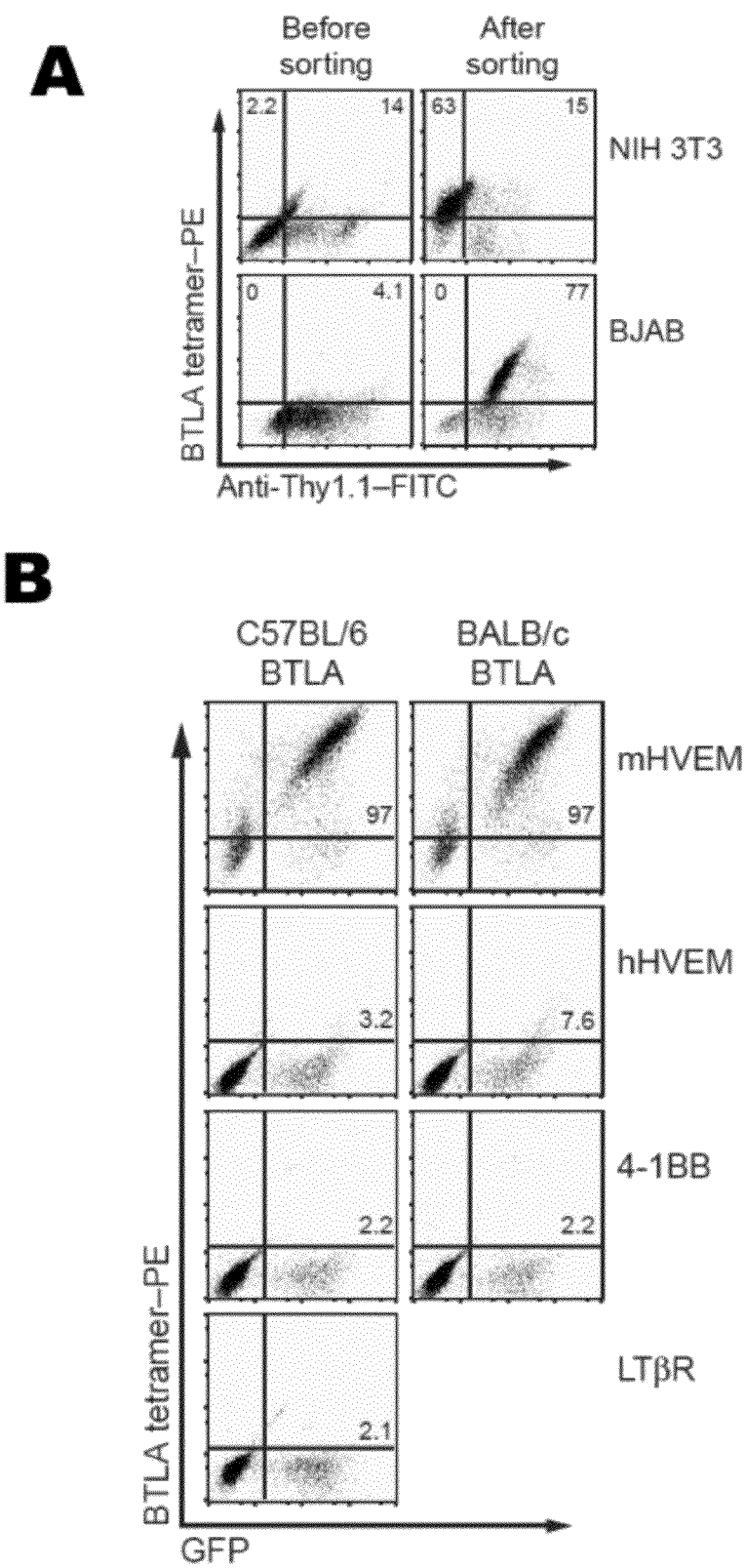
FIG. 36 HVEM is a ligand for BTLA. (A) NIH 3T3 cells and BJAB cells were transduced with splenocyte cDNA libraries and were directly stained with anti-Thy1.1-FITC and the C57BL/6 BTLA tetramer-phycoerythrin (Before sorting). These cells were sorted for the highest 0.5% population of BTLA tetramer staining with BTLA-phycoerythrin tetramer and Thy1.1-FITC and were subjected to an additional three rounds of similar sequential purification. After the fourth round of sorting, cell populations were expanded and cells were stained (After sorting). Numbers in each quadrant indicate the percentage of live cells in the indicated gate. (B) BJAB cells were transduced with the retroviruses mHVEM-IRES-GFP (mHVEM; mouse), hHVEM-IRES-GFP (hHVEM; human), 4-1 BB-IRES-GFP (4-1 BB; mouse) and LTβR-1RES-GFP (LTβR; mouse) and were stained with C57BL/6 BTLA tetramer-phycoerythrin or BALB/c BTLA tetramer-phycoerythrin. Numbers in dot plots indicate the percentage of BTLA tetramer staining in the GFP-positive population. (C, D) HVEM activates BTLA phosphorylation and SHP-2 association. EL-4 cells (EL4), BJAB cells expressing GFP (BJAB-GFP) or BJAB cells expressing mouse HVEM (BJAB-mHVEM) were added (+) or not added (−) for 4 min at 37° C. at a density of $25\times10^6$ cells/ml. Cells were left untreated (−) or were treated (+) with pervanadate ($VO_4$) for 4 min. Total cell lysates were prepared and were immunoprecipitated with 6A6 (anti-mouse BTLA), and immunoblots were probed for SHP-2 (C) or for phosphotyrosine (D) in immunoprecipitates (IP) or in lysates without immunoprecipitation. Immunoblots using the isotype control for immunoprecipitation were negative for SHP-2 association (data not shown). Data in C and d are representative of four independent experiments. (E) BJAB cells were transduced with retrovirus mHVEM-ires-GFP or hHVEM-ires-GFP and were stained with human IgG1 isotype control (hIgG1), mB7x-Fc, mBTLA-Fc or hBTLA-Fc followed by anti-human IgG-phycoerythrin. Numbers in dot plots show the percentage of fusion protein staining in the GFP-positive population.

We constructed a retroviral cDNA library from lymphocytes and transduced two host cell lines, BJAB and NIH 3T3, that were negative for BTLA tetramer binding (FIG. 36A). After four successive rounds of sorting, we obtained lines uniformly positive for BTLA tetramer staining, which we used to amplify retrovirus-specific inserts. From BJAB cells, we obtained a predominant RT-PCR product that we identified as mouse HVEM. From NIH 3T3 cells we also obtained mouse HVEM as the main component of RT-PCR isolates. Among the minor retroviral inserts identified from NIH 3T3 cells, 4-1 BB was the only transmembrane receptor; it also belongs to the TNFR superfamily.

We next tested these isolates as candidates for direct interactions with BTLA tetramers. We expressed full-length cDNA clones of mouse HVEM, human HVEM, mouse 4-1 BB and mouse LTI3R, which binds the same ligands (LIGHT and LTα) as HVEM, in BJAB cells and analyzed these cells for binding to BTLA tetramers. We specifically constructed BTLA tetramers from both the C57BL/6 and BALB/c alleles to identify any potential allelic differences in binding (FIG. 36B). We found specific binding of both forms of BTLA tetramers to green fluorescent protein (GFP)-positive BJAB cells expressing mouse HVEM but not to BJAB cells expressing human HVEM, mouse 4-1 BB or mouse LTI3R or to GFP-negative uninfected BJAB cells.

HVEM Induces BTLA Phosphotylation

We next sought to determine if HVEM could induce BTLA phosphorylation (FIG. 36C, D). We analyzed BTLA phosphorylation in EL4 cells using immunoprecipitation immunoblot analysis as described above. EL4 cells had low expression of BTLA but no detectable HVEM, as assessed by BTLA tetramer binding. We therefore examined EL4 cells for BTLA phosphorylation and SHP-2 coimmunoprecipitation after contact with mouse HVEM expressed by BJAB cells. EL4 cells alone showed neither coimmunoprecipitation of SHP-2 with BTLA (FIG. 36C) nor direct tyrosine phosphorylation of BTLA (FIG. 36D). Mixing of EL4 cells with HVEM-expressing BJAB cells induced both coimmunoprecipitation of SHP-2 with BTLA and tyrosine phosphorylation of BTLA. In contrast, mixing EL4 cells with HVEMnegative BJAB cells induced neither coimmunoprecipitation of SHP-2 with BTLA nor BTLA phosphorylation. As controls, pervanadate treatment of EL-4 cells induced coimmunoprecipitation of SHP-2 and tyrosine phosphorylation of BTLA, but BJAB cells alone, either. HVEM-negative or expressing HVEM, showed neither SHP-2 coimmunoprecipitation nor BTLA phosphorylation. Thus, these results show that HVEM can induce BTLA tyrosine phosphorylation and association with SHP-2.

HVEM-BTLA Interactions are Conserved in Human

Because tetramers of mouse BTLA bound mouse HVEM but not human HVEM, we sought to determine if the BTLA-HVEM interaction was conserved in humans. Therefore, we generated a human BTLA-Fc fusion protein and characterized its interactions with mouse and human HVEM (FIG. 36E). The mouse BTLA-Fc fusion protein bound to BJAB cells expressing mouse HVEM but not cells expressing human HVEM, confirming the data obtained with mouse BTLA tetramers (FIG. 36B). In addition, the human BTLA-Fc fusion protein bound to BJAB cells expressing human HVEM (FIG. 36E). The human BTLA-Fc fusion protein also bound, although more weakly, to BJAB cells expressing mouse HVEM. These interactions were specific, as the isotype control antibody and the B7x-Fc fusion protein did not bind to BJAB cells expressing either mouse or human HVEM. Thus, the interaction between BTLA and HVEM occurs in human lymphocytes, as it does in mouse lymphocytes. Also, although cross-species interactions are noted for human BTLA and mouse HVEM (FIG. 36E), it seems that this cross-species interaction is weaker than the intraspecies interaction.

BTLA Interacts with the CRD I Region of HVEM

Figure 37:
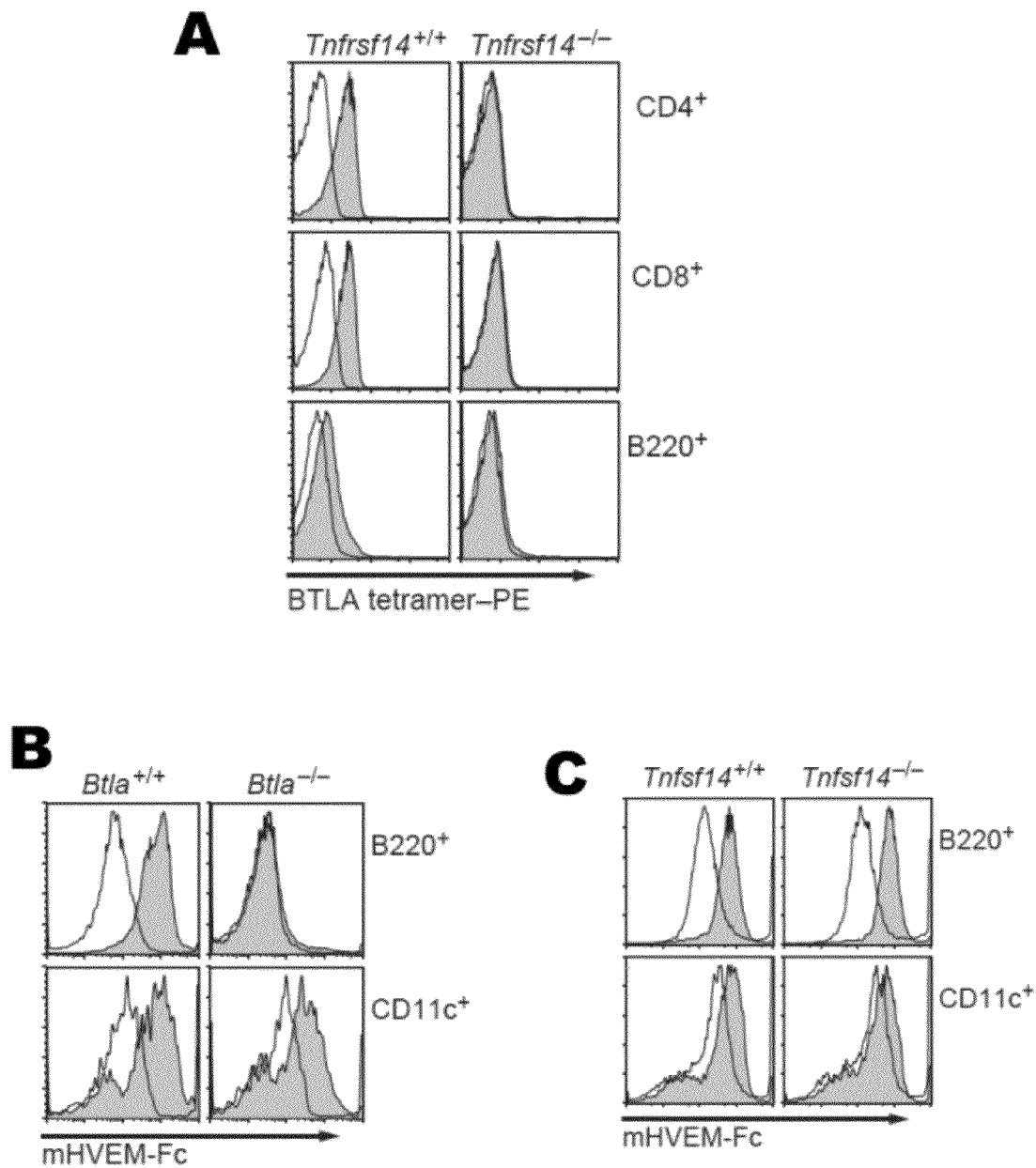
FIG. 37 HVEM is the unique ligand for BTLA and interacts through CRD1. (A) Splenocytes from wild-type (Tnfrsf14+/+) or HVEM-deficient (Tnfrsf14−/−) mice were stained with anti-CD4-FITC(CD4+), anti-CD8-FITC(CD8+) or anti-B220-FITC (B220+) and either C57BL/6 BTLA tetramer-phycoerythrin (shaded histograms) or streptavidin-phycoerythrin alone (open histograms). (B) Splenocytes from wild-type (Btla+/+) and Btla−/− mice were stained with anti-B220-FITC (top) or anti-CD11c-FITC (bottom) and with either mHVEM-Fc (shaded histograms) or isotype control human IgG1 (open histograms) followed by anti-human IgG-phycoerythrin. (C) Splenocytes from wild-type (Tnfsf14+/+) and Tnfsf14−/− mice were stained with B220-FITC (top) or CD11c-FITC (bottom) and mHVEM-Fc or isotype control human IgG1 (open histograms), followed by anti-human IgG phycoerythrin. (D) BJAB cells were left uninfected or were transduced with retroviruses expressing mouse HVEM-GFP fusion protein (mHVEM-GFP), the HVEM deletion mutant lacking N-terminal CRD1 as a GFP fusion protein (mHVEMCRDI-GFP), intact human HVEM (hHVEM-IRES-GFP) or chimeric HVEM containing mouse CRD1 linked to human CRD2 (m/hHVEM-IRES-GFP). Left, cells stained with BTLA tetramer-phycoerythrin (shaded histograms) or streptavidin-phycoerythrin alone (open histograms); right, cells stained with either anti-hHVEM (shaded histograms) or a mouse IgG1 isotype control (9E10) followed by goat anti-mouse IgG1-phycoerythrin. Single-color histograms were gated on GFP-positive live cells. Right margin, composition of the HVEM constructs, with mouse CRDs (open ovals) and human CRDs (shaded ovals).

HVEM is a member of the TNFR superfamily and interacts with the two known TNF family members LIGHT and LTα. Because HVEM has multiple ligands, we sought to determine whether we could detect additional ligands for BTLA. Thus, we compared binding of BTLA tetramers to wild-type and HVEM-deficient lymphocytes (FIG. 37A). BTLA tetramers showed no detectable specific binding to HVEM-deficient CD4+ or CD8+ T cells but showed the expected binding to wild-type T cells. Even the low binding of BTLA tetramer to B cells was reduced to undetectable amounts in HVEM-deficient B cells (FIG. 37A). Thus, we found no evidence of additional ligands for BTLA in mice.

Figure 37D:
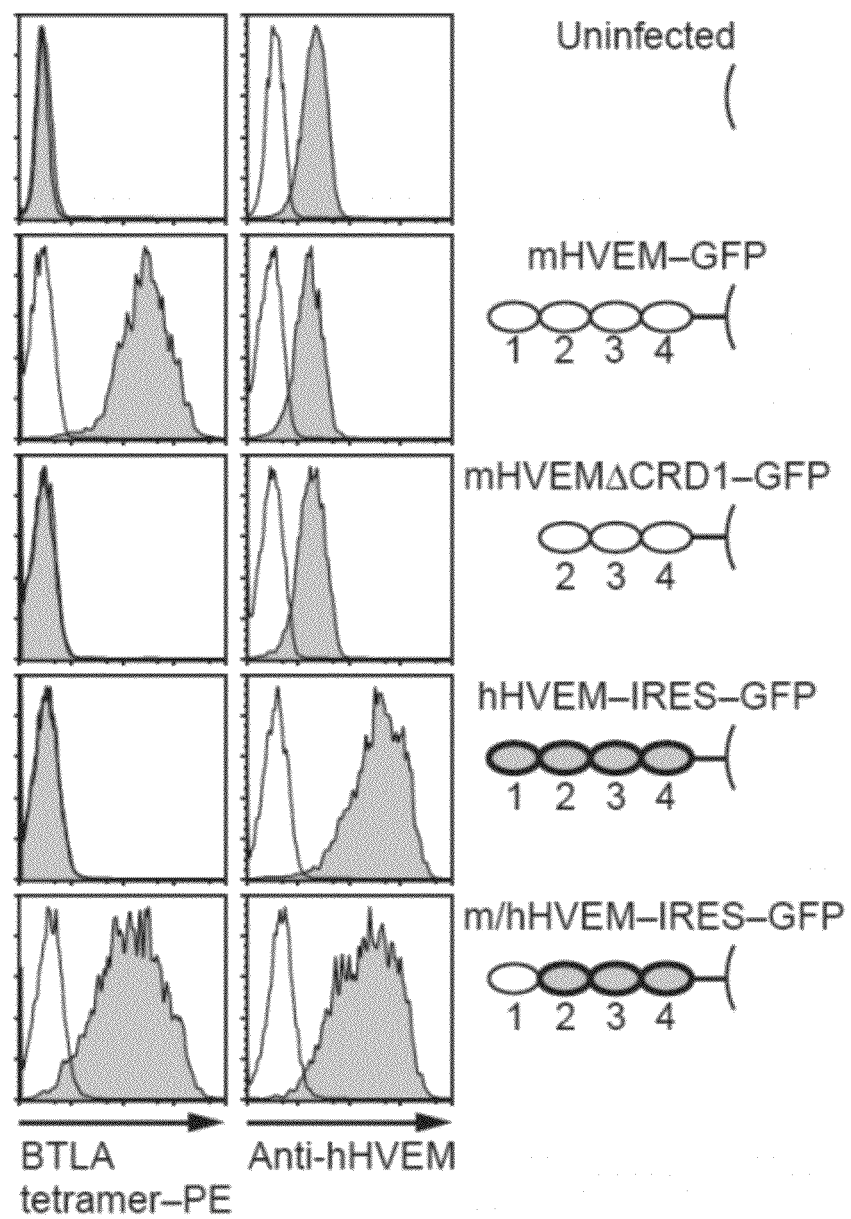

The interaction between HVEM and LIGHT can be detected with an HVEM-Fc fusion protein containing the four extracellular CRD regions of HVEM fused to the Fc region of human IgG1. We therefore sought to determine whether this HVEM-Fc fusion protein can also bind BTLA (FIG. 37D). Because LIGHT is expressed by CD11c+DCs but not by B220+ B cells, we compared the binding of HVEM-Fc fusion protein to B cells and DCs from wild-type and BTLA-deficient mice (FIG. 37B). The HVEM-Fc fusion protein bound to wild-type B cells but not to Btla–/– B cells. In contrast, the HVEM-Fc fusion protein bound to wild-type DCs with only slightly reduced binding to Btla–/– DCs. We next compared the binding of HVEM-Fc fusion protein to wild-type and LIGHT-deficient (Tnfsf14–/–) B cells and DCs (FIG. 37C).

The HVEM-Fc fusion protein bound to wild-type and Tnfsf11–/– B cells and DCs with nearly equal intensity. In addition, HVEM expression was actually increased in Btla–/– mice compared with that in wild-type mice. This result might indicate that endogenous HVEM expression is regulated by interaction with BTLA, similar to the reported regulation of HVEM expression by LIGHT. Furthermore, this result formally shows that HVEM expression does not require BTLA as a 'chaperone'. These results might suggest that BTLA is the only ligand for HVEM on B cells, but such conclusions based solely on soluble staining reagents may be misleading, and it is possible that HVEM could also interact with other unknown molecules on B cells. For DCs, it seems that both BTLA and LIGHT are ligands for HVEM.

We sought to identify which domains of HVEM are involved in BTLA interactions. HVEM has four extracellular CRDs; it binds LIGHT and LTα through CRD2 and CRD3 and binds herpes glycoprotein D through CRD1. We constructed a series of HVEM mutants, including a mouse HVEM GFP fusion protein, an HVEM deletion mutant lacking the N-terminal CRD1 as a GFP fusion protein, an intact human HVEM, and a chimeric HVEM containing mouse CRD1 linked to human CRD2. We expressed this panel of HVEM mutants in BJAB cells and examined binding of the mouse BTLA tetramer (FIG. 37D). As expected, the BTLA tetramer did not bind uninfected BJAB cells but bound to wild-type mouse HVEM. However, the mouse BTLA tetramer did not bind to the HVEM mutant lacking CRD1. In addition, BTLA tetramer did not bind to human HVEM but did bind to the mouse-human chimeric HVEM (FIG. 37D). As a control, we assessed the amounts of human HVEM expressed by these cell lines (FIG. 37D), confirming expression of the human and chimeric HVEM molecules. These results indicate an important function for the CRD1 domain of mouse HVEM for BTLA interactions but do not exclude the possibility of a contribution by other domains.

HVEM Inhibits Antigen-Driven T Cell Proliferation

Figure 38:
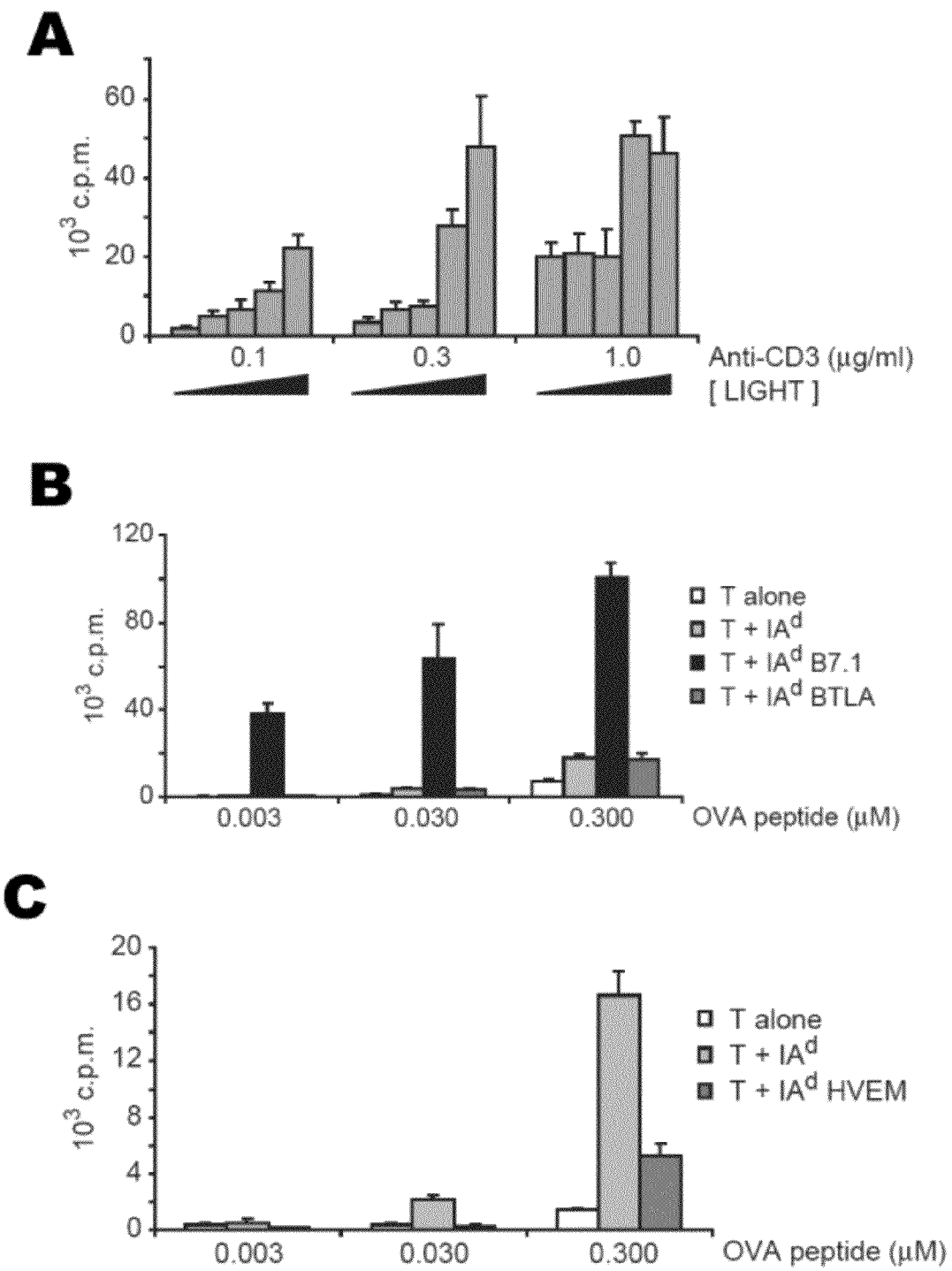
FIG. 38 HVEM expression on APCs inhibits T cell proliferation. (A) CD4+ cells were purified from BALB/c mice by magnetic separation and were stimulated ($1\times10^6$ cells/ml) with plate-bound anti-CD3 (2C11; dose, horizontal axis) and increasing concentrations (wedges; 0, 0.3, 1.0, 3.0 and 10.0 μg/ml) of plate-bound LIGHT. Cultures were pulsed with [$^3$H]thymidine at 48 h and were collected at 60 h. Data represent c.p.m. s.d. from one of three similar experiments. (B) CD4+ T cells from DO11.10 mice were purified by magnetic separation, followed by cell sorting for CD4+B220-CD11c- cells to more than 98% purity, and were added to cultures alone (T alone) or with (T+) CHO cells expressing I-Ad, I-Ad and B7.1, or I-Ad and BTLA, plus various concentration of OVA peptide (horizontal axis), and proliferation was measured as described in A. (C) T cells prepared as described in b were cultured alone or with CHO cells expressing I-Ad, or I-Ad and HVEM, plus various concentrations of OVA peptide, and proliferation was measured as described in A. (D) T cells prepared as described in b were cultured alone or with CHO cells expressing I-Ad, or I-Ad and B7.1, or I-Ad, B7.1 and HVEM, and were activated with various concentration of OVA peptide. Proliferation was measured as described in A.

HVEM is expressed by several types of cells, including T cells, B cells and DCs, complicating the analysis of potential interactions between cells expressing LIGHT, BTLA and HVEM. Thus, we first sought to confirm the reported costimulatory effects of LIGHT on CD4+ T cells in our system. We stimulated highly purified CD4+ T cells with increasing amounts of anti-CD3 in the presence of various concentrations of plate-bound LIGHT (FIG. 38A). At suboptimal concentrations of anti-CD3 stimulation, LIGHT strongly augmented T cell proliferation in a dose-dependent way. At the highest dose of anti-CD3, the costimulatory effect of LIGHT was reduced slightly because of an increase in the LIGHT-independent proliferation. These data confirm reports that LIGHT engagement of HVEM provides positive costimulation.

We next tested whether BTLA or HVEM expression by antigen-presenting cells (APCs) inhibited or activated T cells. For this, we produced a panel of Chinese hamster ovary (CHO) cells expressing various combinations of 1-Ad and B7-1 (ref. 18) plus either BTLA or HVEM using retrovirus transduction and cell sorting. We confirmed expression of 1-Ad, B7-1, BTLA and HVEM by these cell lines using flow cytometry. We sought to determine if BTLA expression by APCs costimulated D011.10 T cells (FIG. 38B). CHO cells expressing I-Ad alone supported minimal T cell proliferation, similar to that seen with T cells and peptide alone. As a positive control, CHO cells expressing I-Ad and B7-1 supported higher proliferation in response to OVA peptide. In contrast, BTLA expression by APCs did not augment T cell proliferation induced by CHO cells expressing I-Ad alone (FIG. 38B), as did expression of B7-1, suggesting that BTLA does not provide costimulation to T cells through HVEM engagement.

Figure 38D:
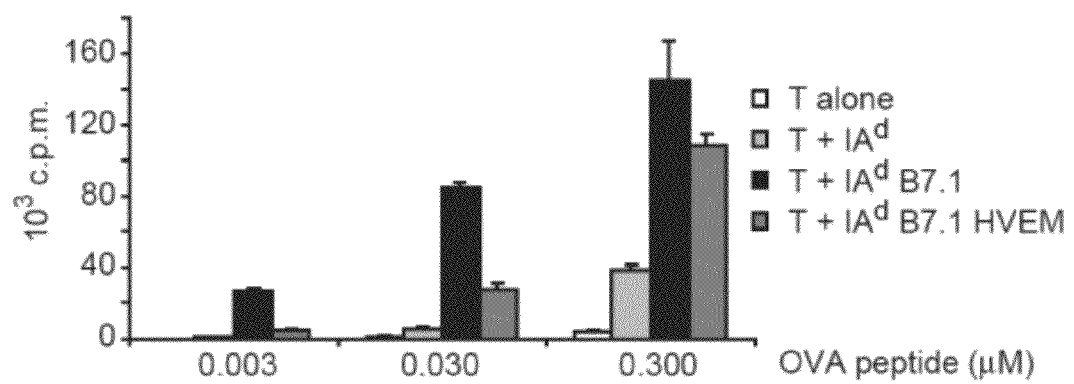

Whereas BTLA, unlike LIGHT, may not activate HVEM, HVEM seems to activate BTLA, as evidenced by BTLA phosphorylation and SHP-2 association (FIG. 36C, D). Thus, we sought to determine whether HVEM expression by APCs influenced T cell proliferation (FIG. 38C). The peptide dose-dependent proliferation supported by CHO cells expressing I-Ad alone was reduced when HVEM was coexpressed on these CHO cells (FIG. 38C). Furthermore, as expected, B7-1 increased T cell proliferation induced by peptide and I-Ad (FIG. 38D), shifting the dose-response to lower concentrations of peptide. Again, coexpression of HVEM on these CHO cells reduced peptide-dependent T cell proliferation. The inhibition produced by HVEM at the highest peptide concentrations was smaller than the inhibition seen with intermediate stimulation.

Figure 39A:
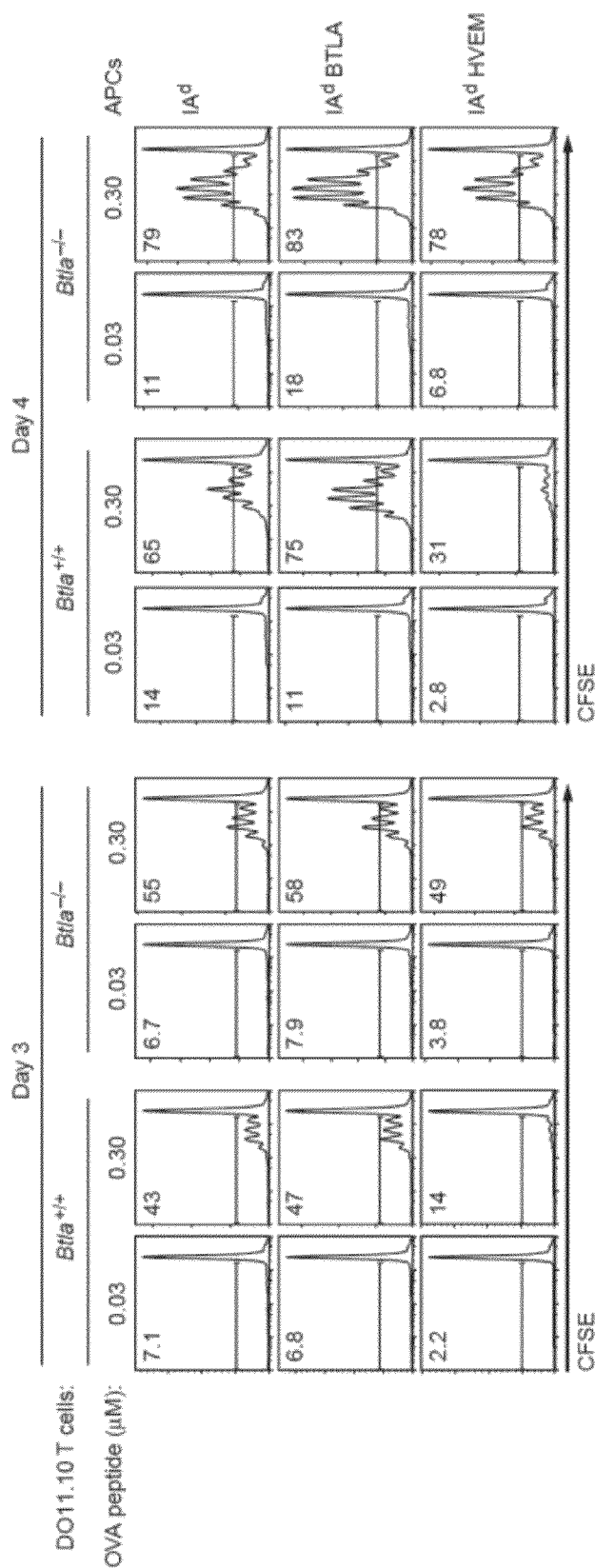
FIG. 39 HVEM inhibits T cell proliferation in a BTLA-dependent way. (A) Highly purified DO11.10 CD4+ T cells from wild-type (Btla+/+) or Btla−/− mice were prepared as described in FIG. 38, were labeled with CFSE and were cultured for 3 or 4 d with CHO cells expressing I-Ad, or I-Ad and BTLA, or I-Ad and HVEM, plus 0.03 or 0.3 μM OVA peptide. Cells were analyzed by flow cytometry. Data are single-color histograms of CFSE gated on CD4+ T cells. Numbers indicate percentage of live cells that have divided at least once, as indicated by the gate drawn. (B) T cells prepared as described in a were cultured for 3 or 4 d with CHO cells expressing I-Ad and B7.1, I-Ad, B7.1 and BTLA, or I-Ad, B7.1 and HVEM, plus 0.03 or 0.3 μM OVA peptide, and were analyzed as described in A. Numbers indicate percentage of live cells that have divided at least once.

We extended this analysis using T cells labeled with carboxyfluorescein diacetate succinimidyl diester (CFSE; FIG. 39). In addition, we tested whether the inhibitory effect of HVEM on T cell proliferation required BTLA by using Btla−/− DO11.10 T cells. Using CHO cells lacking B7-1 expression, we did not note T cell proliferation at the lowest dose of OVA peptide (0.03 µM) on days 3 and 4 (FIG. 39A). However, higher peptide concentrations (0.3 µM) induced T cell proliferation on days 3 and 4. In these conditions, expression of BTLA on CHO cells had no effect on T cell proliferation at anytime. However, expression of HVEM on CHO cells greatly reduced T cell proliferation, which occurred only in wild-type DO11.10 T cells, not Btla−/− T cells, and was evident on days 3 and 4 after activation.

Figure 39B:
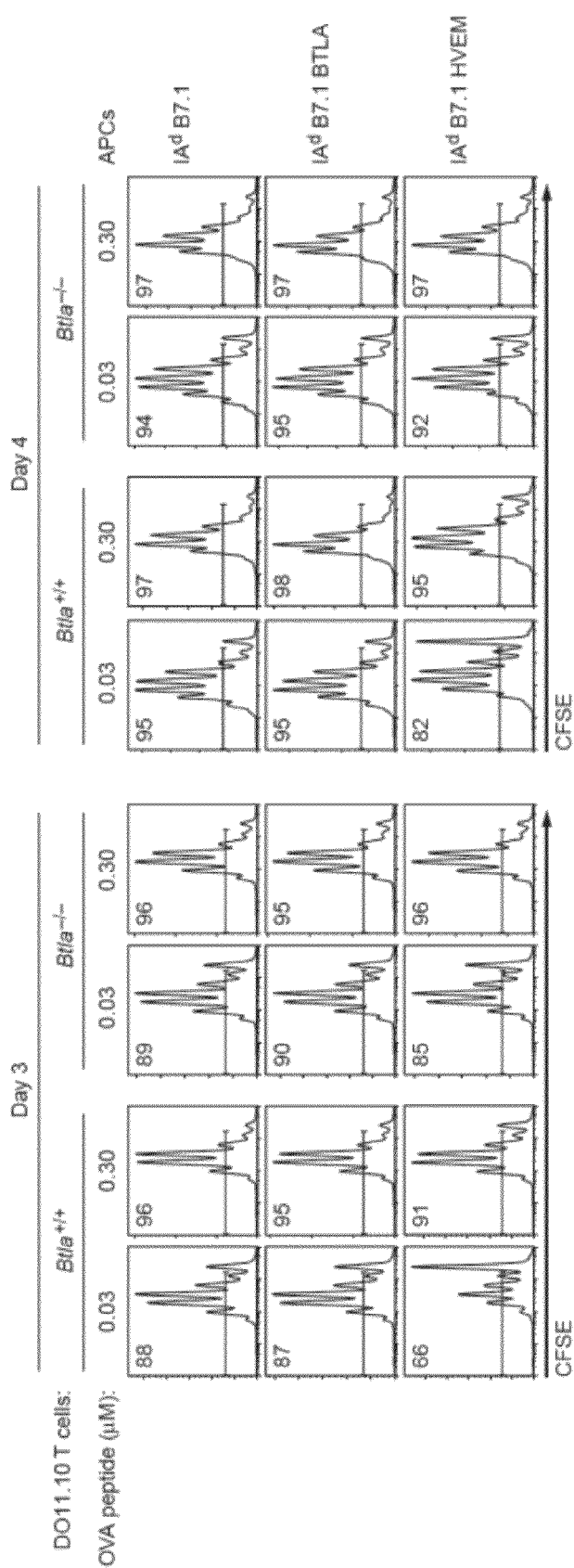

We next examined the effects of HVEM on T cell proliferation in response to antigen presentation by CHO cells expressing B7-1 (FIG. 39B). Again, B7-1 increased T cell proliferation induced by peptide and I-Ad, shifting the dose-response to lower concentrations of peptide, as demonstrated by larger numbers of cellular divisions at lower doses of peptide; this was clearly evident on day 3 as well as day 4. In these conditions, coexpression of BTLA on CHO cells had no effect on T cell proliferation. In contrast, coexpression of HVEM on CHO cells caused a reduction in proliferation of wild-type DO11.10 T cells, but this was evident only at the lowest peptide dose and was evident only on day 3, not day 4, after T cell activation. This inhibition of T cell proliferation was specific to BTLA, as we found it only in wild-type but not Btla−/− T cells. In summary, HVEM inhibits both costimulation-independent and costimulation-dependent proliferation, but is more effective in blocking activation of antigen stimulated T cells at low B7-1 expression. Furthermore, HVEM-mediated inhibition of T cell proliferation requires BTLA expression by T cells.

Methods for Example 13.

Mice

C57BL/6 and BALB/c mice (Jackson Labs) were bred in our facility. Btla−/− mice were backcrossed to BALB/c for nine generations and were subsequently crossed onto the DOI 1.10 T cell receptor-transgenic background. LIGHT-deficient mice were previously described and HVEM-deficient (Tn-frsfl4−/−) mice will be described elsewhere (data not shown).

Plasmids and Retroviral Constructs.

The sequences of all oligonucleotides are provided in Supplementary Table 1 online Sedy et al., Nature Immunology (2005) 6:90-98. For preparation of B7x-B7h-GFP-RV, a PCR product made with primers 5'Bgl2 mB7x and B7xB7h bottom using IMAGE cDNA clone 3709434 as the template, plus a PCR product made with primers B7xB7h top and 3'RI GFP using the B7h-GFP plasmid (a gift from W. Sha, University of California, Berkeley, Calif.) as the template, were annealed and amplified with Pfu polymerase with primers 5'Bgl2 mB7x and 3'R1 GFP. This product, encoding the B7x extracellular domain, B7h transmembrane and cytoplasmic domains fused to GFP, was digested with BglII and EcoRI and was cloned into IRES-GFP-RV that had been digested with BglII and EcoRI.

The plasmid huHVEM-IRES-GFP-RV was produced by amplification of huHVEM with primers 5'Bgl2 huHVEM and 3'Xho1 huHVEM using IMAGE cDNA clone 5798167 (Invitrogen) as the template, followed by digestion with BglII and XhoI and ligation into Tb-lym-IRES-GFP-RV that had been digested with BglII and XhoI, replacing the Tb-lym cDNA with that of huHVEM. Similarly, m4-1 BB-IRES-GFP-RV was prepared with primers 5'Bgl2 m4-1BB and 3'Xho1 m4-1BB using library plasmid as the template, followed by digestion with BglII and XhoI and ligation into Tb-lym-IRES-GFP¬ RV. The plasmid mLT R-IRES-GFP-RV was prepared with primers 5'Bgl2 mLT R and 3'SalI mLT R using IMAGE cDNA clone 5293090 (Invitrogen) as the template, followed by digestion with BglII and SalI and ligation into Tb-lym-IRES-GFP-RV. The plasmid mHVEM-FL-IRES-GFP-RV was similarly prepared with primers 5'Bgl2 mHVEM and 3'Xho1 mHVEM using, as the template, cDNA from library infected BJAB cells sorted for BTLA tetramer binding, followed by digestion with BglII and XhoI and ligation into Tb-lym-IRES-GFP-RV. Three amino acid changes (N58S, K92R and E128G) in mouse HVEM cDNA cloned from the retrovirus library, compared with that of mouse HVEM cDNA from the 129 SvEv mouse strain, were implemented by Quick Change mutagenesis (Stratagene) to generate mHVEM(129)-IRES-GFP-RV with serial application of the primers S—N top plus S—N bot; R-K top plus R-K bot; and G-E top plus G-E bot.

The plasmid mHVEM-FL-GFP-RV was made from two PCR products, with primers 5'Bgl2 mHVEM and mHVEM/GFP bot using mHVEM-FL-IRES-GFP-RV as the template, and primers mHVEM/GFP top and 3'GFP+Sal using mHVEM-FL-IRES-GFP-RV as the template; the PCR products were annealed, amplified with primers 5'Bgl2 mHVEM and 3'GFP+Sal, digested with BglII and SalI and ligated into IRES-GFP-RV that had been digested with BglII and SalI. The plasmid mHVEM-FL-GFP-RVCRD1 was made by Quick Change mutagenesis from mHVEM-FL-GFP-RV with primers mHVEM dI top and mHVEM dI bot. The plasmid m/hHVEM-IRES-GFP-RV (mouse CRD1 fused to human CRD2) was made from two PCR products, with primers 5'Bgl2 mHVEM and m/hHVEM bot using mHVEM-FL-IRES-GFP-RV as the template, and primers m/hHVEM top and 3'Xho hHVEM using hHVEM-IRES-GFP-RV as the template; the PCR products were annealed, amplified with primers 5'Bgl2 mHVEM and 3'Xho huHVEM, digested with BglII and XhoI and ligated into Tb-lym-IRES-GFP-RV that had been digested with BglII and XhoI. C57BL/6-BTLA-GFP-RV, a BTLA-GFP chimera, was prepared from two PCR products, with primers J10RV1 (Bgl 2) and 3'J10+10 using C57BL/6 BTLA cDNA as the template, and primers 5'GFP+10 and 3'GFP+Sal using GFP cDNA as the template; the PCR products were annealed, amplified with J10RV1 (Bgl 2) and 3'GFP+Sal, digested with BglII and SalI and ligated into Tb-lym-IRES-GFP-RV that had been digested with BglII and XhoI. A cytoplasmic deletion of this construct, BTLA-trunc-GFP-RV, was made by site-directed mutagenesis (Stratagene) with primers mjl ltrunc top and mj11trunc bottom.

PD-1-GFP-RV was made by amplification of the PD-1 coding region with primers PD15' and PD13' using PD-1 cDNA as the template (a gift from T. Honjo, Kyoto University, Kyoto, Japan); the PCR product was digested with BglII and BamHI and was cloned into AIB3-GFP MSCV that had been digested with BglII and BamHI (a gift from W. Shay. Similarly, PD-L1-GFP-RV was made by amplification of the region encoding PD-L1 with primers PD-L1G5' and PD-L1G3' using PD-L1 cDNA (a gift from T. Honjo) as the template; the PCR product was digested with BglII and BamHI and was ligated into AIB3-GFP MSCV.

PD-1 pET28 was made by amplification of the immunoglobulin domain of PD-1 with primers PD1 Tet5' and PD1 Tet3' using PD-1-GFP-RV plasmid as the template, followed by digestion with NcoI and BamHI and ligation intoMLL1-pET28 (a gift from D. Fremont, Washington University, St. Louis, Mo.) that had been digested with NcoI and BamHI. Similarly, B6-BTLA pET28 was made by amplification of the extracellular immunoglobulin domain of BTLA with primers J11TetMus5' and J11TetB63' using C57BL/6 BTLA-GFP-RV plasmid as the template, followed by digestion with NcoI and BamHI and ligation into MLL1-pET28. Similarly, BALB-BTLA pET28 was made with primers J11TetMus5' and J11TetWEHI3' using mJ11W1 as the template, and digestion with NcoI and BamHI and ligation into MML1-pET28. The immunoglobulin domain was 'corrected' to authentic BALB/c allelic sequence (data not shown) by serial mutagenesis with primers W1e23k5' and W1e23k3' followed by primers W1 h38n3B and W1 h38n5C.

Fc Fusion Proteins

For the creation of CD47-Fc-αTP-ires-GFP-RV, a bicistronic retroviral vector for Fc fusion proteins, CP318 (a gift from Lewis Lanier, University of California, San Francisco, Calif.) was digested with PflF I and NotI, treated with Vent polymerase and ligated into mIL-12R-ires-GFP-RV that had been digested with BglII and XhoI and treated with mung bean nuclease. The plasmids mBTLA-Fc-αTP-ires-GFP-RV, mB7x-Fc-αTP-ires-GFP-RV, mPD-L1-Fc-αTP-ires-GFP-RV and hBTLA-Fc-αTP-ires-GFP-RV were made by ligation of the following XhoI-digested PCR products containing the immunoglobulin domains regions of these genes into the XhoI site of CD47-Fc-αTP-ires-GFP-RV. The product mBTLA was made with primers 5'xho mJI 1 dodecamer and 3' xho mJ 11 dodecamer using as a template the C57BL/6 splenocyte phage library (Stratagene). The product mB7x was made with primers 5'xho mB7x dodecamer and 3'xho mB7x dodecamer using IMAGE cDNA clone 3709434 (Invitrogen) as the template. PD-LI was made with primers 5'xho mPDL2 dodecamer and 3'Xho PDL1 dodecamer using pBacPAK8-PDL1 (a gift from T. Honjo) as the template. Human BTLA was made with primers 5'Xho hJ111g and 3'Xho hJH Ig using hJ11(corr)ires-GFP-RV as the template.

Fc fusion proteins were produced by transfection of Phoenix E cells, were purified with Affi¬prep protein A columns (Biorad) and were dialyzed against PBS and stored at –70° C. For flow cytometry, cells were stained with 200 ng of purified Fc-fusion protein or, for hBTLA-Fc fusion protein, 1 ml of supernatant, followed by phycoerythrin-conjugated anti-human IgG (heavy plus light) that had been adsorbed against proteins from mouse, rat, cow and other species (Jackson Immunoresearch), and anti-mCD4-tricolor (Caltag) and anti-mB220-fluorescein isothiocyanate (FITC; BD-Pharmingen).

Production of Tetramers

Tetramers produced with plasmid PD-1 pET28, B6-BTLA pET28 or BALB-BTLA pET28 were transformed into BL21-CodonPlus (DE3) RIPL Competent Cells (Stratagene) essentially as described. Purified proteins were biotinylated in vitro with BirA ligase (Avidity), purified by gel filtration and concentrated. Tetramers were formed by the addition of biotinylated protein to streptavidin-phycoerythrin at a molar ratio of 1:4.

Cell Lines

BJAB and NIH 3T3 cells were from A. Chan (Washington University, St. Louis, Mo.); EL-4 cells were from T. Ley (Washington University, St. Louis, Mo.); 293T cells were from R. Schreiber (Washington University, St. Louis, Mo.); CHO cells were from A. Sharpe (Harvard University, Boston, Mass.); and Phoenix A and E packaging cells were from American Type Culture Collection. Retrovirus constructs were packaged either in Phoenix A or E cells by calcium phosphate transfection as described. CHO cells were transduced by retrovirus packaged by transfection of 293T cells with pYITG plus pCGP (a gift from W. Sha) and were sorted for GFP to more than 95% purity, followed by staining with 6A6 (anti-BTLA) or BTLA-phycoerythrin tetramers.

Retrovirus Library

Purified BALB/c and C57BL/6 splenocytes were left unstimulated or were activated for 48 h with plate-bound anti-CD3 (500A.2 ascites) or soluble anti-IgM (Jackson Immunoresearch), then RNA was purified (RNeasy mini kit; Qiagen) and mRNA was made with the Nucleotrap mRNA purification kit (Clontech), full-length cDNA was made with the SMART cDNA Library Construction Kit (Clontech) and double-stranded cDNA was made by long-distance PCR with 5'PCR primer and CDS III/3'PCR primer; the PCR products were digested with Sfi1, size fractionated, amplified cDNA ligated into Sfi1-digested MSCV-ires-Thy1.1 retrovirus vector (a gift from W. Sha) and were transduced into XL-10 gold (Stratagene) for a library transcript complexity of $2 \times 10^6$. The library plasmid was purified without further amplification by CsCl gradient ultracentrifugation. Infected NIH-3T3 cells ($8 \times 10^6$) and infected BJAB cells ($6 \times 10^6$) were generated from retrovirus made by calcium phosphate transfection of Phoenix E cells; the total number of infected cells was assessed by anti-Thy1.1-FITC (eBioscience) staining. Serial rounds of cell sorting used anti-Thy1.1-FITC and BALB/c and C57BL/6 BTLA tetramers. When the sorted cells were more than 80% positive for Thy1.1 and BTLA tetramer, RNA was prepared and reverse-transcribed, cDNA was amplified with Taq polymerase and primers Sfi 5' and Sfi 3', and PCR products were cloned into pGEM-T Easy (Promega).

T Cell Purification and Stimulation

T cells were purified (>90%) with anti-CD4 magnetic beads (Miltenyi) and, where indicated (FIGS. 38B-D, 39) by subsequent sorting for populations that were negative for B220-FITC and CD11c– phycoerythrin and positive for CD4-CyChrome (>98%). For T cell stimulation with anti-CD3 and LIGHT, 2C11 (BD Pharmingen) was coated onto 96-well plates, followed by LIGHT (PeproTech) at the indicated doses (FIG. 38A). Purified T cells were plated at a density of $1 \times 10^6$ cells/ml in 100 μl media per well. CHO cells were treated in media for 16 h at 37° C. with 50 μg/ml of mitomycin C (Sigma), were washed twice in PBS and were plated at a density of $1 \times 10^6$ cells/ml in 100 μl media in 96-well plates for proliferation assays or in 1 ml media in 24-well plates for CFSE analysis. For proliferation assays, purified T cells were plated directly onto CHO cells at a density of $1 \times 10^6$ cells/ml in 100 μl media and OVA peptide. After 48 h, cells were pulsed for 12 h with 1 μCi/well of [$^3$H]thymidine. For CFSE analysis, purified T cells were washed three times with PBS, were incubated for 8 min at 20° C. with 1 μM CFSE (Molecular Probes), were 'quenched' with fetal calf serum, were washed twice with media and were plated directly onto CHO cells at a density of $1 \times 10^6$ cells/ml in 1 ml media plus OVA peptide. After 3 and 4 d, cells were stained with CD4-FITC and were analyzed by flow cytometry.

Immunoblot Analysis

Pervanadate stimulation was done as described. For cell-mixing experiments, 25×10$^6$ EL4 cells were mixed with 25×10$^6$ BJAB cells expressing GFP or 25×10$^6$ BJAB cells expressing mouse HVEM in 1 ml for 4 min at 37° C. and were lysed as described. Extracts were precleared with protein G-Sepharose (Pharmacia), followed by immunoprecipitation with 9 µg of 6A6 (anti-mBTLA) or isotype control Armenian hamster IgG (Santa Cruz) and 40 ul protein G-Sepharose (Pharmacia), then were washed and analyzed by SDS-PAGE. Immunoblot analyses for SHP-2 and phosphotyrosine were done as described in Watanabe et al, Nat. Immunol. (2003) 4:670-679 and Gavrieli et al, Biochem. Biophys. Res. Commun. 312:1236 1243 (2003).

For further details regarding Example 13, including references, see Sedy et al., Nat. Immunol., 6:90-98, which is expressly incorporated herein in its entirety by reference.

Example 14

BTLA Polymorphism and BTLA Binding Antibodies

Allelic Polymorphisms in BTLA

We previously generated BTLA cDNA from several sources, including from the cell line WEHI 231, a commercial murine C57BL/6 splenocyte cDNA library, and 129SvEv mice, finding several polymorphisms within the BTLA Ig domain coding sequence. To determine the basis of differences, we sequenced the coding region for the BTLA Ig domain from genomic DNA of several inbred and wild mouse strains (FIG. 40). Among 23 strains, we identified three distinct alleles of BTLA, differing in their predicted amino acid sequence and potential predicted disulphide bonding pattern (FIG. 40A). The allele represented by BALB/c was present in CBA/J, SJL/J, New Zealand White (NZW), BXSB, C3H/J, New Zealand Black (NZB/BinJ), NOD, 129SvEv, and 129SWJ (FIG. 40B). A second allele, represented by the strains MLR/Ipr, AKR, SWR, CALB/RK, and DBA/2J, differed from the BALB/c allele at only one amino acid, containing histidine rather than asparagine at residue 38 of the BTLA protein. These two alleles each have five cysteine residues within the Ig domain, predicting two disulfide bonds and one unpaired cysteine. The third allele, represented by C57BL/6, was also present in B10.PL and several wild-derived inbred strains, and differed from the BALB/c and MLR/Ipr alleles at 10 and 11 amino acid residues, respectively (FIG. 40A). Notably, the C57BL/6 allele has a cysteine at amino acid residue 49, making six total cysteine residues with three predicted disulfide bonds in the BTLA Ig domain. As a control, we found no sequence polymorphisms in the PD-1 Ig domain from BALB/c, MLR/Ipr, and C57BL/6 (data not shown).

Generation of Allele-Specific Mabs to Murine Btla

Figure 41:
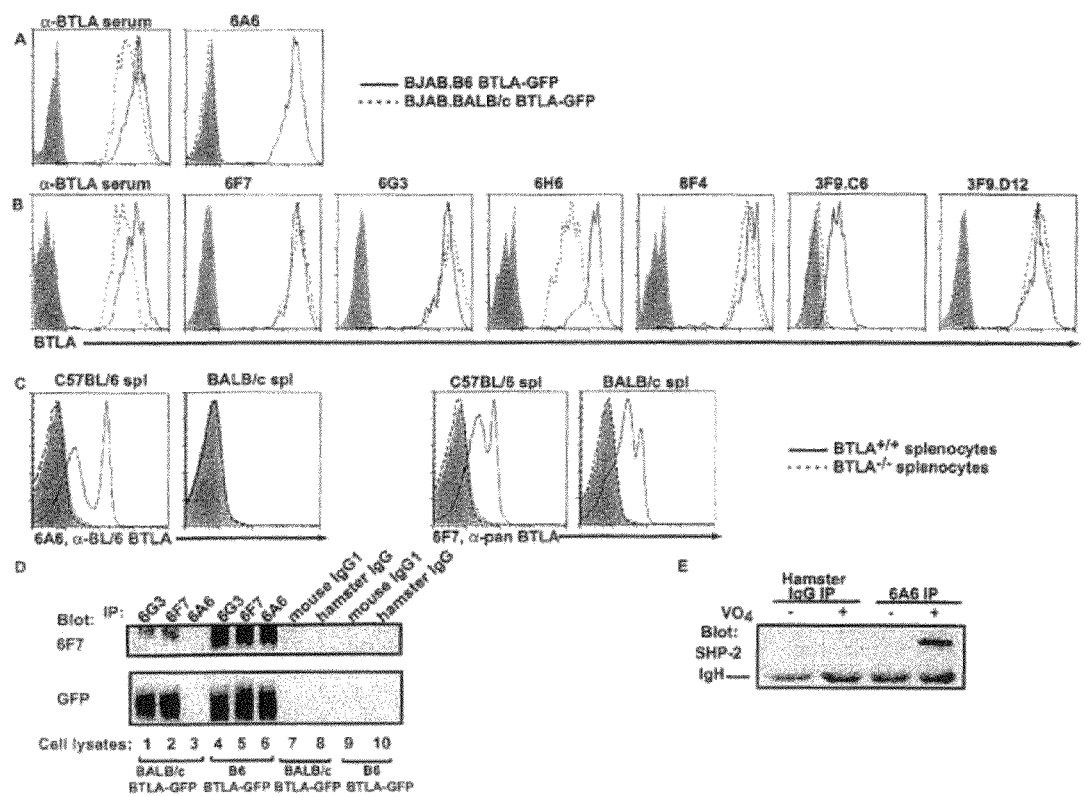
FIG. 41 Production of mAbs to allelic variants of murine BTLA. A and B, BJAB cells were stably transfected with retroviral constructs expressing the extracellular/transmembrane domains of BTLA from C57BL/6 (BJAB.B6 BTLA-GFP, solid histogram) or BALB/c (BJAB.BALB/c BTLA-GFP, dotted histogram) as GFP fusion proteins. Cells were stained with the indicated purified mAbs or postimmune serum (hamster anti-BTLA (A) serum, mouse anti-BTLA (B) serum). Secondary staining was with either anti-hamster IgG (A) or anti-mouse Ig (B). Histograms shown are gated on GFP+ BJAB. B6 BTLA-GFP or BJAB.BALB/c BTLA-GFP cells stained separately. Shaded histogram for the hamster and mouse immune serum are controls using normal hamster serum or normal mouse serum to stain a mixture of BJAB. B6 BTLA-GFP and BJAB.BALB/c BTLA-GFP cells. Shaded histogram for mAb staining shows the isotype control of either hamster IgG (A) or murine IgG1 (B) staining a mixture of cells. C, Splenocytes from C57BL/6 or BALB/c wild-type mice (solid histogram) or BTLA−/− mice (dotted histogram) were stained with 6A6 (left) or 6F7 (right). BTLA−/− staining was equivalent to that of the isotype control (shaded histogram). D, Lysates from $25\times10^6$ cells BJAB. B6 BTLA-GFP or BJAB.BALB/c BTLA-GFP cells were immunoprecipitated (IP) with 10 µg of the indicated Ab and Western blots probed (Blot) with either 6F7, or with anti-GFP Ab, as indicated. As controls, cell lysates were immunoprecipitated with mouse or hamster IgG as indicated (lanes 7-10). E, EL4 cells were incubated in the absence (−) or presence (+) of pervanadate for 4 min at 37° C., and lysed in 1% Triton X-100 lysis buffer, immunoprecipitated (IP) with 6A6 or isotype control Ab (PIP anti-GST) and Western blots probed (Blot) with anti-SHP-2 as described.

To generate anti-BTLA mAbs, we immunized Armenian hamsters and BTLA−/− BALB/c mice with recombinant Ig domain of the C57BL/6 BTLA allele. To allow the identification of Abs that could potentially recognize either the BALB/c or C57BL/6 allele of BTLA, hybridoma supernatants were screened for binding to BJAB cells expressing either the C57BL/6 or BALB/c allele of BTLA as a GFP fusion protein. One hamster anti-BTLA Ab, 6A6, was identified that reacted only with the C57BL/6, but not the BALB/c, allele of BTLA (FIG. 41A). The majority of the murine anti-BTLA mAbs reacted with both the C57BL/6 and BALB/c BTLA alleles, including 6F7, 6G3, 8F4, and 3F9.D12 (FIG. 41B). One murine Ab, 3F9.C6, reacted only with C57BL/6 BTLA, and not with BALB/c BTLA. Another Ab, 6H6, reacted with both alleles, but stained the C57BL/6 allele more highly than the BALB/c allele. For each of these Abs, staining was observed on wild type splenocytes, but not splenocytes of BTLA−/− mice (FIG. 41C, and data not shown), suggesting that these Abs in fact recognize BTLA, and react with native BTLA as well.

To further assess how these Abs interact with BTLA, we characterized their behavior in IP and Western blot analysis (FIGS. 41D and E). The pan-specific Abs 6F7 and 6G3 each specifically immunoprecipitated both the C57BL/6 and BALB/c BTLA-GFP fusions proteins from BJAB cells (FIG. 41O, bottom panel). Importantly, the C57BL/6-specific 6A6 Ab did immunoprecipitate the C57BL/6 BTLA allele, but not the BALB/c allele (FIG. 41O, compare lanes 3 and 6), indicating that the allelic specificity observed by FACS analysis extends to its behavior in IP Western blot analysis. Also, these interactions seen in IP Western blot analysis were specific because no BTLA was immunoprecipitated using mouse or hamster IgG1 as an isotype control (FIG. 41O, lanes 7-10).

Notably, although equivalent amounts of each BTLA allele were immunoprecipitated when assessed by immunoblotting for the GFP epitope of the fusion proteins, detection of the Ig domain by IP Western blot analysis was not equally efficient. Following immunoprecipitation, the C57BL/6 BTLA Ig domain was detected much more strongly than the BALB/c allele by 6G3 and 6F7, both pan-specific anti-BTLA Abs, (FIG. 41O, top panel, lanes 1, 2, and 4-6). These results may indicate differential sensitivity between alleles for recognition or detection of the Ig domains, even using pan-specific Abs, which could result from differential sensitivity to denaturation of the antigenic epitope. Whatever the cause, it is necessary to consider this fact when using IP Western blot analysis in comparing BTLA from varying allelic backgrounds. Finally, certain Abs allow coimmunoprecipitation of BTLA-associated proteins. For example, IP Western blot analysis using 6A6 reproduces the known specific and inducible coassociation of SHP-2 with BTLA following pervanadate treatment (FIG. 41E).

Mapping Antigenic Epitopes Recognized by Anti-BTLA Abs

Figure 42A:
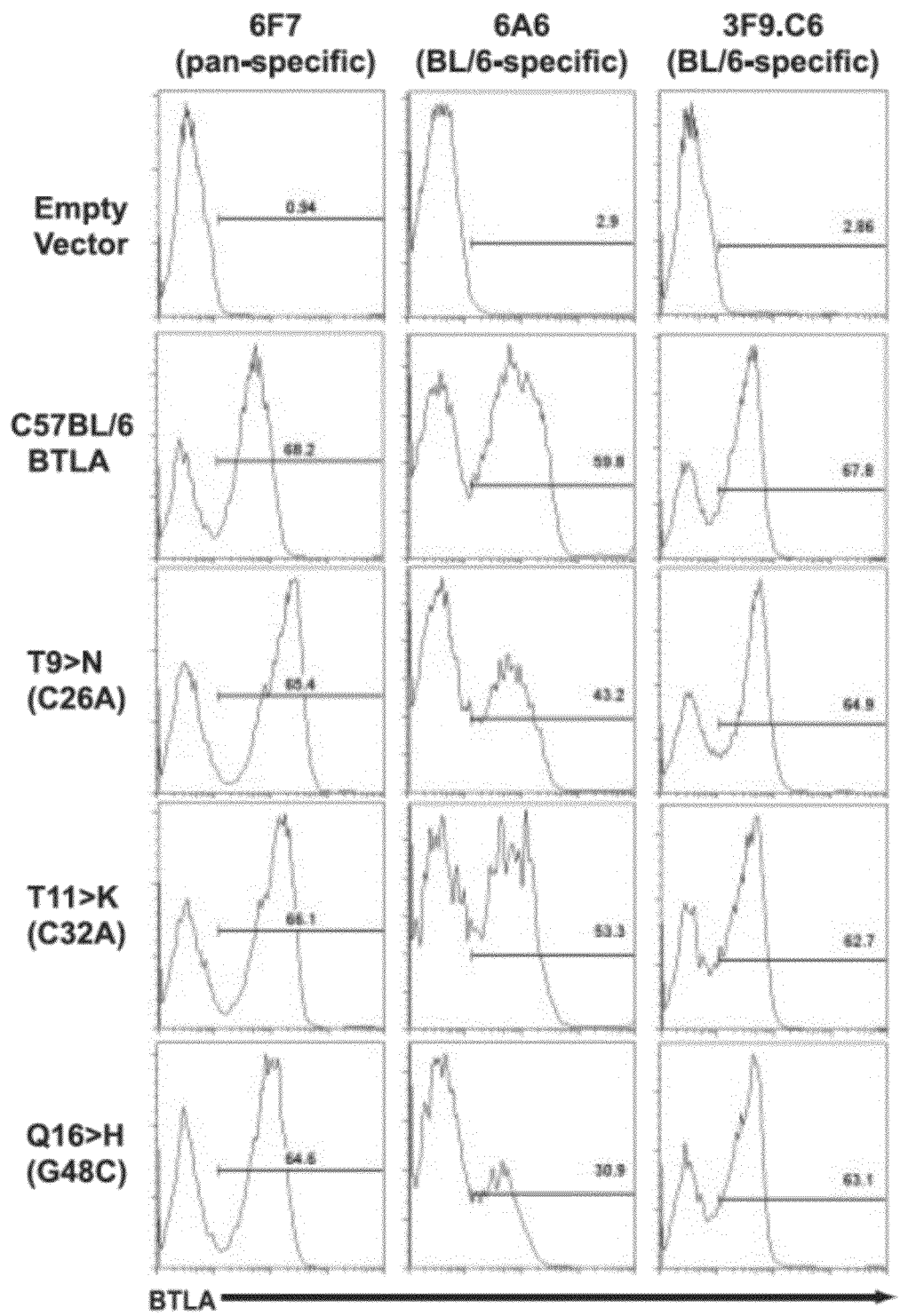
FIG. 42 Mapping epitopes recognized by BTLA Abs using Yeast Display (A and B). A panel of yeast cells expressing the indicated BTLA Ig domain Aga2 fusion proteins was analyzed for Ab staining. As a positive control, expression of the fusion protein was confirmed first for each line using staining with anti-HA Ab specific for the HA-tag incorporated into the BTLA-Aga2 fusion protein, and was positive for each line tested (data not shown). Yeast cells were stained with the anti-BTLA Ab indicated on top of each column. The amino acid substitutions (and corresponding nucleotide substitutions) in each yeast line are indicated on the left. Single-color histograms are marked (*) to indicate mutations that are not recognized by the corresponding Ab.
Figure 42B:
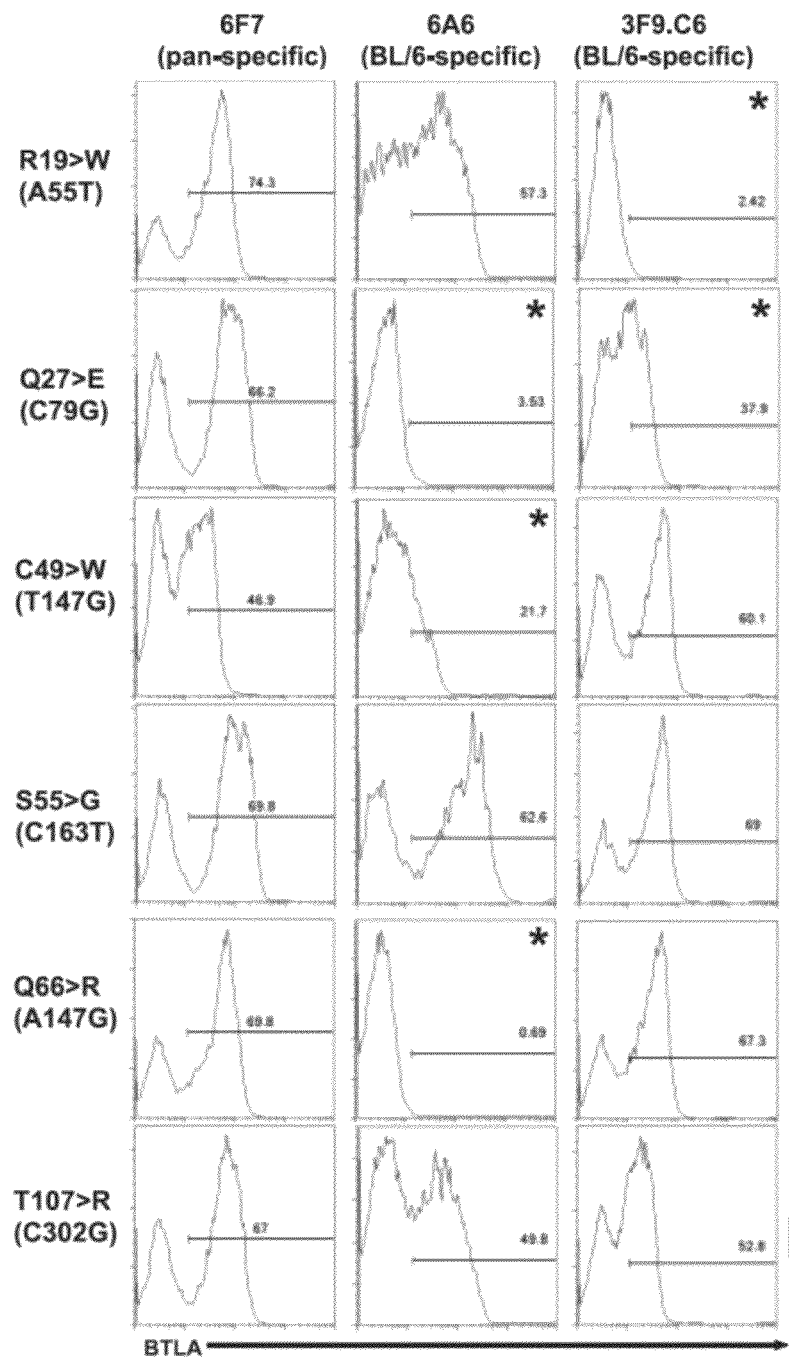

To map which of the polymorphic residues differing between BALB/c and C57BL/6 BTLA were involved in strain-specific reactivity of 6A6 and 3F9.C6, we used yeast display technology. We first expressed the BTLA Ig domain as an Aga2 fusion protein, and then generated a series of mutant BTLA Ig domains with single amino acid substitutions at the polymorphic residues, replacing BALB/c residues into the C57BL/6 allele one residue at a time (FIG. 42). This series of wild type and mutant BTLA proteins were then analyzed for reactivity with pan-specific anti-BTLA mAbs and two B6-specific Abs, 6A6 and 3F9.C6 (FIG. 42). As a positive control, we confirmed that the pan-specific anti-BTLA mAb 6F7 recognized the wild type C57BL/6 BTLA Ig domain, and also recognized each of the single residue substitutions of BTLA (FIG. 42, left column), as expected for pan-specific reactivity. In contrast, the two C57BL/6-specific Abs recognized some, but not all of BTLA mutants. Specifically, 6A6 showed a very selective loss of reactivity only with the Q27E, C49W, and Q66R substitutions, indicating that these residues are involved in the strain-specific recognition of BTLA. A distinct pattern of reactivity was observed with 3F9.C6, with a selective loss of reactivity with the R107W substitution and reduced reactivity with the Q27E substitution. Also, whereas 6A6 reactivity is sensitive to the C49W substitution, which disrupts one of three predicted disulphide bonds, 3F9.C6 reactivity remains in this substitution. These results indicate that the C57BL/6 specificity of these two Abs derive from interactions with the distinct, but polymorphic, region of the BTLA Ig domain.

In summary, at least two of the BTLA alleles can be distinguished by their antigenic structure, as shown by two C57BL/6-specific anti-BTLA Abs. Importantly, we also identified several pan-specific anti-BTLA Abs, which now allow direct comparisons of the fine specificity of tissue expression of native BTLA expression between various murine strains.

Distribution and Expression of Murine BTLA

Figure 43:
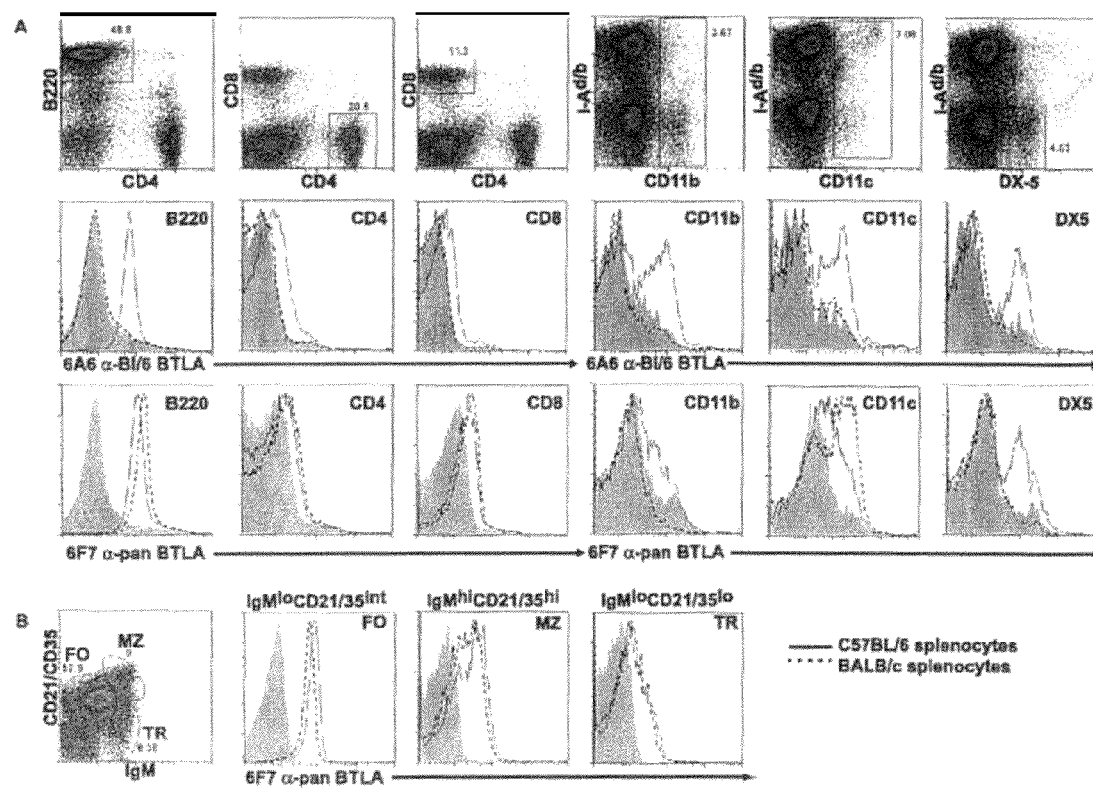
FIG. 43 BTLA shows broad and allelic-specific expression on lymphoid cell populations. A, Four-color FACS analysis was conducted on splenocytes from C57BL/6 (solid histogram) or BALB/c (dotted histogram). Two-color histograms (upper row) of the indicated markers used to gate cells for single-color histograms of 6A6 (middle row) or 6F7 (lower row) staining are shown. In the columns one, two, and three, cells were stained with anti-B220 allophycocyanin, anti-CD4 CyChrome, anti-CD8 FITC, and either biotinylated b-6A6 or b-6F7 followed by SA-PE secondary. In columns four, five, and six, cells were stained with anti-I-Ad PE (BALB/c cells) or anti-1-Ab PE (C57BU6 cells), and anti-CD11b FITC (fourth column), CD11c-FITC (fifth column), or anti-DX-5 FITC (sixth column), and b-6A6 or b-6F7 followed by SA-CyChrome secondary. Shaded histograms are staining of a mixture of C57BL/6 and BALB/c splenocytes using isotype controls of biotinylated hamster IgG (middle row) and mouse IgG1 (lower row). The numbers shown in top panels are the percentage of live cells within the indicated gate. The identity of the gated population is indicated in the panel. B, C57BL/6 and BALB/c splenocytes were stained with Abs to identify the following B cell populations: follicular B cells (FO), IgMlowCD21/CD35int; marginal zone (MZ), IgMhighCD21/CD35high; transitional (TR), IgMlowCD21/CD35low. Staining with the pan-BTLA-specific Ab 6F7 revealed equivalent BTLA levels between strains for all subsets.

In our previous studies, we were restricted to analyzing BTLA expression either by mRNA expression or by using epitope-tags because we lacked Abs to native BTLA. Conceivably, we failed to detect low but physiologically important levels of BTLA on certain lymphocyte subsets for this reason. Thus, we examined BTLA surface expression on various lymphoid subsets again, using both allele-specific Ab 6A6 and pan-specific Ab 6F7 (FIG. 43).

First, BTLA was expressed uniformly on B cells at levels that were similar for C57BL/6 and BALB/c mice (FIG. 43A). CD4+ and CD8+ T cells expressed lower levels of BTLA compared with B cells, but again, at levels that were similar for C57BL/6 and BALB/c mice. For 6A6, we found that a subpopulation of CD11b+ cells, CD11c+ dendritic cells, and DX5+ cells were positive for BTLA expression, and again identified only in C57BL/6 cells as expected (FIG. 43A, middle row). Using the pan-specific 6F7 Ab, we found that B cells express the highest levels of BTLA, again at levels similar between C57BL/6 and BALB/c mice, with lower levels expressed in CD4 and CD8 T cells (FIG. 43A, lower row). Interestingly, using the pan-specific reagent 6F7, we found that BTLA was expressed on CD11c+ BALB/c cells at levels similar to CD11c+ C57BL/6 cells, but that BTLA was only expressed on CD11b+ macrophages and DX5+ NK cells from C57BL/6 mice, but not in BALB/c mice (FIG. 43A, lower row). The fact that 6F7 detects BTLA expression on B cells, T cells, and CD11c+ cells from both BALB/c and C57BL/6 mice serves as a control for its ability to bind BTLA from both strains. Thus, the selective binding of 6F7 to DX5+ and CD11b+ cells only in C57BL/6, not BALB/c mice, indicates a difference between these strains for BTLA expression by these cell types. Thus, these strains appear to have a distinct difference in the cell types expressing detectable BTLA, explaining the differences between BTLA expression reported previously.

We also examined BTLA expression in splenic B cell populations (FIG. 43B). BTLA expression was detected at the highest levels on follicular B cells (1gMlowCD21/CD35int), and at reduced levels on marginal zone B cells (1gMhighCD21/CD35high) and transitional B cells (1gMlowCD21/CD35low) (FIG. 43B). Notably, because the 6F7 pan-specific Ab was used for analysis, we can also conclude that the levels on each subpopulation of B cells are similar between C57BL/6 and BALB/c mice (FIG. 43B).

Figure 44:
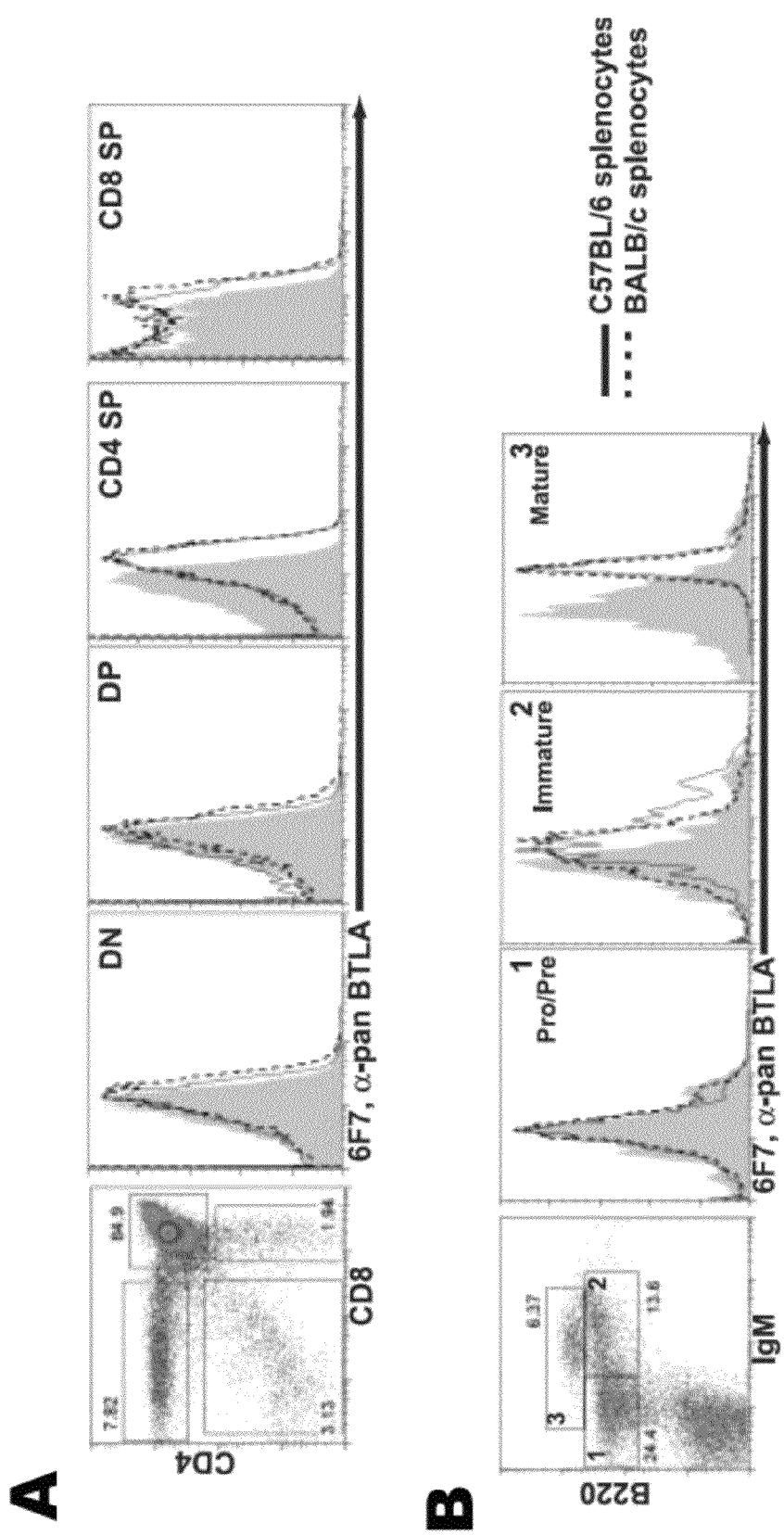
FIG. 44 BTLA is expressed during late stages of B and T lymphocyte development. A, Thymocytes from C57BL/6 (solid histogram) or BALB/c (dotted histogram) mice were stained with a combination of markers, anti-B220 RTC, anti-CD11c FITC, anti-CD11b FITC, anti-GR-1 FITC, anti-DX-5 FITC, CD4-CyChrome, CD8-PE, and either biotinylated (b)-6A7 or b-mouse IgG1, and SA allophycocyanin. The two-color histogram (first panel) is gated on marker (FITC)-negative live cells, and the numbers indicate the percentage of cells in the indicated gates. Single-color histograms for each gate are shown for b-6F7/SA-allophycocyanin staining for CD4-CD8-double negative (DN), CD4+CD8+ double positive (DP), CD4+ single positive (CD4 SP), or CD8+ single positive (CD8 SP) populations. Shaded histograms are staining the b-mouse IgG1 isotype control. B, Bone marrow cells were stained with anti-B220 allophycocyanin, anti-IgM PerCp Cy5.5, either b-6F7 or murine IgG1-biotin, and SA-PE. The numbers are the percentage of live gated cells within the three numbered gates. BTLA expression is shown in the single-color histograms for each gate; gate 1, Pre-B cells and Pro-B cells (IgM-B220low); gate 2, Immature B cells (IgM+B220low); gate 3, Mature B cells (IgM+B220high). Shaded regions are mouse IgG1 isotype control staining.

We next examined BTLA expression in thymocyte and B cell development (FIG. 44). In thymus, BTLA was expressed at highest levels on mature CD4+ T cells, and at slightly reduced levels on CD8+ T cells (FIG. 44A). BTLA expression on immature CD4-CD8- T cells or CD4+CD8+ double positive T cells was nearly undetectable (FIG. 44A). In bone marrow, BTLA was expressed at the highest levels on B220highIgM+ mature B cells (FIG. 44B), and was detected at relatively low levels on B220low/IgM+ immature B cells. BTLA expression was undetectable on B220+1gM− pro-B cells and pre-B cells. Further, we found no differences between C57BL/6 or BALB/c mice for the levels of BTLA expression on the thymocyte and bone marrow populations.

Figure 45:
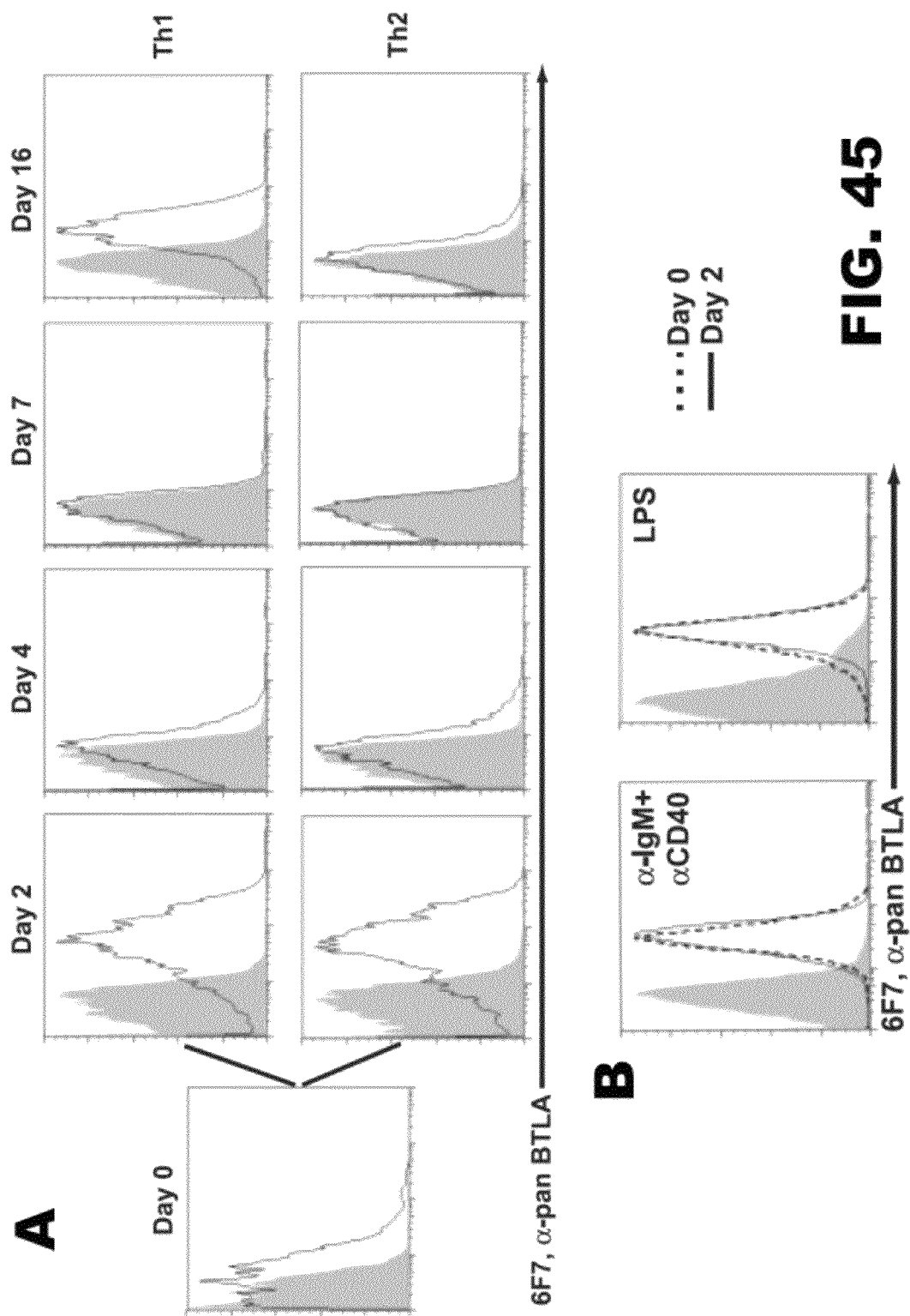
FIG. 45 BTLA expression during CD4+ T cell activation and Th1 polarization. A, DO11.10 transgenic T cells were purified by cell sorting and activated with 0.3 µM OVA peptide 324-336 under Th1 or Th2 conditions (see Materials and Methods Examples). Cells were harvested either before activation (Day 0) or on the indicated day following primary activation, and stained with KJ1-26 Tricolor, b-6F7, and SA-PE. T cells were restimulated with OVA peptide on day 7 and day 14. B, BALB/c splenocytes were stimulated with 10 µg/ml anti-IgM and 5 µg/ml anti-CD40 (left) or 1 µg/ml LPS (right). Single-color histograms of B220+ cells (anti-B220-FITC) are shown for b-6F7/SA-PE staining on day 0 (dotted histogram) and day 2 (solid histogram) after activation. Shaded histograms are the biotinylated mouse IgG1 isotype control.

Finally, we examined the BTLA expressed on CD4+ T cells under various conditions of activation and polarization by cytokines (FIG. 45A). BTLA surface expression on resting CD4+ T cells was induced by 10-fold on day 2 following activation with Ag and APCs, decreased by day 4, and was nearly undetectable by day 7 after activation (FIG. 45A). The rapid increase in BTLA expression by day 2 on Ag-activated CD4+ T cells occurred both in Th1-inducing or Th2-inducing conditions (FIG. 45A). Upon secondary T cell activation, BTLA was again highly induced 2 days following activation, again in both Th1 and Th2 cultures (data not shown). However, tertiary activation of T cells revealed selective induction in the Th1 cultures, but not in the Th2 cultures (FIG. 45A). These results suggest that BTLA expression on CD4+ T cells is initially controlled primarily by T cell activation and not by factors governing Th1 or Th2 differentiation. The delayed loss of BTLA inducibility in Th2 cells might suggest a silencing process rather than a Th1-specific pathway for induction, which would be consistent with our initial finding that BTLA expression is not dependent on Stat4 or Stat1. Finally, the rapid modulation of BTLA expression, peaking on day 2 and extinguished by day 7, suggests that it may act in the mid-phases of T cell activation following interactions with APCs.

In contrast to the activation-dependent expression of BTLA seen in CD4+ T cells, BTLA expression on B cells was maintained at high levels throughout activation by LPS or anti-IgM stimulation (FIG. 45B). These results differ slightly from the reported 3- to 10-fold decrease in BTLA expression following LPS activation of B cells. Nonetheless, our results agree with that report in the finding of high levels of BTLA expression on B220+ B cells in the periphery, and to some degree, the constitutive nature of its expression.

Selective Induction of BTLA on Anergic T Cells

Previously, a method of anergy induction for naive CD4+ T cells was developed that involves adoptive transfer of Ag-specific CD4+ T cells into recipients expressing Ag on somatic tissues. Specifically, clone 6.5 transgenic T cells, reactive to HA peptide 110-120 presented by I-Ad, become anergic when transferred into recipient mice expressing a membrane bound form of HA targeted for expression on lung and prostate tissue. We analyzed BTLA expression following T cell transfer on various days after transfer using Affymetrix gene arrays and FACS (FIGS. 46, A and B). We found that BTLA mRNA was highly induced in these anergic CD4+ T cells in this system, compared with CD4+ T cells activated by Ag-expressing vaccinia virus (FIG. 46A). At 2 days after transfer, BTLA expression by T cells undergoing anergy induction was twice the level of naive T cells, and significantly higher than activated T cells. This induction was more evident by day 3 and day 4 following transfer, with BTLA expression about 3-fold higher than in naive T cells. By contrast, BTLA levels were substantially reduced in fully activated T cells compared with naive or anergic T cells at these times (FIG. 46A). As a control, myosin Vila, a constitutive "housekeeping" gene, showed essentially no change in these three conditions over these times. Thus, BTLA mRNA appears to decline more rapidly than BTLA surface protein in activated T cells because activated T cells express peak BTLA surface levels at day 2 (FIG. 45), but show reduced BTLA mRNA (FIG. 46B). These observations are consistent with the reduced BTLA surface expression by day 4 and the essentially undetectable BTLA expression by day 7.

Figure 46C:
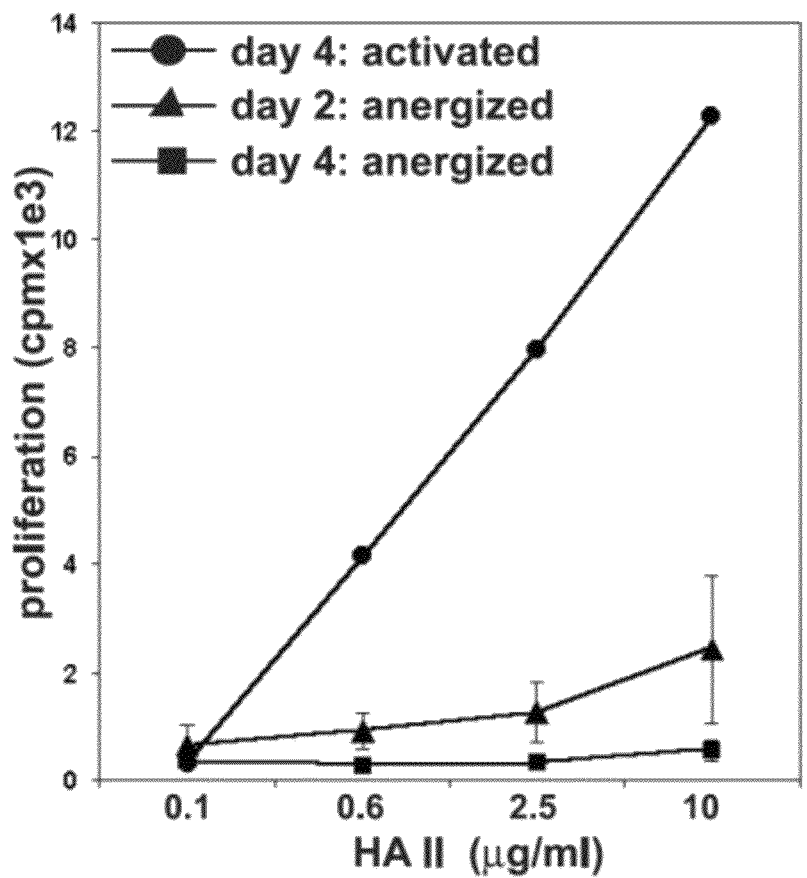
FIG. 46 BTLA is induced on anergic CD4+ T cells, but not CD4+CD25+ regulatory T cells. A, HA-TCR T cells were transferred into and subsequently harvested from B10.D2 mice (naive), C3-HAhigh mice (anergized) or B10.D2 mice infected with vaccinia-HA (activated) on days 2, 3, 4, or 7 after transfer as indicated. After harvest, T cells were isolated using combined magnetic bead and fluorescence sorting, and cDNA probe prepared and hybridized to Affymetrix microarrays M174A, M174B, and M174C. Relative BTLA expression intensity was determined using a latin-squares approach in Affymetrix Microarray Suite, version 5.1. software. Expression of myosin Vila gene is shown as a control. B, CFSE-labeled HA-TCR T cells were adoptively transferred into B10.D2 mice (naive), C3-HAhigh mice (anergized), or B10.D2 mice immunized with vaccinia-HA (activated), and harvested on day 6 as in A. Cells were stained with anti-CD4 allophycocyanin, anti-Thy1.1 PerCP, and either b-6F7 or murine IgG1-biotin, and SA-PE. BTLA expression is shown as single-color histogram for CFSE+ (naive) or CFSE− (activated and anergized) for CD4+ Thy1.1+ donor cells. C, Splenocytes harvested from recipients as in A were restimulated with HA peptide and proliferation measured on day 2. D, Splenocytes and lymph node cells from BALB/c mice were enriched for CD25− negative and CD25− positive populations using anti-CD25-PE and magnetic beads as described in Materials and Methods, and stained with anti-CD4-Cychrome, and biotin-conjugated 6F7, or biotin-IgG1, followed by SA-allophycocyanin. Two-color dot plots are shown for CD25 and CD4 (left panels), or single-color histograms gated on CD4+ cells for 6F7 (middle panels) or anti-PD-1 (right panels) for the CD25− (top row) and CD25+ (bottom row) fractions. For BTLA staining, histograms are shown for both the freshly isolated cells (thin histogram) and 36 h anti-CD3-activated cells (thick histogram). Shaded histograms are the staining of the mouse IgG1 isotype control. E, Cells isolated in D were stimulated with the indicated amount of anti-CD3 and proliferation measured after 2 days.
Figure 46D:
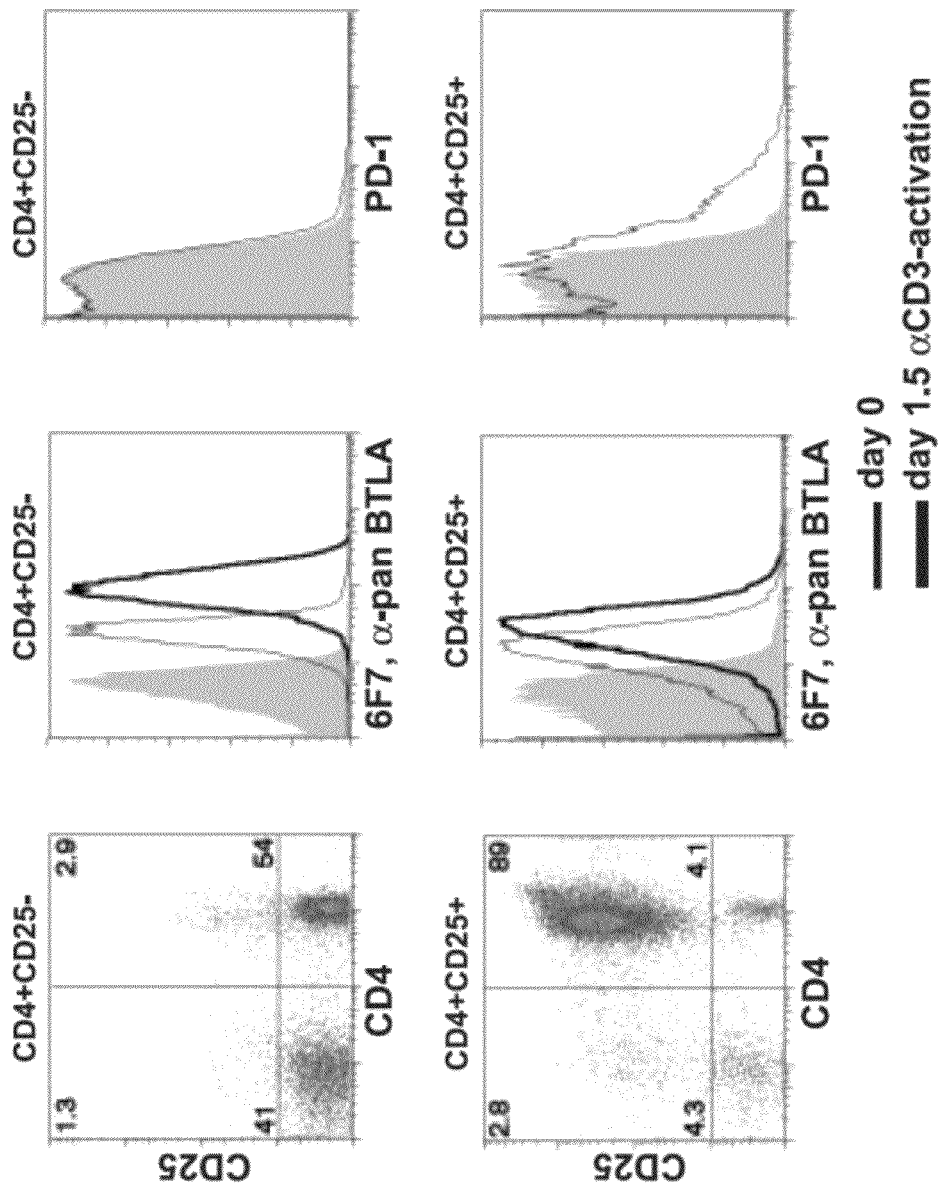
Figure 46E:
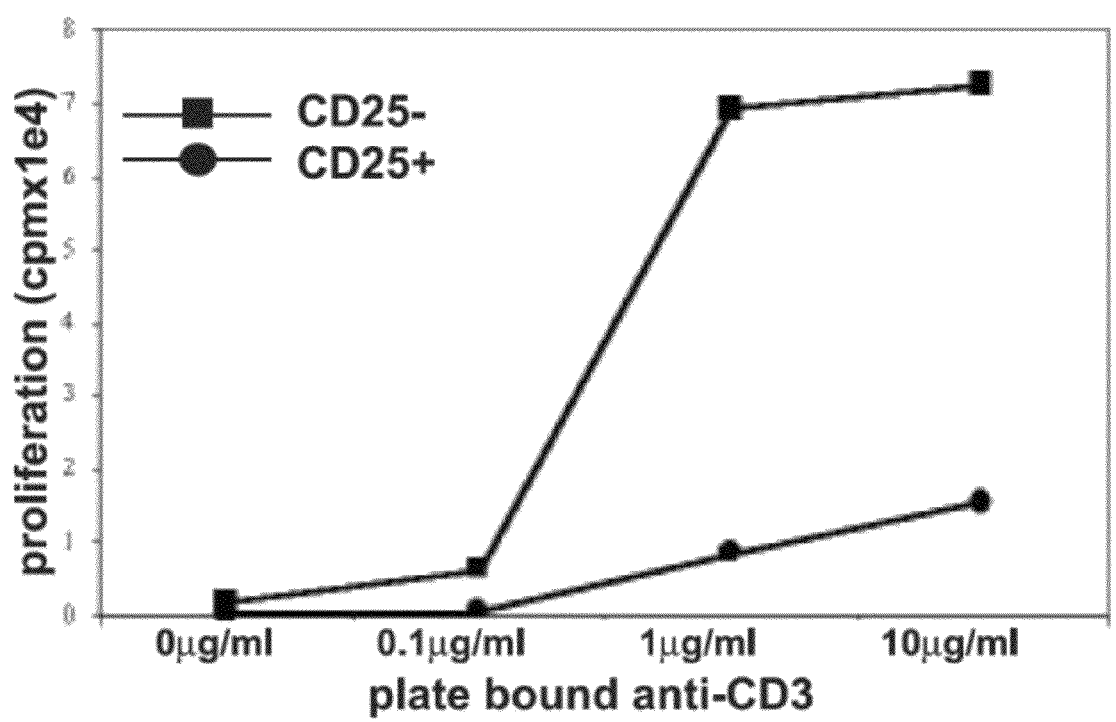

We next measured BTLA expression by FACS under conditions of anergy induction or activation (FIG. 14B). Notably, the highest levels of BTLA surface expression coincided with induction of anergy in vivo. Specifically, 6 days after transfer, anergic T cells expressed about 10-fold higher BTLA than naive T cells, and about 3-fold higher than in vivo-activated T cells (FIG. 46B). We verified that the CD4+ T cells transferred into HA-expressing recipients did become anergic as defined by lack of proliferation (FIG. 46C), consistent with previous reports. For comparison, we also wished to evaluate BTLA expression on conventional naive CD4+ T cells (CD4+ CD25−) T cells or T regulatory cells (CD4+CD25+) either as resting cells ex vivo or after in vitro activation with anti-CD3 (FIG. 46D). As expected, BTLA was expressed at low levels on naive T cells, and was induced about 10-fold 36 h after anti-CD3 treatment. Freshly isolated T regulatory cells expressed similar levels of BTLA as freshly isolated naive CD4+ T cell, but showed only a slight increase after treatment with anti¬CD3 (FIG. 46D). As a control, we confirmed that T regulatory cells, but not naive T cells, expressed PD-1, consistent with previous reports. As a further control, we showed that the isolated CD25+ T regulatory cells failed to proliferate in vitro, in contrast to the robust proliferation of freshly isolated naive T cells (FIG. 46E). In summary, BTLA shows a pattern of expression that is somewhat distinct from that of CTLA-4 and PD-1 in terms of its response to anergy induction and expression by T regulatory cells.

Role of BTLA in T cell-independent Ab Responses

Figure 47:
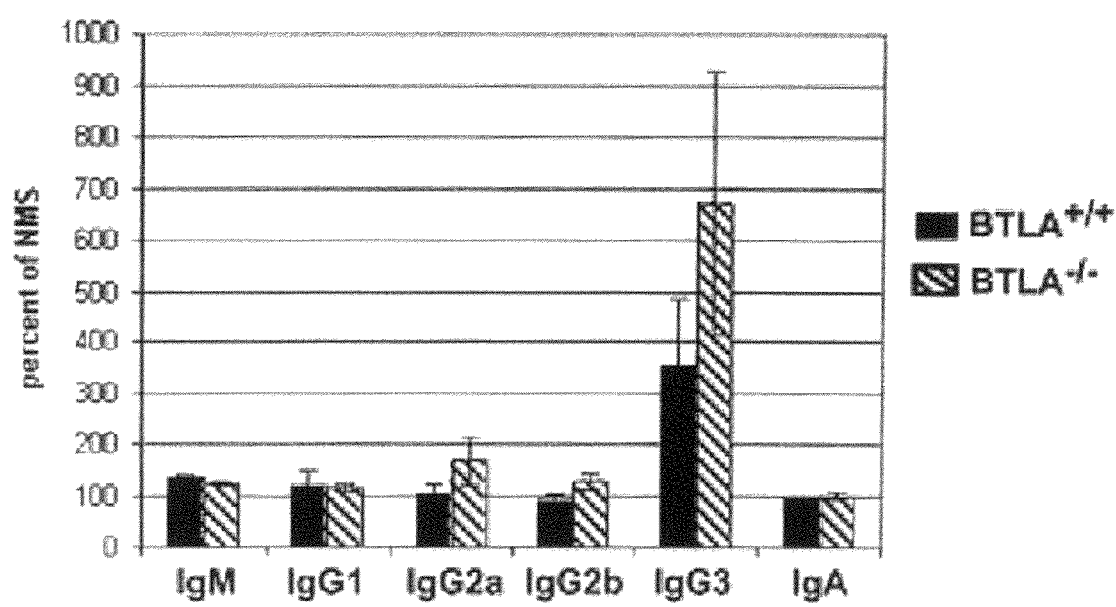
FIG. 47 BTLA−/− mice have modestly augmented IgG3 responses to T-independent Ag. 129SvEv wild-type mice or BTLA−/− mice (n=5) were immunized with 50 µg NP-Ficoll in alum by i.p. injection. At day 14, relative isotype-specific anti-NP Ab titer in serum was determined by ELISA. Data are shown as the percentage of the Ab titer produced in serum of naive BTLA+/+ or BTLA−/− mice. Mean±SD is shown.
Figure 48:
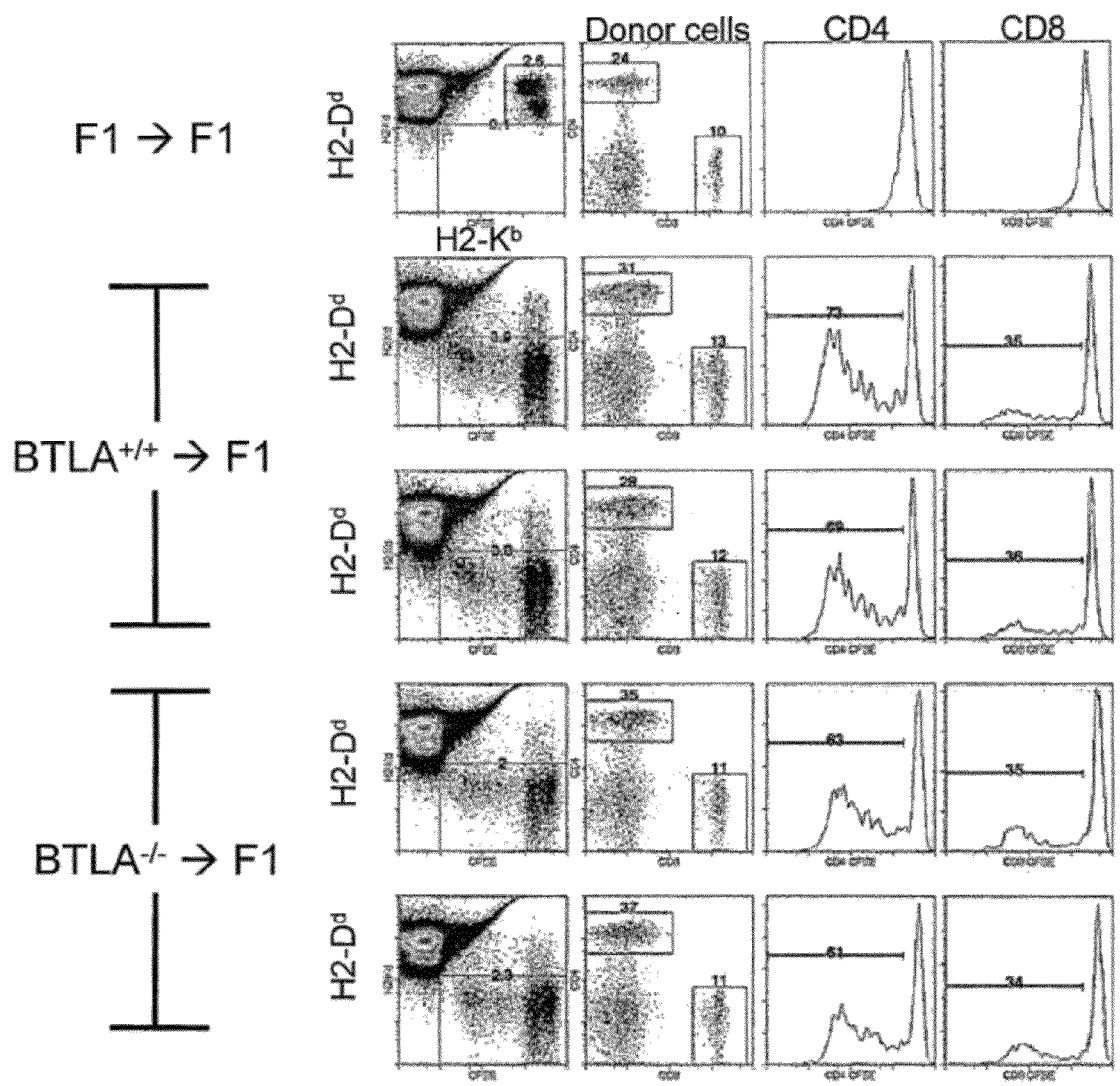
FIG. 48 BTLA−/− parental cells engraft and initially expand.
Figure 49:
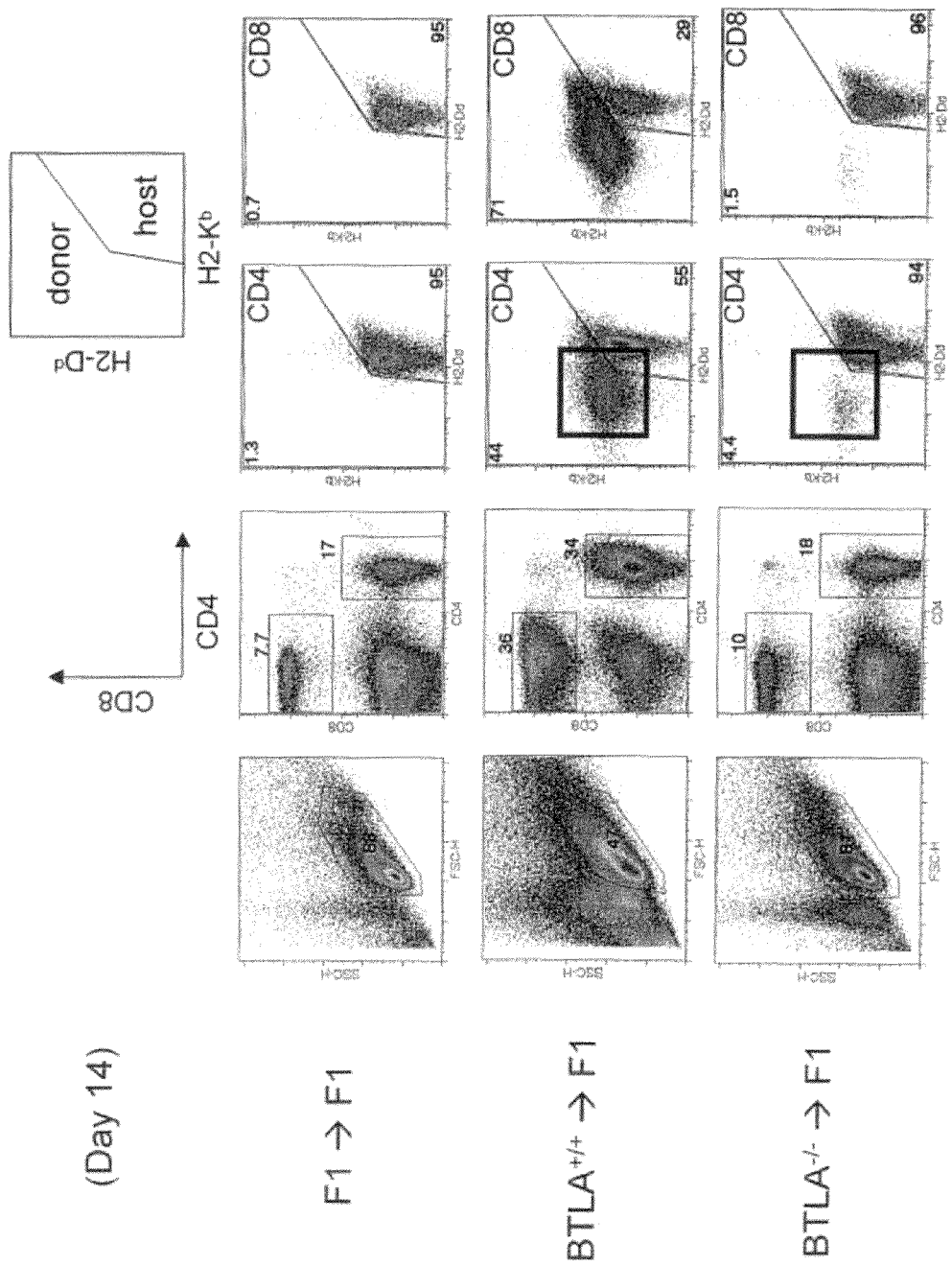
FIG. 49 BTLA−/− parental cells fail to survive following transfer.
Figure 50:
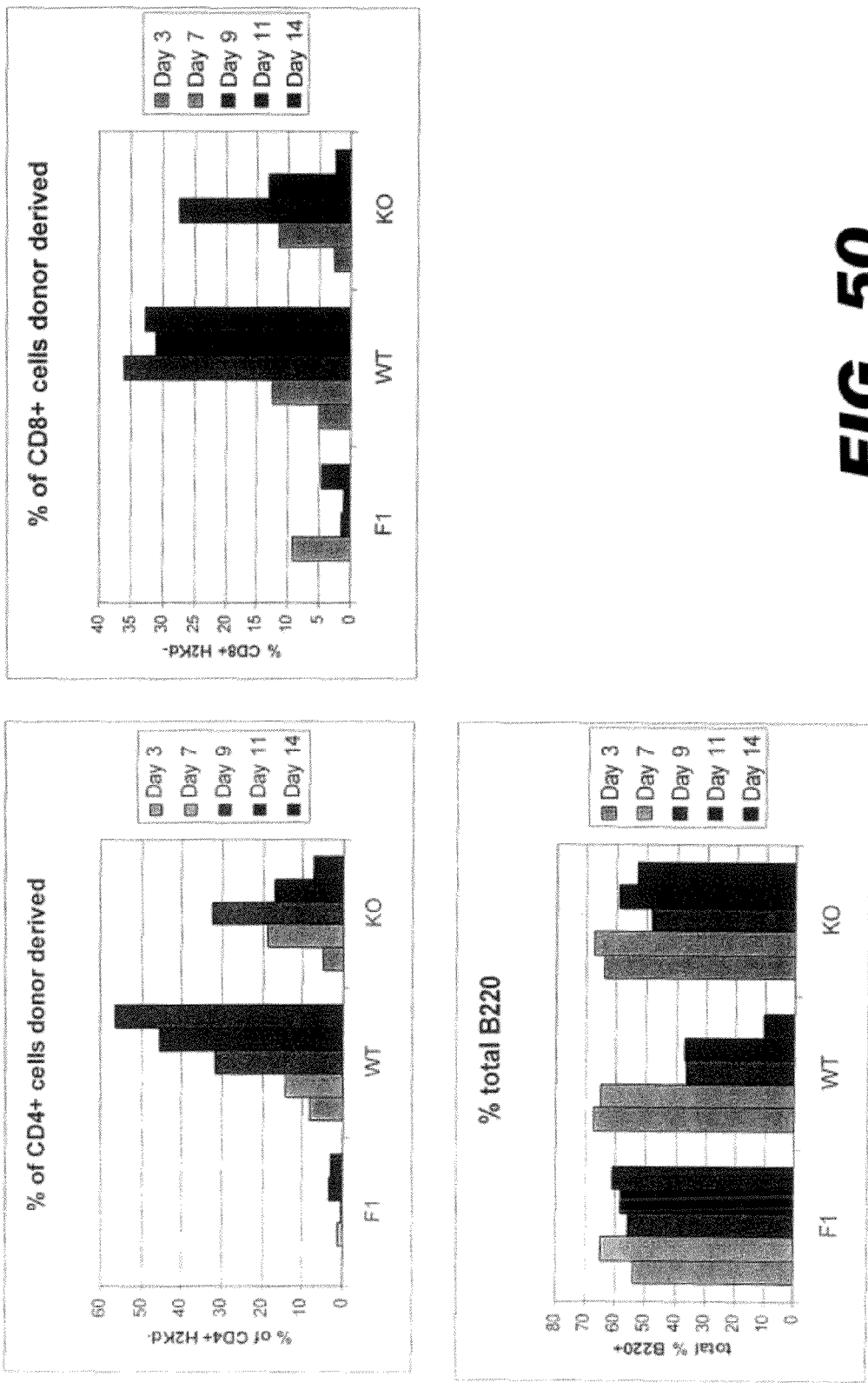
FIG. 50 BTLA−/− cells do not persist as GHVD progresses until about day 9, the expansion of WT and BTLA KO donor T cells is similar; At later times, BTLA−/− show rapid decrease is the number of remaining donor cells.
Figure 51:
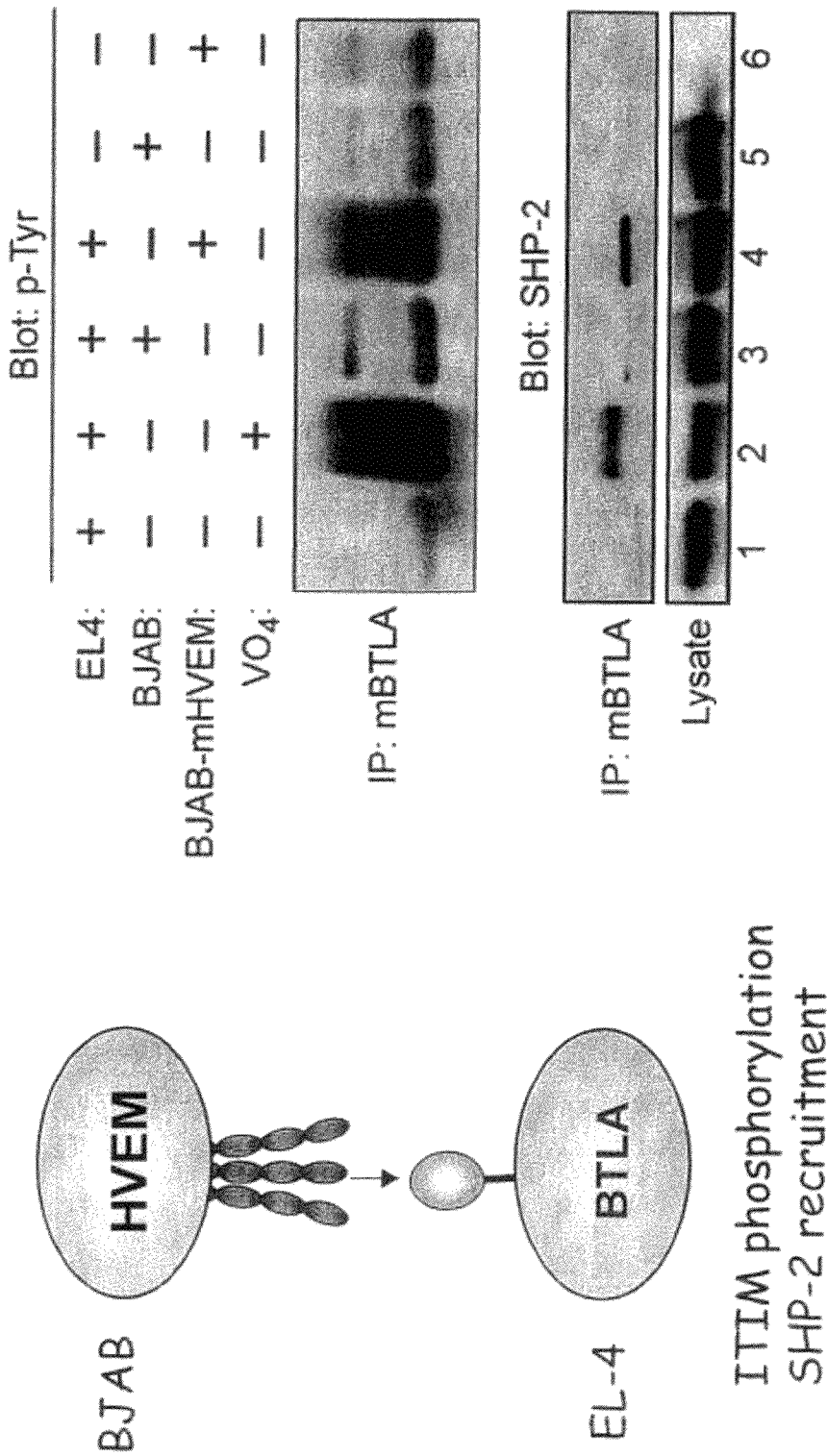
FIG. 51 HVEM induces BTLA-phosphorylation and SHP-2 recruitment in trans.
Figure 52:
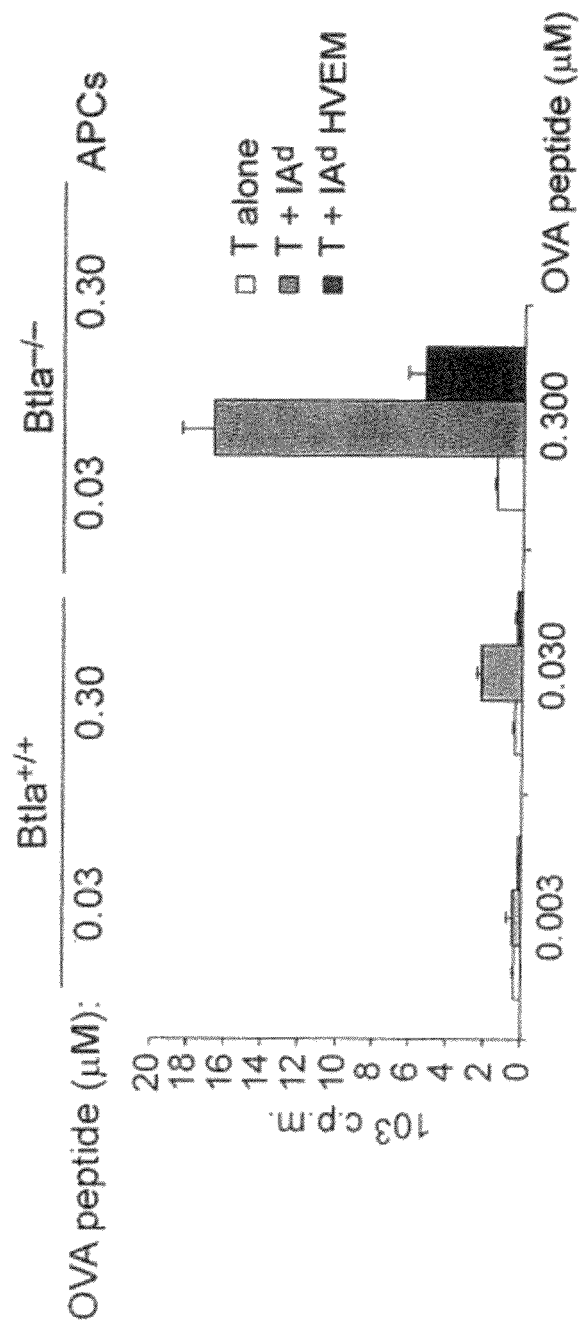
FIG. 52 HVEM on APCs inhibits T cell proliferation through BTLA. HVEM on APCs inhibits T cell proliferation. HVEM does not inhibit BTLA−/− T cells.
Figure 53:
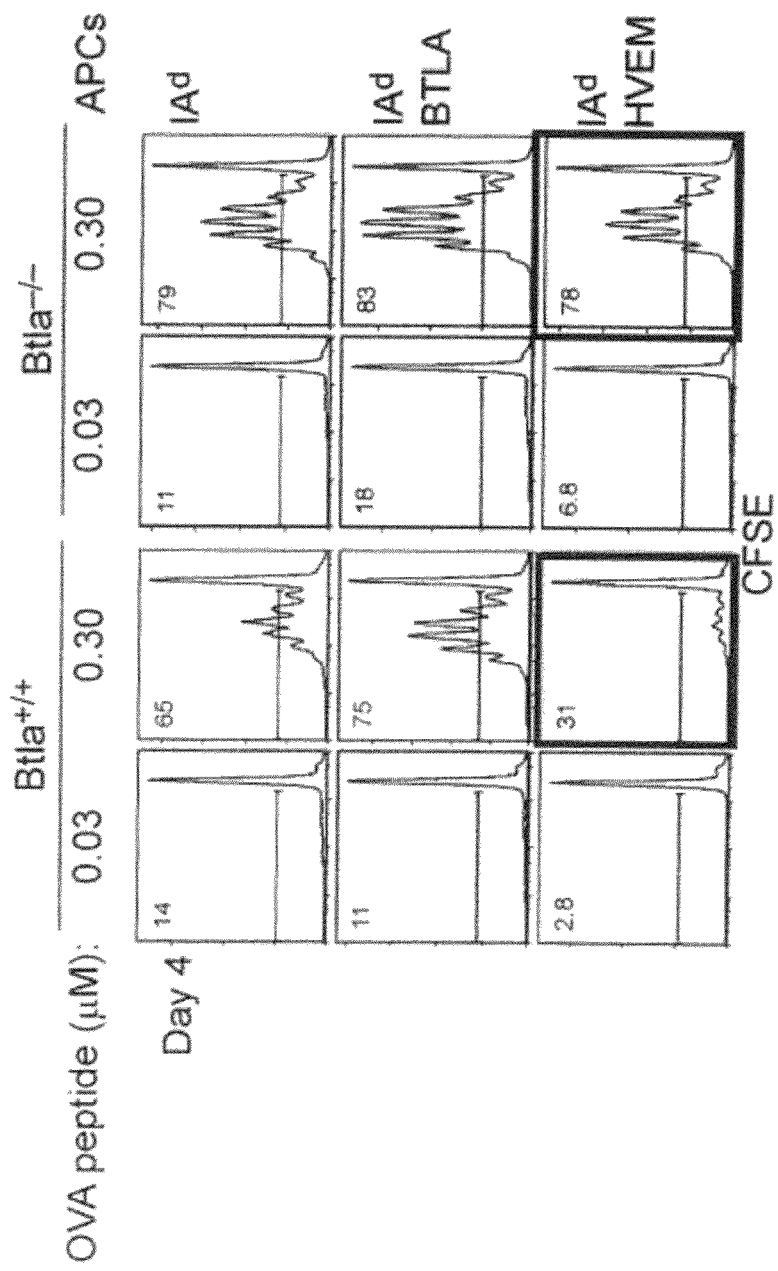
FIG. 53 HVEM on APCs inhibits T cell proliferation through BTLA.
Figure 54:
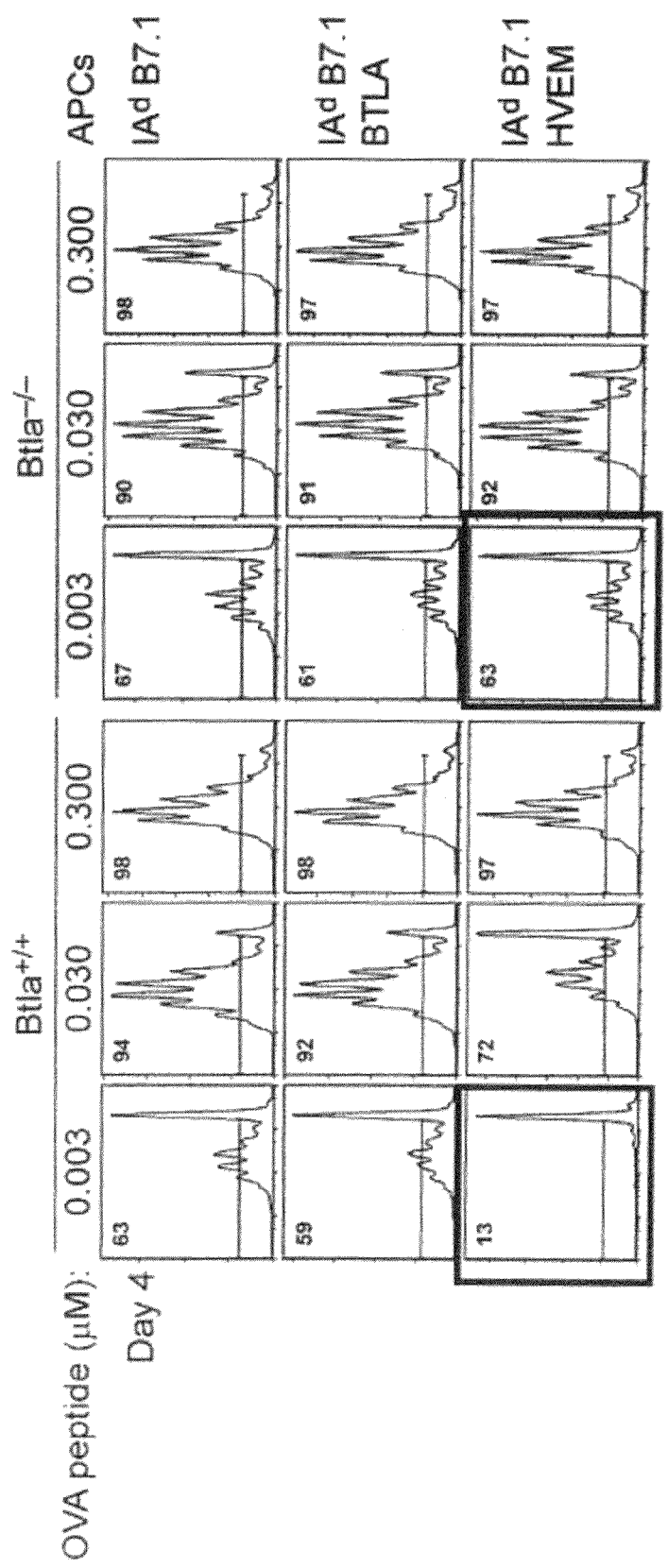
FIG. 54 HVEM inhibition is overcome by strong costimulation. HVEM inhibition of T cells is less with stronger co-stimulation. HVEM inhibition of T cells is less at highest antigen doses.

Our initial analysis of BTLA was motivated by consideration of its role in T cell activation. However, the fact that B cells express the highest level of BTLA, and the constitutive nature of this expression, motivated a second examination of its effect on Ab production. In our study, we examined T cell-independent Ab responses using immunization with NP-Ficoll in wild-type mice or BTLA−/−129SvEv mice, which express the BALB/c allele of BTLA. We immunized cohorts of mice with one injection of NP-Ficoll in alum and measured production of anti-NP Abs of specific isotypes on day 14 (FIG. 47). For the isotypes IgM, IgG1, IgA, we found no specific changes in levels of anti-NP Abs. For IgG2a or IgG2b, we found only slight increases in anti-NP Abs in the BTLA−/− compared with wild-type mice. However, for Abs of the IgG3 isotype, which is primarily associated with T-independent responses, we found an about 2-fold increased in anti-NP-specific Abs in BTLA−/− mice compared with wild-type mice. The size of this difference is consistent with the relatively modest increases in B cell and T cell proliferation responses described for BTLA−/− cells previously by both our report and by others, and is consistent with an inhibitory rather than activating role of BTLA. However, the relatively modest magnitude of this effect could also be an indication that BTLA expression by B cells may serve a purpose other than cell-intrinsic signaling, such as perhaps delivery of a signal toward cells expressing ligands for BTLA.

Methods for Example 14

The following Abs used for FACS analysis were from BD Pharmingen: CD4-CyChrome (RM4-5), CD8-FITC (53-6.7), B220-allophycocyanin (RA3-6B2), CD11b-FiTC (M1/70), CD11c-FITC(HL3), DX5-FITC, I-Ad-PE (AMS-32.1), I-Ab-PE (AF6-120.1), IgM-PerCP Cy5.5 (R6.60.2), CD21/CD25-FITC (7G6), CD25-allophycocyanin (PC61), CD62 ligand-FITC (MEL-14), Thy1.1-PerCP (OX-7), goat anti-mouse Ig-PE, mouse anti-Armenian/Syrian hamster IgG-PE (mixture), Streptavidin (SA)-PE, SA-CyChrome, and SA-aliophycocyanin. KJ1-26 Tricolor, hamster IgG-biotin, and murine IgG1-biotin were from Caltag Laboratories. All FACS analysis included an initial incubation with 2.4G2 (anti-CD16/CD32; BD Pharmingen) to block Fc receptor interactions. DO11.10 TCR transgenic mice were as described. C3 hemagglutinin (HA) high mice were as described. Immunoprecipitation (IP) Western blot analysis was conducted as previously described. Conditions used to induce Th1 and Th2 development were as previously described.

Sequencing of BTLA and PD-1 Ig domains

Exon 2 of BTLA or PD-1, encompassing the Ig domain, was amplified by PCR from genomic DNA from a panel of mouse strains previously described (23) using Easy-A High Fidelity PCR Cloning Enzyme (Stratagene) and the following intronic primers: BTLA (sense) ATGGTCCTTCTAAGAGT-GAAC (SEQ ID NO: 70), (antisense) ATAGATG-GTCTGGGGTAGATC (SEQ ID NO: 71) and PD-1 (sense) CAGGCTCCTTCCTCACAGC (SEQ ID NO: 72), (antisense) CTAAGAGGTCTCTGGGCAG¬3'(SEQ ID NO: 73).

PCR products were cloned into the pGEM-T Easy vector (Promega) and inserts from at least three individual subclones from each strain were sequenced using the T7 universal primer.

Generation of Soluble BTLA Ig Domain

The Ig domain of C57BL/6 BTLA was PCR amplified from cDNA using the following primers: BTLA (sense) CAT-GCCATGGAGAAAGCTACTAAGAGGAAT (SEQ ID NO: 74) and BTLA (antisense) CGGGATCCTGAA-GAGTTTTGAGTCCTTTC-3' (SEQ ID NO: 75). The product was subcloned into the pET28 vector (Novagen) that had been modified to contain a BirA biotinylation sequence (GGGLNDIFEAQKI EWHE) (SEQ ID NO: 76) onto the C terminus of the BTLA Ig domain. Proteins were expressed as insoluble inclusion bodies in BL21 (DE3) Codon Plus RIL cells (Stratagene) and refolded as described.

Production of mAbs to BTLA

Armenian hamsters or BALB/c background BTLA−/− mice were immunized with 100 μg of refolded C57BL/6 BTLA Ig domain protein in CFA, boosted biweekly with 100 μg of protein in IFA, and received a final i.v. boost 3 days before fusion. Splenocytes were fused with the P3X63Ag8 myeloma, and hybridoma supernatants screened for binding to BJAB cells expressing either C57BL/6 or BALB/c BTLA Ig domains as GFP fusion proteins. The BTLA¬GFP chimera was prepared by splicing by overlap extension (SOEing). A PCR fragment containing the BTLA cDNA with a 3' tail annealing to the 5' end of GFP was amplified by PCR made using Vent polymerase, the primers J10RV1-BglII (AGCTCTGAAGATCTCTAGGGAGGAAG) (SEQ ID NO: 77) and 3' J 10+10 (CCTTGCTCACACTTCTCACA-CAAATGGATGC) (SEQ ID NO: 78) with DOI 1.10 BTLA cDNA as template. A second fragment containing GFP cDNA, without its start codon, with a 5' tail annealing to the 3' end of BTLA was amplified by PCR using Vent polymerase and the primers 5' GFP+10 (TGTGAGAAGTGTGAG-CAAGGGCGAGGAGC) (SEQ ID NO: 79) and 3' GFP+Sal (ACGCGTCGACTTACTTGTACAGCTCGTCCATG) (SEQ ID NO: 80) with the GFP cDNA as template. The chimeric BTLA-GFP fusion cDNA was amplified by PCR from a mixture of these two PCR fragments using the primers J10RV1-BglII and 3' GFP+Sal, digested with BglII and SalI, and cloned into the BglII/SalI sites of IRES-GFP-RV to produce DO11.10-BTLA-GFP-RV. A cytoplasmic deletion was made using site directed mutagenesis (Stratagene) and the primers mj11 trunc top (GTTGATATTCCAGTGAG-CAAGGGCGAGGAG) (SEQ ID NO: 81) and mj11 trunc bottom (CTTGCTCACTGGAATATCAACCAGGT-TAGTG) (SEQ ID NO: 82) to produce DO11.10-BTLA-trunc-GFP-RV. The C56BL/6 version of BTLA trunc-GF-PRV was made by purifying a natural BglII/BamHI fragment from a BTLA cDNA cloned from a mouse spleen cDNA phage library (Stratagene). This fragment was then cloned into the Bg111/BamHI digested D011.10-BTLA trunc-GFP-RV to produce C57BL/6-BTLA trunc-GFP-RV.

Positive hybridomas were expanded and Abs purified using MAPS II-protein A columns. Hamster monoclonal 6A6 is of the IgG isotype, whereas all murine Abs are IgG1κ. Unless otherwise stated, all Abs were biotinylated using EZ-Link Sulfo-NHS-LC-biotin (Pierce) and detected with SA-conjugated fluorochromes. This procedure eliminated secondary Ab cross-reactivity with murine cells.

Yeast Display Mapping

The Ig domain of the C57BL/6 BTLA allele was amplified from cDNA using the primers 5'-GGAATTCCATATG-CAGCCAAGTCCTGCCTG-3' (SEQ ID NO: 83) and 5'-CATGCTAGCGAGAAAGCTACTAAGAGGAA-3' (SEQ ID NO: 84) and subcloned into the NdeI and the NheI sites of the pCT302-AGA2d vector to create an HA-tagged fusion to the Aga2 peptide. QuickChange mutagenesis was used to introduce mutations into this construct using the following primer pairs: C26At, CAGTGCAACTTAATATTACGAG-GAATTCCAAACAG (SEQ ID NO: 85); C26Ab, CTCG-TAATATTAAGTTGCACTGGACACTCTT (SEQ ID NO: 86); C32At, GCAACTTACTATTAAGAGGAATTCCAAA-CAGTCTGC (SEQ ID NO: 87); C32Ab, AATTCCTCT-TAATAGTAAGTTGCACTGGACA (SEQ ID NO: 88); G48Ct, GAATCCCAAACACTCTGCCAGGACAG-GAGAGT (SEQ ID NO: 89); G48Cb, CTGGCAGAGT-GTTTGGAATTCCTCGTAATAG (SEC) ID NO: 90); A55Tt, ACAGTCTGCCTGGACAGGAGAGTTATT-TAAAATT (SEC) ID NO: 91); A55Tb, TCCTGTCCAG-GCAGACTGTTTTGAATTCCT (SEC) ID NO: 92); C79Gt, GAGTTATTTAAAATTGAATGTCCTGT-GAAATACTGTGT (SEC) ID NO: 93); C79 Gb, AGGACAT-TCAATTTTAAATAACTCTCCTGTCC (SEC) ID NO: 94); T147Gt, ATGGAACAATCTGGGTACCCCTTGAGGT-TAGCC (SEC) ID NO: 95); T147 Gb, GGGTACCCAGAT-TGTTCCATTGTGCTTAC (SEC) ID NO: 96); A163G/T168Gt, TTGAGGTTGGCCCGCAGCTATACACTAG (SEC) ID NO: 97); A163/T168 Gb, GCTGCGGGCCAAC-CTCAAGGGGTACACAGA (SEC) ID NO: 98); A197Gt, TTGGGAAGAAAATCGATCAGTTCCGGTTTTTGTTCT (SEC) ID NO: 99); A197 Gb, AACTGATCGATTTTCTTC-CCAACTAGTGTA (SEC) ID NO: 100); C320Gt, ATCCAT-GTGAGAGAAAGGACTCAAAACTCTTCA (SEC) ID NO: 101); and C320 Gb, AGTCCTTTCTCTCACATG-GATGGTTACTGAATG (SEC) ID NO: 102).

Transformation of EBY100.Aga1 yeast with each construct resulted in surface expression of the BTLA mutant. Expression level was confirmed by anti-HA staining. Yeast cells were stained with anti-BTLA Abs as indicated to determine mutations that abolished Ab recognition.

CD4+ T Cell Activation and Expression Analysis

DO11.10 TCR transgenic cells were activated with 0.3 μM OVA peptide (amino acids 323-339) and irradiated (2000 rad) BALB/c splenic APCs as described. Th1 conditions consisted of heat-killed *Listeria monocytogenes*, IL-2 (40 U/ml; Takeda Chemical Industries), and 10 μg/ml anti-IL-4 (11 B11). Th2 cells were differentiated in 100 U/ml IL-4, 3 μg/ml anti-IL-12 (TOSH), and IL-2. Cells were restimulated with Ag and APCs on days 7 and 14. Th1/Th2 phenotypes were confirmed at days 7 and 14 by intracellular cytokine staining for IFN-γ and IL-4.

Gene Microarray

Anergic T cells were isolated by adoptively transferring $2.5 \times 10^6$ Thy1.1+HA-specific T cells to recipient mice (C3-HAhigh) as previously described. After 4 days in vivo, animals were sacrificed via CO2 asphyxiation. Spleens were harvested, and subjected to ACK lysis. Adoptively transferred HA-specific T cells were enriched by binding the resulting cells with Abs to CD8a, B220 (RA3-6B2) and Thy1.2 (30-H12), followed by incubation with SA-conjugated magnetic microbeads (Miltenyi Biotec). Unwanted cells were depleted by passage over LS columns (Miltenyi Biotec) according to the manufacturer's protocol. The remaining cells were stained with an Ab to Thy1.1 (OX-7) and further enriched using fluorescence-based cell sorting on a FACSVantage TurboSort (BD Biosciences). The resulting populations were between 95 and 99% pure. Cells were kept at 4° C. throughout the enrichment procedure. In vitro assays confirmed the anergic phenotype of the sorted cells (data not shown). All Abs were purchased from BD Pharmingen. This procedure specifically avoids ligation of the TCR or CD4 during the isolation process. Activated, memory and naive clonal T cells were isolated in an analogous manner, using a specific viral construct (vaccinia-HA) to activate the cells after adoptive transfer to nontransgenic B10.d2 mice. RNA was isolated from each T cell population using the RNAeasy kit according to the manufacturer's instructions (Qiagen), and cRNA probe was prepared. Fragmented cRNA was hybridized to mouse GeneChips MU174A, MU174B, and MU174C per Affymetrix standard hybridization protocol. Each chip contained about 12,000 different genes (chip A) per expressed sequence tag (EST) with (chips B and C), for a total of about 36,000 genes per EST from the three chips. A single gene/EST was represented by a probe set defined by 16-20 perfect match oligonucleotides that span the length of the gene, as well as 16 oligonucleotides with 1 by mismatch. The intensity of a gene was determined by evaluating the perfect match and mismatch intensities, as described in Affymetrix Microarray Suite, version 5.1 software (Affymetrix). The experiment was replicated once, for a total of two replicate intensities within each condition. To identify probe sets associated with an anergic phenotype, we used the hypothesis-based analysis of microarrays algorithm as previously described with the boolean hypothesis day 4 anergy > naive AND day 4 anergy > day 4 activation.

Assessment of Anergy by Proliferation

On indicated days following transfer of HA-TCR transgenic T cells, $20 \times 10^6$ splenocytes were incubated with increasing doses of HA peptide. Proliferation was assayed after 48 h, with a [$^3$H]thymidine pulse in the final 12 h.

BTLA Expression by Naive, Activated, and Anergic CD4+ T Cells

HA-TCR transgenic T cells were enriched by depletion of CD8+ and B220+ cells as earlier described. Cells were CFSE-labeled as previously described before adoptive transfer of $2.5 \times 10^6$ clonotypic cells via tail vein injection. Cells were stained with anti-Thy1.1 PerCP and the anti-BTLA Ab 6F7-biotin, followed by SA-PE.

Purification and Activation of CD44-CD25+ T Regulatory Cells

Splenocytes and lymph node cells from BALB/c mice were isolated. Following erythrocyte lysis, B220+ cells were depleted by magnetic separation with anti-B220 Microbeads (Miltenyi Biotec). The negative fraction was stained with CD25-PE (BD Pharmingen) and anti-PE Microbeads (Miltenyi Biotec) and magnetically separated into CD25+ and CD25− fractions. Enrichment was assessed by FACS as shown (see FIG. 46D). Contaminating non-CD4+ cells were mainly B220+ or CD8+ cells. To activate T cells, $1 \times 10^6$ cells/ml of each fraction were cultured on flat-bottom plates coated with 10 μg/ml 2C11 (anti-CD3; BD Pharmingen) for 48 h. Cells were pulse with 1 μCi/well [$^3$H]thymidine for an additional 12 h.

Ab Response to NP-Ficoll

Eight-week-old BTLA+/+ and BTLA−/− littermate mice on the 129SvEv background were immunized i.p. with 50 μg of nitrophenyl (NP)-Ficoll (Biosearch Technologies) in Imject alum (Pierce). Sera were collected on day 14, and the titers of anti-NP were determined by ELISA using NP25-BSA (Biosearch Technologies) for Ab capture and the Southern Biotechnology clonotyping/HRP kit for IgG subclass-specific ELISA (Southern Biotechnology Associates).

For further details regarding Example 14, including references, see Hurchla et al., J. Immunol., 174: 3377-3385, 2005, which is expressly incorporated herein in its entirety by reference.

Example 15

BTLA-HVEM Effects in Graft Survival

Figure 61:
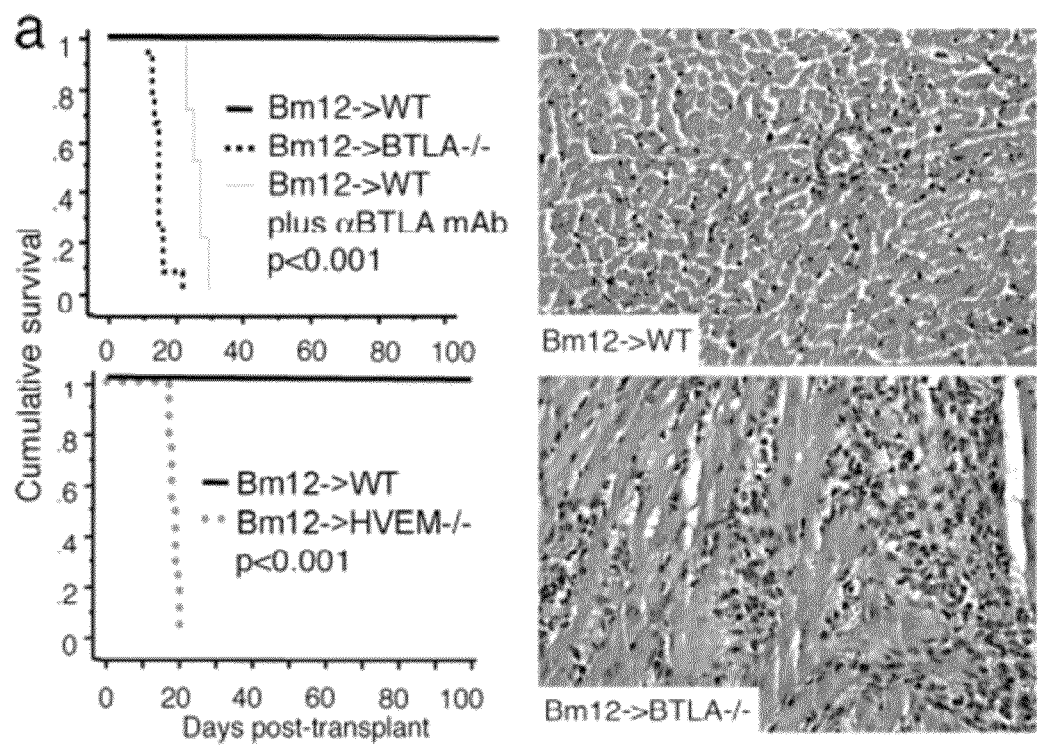
FIG. 61 shows graphs and micrographs illustrating that BTLA and HVEM, but not PD-1, regulate the survival of partially MHC-mismatched cardiac allografts. A, The lack of BTLA or HVEM, or administration of a neutralizing anti-BTLA mAb, led to rejection of all MHC class II-mismatched cardiac allografts within 3-4 wk of transplantation, whereas wild-type (WT) recipients accepted Bm12 allografts indefinitely. Data were generated from six to 12 allografts/group; p<0.001 for BTLA−/−, HVEM−/−, or anti-BTLA mAb-treated group vs respective WT controls. Panels at the right show acute cellular rejection of Bm12 allografts harvested 2 wk after transplant from BTLA−/−, but not WT, recipients (H&E-stained paraffin sections; original magnifications, ×300). B, In contrast to BTLA and HVEM, a lack of PD-1 still allowed >80% long-term survival of MHC class II-mismatched cardiac allografts (p<0.05 compared with isotype-treated WT control), and an absence of both PD-1 and BTLA (DKO) led to only a minor acceleration of allograft rejection compared with lack of BTLA alone (p<0.05 vs BTLA−/− alone) in B6 recipients of Bm12 cardiac allografts. Data were generated from four to eight allografts per group. C, Lack of BTLA led to rejection of all MHC class I-mismatched cardiac allografts, whereas WT recipients accepted Bm1 allografts indefinitely. Data were generated from 6 to 12 allografts/group (p<0.001). Panels at the right show histologic evidence of developing cellular rejection of BmI allografts harvested 4 wk after transplant from BTLA−/−, but not WT, recipients (H&E-stained paraffin sections; original magnifications, ×300).
Figure 61:
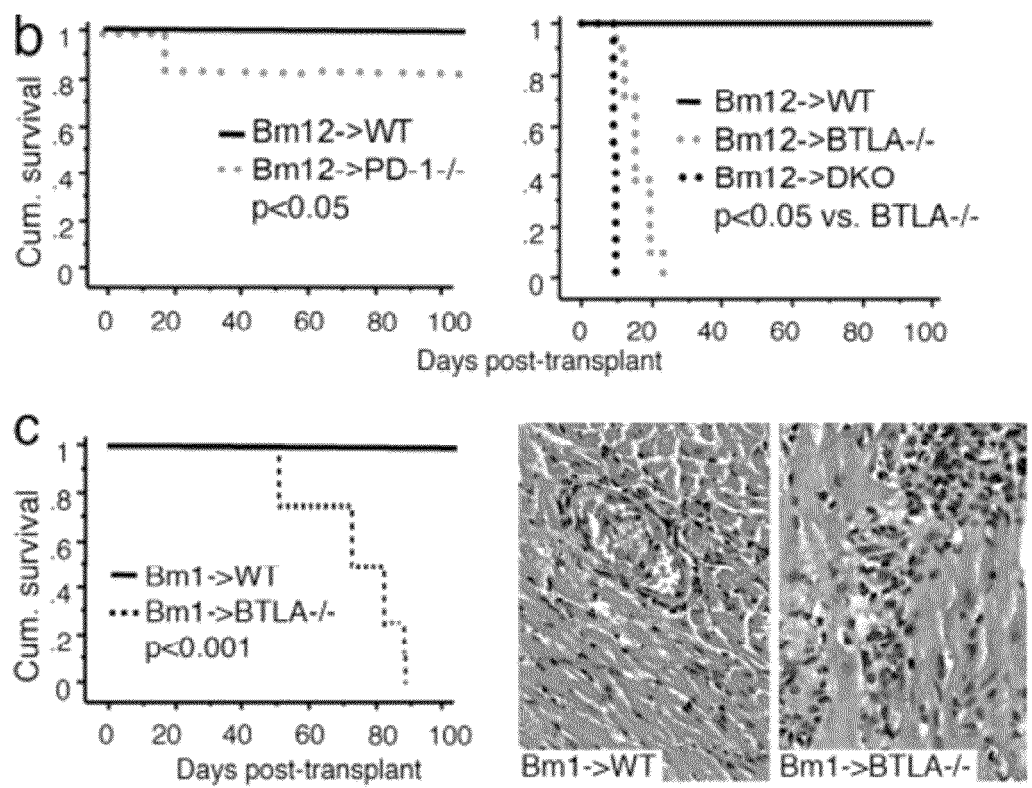

BTLA and HVEM Regulate Acceptance of Partially MHC-Mismatched Cardiac Allografts Primarily vascularized cardiac allografts are the most frequent organ transplant undertaken in mice and may be performed across full MHC disparities, with rejection in 7-8 days, or across MHC class I or II disparities, which leads to long-term survival (>100 days). The basis for this unexpectedly long-term survival of cardiac transplants across partial MHC disparities is unknown and has received little attention. As anticipated from the literature, we indeed found that cardiac allografts performed across an MHC class II mismatch (Bm12 B6) survived long term in wild-type recipients (mean survival time (MST), >100 days; n=6). Histologic assessment of these allografts harvested at 2 wk after transplant showed preservation of myocardial architecture and generally only sparse mononuclear cell infiltration (FIG. 61A). In contrast, BTLA−/− recipients rejected Bm 12 cardiac allografts by 2-3 wk after transplant (MST, 14.3±3.8 days; n=12; p<0.001), and histology showed a marked increase in leukocyte infiltration and myocardial injury (FIG. 61A). In addition, comparable abrogation of Bm12 allograft survival was seen with mAb targeting of BTLA in wild-type recipients (MST, 23.2±3.2; n=6; p<0.001) or by engraftment of recipients lacking the BTLA ligand, HVEM (MST, 17.4±4.2 days; n=8; p<0.001; FIG. 61A). Thus, BTLA and HVEM are required to allow long-term survival of partially mismatched cardiac allografts. In contrast to results obtained with BTLA−/− recipients, PD-1−/− recipients receiving Bm12 cardiac allografts exhibited an 80% long-term allograft survival (FIG. 61B), although we did observe a minor role for PD-1 in regulating responses to Bm12 cardiac allografts. Dual BTLA−/− and PD-1−/− knockout mice (DKO) mice rejected Bm12 donor hearts more rapidly (MST, 10.5+1.5 days; n=4) than singly deficient BTLA−/− recipients (p<0.05) or wild-type controls (p<0.0001; FIG. 61B).

Like MHC class II-mismatched grafts, MHC class I-mismatched (Bm1 B6) cardiac allografts survived long term when transplanted to wild-type B6 mice, but were rejected in BTLA−/− mice (FIG. 61C). Furthermore, in contrast to wild-type B6 recipients, the MHC class 1-mismatched allografts in BTLA−/− recipients showed increased mononuclear cell infiltration and progressive tissue damage indicative of the development of cellular rejection (FIG. 61C). PD-1−/− recipients receiving Bm1 cardiac allografts had 100% long-term allograft survival (data not shown). Collectively, these findings indicate that BTLA, in contrast to PD-1, is capable of inhibiting the generation of a functional allogeneic immune response in the context of partial MHC mismatches.

BTLA Suppresses MHC Class II-Dependent T Cell Responses

Figure 62:
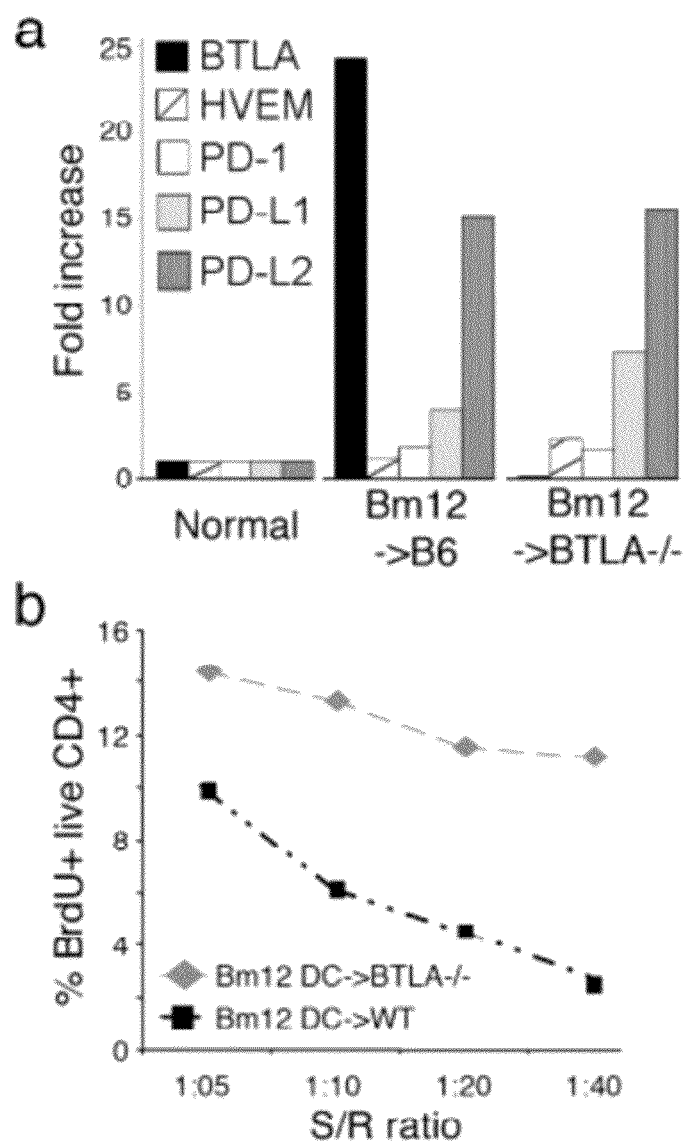
FIG. 62 shows graphs illustrating that BTLA suppresses T cell responses to MHC class II alloantigens. A, Intragraft mRNA expression of BTLA, PD-1, and ligands was determined by qPCR; data are expressed as the fold increase compared with naive heart and are representative of three separate experiments (Bm123B6 cardiac allografts). B, Compared with wild-type (WT) CD4+ T cells, CD4+ T cells from BTLA−/− mice had markedly enhanced proliferative responses to Bm12 APC. Data at 72 h are expressed as a percentage of live BrdU+ CD4 cells at each stimulator (S) to responder (R) ratio (pooled triplicate wells). C, Assessment of alloactivation-induced CD4+ T cell proliferation at 72 h induced by irradiated Bm12 APC; the percentage of dividing CD4+ T cells was determined by CFSE dilution. D, Markedly increased proliferation of CFSE-labeled BTLA−/− CD4+ T cells 72 h after transfer into irradiated Bm12 hosts. Data are representative of two experiments with similar results. E, Marginally increased proliferation of CFSE-labeled BTLA−/− CD8+ T cells 72 h after transfer into irradiated Bm12 hosts. Data are representative of two experiments with similar results. F, Significantly increased responder frequency in BTLA−/− recipients of class II-mismatched cardiac allografts, as shown by harvesting of recipient spleens 10 days after transplant and stimulation of recipient splenocytes in vitro with irradiated Bm12 ($p<0.001$ at all ratios) or B6 DC (syngeneic control) for 24 h. Donor-specific responder frequency was expressed as the number of IFN-γ spot-forming cells (SFC) per $1\times10^6$ splenocytes, and data (mean±SD) are representative of two experiments.
Figure 62:
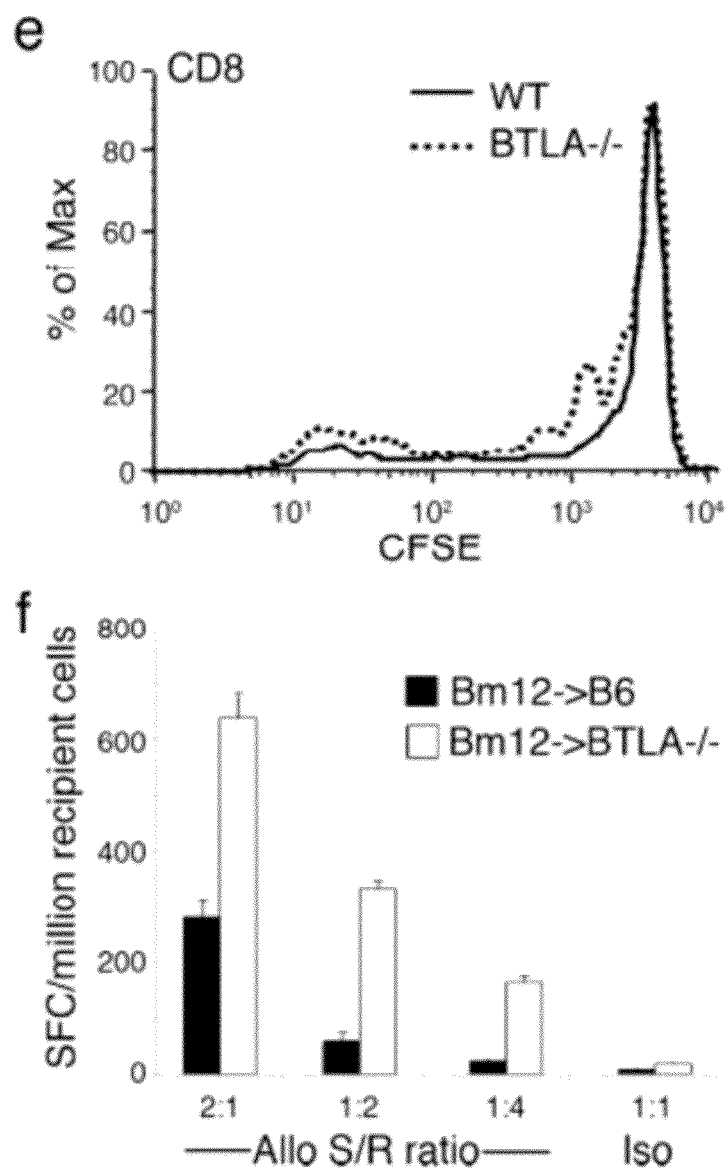

The unexpected rejection of Bm12 allografts by BTLA−/−, but not PD-1−/−, mice suggested that BTLA and PD-1, or their ligands, might be differentially expressed in partially MHC-mismatched allografts. BTLA mRNA expression within Bm12 allografts was 20-fold higher than PD-1 at 7 days after transplant, whereas no BTLA expression was detected within Bm12 hearts engrafted into BTLA−/− recipients, indicating BTLA expression primarily by infiltrating host leukocytes (FIG. 62A). Comparable BTLA expression was observed within long-surviving allografts (data not shown). Unlike BTLA, only very low levels of PD-1 were detected in Bm12 allografts in either wild-type or BTLA−/− recipients (FIG. 62A). No differences in the levels of expression of HVEM, PD-L1, or PD-L2 were seen between wild-type and BTLA−/− recipients (FIG. 62A). These data suggest that in the Bm12 B6 model, BTLA is the predominant inhibitory receptor expressed by infiltrating alloreactive T cells, and that in the absence BTLA, there is no compensatory increase in expression of additional inhibitory molecules.

We next studied the in vitro and in vivo responses of T cells from wild-type and BTLA−/− mice to MHC class II Ags. First, we examined the in vitro proliferation of purified wild-type or BTLA−/− CD4+ T cells cocultured with irradiated Bm12 DC. Proliferation of BTLA−/− T cells was increased compared with that of wild-type T cells, as measured by either BrdU incorporation (FIG. 62B) or CFSE dilution (FIG. 62C). To assess in vivo responses, 40 million CFSE-labeled wild-type or BTLA−/− splenocytes were adoptively transferred into irradiated Bm12 hosts, and donor CD4+ T cell proliferation was assessed. Although a large portion of wild-type CD4+ T cells remained undivided 72 h after adoptive transfer, almost all BTLA−/− CD4+ T cells had entered the cycle and proceeded through several rounds of division (FIG. 62D). Hence, BTLA regulates CD4+ T cell alloactivation and proliferative responses to MHC class II Ags.

MHC class II-restricted CD4+ T cell proliferation dominates host alloresponses in the Bm12 B6 model, although host responses are known to include stimulation of CD8+ precursor CTL by class II-restricted CD4+ T cells. We found that although proliferative responses of CD8+ T cells in irradiated Bm12 hosts were low compared with those of CD4 cells, the alloactivation and proliferation of CD8+ T cells from BTLA−/− mice were marginally increased over control cells in this assay system (FIG. 62E). We examined recipient anti-donor responder frequencies by ELISPOT, with the readout of IFN-spot-forming cells by recipient splenocytes. BTLA−/− recipient splenocytes had significantly higher anti-donor responder frequencies when challenged with Bm12 APCs (FIG. 62F), consistent with the increased allogeneic proliferation in vitro and the accelerated graft rejection in vivo of T cells from BTLA−/− mice.

Minor Role of BTLA in Fully MHC-Mismatched Alloresponses

Figure 63:
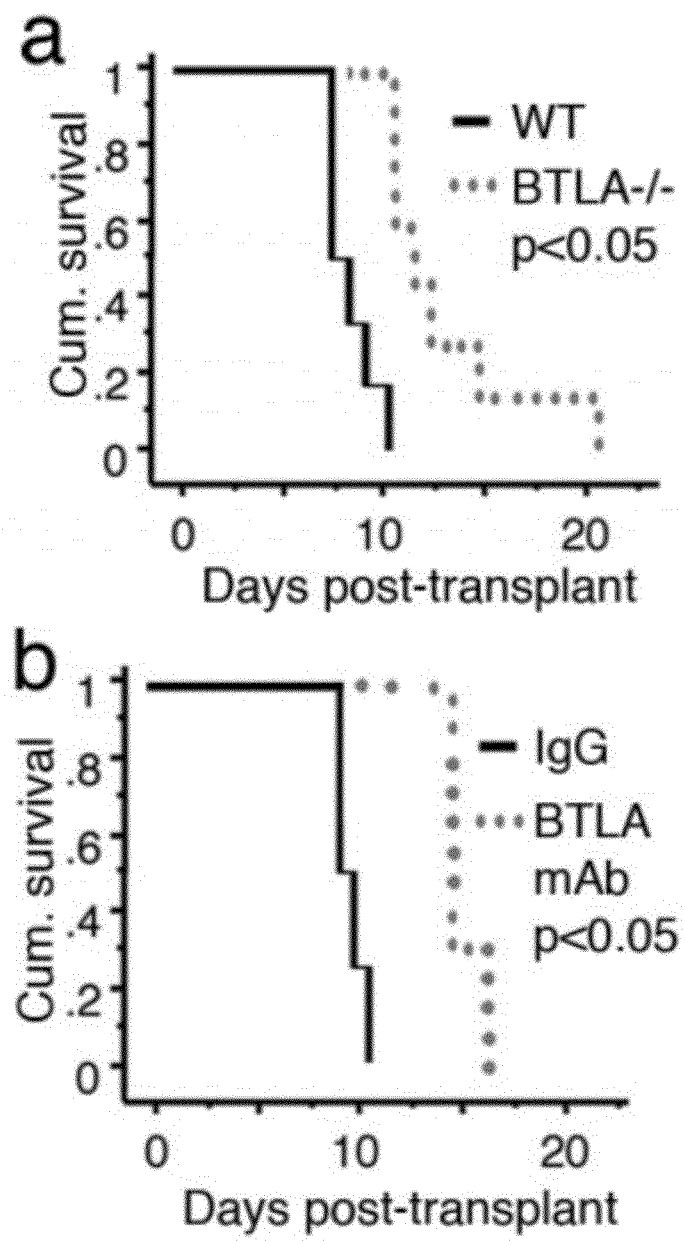
FIG. 63 shows graphs and photographic images demonstrating that BTLA targeting prolongs survival of fully MHC-mismatched cardiac allografts. Targeting of BTLA significantly prolonged BALB/c cardiac allograft in fully allogeneic B6 recipients, as shown using BTLA−/− recipients (A) and anti-BTLA mAb in wild-type (WT) mice (B). C, In addition, a subtherapeutic course of rapamycin (RPM; 10 μg/kg/day, i.p., for 14 days) significantly prolonged cardiac allograft survival compared with either identically treated WT mice or BTLA−/− controls. Allograft survival data in A-C were obtained from six to eight transplants per group. D, BALB/c hearts transplanted to WT or BTLA−/− B6 mice were harvested 7 days after transplant for qPCR. Data from three allografts per group are expressed as the fold increase compared with native heart. E, Western blots of CXCR3 and IP-10 proteins, using extracts of three allografts per group. The effects of targeting BTLA, alone or in combination with low dose RPM, on allogeneic T cell proliferation and cytokine production were determined by adoptive transfer of CFSE-labeled splenocytes from WT or BTLA−/− mice to B6D2F1 hosts, and recipient spleens were harvested at 72 h. The responses of donor T cells were identified by gating on Kd-Dd-cells. Data are shown as an overlay of CFSE histograms (F) and analysis of intracellular cytokine production (G). The figure in each box is the percentage of the indicated population, and data are representative of two experiments with similar results.
Figure 63C:
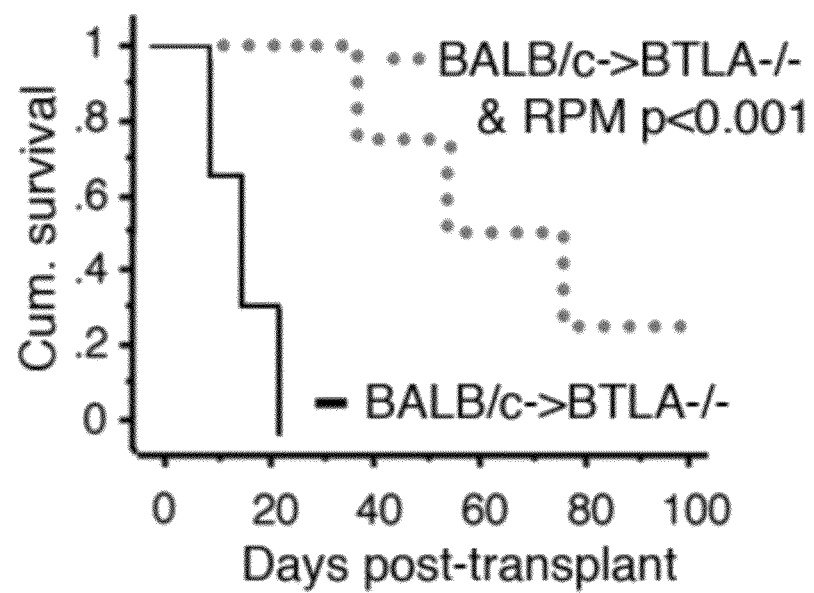

We next tested whether BTLA played a similar dominant role in regulating responses to fully MHC-mismatched cardiac allografts as it did for partially MHC-mismatched cardiac allografts. Wild-type recipients (B6, H-2b) rejected cardiac grafts (BALB/c, H-2d) in 7-10 days (MST, 8±1 days; n=6), whereas BTLA−/− recipients showed a small and unexpected prolongation of graft survival (MST, 12±5 days; n=6; p<0.05; FIG. 63A). In addition, wild-type mice treated with a neutralizing anti-BTLA mAb showed a similar prolongation of allograft survival (MST, 13±1 days; n=4; p<0.05) compared with control IgG treated recipients (MST, 8+1 days; n=4; FIG. 63B). Furthermore, addition of a subtherapeutic course of rapamycin prolonged graft survival in wild-type mice by a few days (MST, 11±2 days; n=6; p<0.05), but significantly prolonged graft survival in BTLA−/− mice (MST, 53±12 days; n=8; p<0.001), with 25% of the latter recipients achieving long-term acceptance (FIG. 63C). Hence, in the case of fully MHC-mismatched cardiac allografts, loss of BTLA did not accelerate allograft rejection, but, rather, caused a surprising, albeit small, increase in allograft survival. By contrast, the presence or the absence of BTLA had no effect on the tempo of rejection of B6 cardiac allografts by BALB/c recipients; all allografts were rejected within 7-10 days (n=4/group; p>0.05).

Figure 63D:
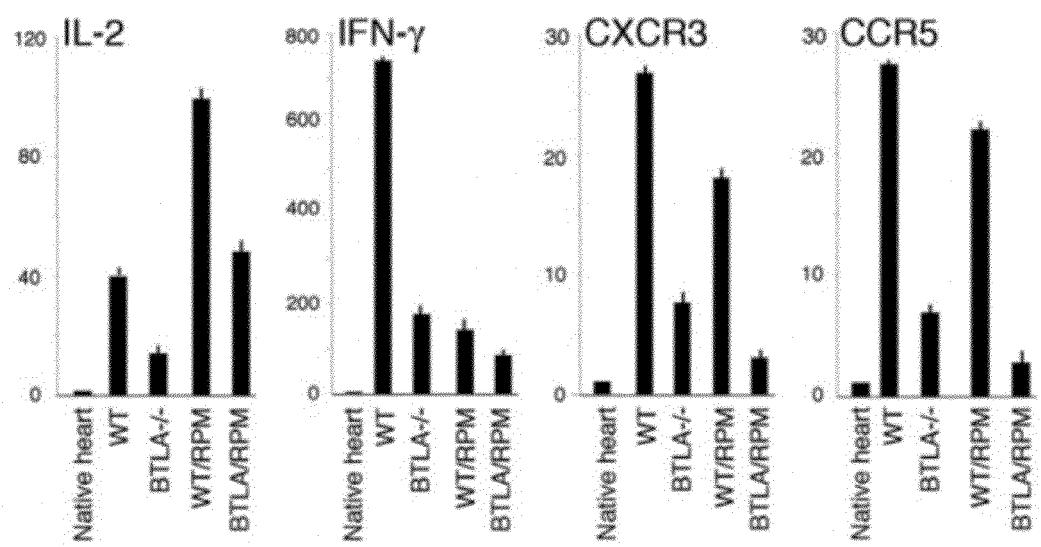
Figure 63E:
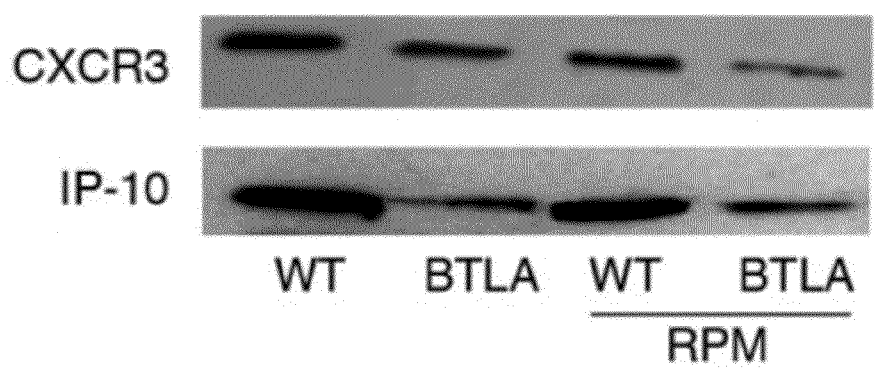

To understand the prolongation of fully MHC-mismatched graft survival, we measured the expression of cytokines and chemokine receptors important to host T cell recruitment in this model, using allografts harvested 7 days after transplant. We found decreases in IL-2 and IFN-mRNA in BTLA−/− recipients compared with wild-type recipients (FIG. 63D). We also found reduced expression of CXCR3 and CCR5 in BTLA−/− recipients compared with wild-type recipients (FIG. 63D). Therapy with rapamycin accentuated differences in cytokine and chemokine receptor mRNA expression between BTLA−/− and wild-type recipients (FIG. 63D). Given a key role for IFN-induced IFN-inducible protein 10 (IP-10) production in promoting CXCR3+ cell recruitment and allograft rejection in this model, we performed Western blotting, which confirmed that allografts in BTLA−/− recipients had reduced IP-10 and CXCR3 proteins compared with wild-type controls, with or without rapamycin therapy (FIG. 63E).

Figure 63F:
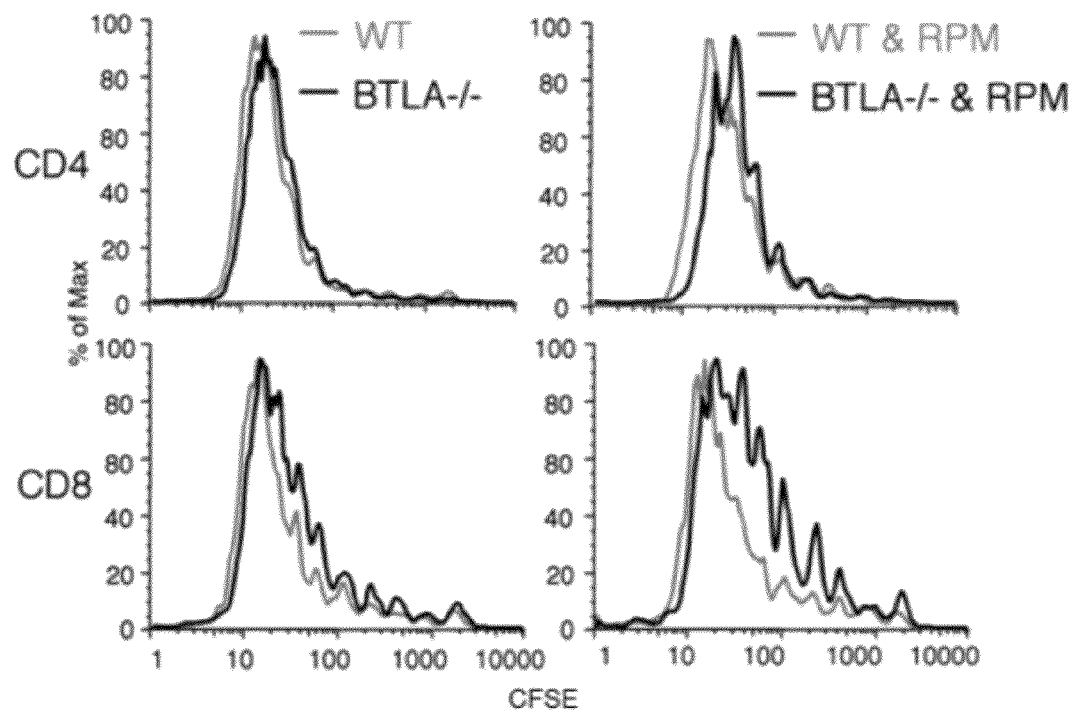
Figure 63G:
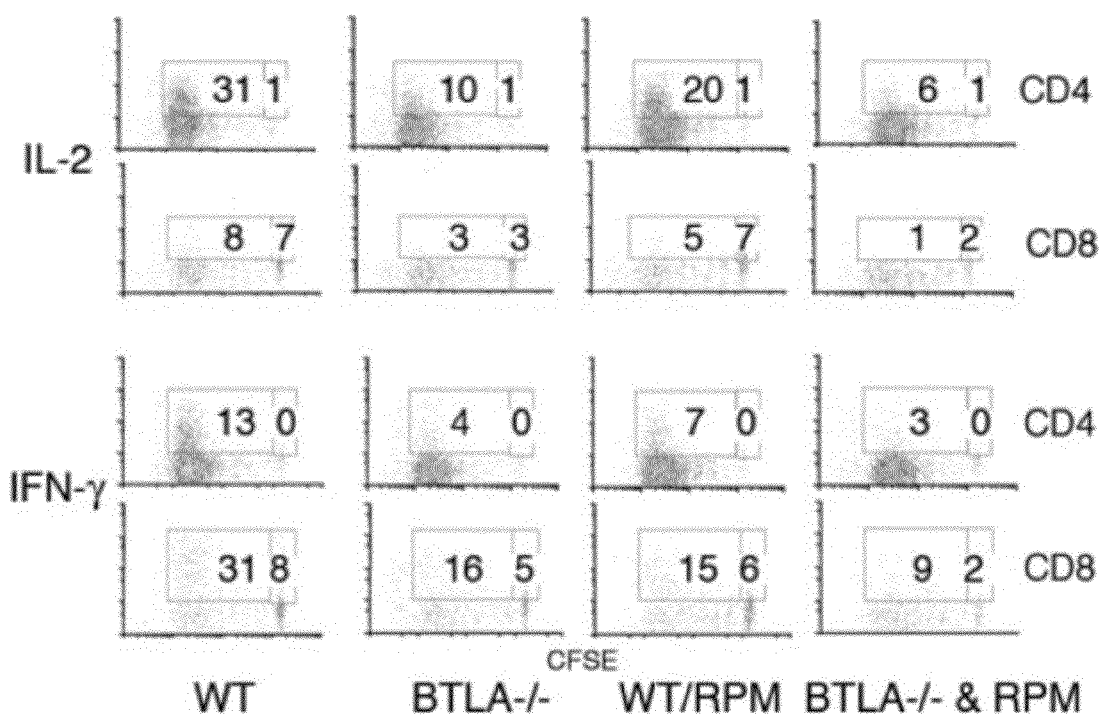

To assess whether the lack of BTLA affected the strong alloactivation and proliferation induced in T cells by 72 h in this model, we used the parent-to-F1 model involving transfer of CFSE-labeled cells across fully allogeneic barriers (FIG. 63F). In this model, the activation and cell cycle progression of CD4+ responses were similar for BTLA−/− and wild-type cells, and CD8+ T cells from BTLA−/− mice were only marginally decreased compared with those from wild-type controls (FIG. 63F). However, the evaluation of intracellular cytokine production by alloreactive T cells showed decreased IL-2 and IFN-production by alloreactive BTLA−/− CD4+ and CD8+ T cells compared with wild-type T cells (FIG. 63G). Again, a subtherapeutic rapamycin dose caused a modest decrease in proliferation of BTLA−/− T cells compared with wild-type T cells, particularly CD8+ responses (FIG. 63F), and decreased production of IL-2 and IFN- by both T cell subsets (FIG. 63G). These data indicate that T cell activation, proliferation, and production of cytokines such as IL-2 and IFN- are decreased in BTLA−/− mice, especially when recipients are treated with limited immunosuppression, and that these impaired responses are associated with modulation of chemokine/chemokine receptor effector pathways.

Involvement of PD-1 and BTLA in Fully MHC-Mismatched Alloresponses

Figure 64:
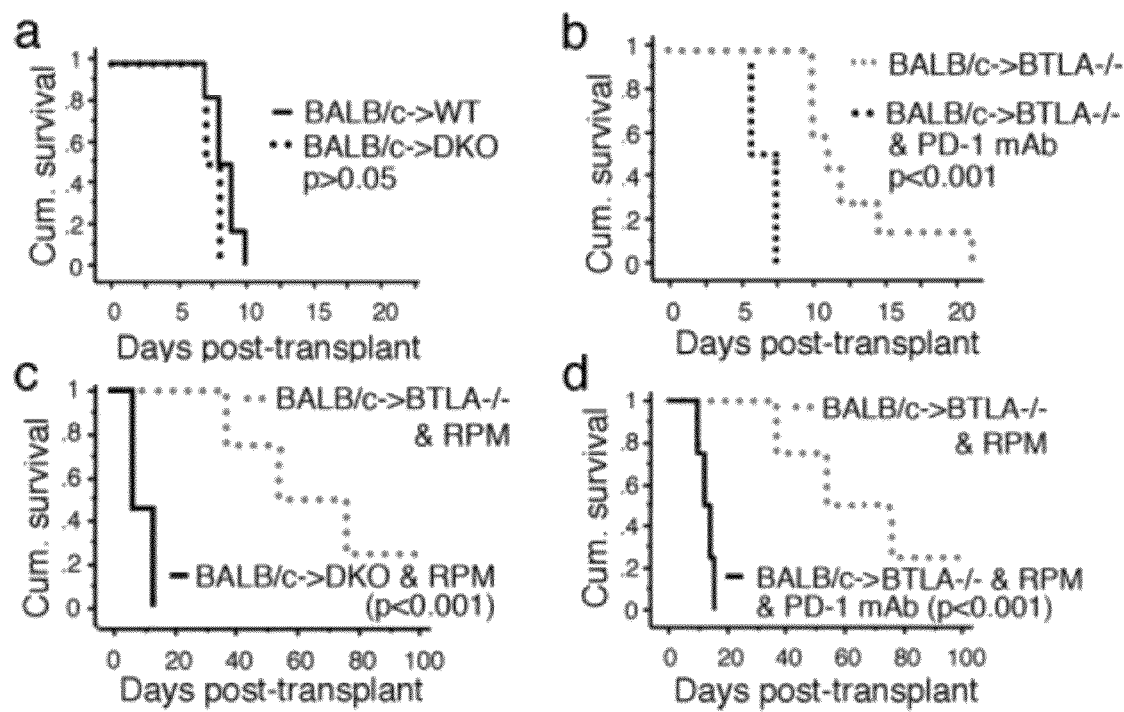
FIG. 64 shows graphs illustrating the dominant role of PD-1 in regulating the survival of fully MHC-mismatched cardiac allografts. A, Dual PD-1/BTLA−/− (DKO) recipients rejected fully MHC-disparate allografts at the same speed as wildtype (WT) recipients. B, Neutralization of PD-1 in BTLA−/− recipients reversed the prolongation of survival seen in BTLA−/− mice ($p<0.001$). c, The dominant role of PD-1 was also seen by the quick rejection of allografts in DKO mice, despite therapy with rapamycin (RPM; 10 μg/kg/day, i.p., for 14 days), in marked contrast to the prolonged survival in BTLA−/− recipients treated with the same dose of RPM ($p<0.001$). D, The key contribution of PD-1, but not BTLA, in promoting the survival of fully MHC-mismatched cardiac allografts in RPM-treated recipients was confirmed by the rapid onset of acute rejection in BTLA−/− recipients treated with anti-PD-1 mAb ($p<0.001$).

In considering explanations for the differing effects of BTLA in the partial MHC-mismatch and full MHC mismatch models, we wondered whether differential reliance on PD-1 between these models might play a role. Therefore, we examined the contributions of both PD-1 and BTLA in the fully MHC-mismatched model (FIG. 64). We found, first, that BALB/c cardiac allografts were rejected at similar rates (p>0.05) by C57BL/6 wild-type mice and DKO mice (FIG. 64A). Second, consistent with the DKO data, mAb blockade of PD-1 increased the rate of rejection of fully MHC-mismatched allografts by BTLA−/− recipients (p<0.001; FIG. 64B). Third, the duration of allograft survival in BTLA−/− recipients receiving subtherapeutic course of rapamycin (MST, 53±12 days; n=8) was markedly decreased by loss of PD-1, as seen by examining either DKO recipients (MST, 12.8±2.2 days; n=4; p<0.001; FIG. 64C) or by mAb Ab blockade of PD-1 in BTLA−/− mice (MST, 14.0±3.5 days; n=4; p<0.001; FIG. 32D). In summary, in contrast to partial MHC-mismatched allografts, the responses against fully MHC-mismatched cardiac allografts are regulated by both BTLA and PD-1.

We next asked whether PD-1 regulated the proliferation and function of T cells responding to fully MHC-mismatched allografts. Analysis by qPCR of BALB/c cardiac allografts harvested on day 7 after transplant from C57BL/6 recipients showed intragraft expression of BTLA, PD-1, and their ligands, HVEM, PD-L1, and PD-L2 (FIG. 65A). By comparison with wild-type recipients, BALB/c allografts harvested from BTLA−/− recipients had increased PD-1 expression (FIG. 65A; p<0.01). In contrast to PD-1 expression, the expression of HVEM, PD-L1, and PD-L2 was not increased in BTLA−/− recipients. These results suggest that in the absence of BTLA, host leukocytes might express more PD-1 in response to allostimulation.

To directly examine PD-1 expression by alloreactive wild-type or BTLA−/− T cells, we adoptively transferred CFSE-labeled splenocytes into irradiated Bm12 (class II-mismatched) or B6D2F1 (fully MHC-mismatched) recipients. At analysis 72 h later, we found that in the MHC class II partial mismatch, PD-1 was weakly expressed by alloreactive CD4+ T cells, but not at all by CD8+ T cells, from wild-type or BTLA−/− mice (FIG. 65B). In contrast, with a full MHC mismatch, PD-1 expression by both CD4+ and CD8+ donor T cells was markedly increased, and the extent of PD-1 expression was higher in BTLA−/− vs wild-type T cells (FIG. 65B). Moreover, treatment with rapamycin reduced PD-1 expression by wild-type T cells, but had only minor effects on PD-1 induction by T cells from BTLA−/− mice (FIG. 65B).

Figure 65:
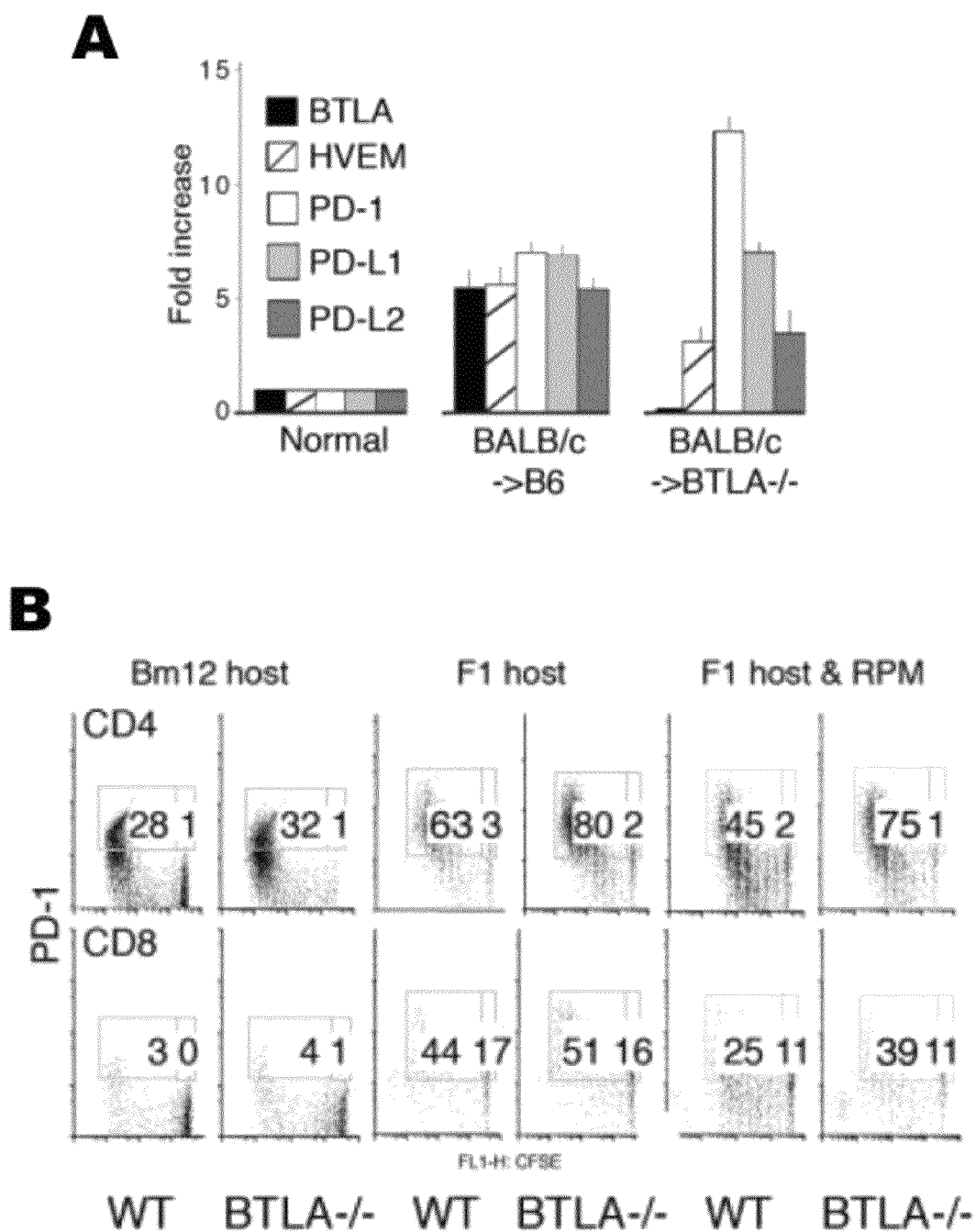
FIG. 65 shows plots that demonstrate increased PD-1 expression and function by alloreactive T cells of BTLA−/− recipients of fully MHC-mismatched cardiac allografts. A, Intragraft mRNA expression of BTLA, PD-1, and ligands was determined by qPCR. Data are expressed as the fold increase compared with naïve heart and are representative of three separate experiments (BALB/c3B6 cardiac allografts). B, PD-1 expression by alloreactive T cells determined by adoptive transfer of CFSE-labeled wild-type (WT) or BTLA−/− splenocytes to irradiated Bm12 or B6D2F1 hosts, with or without added rapamycin (RPM; 0.01 mg/kg, i.p., for 3 days). Figures indicate the percentages of PD-1 cells in the divided and undivided donor T cell populations. C, Increased proliferation of CFSE-labeled T cells from DKO mice or PD-1−/− mice vs WT or BTLA−/− controls after adoptive transfer to F1 hosts, with or without RPM therapy. Analysis of corresponding intracellular cytokine production by the groups shown in C was undertaken, alone (D) or in conjunction with RPM therapy (E). Cells were stained with Kd-PE and CD4- or CD8-PerCP, and IL-2 or IFN-γ APCs and donor cells were identified as the Kd-Dd-population; the percentage of each indicated population is shown.
Figure 65C:
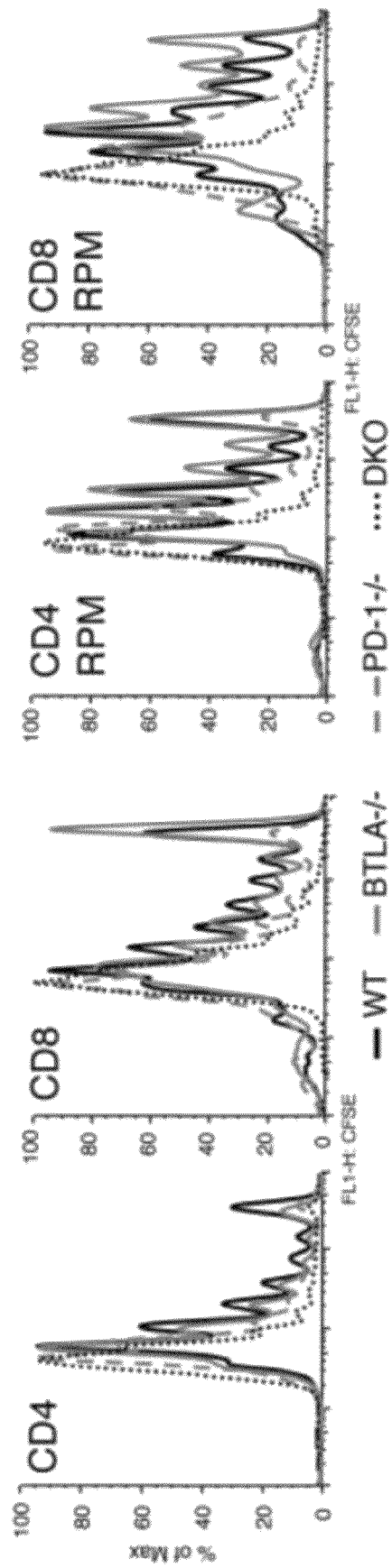
Figure 65D:
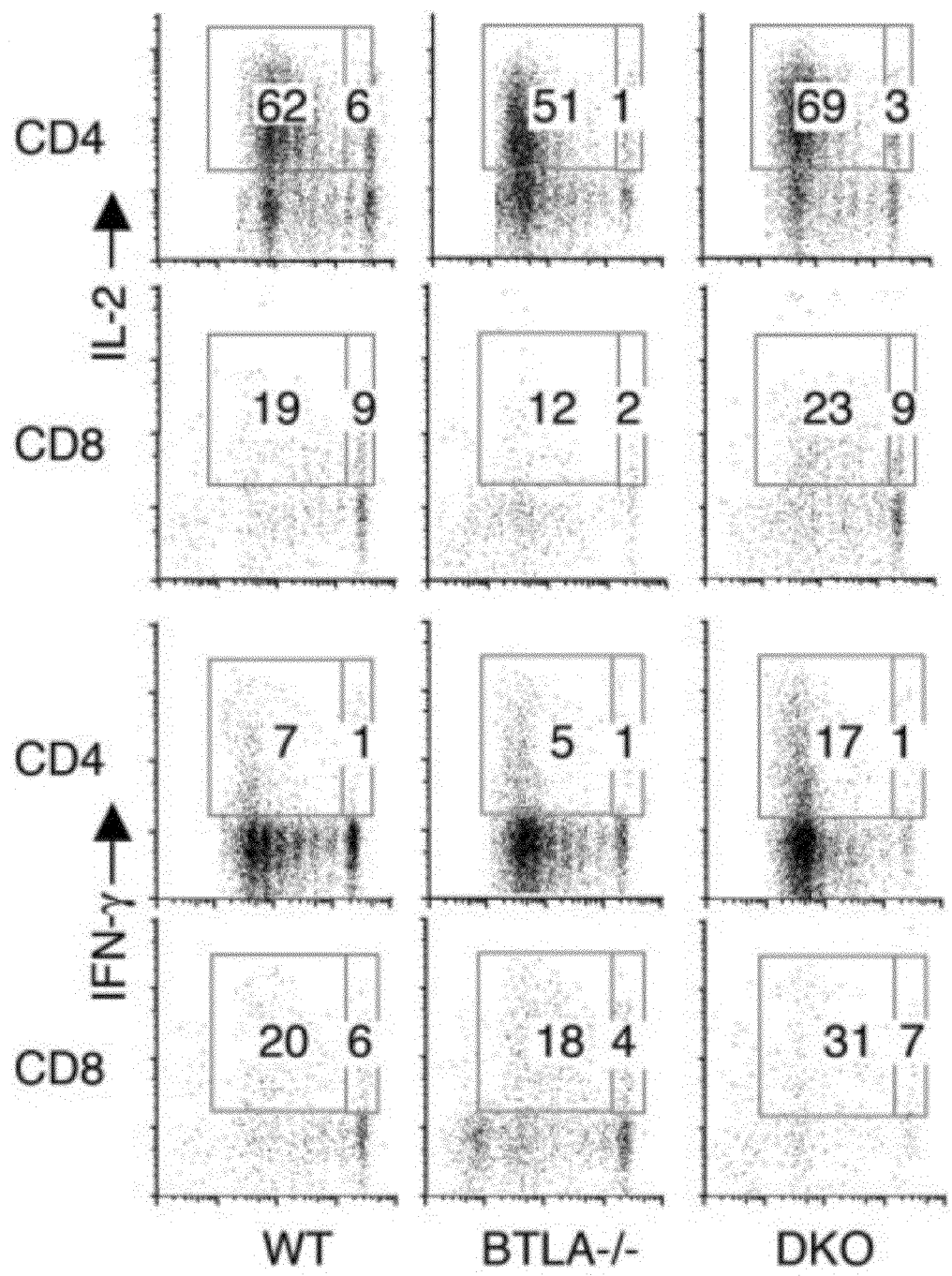
Figure 65E:
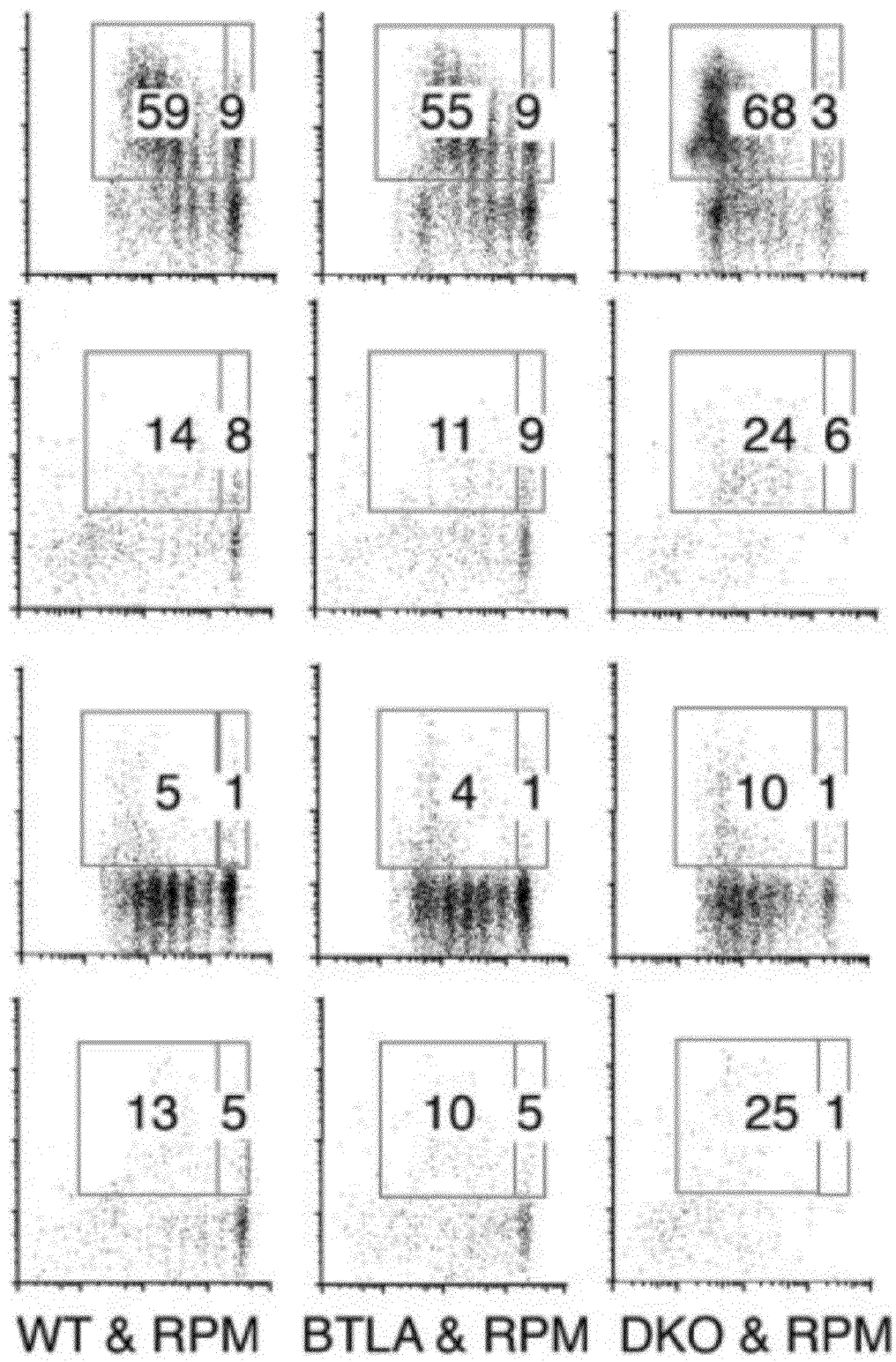
Figure 66:
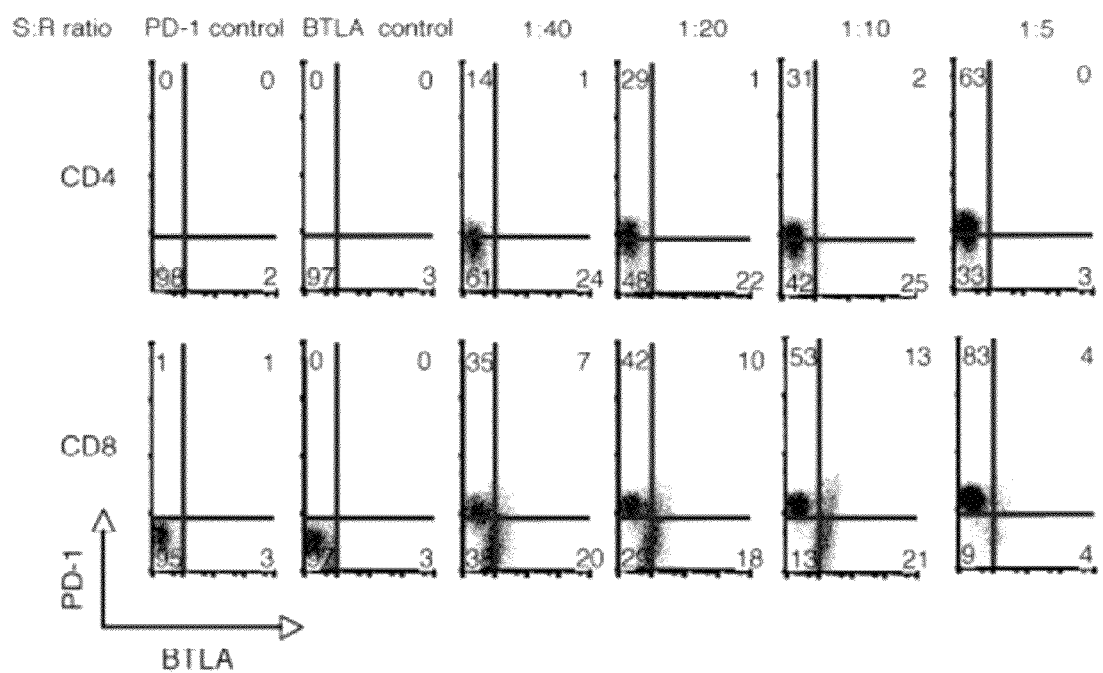
FIG. 66 shows graphs illustrating that as the strength of T cell signaling increases, PD-1 induction predominates over that of BTLA. Increasing T cell activation by mature fully allogeneic BALB/c bone marrow-derived DC leads to increasing expression of PD-1, rather than BTLA, by C57BL/6 CD4 and CD8 T cells, as shown by flow cytometric analysis of cells cultured at varying stimulator (S) to responder (R) ratios for 72 h. Data are representative of three such experiments.

Lastly, we used in vivo and in vitro approaches to examine the roles of BTLA and PD-1 in regulating T cell proliferation and cytokine production in response to fully MHC-mismatched allostimulation (FIG. 65, C-E). Compared with wild-type or BTLA−/− cells, DKO cells showed enhanced proliferation (FIG. 65C) and Th1 cytokine production (FIG. 65D). Therapy with rapamycin decreased the alloactivation-induced proliferation (FIG. 33C) and cytokine production (FIG. 65E) of CD4+ and CD8+ T cells from wild-type and BTLA−/− donors, but did not block these events in DKO CD4+ or CD8+ T cells (FIGS. 65, C and E). Indeed, the production of IL-2 and IFN- was increased in DKO T cells compared with wild-type and BTLA−/− T cells (FIG. 65D), including in the presence of rapamycin therapy (FIG. 65E). Collectively, these data indicate that 1) PD-1 expression is highly induced on the surfaces of alloreactive CD4+ and CD8+ T cells upon exposure to fully MHC-disparate allografts; 2) the levels of PD-1 on alloreactive CD4+ and CD8+ T cells are still further increased in the absence of BTLA; and 3) increased PD-1 expression is associated with inhibitory effects on the alloantigen-induced production of cytokines such as IL-2 and IFN-. In associated in vitro studies, as T cell activation increased in response to allogeneic DC (FIG. 66), the induction of PD-1 was increasingly apparent compared with that of BTLA. BTLA up-regulation occurred upon T cell activation, but did not show expansion comparable with that of PD-1 with increasing T cell activation, suggesting that the strength of T cell activation determines the relative importance of these two pathways.

Methods for Example 15
Mice

BTLA−/− b PD-1−/−, and dual BTLA−/− and PD-1−/− mice were backcrossed for more than eight generations on a C57BL/6 background; HVEM−/− mice were generated by homologous recombination and backcrossed more than five generations on a B6 background. Wild-type C57BL/6 (H-2b), BALB/c (H-2d), C57BL6/DBA FI (H-2b/d), Bm12 (B6.C—H2bm12/KhEg), and BmI (B6.C—H2bmI/ByJ) mice were purchased from The Jackson Laboratory, housed in specific pathogen-free conditions, and used for studies approved by the institutional animal care and use committee of Children's Hospital of Philadelphia.

An Armenian hamster anti-mBTLA neutralizing mAb, 6A6, was described previously in Sedy et al. Nature Immunol. 6:90-98 (2005), and we purchased mAbs for flow cytometry (BD Pharmingen) and Abs for Western blotting (Santa Cruz Biotechnology). Labeling of cells with CFSE (Molecular Probes) was undertaken as previously reported.

Quantitative PCR (qPCR)

We performed qPCR as previously described. Briefly, RNA was extracted with TRIzol (Invitrogen Life Technologies), RT of random hexamers was performed with an ABI PRISM 5700 unit (Applied Biosystems), and specific primer and probe sequences for target genes were used for qPCR amplification of total cDNA (TaqMan PDAR; Applied Biosystems). Relative quantitation of target cDNA was determined using a control value of 1; the sample cDNA content was expressed as the fold change from the control value. Differences in cDNA input were corrected by normalizing signals obtained with specific primers to ribosomal RNA; nonspecific amplification was excluded by performing RT-PCRs without target cDNA.

Flow Cytometry

Alloreactive T cells were generated by i.v. injection of $40\times10^6$ CFSE-labeled B6 spleen and lymph node cells into B6/DBA F1 recipients, a parent F1 MHC mismatch in which only donor cells respond. Splenocytes harvested after 3 days were incubated with CD4-PE, CD8-PE, CD25-PE, CD44-PE, CD62L-PE, PD-1-PE, ICOS-PE, and biotin-conjugated anti H-2 Kd and anti-H-2Dd mAb. Donor alloreactive T cells were identified by gating on H-2 Kd and H-2Dd cells (FACSCalibur; BD Biosciences), and their proliferation was assessed by CFSE division profiles. For intracellular cytokine staining, splenocytes ($3\times10^6$/ml) were treated with Golgi-Stop (BD Pharmingen), stimulated for 4 h with PMA (3 ng/ml) and ionomycin (1 µM) in 24-well plates in complete medium (RPMI 1640, 10% FCS, 100 U/ml penicillin, 100 µg/ml streptomycin, and 50 µM 2-ME), and stained with cell surface markers (CD4-PE or CD8-PE, biotin-conjugated H-2 Kd or H-2Dd, followed by streptavidin-PerCP), fixed, and stained with IFN-allophycocyanin or IL-2-allophycocyanin after permeabilization (Perm-Wash buffer; BD Pharmingen).

In Vitro Cellular Assays

For propagation of bone marrow-derived DC, bone marrow cells harvested from the femurs and tibia were cultured for 5-7 days in 24-well plates ($2\times10^6$/well) in medium plus mouse GM-CSF (5 ng/ml) and IL-4 (10 ng/ml). One-way MLR cultures were performed in triplicate, using magnetic column-eluted splenic T cells ($2\times10^5$/well) as responders and gamma-irradiated (20 Gy) DC as stimulators. Cultures were maintained in complete medium for 72-96 h, and T cell proliferation was determined by BrdU incorporation or CFSE dilution profile. BrdU staining with a BrdU labeling kit (BD Pharmingen) was performed using the manufacturer's instructions. Cells were pulsed with BrdU, treated with FcR-blocking CD16/CD32 mAbs, stained with cell surface markers, fixed, permeabilized, treated with DNase/Triton X-100, stained with anti-BrdII mAb, and analyzed by flow cytometry.

ELISPOT

Immunospot assays for IFN- were performed by coating ELISPOT plates (BD Pharmingen) with anti-IFN-mAb, blocking, and addition of responder cells isolated from cardiac transplant recipients plus donor splenocytes or bone marrow-derived DC as stimulators; recipient splenocytes or DC were used as syngeneic controls. At 24 h, cells were discarded, and wells were washed, followed by biotinylated anti-IFN-mAb, streptavidin-HRP, and substrate. Spots were counted using an Immunospot Analyzer (Cellular Technology), and recipient anti-donor responder frequency was determined as the number of IFN-spot-forming cells per-106 106 splenocytes.

Western Blots

Grafts were sonicated in lysis buffer containing Triton X-100 and protease inhibitors, followed by centrifugation and assay of supernatant protein content. Proteins were reduced, separated by SDS-PAGE, and transferred to nitrocellulose membranes. Membranes were blocked, incubated with primary and HRP-linked secondary Abs, and, after the substrate reaction, analyzed using National Institutes of Health Image.

Transplantation

Intra-abdominal vascularized cardiac allografting was performed as previously described using 6- to 8-wk-old mice. Briefly, donor ascending aorta and pulmonary artery were anastomosed end-to-side to recipient infrarenal aorta and inferior vena cava, respectively. Graft survival was assessed twice daily by abdominal palpation; rejection was defined as total cessation of cardiac contraction and was confirmed by histology.

Immunopathology

Portions of harvested allografts were fixed in formalin, paraffin-embedded or snap-frozen, and analyzed by immunoperoxidase staining with mAbs and an Envision kit (DakoCytomation).

Statistics

Allograft survival was used to generate Kaplan-Meier survival curves, and comparison between groups was performed by log-rank analysis.

For further details regarding Example 15, including references, see Tao et al., J. Immunol., 175:5774-5782, 2005, which is expressly incorporated herein in its entirety by reference.

Example 16

BTLA-HVEM Effects in Asthma

Regulated Expression of PD-1 and BTLA During Acute Allergic Airway Inflammation.

Figure 57:
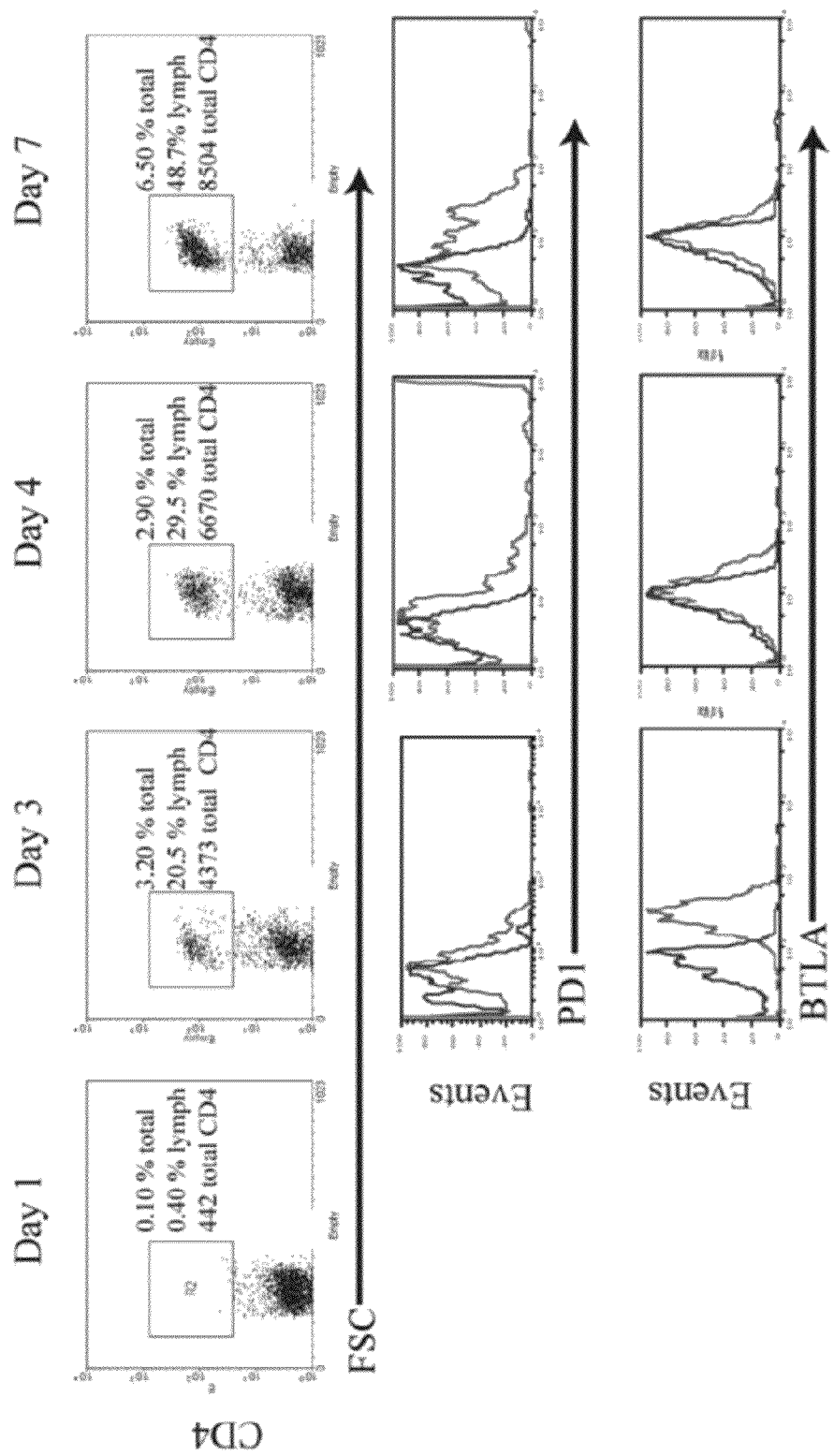
FIG. 57 PD-1 and BTLA are expressed on BAL CD4 T cells: C57BL/6 mice were sensitized and challenged with Ovalbumin. On days 1, 3, 4, and 7 following challenge, groups of mice were euthanized and the cells recovered in the BAL analyzed for expression of CD4 and PD-1 or BTLA by 2-color flow cytometry. The percentage of cells positive for CD4 as a fraction of either the total sample or of the lymphocyte gate as well as the total number of CD4+ cells recovered is indicated in each box. Histograms of PD-1 or BTLA expression on the CD4+ cells are shown for days 3, 4 and 7. Representative data of 3 independent experiments is presented.

We first determined the kinetics of lymphocyte accumulation and receptor expression in vivo by examining the cells recovered in the bronchoalveolar lavage (BAL) fluid. Mice were systemically sensitized and challenged with OVA. At 1, 3, 4, or 7 days following challenge groups of mice were euthanized and BAL performed. On 1 day following challenge, few CD4+ T cells were found in the BAL fluid. Significantly increased numbers of CD4 T cells appeared by day 3 which peaked by day 7 post-challenge (FIG. 57). We next examined the expression of PD-1 and BTLA on CD4 T cells recovered in the BAL fluid. Consistent with previous reports that PD-1 expression is induced on activated cells, we found that PD-1 expression gradually increased, being detectable on day 3 and reaching its maximum on day 7 following challenge. BTLA expression exhibited a reciprocal pattern with expression being greatest on day 3 and nearly undetectable by day 7 (FIG. 57).

Figure 58:
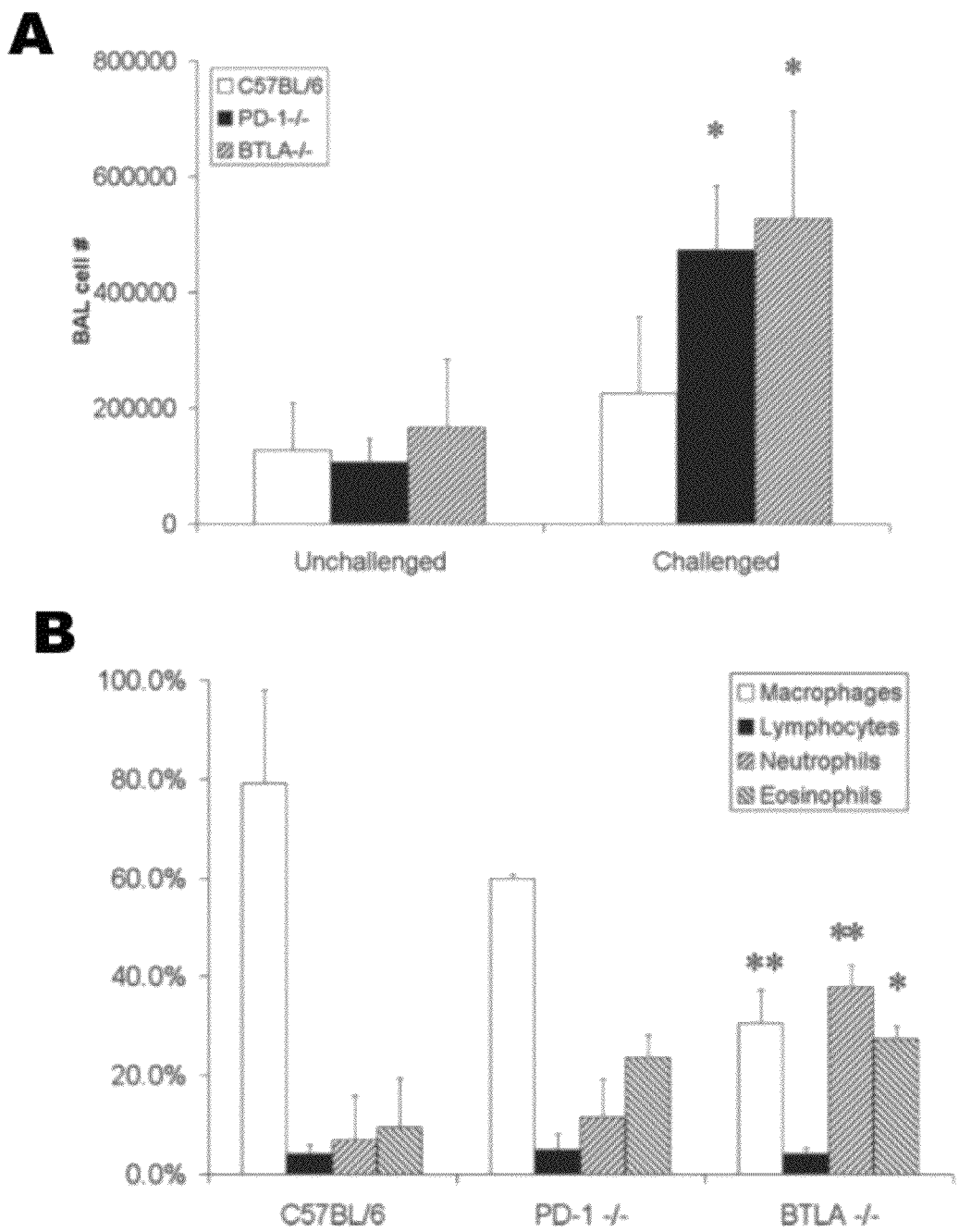
FIG. 58 PD-1 and BTLA have a minor effect on acute allergic airway inflammation: C57BU6, PD-1−/− and BTLA−/− mice (n=5 per group) were sensitized ad challenged with OVA. 3 days following challenge, the mice were euthanized and samples collected for analysis. (A) Total cell counts in the BAL fluid. (B) Differential analysis of the cell types present in the BAL. (C) Representative fields of H and E stained sections (40× magnification). *=P<0.05 **=P<0.005 compared to C57BU6 by 2 tailed T test. Representative data from 5 independent experiments is shown.
Figure 58C:
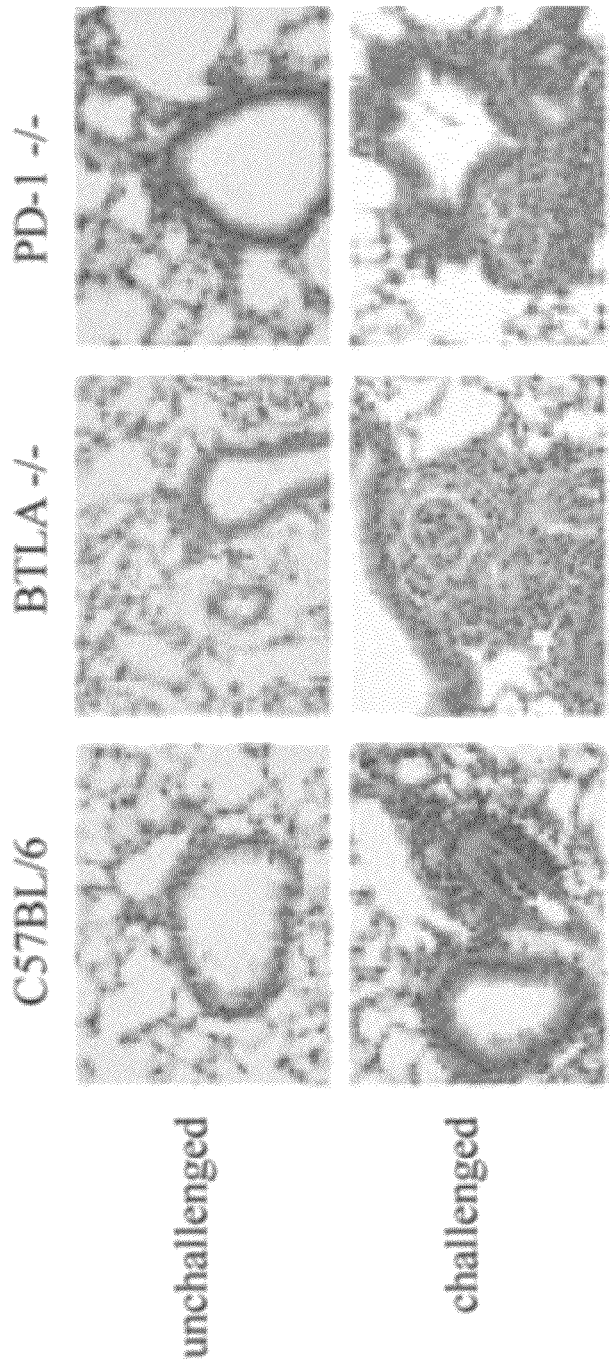

Given the distinct patterns of expression of these receptors on BAL T cells, we next examined the phenotype of mice deficient either BTLA or PD-1 in the acute allergic airway inflammation model (FIG. 58). Both BTLA-deficient and PD-1-deficient mice showed some increase in inflammatory cell recruitment compared to wild type mice (FIGS. 58A and B). All genotypes had a mixed inflammatory cell infiltrate, although there was an increased percentage of neutrophils and eosinophils in the BTLA-deficient mice (FIGS. 58A and B). Examination of the lung tissues revealed a mild increase in the intensity of inflammatory infiltrates in PD-1 and BTLA-deficient animals compared to wild type controls. Thus, while PD-1 and BTLA have been reported as being potent inhibitory receptors, we found only a relatively mild increase in the inflammatory response following of acute allergic airway inflammation in the absence of either of these inhibitory receptors.

Delayed Expression of Ligands for BTLA and PD-1 in Acute Allergic Airway Inflammation.

Figure 59:
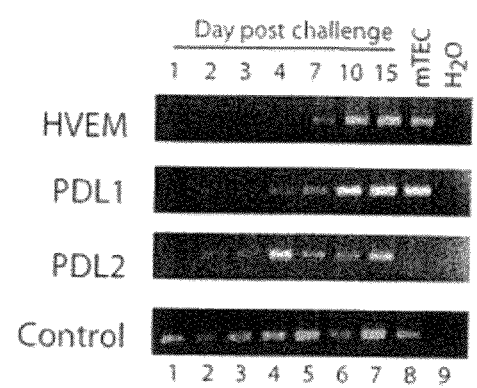
FIG. 59 Expression of the ligands for PD-1 and BTLA during allergic airway inflammation: Total RNA was isolated from whole lungs of allergen challenged mice on the indicated days post-challenge or from primary cultured murine tracheal epithelial cells (mTEC). RT-PCR was performed using specific primers that spanned intronic sequences of each gene. Shown is representative data from 2 independent experiments.

Given the documented inhibitory activity of BTLA and PD-1 in vivo, we were surprised that the absence of either of these receptors did not have a greater effect on acute airway inflammation. We therefore speculated that the ligands for these receptors might not be expressed thereby not allowing this axis of regulation to be apparent. We examined the expression of mRNA for Herpes Virus Entry Mediator (HVEM), the ligand for BTLA, and PD-L1 and PD-L2, the ligands for PD-1, during an extended time course of airway inflammation (FIG. 59). Expression of HVEM message was nearly undetectable in the first four days of acute allergic airway inflammation following challenge but became apparent by day 7 and was maximal by day 10 and 15 (FIG. 57, upper panels). Likewise, the expression of PD-L1 was first detectable at day 2, but remained relatively low in expression until approximately day 7 to day 10. Expression of PD-L2, a second ligand for PD-1, was maximum at day 4 following intranasal challenge, and declined subsequently. Interestingly, both HVEM and PDL1 were detectable in RNA samples obtained from cultured murine tracheal epithelial cells (mTEC), suggesting that the source of ligand may be non-immune cells of the lung.

BTLA and PD-1 Limit the Duration of Acute Allergic Airway Inflammation.

Figure 60A:
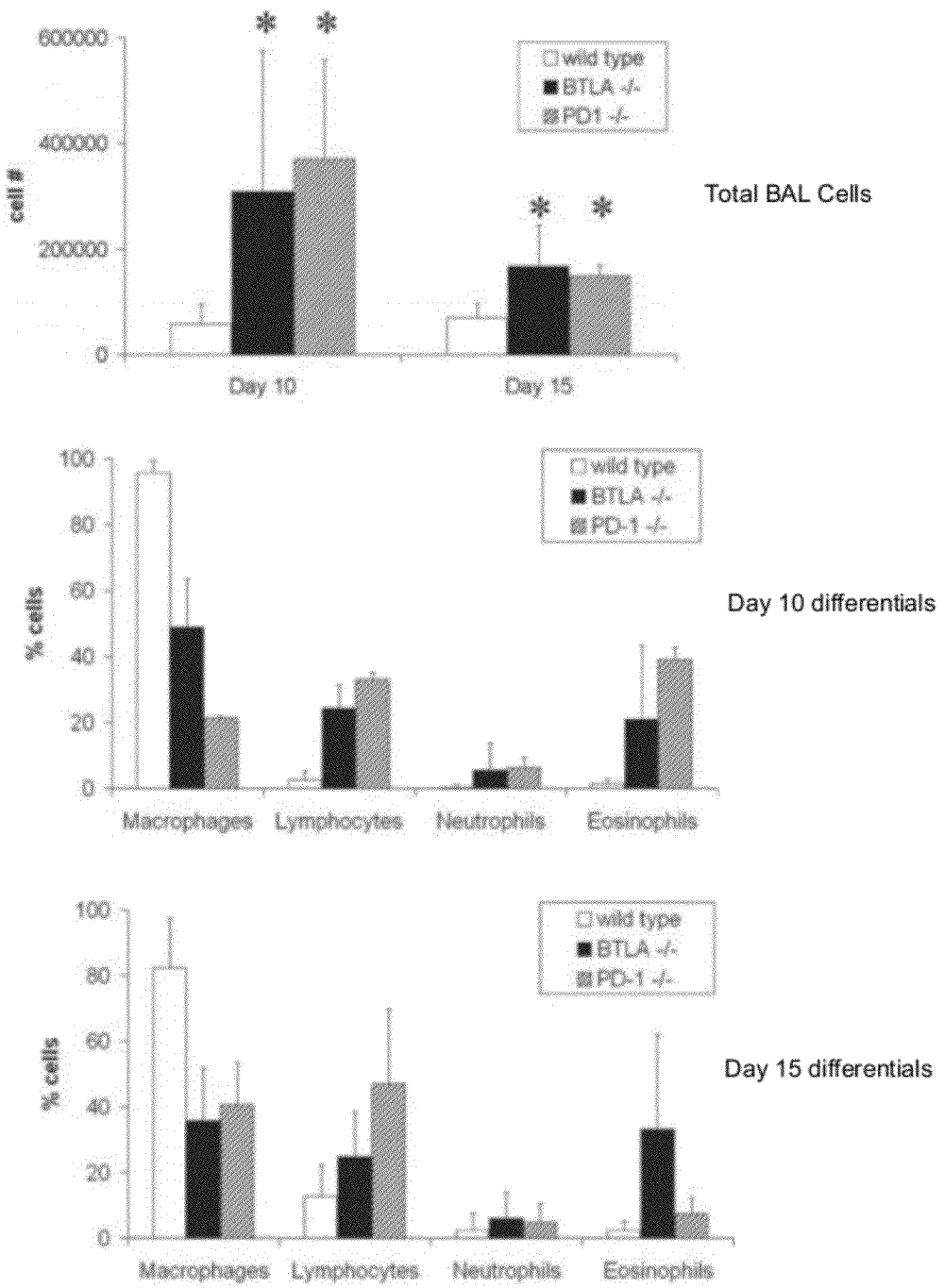
FIG. 60 shows that PD-1 and BTLA-deficient mice have a prolonged duration of airway inflammation: C57BL/6, PD-1−/− and BTLA−/− mice were sensitized and challenged with OVA. On days 10 and 15 cohorts of mice (n=5/group) were euthanized and samples collected for A) analysis of the BAL and B) histology. *=p<0.05 compared to C57BL/6 using a 2 tailed T-test.
Figure 60B:
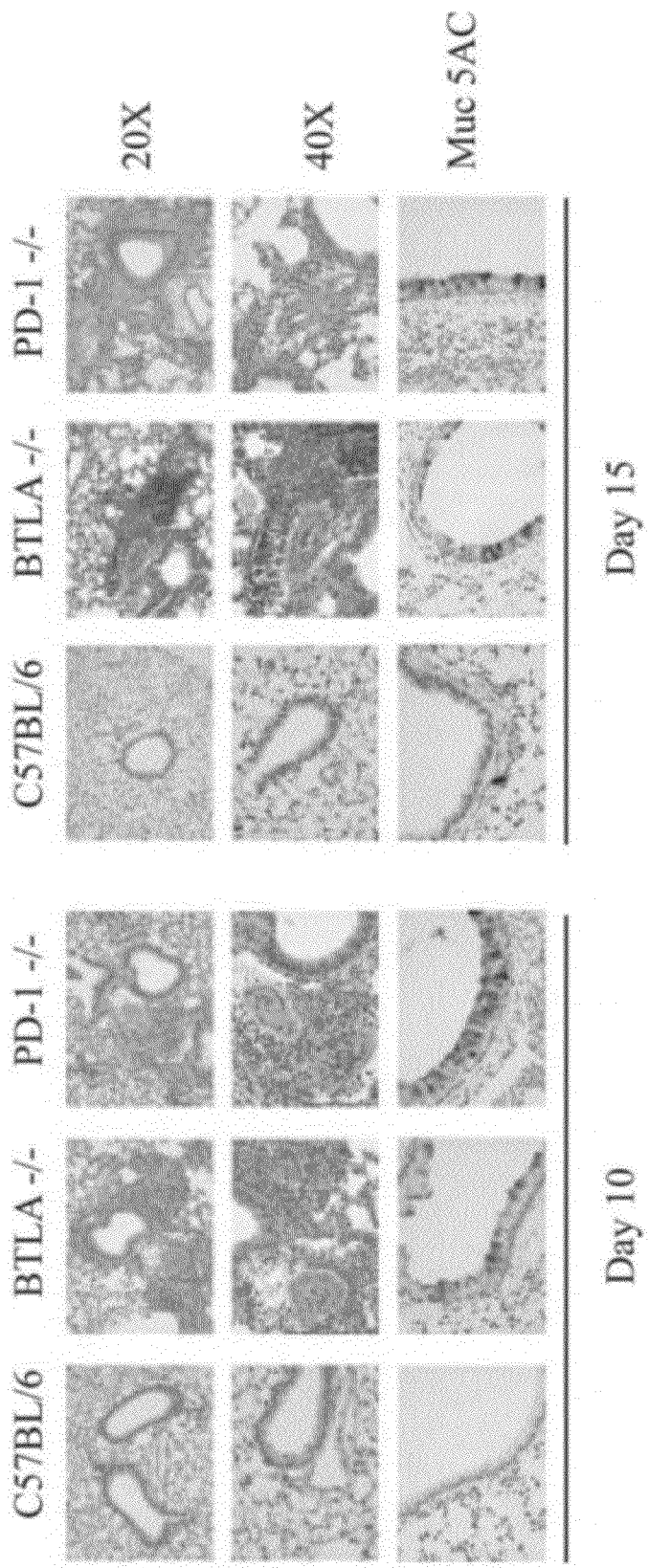

Because the ligands for PD-1 and BTLA were maximally expressed in the second week following intranasal challenge, we next examined BAL cell numbers and compositions at day 10 and day 15 following intranasal challenge (FIG. 60). Wild type mice had completely resolved the inflammation, as evidenced by a low number of cells recovered in the BAL fluid and histology at days 10 and 15 following challenge. In stark contrast, mice deficient in BTLA and PD-1 showed a persistent increase in BAL cells on day 10 following intranasal challenge. Furthermore, the composition of these cells in this fluid revealed a greater proportion of lymphocytes and eosinophils in comparison to the few cells in the wild type mice, which consisted predominantly of macrophages. Even on day 15, examination of BTLA-deficient mice revealed the continued presence increased numbers of lymphocytes and eosinophils: Direct histological examination of H and E stained sections also demonstrated persistent inflammation in the lungs of both PD-1 and BTLA-deficient mice at days 10 and 15, whereas the wild type mice had complete resolution in this time frame. Thus, these receptors are critical for the normal resolution of airway inflammation.

T cell dependent immune responses are determined by the coordinate integration of signals derived from both cell:cell interactions and soluble mediators. We have recently described a novel role for CD28 signaling not only in the early priming phase but also in maintenance of the effector phase of allergic airway inflammation. These studies focused on an acute model, acting between days 1 and 3. By contrast, the present results show that the inhibitory receptors BTLA and PD-1 exert a slight effect in attenuating the degree of acute inflammation but have a profound effect on the duration of inflammation, suggesting they act to terminate the immune response. We also observed a temporal regulation of expression of the ligands for these receptors during the course of the inflammatory response. Therefore, these data support that the regulated expression of inhibitory receptors on lymphocytes and their ligands in the lung are critical for the proper termination of the acute inflammatory response. In the absence of the inhibitory receptors on lymphocytes, the normally self limited acute inflammatory response progresses to a chronic infiltrate that persists for at least 15 days. We propose, based on these findings, that abnormalities in this axis could play a role in pathologic situations such as chronic persistent asthma and may represent novel targets for therapeutic intervention.

Methods for Example 16.

Mice

BTLA-deficient mice were generated as previously described. PD-1 deficient mice were obtained from Tasuka Honjo (Kyoto University, Kyoto Japan). C57BL/6 mice were purchased from Jackson Laboratories (Bar Harbor, Me.). All mice were housed in specific pathogen free facilities at Washington University School of Medicine. All animal studies have been approved by the Washington University Animal Studies Committee.

Antibodies

Anti-BTLA antibody (Clone 6F7, mouse IgG1) was generated as previously described. Anti-PD-1 and anti-CD4 antibodies were purchased from Ebiosciences. Flow cytometric analysis was performed on a FacsCalibur cytometer using Cellquest software (Becton Dickinson Corporation). Analysis was performed using FloJo software.

RT-PCR

Total RNA was extracted from lung tissue of control or allergen challenged mice using Trizol (Invitrogen). Random primed cDNA was prepared using the Retroscript kit (Ambion). Specific primers for PDL1, PDL2 and HVEM were designed that spanned intronic sequences. Control primers amplify ribosomal S15 RNA and are provided with the Retroscript Kit.

Experimental Allergic Airway Inflammation

Mice were sensitized and challenged with Ovalbumin as previously described. Briefly, mice were injected i.p. with Ova adsorbed to alum on days 0 and 7. On day 14 they received an intranasal challenge of 50 pi of 1% Ova in the morning and afternoon. Samples were collected as previously described on the indicated days following inhaled challenge.

Preparation of murine tracheal epithelial cells: Primary mouse airway epithelial cells were cultured and differentiated using an established high fidelity model of the mouse airway. Briefly, epithelial cells were harvested from mouse tracheas of C57/Bl6 strain mice (5-6 weeks old) using pronase digestion. Cells were purified by differential adherence of fibroblasts to yield a preparation composed of greater than 99% epithelial cells determined by expression of cytokeratin. Mouse tracheal epithelial cells (MTEC) were cultured in the presence of growth factor supplemented media on semi-permeable membranes (Transwell, Corning-Costar, Corning, N.Y.). Media was maintained in upper and lower chambers until the transmembrane resistance was greater than 1,000 Ohms·cm2 indicating tight junction formation. Media was then removed from the upper chamber to establish an air-liquid interface (ALI) condition used for epithelial cell differentiation. Cells were differentiated for at least 7 days at ALI to generate a multilayer model of the airway composed of ciliated, secretory, and basal airway epithelial cells. RNA was prepared from day 7 ALI cultures using Trizol reagent.

Example 17

Effect of BTLA Loss of Function on Humoral Response

We immunized cohorts of mice with one injection of NP-Ficoll in alum and measured production of anti-NP antibodies of specific isotypes on day 14. For the isotypes IgM, IgG1, IgA, we found no specific changes in levels of anti-NP antibodies. For IgG2a or IgG2b, we found only slight increases in anti-NP antibodies in the BTLA-/- compared to wild type mice. However, for antibodies of the IgG3 isotype, which is primarily associated with T-independent responses, we found approximately a two-fold increased in anti-NP specific antibodies in BTLA-/- mice compared to wild type mice.

In addition, spontaneous germinal centers have been observed at a higher frequency than control in aging BTLA-/- mice.

Example 18

BTLA Modulates Response to Viral Infection

Wildtype and BTLA knockout mice were infected with Sendai virus and monitored for three weeks. BTLA knockout mice maintained higher body weight and exhibited greater survival following infection with Sendai virus. Similar results were obtained using West Nile virus.

What is claimed is:

1. A method of inhibiting lymphocyte proliferation, the method comprising exposing lymphocytes to an isolated antibody that specifically binds to an epitope on a BTLA protein, the BTLA protein having an amino acid sequence set forth in SEQ ID NO: 8.

2. A method of inhibiting T cell proliferation, the method comprising exposing T cells to an isolated antibody that specifically binds to an epitope on a BTLA protein, the BTLA protein having an amino acid sequence set forth in SEQ ID NO: 8.

3. A method of inhibiting CD4+ T cell proliferation, the method comprising exposing CD4+ T cells to an isolated antibody that specifically binds to an epitope on a BTLA protein, the BTLA protein having an amino acid sequence set forth in SEQ ID NO: 8.

4. A method of inhibiting Th1 cell proliferation, the method comprising exposing Th1 cells to an isolated antibody that specifically binds to an epitope on a BTLA protein, the BTLA protein having an amino acid sequence set forth in SEQ ID NO:6.

5. A method of inhibiting CD4+ T cell proliferation, the method comprising exposing CD4+ T cells to an isolated antibody which specifically binds to the polypeptide of SEQ ID NO: 8, wherein said antibody is an agonist antibody that inhibits CD4+ T cell proliferation.

* * * * *